United States Patent [19]

Shuto et al.

[11] Patent Number: 5,264,448
[45] Date of Patent: Nov. 23, 1993

[54] AMIDE COMPOUND AND ITS PRODUCTION AND USE

[75] Inventors: Akira Shuto; Hirosi Kisida, both of Takarazuka; Naoto Meki, Kobe; Tomotoshi Imahase, Takarazuka; Hiroaki Fujimoto; Kimitoshi Umeda, both of Toyonaka, all of Japan

[73] Assignee: Sumitomo Chemical Company, Limited, Osaka, Japan

[21] Appl. No.: 777,497

[22] Filed: Oct. 17, 1991

Related U.S. Application Data

[62] Division of Ser. No. 506,336, Apr. 9, 1990, abandoned.

[30] Foreign Application Priority Data

Apr. 19, 1989 [JP] Japan .................. 1-101203
Dec. 25, 1989 [JP] Japan .................. 1-337698

[51] Int. Cl.$^5$ .................. C07D 263/16; A01N 43/76
[52] U.S. Cl. .................. 514/324; 548/236
[58] Field of Search .................. 548/236; 514/374

[56] References Cited

U.S. PATENT DOCUMENTS

| 4,861,777 | 8/1989 | Okada | 514/234.5 |
| 4,950,668 | 8/1990 | Okada | 514/232.5 |
| 5,103,014 | 4/1992 | Musser | 548/204 |

FOREIGN PATENT DOCUMENTS

| 296673 | 12/1988 | European Pat. Off. | 548/200 |
| 2001623 | 2/1979 | United Kingdom. | |
| 2058748 | 4/1981 | United Kingdom. | |
| 2149402 | 6/1985 | United Kingdom. | |

*Primary Examiner*—Robert Gerstl
*Attorney, Agent, or Firm*—Stevens, Davis, Miller & Mosher

[57] ABSTRACT

The present invention relates to certain novel amide compound represented by the formula of

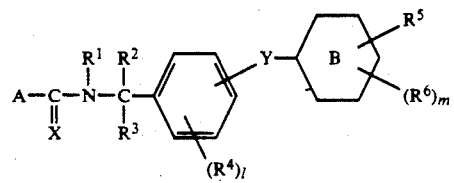

wherein A is an oxazole and, X, $R^1$, $R^2$, $R^3$, $R^4$, Y, the ring B, $R^5$, $R^6$, l and m are the same as defined in the present specification, its production and an insecticidal and/or acaricidal composition containing it as an active ingredient.

7 Claims, No Drawings

AMIDE COMPOUND AND ITS PRODUCTION AND USE

This application is a division of application Ser. No. 07/506,336, filed Apr. 9, 1990, now abandoned.

The present invention relates to a novel amide compound, its production, and insecticidal and acaricidal composition containing it as an active ingredient.

It has been disclosed in the specifications of EP-289879-A and EP-307801-A that certain kinds of amide compounds have an insecticidal, acaricidal activities.

These compounds are, however, not necessarily sufficient in view of their activities, spectra and others.

Under such circumstances, the present inventors have made extensive research to develop compounds having an excellent insecticidal, acaricidal activities, and resultantly have found that amide compounds represented by the later-mentioned formula [I] have excellent insecticidal, acaricidal activities, and have accomplished the present invention.

The present invention provides an amide compound represented by the formula [I] [hereinafter referred to as the compound of the present invention], its production, and insecticidal and acaricidal composition containing it as an active ingredient:

An amide compound represented by the formula [I] of

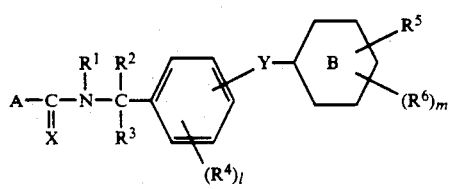

wherein $R^1$ is a hydrogen atom an alkyl group of 1–4 carbons, an alkylcarbonyl group of 1–8 total carbons or a group represented by the formula of $$-S(O)_nR^7;$$

$R^2$ is a hydrogen atom, an alkyl group of 1–4 carbons or a cyano group;

$R^3$ is a hydrogen atom or an alkyl group of 1–4 carbons;

$R^4$ is a hydrogen atom, a halogen atom or an alkyl group of 1–4 carbons;

$R^5$ is a halogen atom, an alkyl group of 1–8 carbons, a haloalkyl group of 1–8 carbons, a cycloalkyl group of 3–8 total carbons, an alkenyl group of 2–8 carbons, an alkynyl group of 2–8 carbons, an alkoxy group of 1–8 carbons, a haloalkoxy group of 1–8 carbons, an alkenyloxy group of 2–8 carbons, a haloalkenyloxy group of 2–8 carbons, an alkynyloxy group of 2–8 carbons, an alkylthio group of 1–8 carbons, a haloalkylthio group of 1–8 carbons, an alkenylthio group of 2–8 carbons, a haloalkenylthio group of 2–8 carbons, an alkynylthio group of 2–8 carbons, an alkoxyalkyl group of 2–8 total carbons, an alkylthioalkyl group of 2–8 total carbons, a (haloalkylthio)alkyl group of 2–8 total carbons, an alkylsulfinyl group of 1–8 carbons, a haloalkylsulfinyl group of 1–8 carbons, an alkylsulfonyl group of 1–8 carbons, a haloalkylsulfonyl group of 1–8 carbons, an alkylsulfonyloxy group of 1–8 carbons, a haloalkylsulfonyloxy group of 1–8 carbons, an alkylamino group of 1–8 carbons, a haloalkylamino group of 1–8 carbons, a dialkylamino group of 2–16 total carbons, an alkanoylamino group of 1–8 carbons, an alkylimino group of 1–8 carbons, an N-alkylformamidino group of 2–8 total carbons, an N-alkylacetamidino group of 3–8 total carbons, an N,N-dialkylformamidino group of 3–16 total carbons, an N,N-dialkylacetamidino group of 4–16 carbons or an alkylsulfonylamido group of 1–8 carbons;

$R^6$ is a hydrogen atom, a halogen atom, an alkyl group of 1–3 carbons, a haloalkyl group of 1–3 carbons, a cycloalkyl group of 3–6 carbons, an alkenyl group of 2–6 carbons, an alkynyl group of 2–6 carbons, an alkoxy group of 1–3 carbons, a haloalkoxy group of 1–3 carbons, an alkenyloxy group of 2–6 carbons, a haloalkenyloxy group of 2–6 carbons, an alkynyloxy group of 2–6 carbons, an alkylthio group of 1–3 carbons, a haloalkylthio group of 1–3 carbons, an alkenylthio group of 2–6 carbons, a haloalkenylthio group of 2–6 carbons, an alkynylthio group of 2–6 carbons, an alkoxyalkyl group of 2–3 total carbons, an alkylsulfinyl group of 1–3 carbons, a haloalkylsulfinyl group of 1–3 carbons, an alkylsulfonyl group of 1–3 carbons, a haloalkylsulfonyl group of 1–3 carbons, an alkylsulfonyloxy group of 1–3 carbons or a haloalkylsulfonyloxy group of 1–3 carbons, provided that $R^5$ and $R^6$ may be linked at their ends, when they are adjacent each other, to form a saturated or unsaturated five- or six-membered ring which contains 0–2 oxygen or sulfur atoms therein and may be substituted with a halogen atom or an alkyl group of 1–4 carbons;

$R^7$ is an alkyl group of 1–18 carbons, a haloalkyl group of 1–18 carbons, or a group represented by the formula of

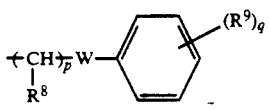

or the formula of

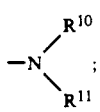

$R^8$ is a hydrogen atom, an alkyl group of 1–4 carbons or a haloalkyl group of 1–4 carbons;

$R^9$ is a hydrogen atom, a halogen atom, an alkyl group of 1–4 carbons, a haloalkyl group of 1–4 carbons, an alkoxy group of 1–4 carbons, a haloalkoxy group of 1–4 carbons, an alkylthio group of 1–4 carbons, a haloalkylthio group of 1–4 carbons, an alkylsulfinyl group of 1–4 carbons, a haloalkylsulfinyl group of 1–4 carbons, an alkylsulfonyl group of 1–4 carbons, a haloalkylsulfonyl group of 1–4 carbons, an alkylsulfonyloxy group of 1–4 carbons, a haloalkylsulfonyloxy group of 1–4 carbons, nitro or cyano group;

$R^{10}$ is an alkyl group of 1–8 carbons, a haloalkyl group of 1–8 carbons, an alkoxyalkyl group of 3–8 total carbons or a (haloalkoxy)alkyl group of 3–8 total carbons;

$R^{11}$ is an alkyl group of 1–8 carbons, a haloalkyl group of 1–8 carbons, an alkoxyalkyl group of 3–8 total carbons, a (haloalkoxy)alkyl group of 3–8 total carbons or a group represented by the formula of

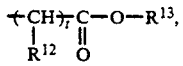

provided that $R^{10}$ and $R^{11}$ may be linked at their ends to form a saturated or unsaturated five- or six-membered ring which contains 0-2 oxygen or sulfur atoms therein and may be substituted with a halogen atom, an alkyl group of 1-4 carbons, an alkoxy group of 1-4 carbons or an alkylthio group of 1-4 carbons;

$R^{12}$ is a hydrogen atom, an alkyl group of 1-8 carbons, a haloalkyl group of 1-8 carbons, an alkoxyalkyl group of 2-8 total carbons or a (haloalkoxy)alkyl group of 2-8 total carbons;

$R^{13}$ is an alkyl group of 1-18 carbons, a haloalkyl group of 1-18 carbons, an alkoxyalkyl group of 3-18 total carbons, a (haloalkoxy)alkyl group of 3-18 total carbons, an alkoxyhaloalkyl group of 3-18 total carbons, an alkylthioalkyl group of 3-18 total carbons, a (haloalkylthio)alkyl group of 3-18 total carbons, a cycloalkyl group of 3-8 carbons which may be substituted with an alkyl group of 1-10 carbons, a cycloalkyl group of 3-8 carbons substituted with a haloalkyl group of 1-10 carbons, a halocycloalkyl group of 3-8 carbons which may be substituted with an alkyl group of 1-10 carbons, a cycloalkyl group of 3-8 carbons substituted with an alkoxy group of 1-10 carbons, or a cycloalkyl group of 3-8 carbons substituted with a haloalkoxy group of 1-10 carbons;

W is an oxygen atom, a sulfur atom, a sulfinyl group or single bond;

l is an integer of 1 or 2;
m is an integer of 1-4;
n is an integer of 0-2;
p is an integer of 1-4;
q is an integer of 1-5;
t is an integer of 0-10;
A is a group represented by the formula of

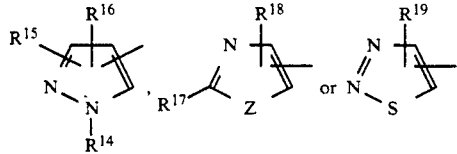

$R^{14}$, $R^{17}$, $R^{18}$ and $R^{19}$ independently are a hydrogen atom, an alkyl group of 1-4 carbons or a haloalkyl group of 1-4 carbons; $R^{15}$ and $R^{16}$ independently are a hydrogen atom, a halogen atom, an alkyl group of 1-6 carbons, a cycloalkyl group of 3-6 carbons, a haloalkyl group of 1-6 carbons, a phenyl group which may be substituted, an alkoxy group of 1-6 carbons, a cycloalkoxy group of 3-6 carbons or a haloalkoxy group of 1-6 carbons, provided that $R^{15}$ and $R^{16}$ may be linked at their ends, when they are adjacent each other, to form a saturated five- or six-membered ring which may be substituted with an alkyl of 1-4 carbons; X and Z independently are an oxygen atom or a sulfur atom; Y is an oxygen atom, a sulfur atom, a sulfinyl, sulfonyl or methylene group, or a group represented by the formula of —$NR^{20}$—;

$R^{20}$ is a hydrogen atom or an alkyl group of 1-4 carbons; and the ring B is a benzene, pyridine or cyclohexane ring.

In the compounds of the present invention represented by the formula (I), the alkyl group of 1-4 carbons denoted by $R^1$ includes, for example, methyl, ethyl, n-propyl, isopropyl, n-butyl, sec-butyl, isobutyl and the like; the alkylcarbonyl group of 1-8 carbons includes, for example, acetyl, propionyl, n-butylyl, isobutylyl, n-valeryl, isobutylcarbonyl, tert-butylcarbonyl, n-hexanoyl, n-heptanoyl, n-octanoyl and the like. The alkyl group of 1-4 carbons denoted by $R^2$ or $R^3$ includes, for example, methyl, ethyl, n-propyl, isopropyl, n-butyl, sec-butyl, isobutyl and the like. The halogen atom denoted by $R^4$ includes, for example, a fluorine atom, chlorine atom, bromine atom and the like; and the alkyl group of 1-4 carbons includes, for example, methyl, ethyl, n-propyl, isopropyl, n-butyl, sec-butyl, isobutyl and the like. The halogen atom denoted by $R^5$ includes, for example, fluorine atom, chlorine atom, bromine atom and the like; the alkyl group of 1-8 carbons includes, for example, methyl, ethyl, n-propyl, isopropyl, n-butyl, sec-butyl, isobutyl, tert-butyl, n-amyl, neopentyl, n-hexyl, n-heptyl, n-octyl and the like; the haloalkyl group of 1-8 carbons includes, for example, difluoromethyl, trifluoromethyl, 2-fluoroethyl, 2,2,2-trifluoroethyl, 1-fluoroethyl, 1,2-difluoroethyl, 3-fluoropropyl, 1-fluoropropyl, 2-fluoropropyl, 4-fluorobutyl, 5-fluoroamyl, 6-fluorohexyl, 7-fluoroheptyl, 8-fluorooctyl, 2-chloroethyl, 3-chloropropyl, 4-chlorobutyl, 3-bromopropyl and the like; the cycloalkyl group of 3-8 carbons includes, for example, cyclopropyl, cyclobutyl, 2-methylcyclopropyl, cyclohexyl, 2-methylcyclohexyl, 1-methylcyclopropyl, 4-methylcyclohexyl, 4-ethylcyclohexyl and the like; the alkenyl group of 2-8 carbons includes, for example, vinyl, allyl, 1-methylvinyl, 1-propenyl, 2-butenyl, 2-methyl-2-propenyl, 2-pentenyl, 3-methyl-2-butenyl, 3,3-dimethyl-1-butenyl, 2-methyl-2-butenyl, 1-hexenyl, 2-hexenyl, 5-hexenyl, 1-heptenyl, 1-methyl-1-hexenyl, 1-octenyl and the like; the alkynyl group of 2-8 carbons includes, for example, ethynyl, propargyl, 1-methylpropargyl, 1-propynyl, 1-butynyl, 3,3-dimethyl-1-butynyl, 1-pentynyl, 1-hexynyl, 1-heptynyl, 1-octynyl and the like; the alkoxyl group of 1-8 carbons includes, for example, methoxy, ethoxy, n-propoxy, isopropoxy, n-butoxy, isobutyloxy, sec-butyloxy, n-amyloxy, 1,2-dimethylpropoxy, 1-ethylpropoxy, neopentyloxy, n-hexyloxy, 4-methylpentyloxy, sec-pentyloxy, n-heptyloxy, n-octyloxy and the like; the haloalkoxyl group of 1-8 carbons includes, for example, difluoromethoxy, trifluoromethoxy, 2-fluoroethoxy, 2,2,2-trifluoroethoxy, 1,1,2,2-tetrafluoroethoxy, 2-chloro-1,1,2-trifluoroethoxy, 2,2-dichloro-1,1-difluoroethoxy, 2,2,3,3,3-pentafluoropropyloxy, 1,1,1,3,3,3-hexafluoro-2-propyloxy, 1,1,2,3,3,3-hexafluoropropyloxy, 3,3,4,4,4-pentafluoro-2-butyloxy, 3-fluoropropyloxy, 4-fluorobutyloxy, 5-fluoroamyloxy, 6-fluorohexyloxy, 7-fluoroheptyloxy, 8-fluorooctyloxy, 2-chloroethoxy, 3-chloropropoxy, 4-chlorobutyloxy, 3-bromopropoxy and the like; the alkenyloxy group of 2-8 carbons includes, for example, vinyloxy, allyloxy, 1-propenyloxy, 2-butenyloxy, 2-methyl-2-propenyloxy, 2-pentenyloxy, 3-methyl-2-butenyloxy, 2-hexenyloxy, 2-heptenyloxy, 2-octenyloxy and the like; the alkynyloxy group of 2-8 carbons includes, for example, ethynyloxy, propargyloxy, 1-methylpropargyloxy, 1-propynyloxy, 2-butynyloxy, 4,4-dimethyl-2-pentynyloxy, 2-pentynyloxy, 2-hexynyloxy, 2-heptynyloxy, 2-octynyloxy and the like; the haloalkenyloxy group of 2-8 carbons includes, for example, 1,2-dichlorovinyloxy, 2,3-dichloroallyloxy, 2-iodo-1-fluorovinyloxy, 2-chloro-1-fluorovinyloxy, 2,2- dichloro-1-fluorovinyloxy, 2,2-dichloro-vinyloxy and the like; the alkylthio group of 1–8 carbons includes, for example, methylthio, ethylthio, n-propylthio, isopropylthio, n-butylthio, isobutylthio, sec-butylthio, tert-butylthio, n-pentylthio, isopentylthio, sec-pentylthio, 2-ethylpropylthio, n-hexylthio, n-heptylthio, n-octylthio and the like; the haloalkylthio group of 1–8 carbons includes, for example, fluoromethylthio, difluoromethylthio, trifluoromethylthio, 2-fluoroethylthio, 2,2,2-trifluoroethylthio, 1,1,2,2-tetrafluoroethylthio, 2-chloro-1,1,2-trifluoroethylthio, 2,2-dichloro-1,1-difluoroethylthio, 2,2,3,3,3-pentafluoropropylthio, 1,1,1,3,3,3-hexafluoro-2-propylthio, 1,1,2,3,3,3-hexafluoropropylthio, 3,3,4,4,4-pentafluoro-2-butylthio, 3-fluoropropylthio, 4-fluorobutylthio, 5-fluoroamylthio, 6-fluorohexylthio, 7-fluoroheptylthio, 8-fluorooctylthio, 2-chloroethylthio, 3-chloropropylthio, 4-chlorobutylthio, 3-bromopropylthio and the like; the alkenylthio group of 2–8 carbons includes, for example, vinylthio, allylthio, 1-propenylthio, 2-butenylthio, 2-methyl-2-propenylthio, 2-pentenylthio, 3-methyl-2-butenylthio, 2-hexenylthio, 2-heptenylthio, 2-octenylthio and the like; the alkynylthio group of 2–8 carbons includes, for example, ethynylthio, propargylthio, 1-methylpropargylthio, 1-propynylthio, 2-butynylthio, 4,4-dimethyl-2-pentynylthio, 2-pentynylthio, 2-hexynylthio, 2-heptynylthio, 2-octynylthio and the like; the haloalkenylthio group of 2–8 carbons includes, for example, 1,2-dichlorovinylthio, 2,3-dichloroallylthio, 2-iodo-1-fluorovinylthio, 2-chloro-1-fluorovinylthio, 2,2-dichloro-1-fluorovinylthio, 2,2-dichloro-vinylthio and the like; the alkoxyalkyl group of 2–8 total carbons includes, for example, methoxymethyl, 2-methoxyethyl, ethoxymethyl, 1-methoxyethyl, 2-ethoxyethyl, 3-methoxypropyl, 2-methoxypropyl, 2-ethoxypropyl, 4-methoxybutyl, 1-methoxypropyl, n-propyloxymethyl, isopropyloxymethyl, 3-n-propyloxypropyl, 4-n-propyloxybutyl, 6-ethoxyhexyl, 5-ethoxypentyl, 4-ethoxybutyl and the like; the alkylthioalkyl group of 2–8 total carbons includes, for example, methylthiomethyl, 2-methylthioethyl, ethylthiomethyl, 1-methylthioethyl, 2-ethylthioethyl, 3-methylthiopropyl, 2-methylthiopropyl, 2-ethylthiopropyl, 4-methylthiobutyl, 1-methylthiopropyl, n-propylthiomethyl, isopropylthiomethyl, 3-n-propylthiopropyl, 4-n-propylthiobutyl, 6-ethylthiohexyl, 5-ethylthiopentyl, 4-ethylthiobutyl and the like; the (haloalkylthio)alkyl group of 2–8 total carbons includes, for example, (trifluoromethylthio)methyl, 2-(bromodifluoromethylthio)ethyl, (2,2,2-trifluoroethylthio)methyl, 1-(trifluoromethylthio)ethyl, 2-(2,2,2-trifluoroethylthio)ethyl, 3-(trifluoromethylthio)propyl, 2-(trifluoromethylthio)propyl, 2-(2,2,2-trifluoroethylthio)propyl, 4-(trifluoromethylthio)butyl, 1-(trifluoromethylthio)propyl, (2,2,3,3,3-pentafluoropropylthio)methyl, (1-methyl-2,2,2-trifluoromethylthio)methyl, 3-(2,2,3,3,3-pentafluoropropylthio)propyl, 4-(2,2,3,3,3-pentafluoropropylthio)butyl, 6-(2,2,2-trifluoromethylthio)hexyl, 5-(2,2,2-trifluoroethylthio)pentyl, 4-(2,2,2-trifluoroethylthio)butyl and the like; the alkylsulfinyl group of 1–8 carbons includes, for example, methylsulfinyl, ethylsulfinyl, n-propylsulfinyl, isopropylsulfinyl, n-butylsulfinyl, 2-butylsulfinyl, 2-methylpropylsulfinyl, 1,1-dimethylethylsulfinyl, n-pentylsulfinyl, 2-pentylsulfinyl, 3-methylbutylsulfinyl, 2-ethylpropylsulfinyl, n-hexylsulfinyl, n-heptylsulfinyl, n-octylsulfinyl and the like; the haloalkylsulfinyl group of 1–8 carbons includes, for example, fluoromethylsulfinyl, difluoromethylsulfinyl, trifluoromethylsulfinyl, 2-fluoroethylsulfinyl, 2,2,2-trifluoroethylsulfinyl, 1,1,2,2-tetrafluoroethylsulfinyl, 2-chloro-1,1,2-trifluoroethylsulfinyl, 2,2-dichloro-1,1-difluoroethylsulfinyl, 2,2,3,3,3-pentafluoropropylsulfinyl, 1,1,1,3,3,3-hexafluoro-2-propylsulfinyl, 1,1,2,3,3,3-hexafluoropropylsulfinyl, 3,3,4,4,4-pentafluoro-2-butylsulfinyl, 3-fluoropropylsulfinyl, 4-fluorobutylsulfinyl, 5-fluoropentylsulfinyl, 6-fluorohexylsulfinyl, 7-fluoroheptylsulfinyl, 8-fluorooctylsulfinyl, 2-chloroethylsulfinyl, 3-chloropropylsulfinyl, 4-chlorobutylsulfinyl, 3-bromopropylsulfinyl and the like; the alkylsulfonyl group of 1–8 carbons includes, for example, methylsulfonyl, ethylsulfonyl, n-propylsulfonyl, 2-propylsulfonyl, n-butylsulfonyl, 2-butylsulfonyl, 2-methylpropylsulfonyl, 1,1-dimethylethylsulfonyl, n-pentylsulfonyl, 2-pentylsulfonyl, 3-methylbutylsulfonyl, 2-ethylpropylsulfonyl, n-hexylsulfonyl, n-heptylsulfonyl, n-octylsulfonyl and the like; the haloalkylsulfonyl group of 1–8 carbons includes, for example, fluoromethylsulfonyl, difluoromethylsulfonyl, trifluoromethylsulfonyl, 2-fluoroethylsulfonyl, 2,2,2-trifluoroethylsulfonyl, 1,1,2,2-tetrafluoroethylsulfonyl, 2-chloro-1,1,2-trifluoroethylsulfonyl, 2,2-dichloro-1,1-difluoroethylsulfonyl, 2,2,3,3,3-pentafluoropropylsulfonyl, 1,1,1,3,3,3-hexafluoro-2-propylsulfonyl, 1,1,2,3,3,3-hexafluoropropylsulfonyl, 3,3,4,4,4-pentafluoro-2-butylsulfonyl, 3-fluoropropylsulfonyl, 4-fluorobutylsulfonyl, 5-fluoropentylsulfonyl, 6-fluorohexylsulfonyl, 7-fluoroheptylsulfonyl, 8-fluorooctylsulfonyl, 2-chloroethylsulfonyl, 3-chloropropylsulfonyl, 4-chlorobutylsulfonyl, 3-bromopropylsulfonyl and the like; the alkylsulfonyloxy group of 1–8 carbons includes, for example, methylsulfonyloxy, ethylsulfonyloxy, 2-propylsulfonyloxy, n-propylsulfonyloxy, n-butylsulfonyloxy, n-pentylsulfonyloxy, n-hexylsulfonyloxy, n-heptylsulfonyloxy, n-octylsulfonyloxy and the like; the haloalkylsulfonyloxy group of 1–8 carbons includes, for example, chloromethylsulfonyloxy, trifluoromethylsulfonyloxy, difluoromethylsulfonyloxy, 2-chloroethylsulfonyloxy, 3-chloropropylsulfonyloxy, 4-chlorobutylsulfonyloxy, 5-chloropentylsulfonyloxy, 6-chlorohexylsulfonyloxy, 7-chloroheptylsulfonyloxy, 8-chlorooctylsulfonyloxy and the like; the alkylamino group of 1–8 carbons includes, for example, N-methylamino, N-ethylamino, N-n-propylamino, N-isopropylamino, N-n-butylamino, N-isobutylamino, N-sec-butylamino, N-n-amylamino, N-neopentylamino, N-n-hexylamino, N-n-heptylamino, N-n-octylamino and the like; the haloalkylamino group of 1–8 carbons includes, for example, N-difluoromethylamino, N-2-chloroethylamino, N-2,2,2-trifluoroethylamino, N-3-chloropropylamino, N-4-chlorobutylamino, N-5-chloropentylamino, N-6-chlorohexylamino, N-7-chloroheptylamino, N-8-chlorooctylamino and the like; the dialkylamino group of 2–16 total carbons includes, for example, N,N-dimethylamino, N-methyl-N-ethylamino, N,N-diethylamino, N-methyl-N-n-butylamino, N,N-di-n-propylamino, N-ethyl-N-n-butylamino, N,N-di-n butylamino, N,N-di-sec-butylamino, N,N-di-isobutylamino, N,N-di-n-amylamino, N,N-di-n-hexylamino, N-N-di-n-heptylamino, N,N-di-n-octylamino, N-methyl-N-n-octylamino and the like; the alkanoylamino group of 1–8 carbons includes, for example, N-formylamino, N-acetylamino, N-propionylamino, N-n-butyrylamino, N-isobutyrylamino, N-valerylamino, N-isovalerylamino, N-n-hexanoylamino, N-n-heptanoylamino, N-n-octanoylamino and the like; the alkylimino group of 1–8 carbons includes, for example, methylimino, ethylimino, 1-propylimino, 2- propylimino, 1-butylimino, 2-butylimino, 1-pentylimino, 2-pentylimino, 1-hexylimino, 2-hexylimino, 1-heptylimino, 2-heptylimino, 1-octylimino, 2-octylimino and the like; the N-alkylformamidino group of 2-8 total carbons includes, for example, N-methylformamidino, N-ethylformamidino, N-n-propylformamidino, N-isopropylformamidino, N-n-butylformamidino, N-n-amylformamidino, N-n-hexylformamidino, N-n-heptylformamidino and the like; the N-alkylacetamidino group of 3-8 total carbons includes, for example, N-methylacetamidino, N-ethylacetamidino, N-n-propylacetamidino, N-isopropylacetamidino, N-n-butylacetamidino, N-isobutylacetamidino, N-n-amylacetamidino, N-n-hexylacetamidino and the like; the N,N-dialkylformamidino group of 3-16 total carbons includes, for example N,N-dimethylformamidino, N-methyl-N-ethylformimidino, N,N-diethylformamidino, N,N-di-n-propylformamidino, N-methyl-N-n-propylformamidino, N,N-di-isopropylformamidino, N,N-di-n-butylformamidino, N,N-di-n-amylformamidino, N,N-di-n-hexylformamidino, N,N-di-n-heptylformamidino and the like; the N,N-dialkylacetamidino group of 4-16 total carbons includes, for example, N,N-dimethylacetamidino, N-methyl-N-ethylacetamidino, N,N-diethylacetamidino, N,N-di-n-propylacetamidino, N-methyl-N-n-butylacetamidino, N,N-di-n-butylacetamidino, N,N-di-n-amylacetamidino, N,N-di-n-hexylacetamidino and the like; and the alkylsulfonylamido group of 1-8 carbons includes, for example, methylsulfonylamido, ethylsulfonylamido, n-propylsulfonylamido, 2-propylsulfonylamido, n-butylsulfonylamido, n-pentylsulfonylamido, n-hexylsulfonylamido, n-heptylsulfonylamido, n-octylsulfonylamido and the like.

The halogen atom denoted by $R^6$ includes, for example, fluorine, chlorine, bromine atoms and the like; the alkyl group of 1-3 carbons includes, for example, methyl, ethyl, n-propyl, isopropyl and the like; the haloalkyl group of 1-3 carbons includes, for example, trifluoromethyl, 2-fluoroethyl, 2,2,2-trifluoroethyl, 1-fluoroethyl, 1,2-difluoroethyl, 3-fluoropropyl, 1-fluoropropyl, 2-fluoropropyl and the like; the cycloalkyl group of 3-6 carbons includes, for example, cyclopropyl, cyclobutyl, and cyclohexyl groups; the alkoxy group of 1-3 carbons includes, for example, methoxy, ethoxy, n-propoxy, isopropoxy and the like; the haloalkoxy group of 1-3 carbons includes, for example, difluoromethoxy, trifluoromethoxy, 2-fluoroethoxy, 2,2,2-trifluoroethoxy, 1,1,2,2-tetrafluoroethoxy, 2-chloro-1,1,2-trifluoroethoxy, 2,2-dichloro-1,1-difluoroethoxy, 2,2,3,3,3-pentafluoropropyloxy, 1,1,1,3,3,3-hexafluoro-2-propyloxy, 2-chloroethoxy, 3-chloropropoxy, 3-bromopropoxy an the like; the alkenyl group of 2-6 carbons includes, for example, vinyl, alkyl, 1-methylvinyl, 1-propenyl, 2-butenyl, 2-methyl-2-propenyl, 2-pentenyl, 3-methyl-2-butenyl, 3,3-dimethyl-1-butenyl, 2-methyl-2-butenyl, 1-hexenyl, 2-hexenyl, 5-hexenyl and the like; the alkynyl group of 2-6 carbons includes, for example, ethynyl, propargyl, 1-methylpropargyl, 1-propynyl, 1-butynyl, 3,3-dimethyl-1-butynyl, 1-pentynyl, 1-hexynyl and the like; the alkenyloxy group having 2-6 carbons includes, for example, vinyloxy, allyloxy, 1-propenyloxy, 2-butenyloxy, 2-methyl-2-propenyloxy, 2-pentenyloxy, 3-methyl-2-butenyloxy, 2-hexenyloxy and the like; the alkynyloxy group of 2-6 carbons includes, for example, ethynyloxy, propargyloxy, 1-methylpropargyloxy, 1-propynyloxy, 2-butynyloxy, 2-pentynyloxy, 2-hexynyloxy and the like; the haloalkenyloxy group of 2-6 carbons includes, for example, 1,2-dichlorovinyloxy, 2,3-dichloroallyloxy, 2-iodo-1-fluorovinyloxy, 2-chloro-1-fluorovinyloxy, 2,2-dichloro-1-fluorovinyloxy, 2,2-dichlorovinyloxy and the like; the alkylthio group of 1-3 carbons includes, for example, methylthio, ethylthio, n-propylthio, isopropylthio and the like; the haloalkylthio group of 1-3 carbons includes, for example, fluoromethylthio, difluoromethylthio, trifluoromethylthio, 2-fluoroethylthio, 2,2,2-trifluoroethylthio, 1,1,2,2-tetrafluoroethylthio, 2-chloro-1,1,2-trifluoroethylthio, 2,2-dichloro-1,1-difluoroethylthio, 2,2,3,3,3-pentafluoropropylthio, 1,1,1,3,3,3-hexafluoro-2-propylthio, 1,1,2,3,3,3-hexafluoropropylthio, 2-chloroethylthio, 2-chloropropylthio, 3-bromopropylthio and the like; the alkenylthio group of 2-6 carbons includes, for example, vinylthio, allylthio, 1-propenylthio, 2-butenylthio, 2-methyl-2-propenylthio, 2-pentenylthio, 3-methyl-2-butenylthio, 2-hexenylthio and the like; the alkynylthio group of 2-6 carbons includes, for example, ethynylthio, propargylthio, 1-methylpropargylthio, 1-propynylthio, 2-butynylthio, 2-pentynylthio, 2-hexynylthio and the like; the haloalkenylthio group of 2-6 carbons includes, for example, 1,2-dichlorovinylthio, 2,3-dichloroallylthio, 2-iodo-1-fluorovinylthio, 2-chloro-1-fluorovinylthio, 2,2-dichloro-1-fluorovinylthio, 2,2-dichlorovinylthio and the like; the alkoxyalkyl group of 2-3 total carbons includes, for examples, methoxymethyl, ethoxymethyl, and methoxyethyl groups; the alkylsulfinyl group having 1-3 carbon atoms includes, for example, methylsulfinyl, ethylsulfinyl, n-propylsulfinyl, 2-propylsulfinyl and the like; the haloalkylsulfinyl group of 1-3 carbons includes, for example, fluoromethylsulfinyl, difluoromethylsulfinyl, trifluoromethylsulfinyl, 2-fluoroethylsulfinyl, 2,2,2-trifluoroethylsulfinyl, 1,1,2,2-tetrafluoroethylsulfinyl, 2-chloro-1,1,2-trifluoroethylsulfinyl, 2,2-dichloro-1,1-difluoroethylsulfinyl, 2,2,3,3,3-pentafluoropropylsulfinyl, 1,1,1,3,3,3-hexafluoro-2-propylsulfinyl, 1,1,2,3,3,3-hexafluoropropylsulfinyl, 3-fluoropropylsulfinyl, 2-chloroethylsulfinyl, 3-chloropropylsulfinyl, 3-bromopropylsulfinyl and the like; the alkylsulfonyl group of 1-3 carbons includes, for example, methylsulfonyl, ethylsulfonyl, n-propylsulfonyl, 2-propylsulfonyl and the like; the haloalkylsulfonyl group of 1-3 carbons includes, for example, fluoromethylsulfonyl, difluoromethylsulfonyl, trifluoromethylsulfonyl, 2-fluoroethylsulfonyl, 2,2,2-trifluoroethylsulfonyl, 1,1,2,2-tetrafluoroethylsulfonyl, 2-chloro-1,1,2-trifluoroethylsulfonyl, 2,2-dichloro-1,1-difluoroethylsulfonyl, 2,2,3,3,3-pentafluoropropylsulfonyl, 1,1,1,3,3,3-hexafluoro-2-propylsulfonyl, 1,1,2,3,3,3-hexafluoropropylsulfonyl, 3-fluoropropylsulfonyl, 2-chloroethylsulfonyl, 3-chloropropylsulfonyl, 3-bromopropylsulfonyl and the like; the alkylsulfonyloxy group of 1-3 carbons includes, for example, methylsulfonyloxy, ethylsulfonyloxy, 2-propylsulfonyloxy, n-propylsulfonyloxy and the like; and the haloalkylsulfonyloxy group of 1-3 carbons includes, for example, chloromethylsulfonyloxy, trifluoromethylsulfonyloxy, difluoromethylsulfonyloxy, 2-chloroethylsulfonyloxy, and 3-chloropropylsulfonyloxy and the like; the alkyl group of 1-18 carbons denoted by $R^7$ includes, for example, methyl, ethyl, n-propyl, isopropyl, n-butyl, sec-butyl, isobutyl, tert-butyl, n-amyl, neo-pentyl, tert-pentyl, 1-methylbutyl, n-hexyl, n-heptyl, n-octyl, 1-methylheptyl, n-dodecyl, n-hexadecyl, n-octadecyl and the like; and the haloalkyl group of 1-18 carbons includes, for example, trifluoromethyl, 2-fluoroethyl, 2,2,2-trifluoroethyl, 1-fluoroethyl, 1,2-difluoroethyl, 3-fluoropropyl, 1-fluoropropyl, 2-fluoropropyl, 4-fluorobutyl, 5-fluoroamyl, 6-fluorohexyl, 7-fluoroheptyl, 8-fluorooctyl, 2-chloroethyl, 3-chloropropyl, 4-chlorobutyl, 3-bromopropyl, 10-fluorodecyl, 12-fluorododecyl, 16-fluorohexadecyl, 18-fluorooctadecyl and the like. The alkyl group of 1-4 carbons denoted by $R^8$ includes, for example, methyl, ethyl, n-propyl, isopropyl, n-butyl, isobutyl and the like; and the haloalkyl group of 1-4 carbons includes, for example, trifluoromethyl, 2-fluoroethyl, 2,2,2-trifluoroethyl, 1-fluoroethyl, 1,2-difluoroethyl, 3-fluoropropyl, 1-fluoropropyl, 2-fluoropropyl, 4-fluorobutyl, 2-chloroethyl, 3-chloropropyl, 4-chlorobutyl; 3-bromopropyl and the like.

The halogen atom denoted by $R^9$ includes, for example, fluorine atom, chlorine atom, bromine atom, and the like; the alkyl group of 1-4 carbons includes, for example, methyl, ethyl, n-propyl, isopropyl, n-butyl, isobutyl, tert-butyl and the like; the haloalkyl group of 1-4 carbons includes, for example, trifluoromethyl, 2-fluoroethyl, 2,2,2-trifluoroethyl, 1-fluoroethyl, 1,2-difluoroethyl, 3-fluoropropyl, 1-fluoropropyl, 2-fluoropropyl, 4-fluorobutyl, 2-chloroethyl, 3-chloropropyl, 4-chlorobutyl; 3-bromopropyl and the like; the alkoxyl group of 1-4 carbons includes, for example, methoxy, ethoxy, n-propoxy, isopropoxy, n-butoxy, isobutyloxy, sec-butyloxy and the like; the haloalkoxyl group of 1-4 carbons includes, for example, difluoromethoxy, trifluoromethoxy, 2-fluoroethoxy, 2,2,2-trifluoroethoxy, 1,1,2,2-tetrafluoroethoxy, 2-chloro-1,1,2-trifluoroethoxy, 2,2-dichloro-1,1-difluoroethoxy, 2,2,3,3,3-pentafluoropropyloxy, 1,1,1,3,3,3-hexafluoro-2-propyloxy, 1,1,2,3,3,3-hexafluoropropyloxy, 3,3,4,4,4-pentafluoro-2-butyloxy, 3-fluoropropyloxy, 4-fluorobutyloxy, 2-chloroethoxy, 3-chloropropoxy, 4-chlobutyloxy, 3-bromopropoxy and the like; the alkylthio group of 1-4 carbons includes, for example, methylthio, ethylthio, n-propylthio, isopropylthio, n-butylthio, isobutylthio, sec-butylthio, tert-butylthio and the like; the haloalkylthio group of 1-4 carbons includes, for example, fluoromethylthio, difluoromethylthio, trifluoromethylthio, 2-fluoroethylthio, 2,2,2-trifluoroethylthio, 1,1,2,2-tetrafluoroethylthio, 2-chloro-1,1,2-trifluoroethylthio, 2,2-dichloro-1,1-difluoroethylthio, 2,2,3,3,3-pentafluoropropylthio, 1,1,1,3,3,3-hexafluoro-2-propylthio, 1,1,2,3,3,3-hexafluoropropylthio, 3,3,4,4,4-pentafluoro-2-butylthio, 3-fluoropropylthio, 4-fluorobutylthio, 2-chloroethylthio, 3-chloropropylthio, 4-chlorobutylthio, 3-bromopropylthio and the like; the alkylsulfinyl group of 1-4 carbons includes, for example, methylsulfinyl, ethylsulfinyl, n-propylsulfinyl, 2-propylsulfinyl, n-butylsulfinyl, 2-butylsulfinyl, 2-methylpropylsulfinyl, 1,1-dimethylethylsulfinyl and the like; the haloalkylsulfinyl group of 1-4 carbons includes, for example, fluoromethylsulfinyl, difluoromethylsulfinyl, trifluoromethylsulfinyl, 2-fluoroethylsulfinyl, 2,2,2-trifluoroethylsulfinyl, 1,1,2,2-tetrafluoroethylsulfinyl, 2-chloro-1,1,2-trifluoroethylsulfinyl, 2,2-dichloro-1,1-difluoroethylsulfinyl, 2,2,3,3,3-pentafluoropropylsulfinyl, 1,1,1,3,3,3-hexafluoro-2-propylsulfinyl, 1,1,2,3,3,3-hexafluoropropylsulfinyl, 3,3,4,4,4-pentafluoro-2-butylsulfinyl, 3-fluoropropylsulfinyl, 4-fluorobutylsulfinyl, 2-chloroethylsulfinyl, 3-chloropropylsulfinyl, 4-chlorobutylsulfinyl, 3-bromopropylsulfinyl and the like; the alkylsulfonyl group of 1-4 carbons includes, for example, methylsulfonyl, ethylsulfonyl, n-propylsulfonyl, 2-propylsulfonyl, n-butylsulfonyl, 2-butylsulfonyl, 2-methylpropylsulfonyl, 1,1-dimenthylethylsulfonyl and the like; the haloalkylsulfonyl group of 1-4 carbons includes, for example, fluoromethylsulfonyl, difluoromethylsulfonyl, trifluoromethylsulfonyl, 2-fluoroethylsulfonyl, 2,2,2-trifluoroethylsulfonyl, 1,1,2,2-tetrafluoroethylsulfonyl, 2-chloro-1,1,2-trifluoroethylsulfonyl, 2,2-dichloro-1,1-difluoroethylsulfonyl, 2,2,3,3,3-pentafluoropropylsulfonyl, 1,1,1,3,3,3-hexafluoro-2-propylsulfonyl, 1,1,2,3,3,3-hexafluoropropylsulfonyl, 3,3,4,4,4-pentafluoro-2-butylsulfonyl, 3-fluoropropylsulfonyl, 4-fluorobutylsulfonyl, 2-chloroethylsulfonyl, 3-chloropropylsulfonyl, 4-chlorobutylsulfonyl, 3-bromopropylsulfonyl and the like; the alkylsulfonyloxy group of 1-4 carbons includes, for example, methylsulfonyloxy, ethylsulfonyloxy, 2-propylsulfonyloxy, n-propylsulfonyloxy, n-butylsulfonyloxy and the like; and the haloalkylsulfonyloxy group of 1-4 carbons includes, for example, chloromethylsulfonyloxy, trifluoromethylsulfonyloxy, difluoromethylsulfonyloxy, 2-chloroethylsulfonyloxy, 3-chloropropylsulfonyloxy, 4-chlorobutylsulfonyloxy and the like.

The alkyl group of 1-8 carbons denoted by $R^{10}$ or $R^{11}$ includes, for example, methyl, ethyl, n-propyl, isopropyl, n-butyl, sec-butyl, isobutyl, n-amyl, 1,2-dimethylpropyl, neopentyl, 1-ethylpropyl, n-hexyl, 4-methylpentyl, sec-pentyl, n-heptyl, n-octyl and the like; the haloalkyl group of 1-8 carbons includes, for example, trifluoromethyl, 2-fluoroethyl, 2,2,2-trifluoroethyl, 1-fluoroethyl, 1,2-difluoroethyl, 3-fluoropropyl, 1-fluoropropyl, 2-fluoropropyl, 4-fluorobutyl, 5-fluoroamyl, 6-fluorohexyl, 7-fluoroheptyl, 8-fluorooctyl, 2-chloroethyl, 3-chloropropyl, 4-chlorobutyl, 3-bromopropyl and the like; the alkoxyalkyl group of 3-8 total carbons includes, for example, 2-methoxyethyl, ethoxymethyl, 1-methoxyethyl, 2-ethoxyethyl, 3-methoxypropyl, 2-methoxypropyl, 2-ethoxypropyl, 4-methoxybutyl, 1-methoxypropyl, n-propyloxymethyl, isopropyloxymethyl, 3-n-propyloxypropyl, 4-n-propyloxybutyl, 6-ethoxyhexyl, 5-ethoxypentyl, 4-ethoxybutyl and the like; the (haloalkoxy)alkyl group of 3-8 total carbons includes, for example, 2-(trifluoroethoxy)ethyl, (2-fluoroethoxy)methyl, (2,2,2-trifluoroethoxy)methyl, 1-(trifluoromethoxy)ethyl, 3-(trifluoromethoxy)propyl, 2-(trifluoromethoxy)propyl, 2-(2,2,2-trifluoroethoxy)propyl, 4-(difluoromethoxy)butyl, 1-(fluoromethoxy)propyl, (3-fluoropropyloxy)methyl, 4-(3-fluoropropyloxy)butyl, 6-(2,2,2-trifluoroethoxy)hexyl, 5-(2-fluoroethoxy)pentyl, 4-(2,2-difluoroethoxy)butyl and the like. The alkyl group of 1-8 carbons denoted by $R^{12}$ includes, for example, methyl, ethyl, n-propyl, isopropyl, n-butyl, sec-butyl, isobutyl, n-amyl, 1,2-dimethylpropyl, neopentyl, 1-ethylpropyl, n-hexyl, 4-methylpentyl, sec-pentyl, n-heptyl, n-octyl and the like; the haloalkyl group of 1-8 carbons includes, for example, trifluoromethyl, 2-fluoroethyl, 2,2,2-trifluoroethyl, 1-fluoroethyl, 1,2-difluoroethyl, 3-fluoropropyl, 1-fluoropropyl, 2-fluoropropyl, 4-fluorobutyl, 5-fluoroamyl, 6-fluorohexyl, 7-fluoroheptyl, 8-fluorooctyl, 2-chloroethyl, 3-chloropropyl, 4-chlorobutyl, 3-bromopropyl and the like; the alkoxyalkyl group of 2-8 total carbons includes, for example, methoxymethyl, 2-methoxyethyl, ethoxymethyl, 1-methoxyethyl, 2-ethoxyethyl, 3-methoxypropyl, 2-methoxypropyl, 2-ethoxypropyl, 4-methoxybutyl, 1-methoxypropyl, n-propyloxymethyl, isopropyloxymethyl, 3-n-propyloxypropyl, 4-n-propyloxybutyl, 6-ethoxyhexyl, 5-ethoxypentyl, 4-ethoxybutyl and the like; and the (haloalkoxy)alkyl of 2-8 total carbons includes, for example, (fluoromethoxy)methyl, 2-(trifluoroethoxy)ethyl, (2-fluoroethoxy)methyl, (2,2,2-trifluoroethoxy)methyl, 1-(trifluoromethoxy)ethyl, 3-(trifluoromethoxy)propyl, 2-(trifluoromethoxy)propyl, 2-(2,2,2-trifluoroethoxy)propyl, 4-(difluoromethoxy)butyl, 1-(fluoromethoxy)propyl, (3-fluoropropyloxy)methyl, 4-(3-fluoropropyloxy)butyl, 6-(2,2,2-trifluoroethoxy)hexyl, 5-(2-fluoroethoxy)pentyl, 4-(2,2-difluoroethoxy)butyl and the like.

The alkyl group of 1-18 carbons denoted by $R^{13}$ includes, for example, methyl, ethyl, n-propyl, isopropyl, n-butyl, sec-butyl, isobutyl, tert-butyl, n-amyl, neopentyl, tert-pentyl, 1-methylbutyl, n-hexyl, n-heptyl, n-octyl, 1-methylheptyl, n-dodecyl, n-hexadecyl, n-octadecyl and the like; the haloalkyl group of 1-18 carbons includes, for example, trifluoromethyl, 2-fluoroethyl, 2,2,2-trifluoroethyl, 1-fluoroethyl, 1,2-difluoroethyl, 3-fluoropropyl, 1-fluoropropyl, 2-fluoropropyl, 4-fluorobutyl, 5-fluoroamyl, 6-fluorohexyl, 7-fluoroheptyl, 8-fluorooctyl, 2-chloroethyl, 3-chloropropyl, 4-chlorobutyl, 3-bromopropyl, 10-fluorodecyl, 12-fluorododecyl, 16-fluorohexadecyl, 18-fluorooctadecyl and the like; the alkoxyalkyl group of 3-18 total carbons includes, for example, methoxymethyl, 2-methoxyethyl, ethoxymethyl, 1-methoxyethyl, 2-ethoxyethyl, 3-methoxypropyl, 2-methoxypropyl, 2-ethoxypropyl, 4-methoxybutyl, 1-methoxypropyl, n-propyloxymethyl, isopropyloxymethyl, 3-n-propyloxypropyl, 4-n-propyloxybutyl, 6-ethoxyhexyl, 5-ethoxypentyl, 4-ethoxybutyl, 7-ethoxyheptyl, 8-ethoxyoctyl, 9-ethoxynonyl, 10-ethoxydecyl, 11-ethoxyundecyl, 12-ethoxydodecyl, 13-ethoxytridecyl, 14-ethoxytetradecyl, 15-ethoxypentadecyl, 16-ethoxyhexadecyl and the like; the (haloalkoxy)alkyl group of 3-18 total carbons includes, for example, 2-trifluoroethoxy)ethyl, (2-fluoroethoxy)methyl, (2,2,2-trifluoroethoxy)methyl, 1-(trifluoromethoxy)ethyl, 3-(trifluoroethoxy)propyl, 2-(trifluoromethoxy)propyl, 2-(2,2,2-trifluoroethoxy)propyl, 4-(difluoromethoxy)butyl, 1-(fluoromethoxy)propyl, (3-fluoropropyloxy)methyl, 4-(3-fluoropropyloxy)butyl, 6-(2,2,2-trifluoroethoxy)hexyl, 5-(2-fluoroethoxy)pentyl, 4-(2,2-difluoroethoxy)butyl, 5-(1,1,2,2-tetrafluoroethoxy)propyl, 6-(2-chloro-1,1,2-trifluoroethoxy)hexyl, 7-(2,2-dichloro-1,1-difluoroethoxy)heptyl, 8-(2,2,3,3,3-pentafluoropropyloxy)octyl, 8-(2-fluoroethoxy)octyl, 9-(1,1,1,3,3,3-hexafluoro-2-propyloxy)nonyl, 10-(1,1,2,3,3,3-hexafluoropropyloxy)decyl, 10-(3,3,4,4,4pentafluoro-2-butyloxy)decyl, 11-(3-fluoropropyloxy)undecyl, 11-(4-fluorobutyloxy)undecyl, 10-(6-fluorohexyloxy)decyl, 16-(2-chloroethoxy)hexadecyl, 15-(3-chloropropyloxy)pentadecyl and the like; the alkoxyhaloalkyl group of 3-18 total carbons includes, for example, 2,2-difluoro-2-methoxyethyl, 2-fluoro-3-methoxypropyl, 2,2-difluoro-3-ethoxypropyl, 4-ethoxy-2,2,3,3-tetrafluorobutyl, 5-ethoxy-2,2,3,3,4,4-hexafluoropentyl, 6-ethoxy-2,2,3,3,4,4,5,5-octafluorohexyl, 4-n-amyloxy-2,2,3,3-tetrafluorobutyl, 6-isobutoxy-2,2,3,3,4,4,5,5-octafluorohexyl, 2,2,3,3,4,4-hexafluoro-5-n-hexyloxypentyl, 4-n-nonyloxy-2,2,3,3-tetrafluorobutyl, 5-n-decyloxy-2,2,3,3,4,4-hexafluoropentyl, 2,2,3,3,4,4,5,5-octafluoro-n-dodecyloxyhexyl and the like; the alkylthioalkyl group of 3-18 total carbons includes, for example, 2-methylthioethyl, 2-ethylthiomethyl, 1-methylthioethyl, 2-ethylthioethyl, 3-methylthiopropyl, 2-methylthiopropyl, 2-ethylthiopropyl, 4-methylthiobutyl, 1-methylthiopropyl, n-propylthiomethyl, isopropylthiomethyl, 3-n-propylthiopropyl, 4-n-propylthiobutyl, 6-ethylthiohexyl, 5-ethylthiopentyl, 4-ethylthiobutyl, 7-ethylthioheptyl, 8-ethylthiooctyl, 9-ethylthiononyl, 11-methylthioundecyl, 11-ethylthioundecyl, 13-ethylthioundecyl, 14-ethylthiotetradecyl, 8-n-heptylthiooctyl, 15-methylthiopentadecyl, 15-ethylthiopentadecyl, 17-methylthiooctadecyl and the like; the (haloalkylthio)alkyl group of 3-18 total carbons include, for example, 2-(trifluoroethylthio)ethyl, (2-fluoroethylthio)methyl, (2,2,2-trifluoroethylthio)methyl, 1-(trifluoromethylthio)ethyl, 3-(trifluoromethylthio)propyl, 2-(trifluoromethylthio)propyl, 2-(2,2,2-trifluoroethylthio)propyl, 4-(difluoromethylthio)butyl, 1-(fluoromethylthio)propyl, (3-fluoropropylthio)methyl, 4-(3-fluoropropylthio)butyl, 6-(2,2,2-trifluoroethylthio)hexyl, 5-(2-fluoroethylthio)pentyl, 4-(2,2-difluoroethylthio)butyl, 5-(1,1,2,2-tetrafluoroethylthio)propyl, 6-(2-chloro-1,1,2-trifluoroethylthio)hexyl, 7-(2,2-dichloro-1,1-difluoroethylthio)heptyl, 8-(2,2,3,3,3-pentafluoropropylthio)octyl, 8-(2-fluoroethylthio)octyl, 9-(1,1,1,3,3,3-hexafluoro-2-propylthio)nonyl, 10-(1,1,2,3,3,3-hexafluoropropylthio)decyl, 10-(3,3,4,4,4-pentafluoro-2-butylthio)decyl, 11-(3-fluoropropylthio)undecyl, 11-(4-fluorobutylthio)undecyl, 10-(6-fluorohexylthio)decyl, 16-(2-chloroethylthio)hexadecyl, 15-(3-chloropropylthio)pentadecyl and the like; the cycloalkyl group of 3-8 carbons which may be substituted by the alkyl group of 1-10 carbons includes, for example, cyclopropyl, 1-methylcyclopropyl, cyclobutyl, cyclopentyl, cyclohexyl, cycloheptyl, cyclooctyl, 1-ethylcyclobutyl, 2-n-decylcyclopentyl and the like; the cycloalkyl group of 3-8 carbons which is substituted by the haloalkyl group of 1-10 carbons includes, for example 1-trifluoromethylcyclopropyl, 3-(3-fluoropropyl)cyclobutyl, 2-(2,2,2-trifluoroethyl)cyclopentyl, 4-(1,2-difluoroethyl)cyclohexyl, 3-(2,2,3,3,4,4,4-heptafluorobutyl)cycloheptyl, 2-(3,3,4,4,5,5,6,6,7,7,8,8,9,9,10,10,10-heptadecafluorodecyl)cyclooctyl and the like; the halocycloalkyl group of 3-8 carbons which may be substituted by the alkyl group of 1-10 carbons includes, for example, 2,2,3,3-tetrafluorocyclopropyl, 2,2,3,3,4,4-hexafluorocyclobutyl, 2,2,3,3,4,4,5,5-octafluorocyclopentyl, 2,2,3,3,4,4,5,5,6,6,7,7,8,8-tetradecafluorocyclooctyl, 1-methyl-2,2,3,3-tetrafluorocyclopropyl, 2-n-nonyl-3,3,4,4,5,5,6,6-octafluorocyclohexyl and the like; the cycloalkyl group of 3-8 carbons which is substituted by the alkoxy group of 1-10 carbons includes, for example, 1-methoxycyclopropyl, 2-ethoxycyclopentyl, 5-n-decylcyclooctyl and the like; and the cycloalkyl group of 3-8 carbons which is substituted by the haloalkoxy group of 1-10 carbons includes, for example, 1-(2,2-difluoroethoxy)cyclopropyl, 2-(2,2,2-trifluoroethoxy)cyclopentyl, 4-(8-fluorooctyloxy)cyclooctyl and the like.

The alkyl group of 1-4 carbons denoted by $R^{14}$, $R^{17}$, $R^{18}$ or $R^{19}$ includes, for example, methyl, ethyl, n-propyl, isopropyl, n-butyl, isobutyl and the like; and the haloalkyl group of 1-8 carbons includes, for example, trifluoromethyl, 2-fluoroethyl, 2,2,2,-trifluoroethyl, 1-fluoroethyl, 1,2-difluoroethyl, 3-fluoropropyl, 1-fluoropropyl, 2-fluoropropyl, 4-fluorobutyl, 2-chloroethyl, 3-chloropropyl, 4-chlorobutyl, 3-bromopropyl and the like.

The halogen atom denoted b $R^{15}$ or $R^{16}$ includes, for example, fluorine atom, chlorine atom, bromine atom and the like; the alkyl group of 1-6 carbons includes, for example, methyl, ethyl, n-propyl, isopropyl, n-butyl, sec-butyl, isobutyl, tert-butyl, n-amyl, neopentyl and the like; cycloalkyl group of 3-6 carbons includes, for example, cyclopropyl, 1-methylcyclopropyl, cyclobutyl, cyclopentyl, cyclohexyl and the like; and the haloalkyl group of 1–6 carbons includes, for example, fluoromethyl, difluoromethyl, trifluoromethyl, 2-fluoroethyl, 2,2,2-trifluoroethyl, 1,2,2,2-tetrafluoroethyl, 1,1,2,2-tetrafluoroethyl, 2,2,3,3-tetrafluoropropyl, 2,2,3,3,3-pentafluoropropyl and the like.

The phenyl group which may be substituted includes, for example, phenyl, 2-fluorophenyl, 3-fluorophenyl, 4-fluorophenyl, 4-methoxyphenyl, 4-tolyl, 4-ethylphenyl, 3-chlorophenyl, 4-chlorophenyl, 4-n-propylphenyl, 4-isopropylphenyl, 4-(1,1,2,2-tetrafluoroethoxy)phenyl, 4-trifluoromethylphenyl, 4-difluoromethoxyphenyl, 2,4-dichlorophenyl and the like; the alkoxyl group of 1–6 carbons includes, for example, methoxy, ethoxy, n-propoxy, isopropoxy, n-butoxy, sec-butoxy, isobutoxy, n-amyloxy, neopentyloxy, n-hexyloxy and the like; and the haloalkoxyl group of 1–6 carbons includes, for example, difluoromethoxy, 2-fluoroethoxy, 2,2,2-trifluoroethoxy and the like; and the cycloalkoxy group of 3–6 carbons includes, for example, cyclopropyloxy, 1-methylcyclopropyloxy, cyclobutyloxy, cyclopentyloxy, cyclohexyloxy and the like.

The alkyl group of 1–4 carbons denoted by $R^{20}$ includes, for example, methyl, ethyl, n-propyl, iso-propyl, b-butyl, isobutyl and the like.

Examples of the insect pests against which the compounds of the present invention are efficacious are Lepidoptera including diamondback moth (*Plutella xylostella*), rice stem borer (*Chilo suppressalis*), rice leafroller (*Cnaphalocrocis medinalis*), armyworms (or cutworms), loopers, common cabbageworm (*Pieris rapae crucivora*), case-making clothes moth (*Tinea translucens*), webbing clothes moth (*Tineola bisselliella*) etc.; Diptera including common mosquito (*Culex pipiens pallens*), Yellow fever mosquito (*Aedes aegypti*), Anopheles mosquitos, Aedes mosquitos, housefly (*Musca domestica*) etc.; Dictyoptera including German cockroach (*Blattella germanica*), smokybrown cockroach (*Periplaneta fuliginosa*), brown cockroach (*Periplaneta brunnea*), American cockroach (*Periplaneta americana*) etc.; Coleoptera including adzuki-bean weevil (*Callosobruchus chinensis*), southern corn rootworm (*Diabrotica undecimpunctata*), northern corn rootworm (*Diabrotica longicornis*), scarab beetles etc.; mites such as two-spotted spider mite (*Tetranychus urticae*), citrus red mite (*Panonychus citri*) and carmine mite (*Tetranychus cinnabarinus*); ticks such as ox tick and other animal parasitic ticks; room dust acari etc.; Hemiptera including planthoppers such as brown planthopper (*Nilaparvata lugens*) and smaller brown planthopper (*Laodelphax striatellus*), leafhoppers such as green rice leafhopper (*Nephotettix cincticeps*), aphids such as green peach aphid (*Myzus persicae*), stink bugs, whiteflies etc.; as well as Hymenoptera, Thysanoptera, Orthoptera and the like. The compounds of the present invention are also efficacious against insect pests which have been increased in their resistance to the existing insecticides and acaricides. They further exhibit preventive and remedial efficacy against various kinds of plant diseases.

The following are typical method for producing the present compound, and a proper method can, of course, be selected in accordance with the kinds of the heterocycle denoted by A and of the functional groups such as $R^1$, $R^2$, $R^5$, $R^6$, X and Y.

Production Method A: Production of an amide compound [I-1] which is represented by the formula [I] but $R^1$ is a hydrogen atom or an alkyl group of 1–4 carbons and X is an oxygen atom.

The amide compound [I-1] is produced by the reaction of a carboxylic compound represented by the formula [II],

[II]

wherein A is the same meanings as defined above, and V is a chlorine atom, a bromine atom, or hydroxy, methoxy, ethoxy, propyloxy or 1-imidazolyl group, with an amine compound represented by the formula [III],

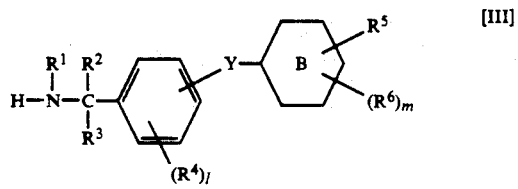

[III]

wherein $R^1$ is a hydrogen atom or an alkyl group of 1–4 carbons, and $R^2$, $R^3$, $R^4$, $R^5$, $R^6$, the ring B, Y, l and m are the same meanings as defined above.

When V in the formula [II] is a chlorine atom, a bromine atom or 1-imidazolyl group, the reaction is carried out in a solvent including ethers such as diethyl ether, tetrahydrofuran and dioxane, aromatic hydrocarbons such as toluene, benzene, xylene, chlorobenzene and pyridine, hydrocarbons such as n-hexane, n-heptane and cyclohexane, halogenated hydrocarbons such as methylene chloride, chloroform, carbon tetrachloride and 1,2-dichloroethane, esters such as ethyl acetate and methyl acetate, water, nitriles such as acetonitrile, polar solvents such as N,N-dimethylformamide, N,N-dimethylacetamide, N-methylpyrrolidone and dimethyl sulfoxide, and mixtures thereof, at a temperature of $-20°$ to $100°$ C., preferably $0°$ to $50°$ C., and normally in the presence of a base including sodium hydroxide, potassium hydroxide, sodium carbonate, potassium carbonate, triethylamine, pyridine and the like with a ratio of 1 to 10 moles based on 1 mole of the carboxylic compound represented by the formula [II].

In case of a two-phase reaction where water is used as the solvent, the reaction rate can be usually accelerated by the use of a phase transfer catalyst including tetra-n-butylammonium bromide, benzyltriethylammonium chloride and the like.

When V in the formula [II] is hydroxy, methoxy, ethoxy or propyloxy group, the reaction is carried out either without solvents or in a high boiling solvent including, for example, polar solvents such as N,N-dimethylformamide, N,N-dimethylacetamide, N-methylpyrrolidone and dimethyl sulfoxide, and aromatic hydrocarbons such as benzene, toluene, xylene and chlorobenzene, at a reaction temperature of $50°$ to $250°$ C.

If necessary and appropriate, acidic substances such as sulfuric acid, benzenesulfonic acid, p-toluenesulfonic acid and activated silica gel or basic substances such as pyridine, triethylamine, sodium ethoxide, sodium methoxide and activated alumina, for example, can be used as a reaction catalyst in an amount of 0.0001 to 1 part by weight based on 1 part by weight of the carboxylic compound represented by the formula [II].

In general, the amine compound represented by the formula [III] is used with a ratio of 0.1 to 10 moles, preferably with a ratio of 0.8 to 1.2 mole, based on 1 mole of the carboxylic compound represented by the formula [II]. A reaction period is normally from 5 minutes to 100 hours, preferably from 30 minutes to 10 hours.

Alternatively, when V in the formula [II] is hydroxy group, the following method is also applicable.

Thus, the carboxylic compound of the formula [II] wherein V is hydroxy group is subjected to a reaction of dehydrating condensation with the amine compound represented by the formula [III] either in the presence or absence of an innert organic solvent and in the presence of a dehydrating agent to produce the subjective present compound. The dehydrating agent includes, for example, carbodiimides such as dicyclohexylcarbodiimide and 1-ethyl-3-(3-dimethylaminopropyl)carbodiimide, inorganic dehydrating agents such as tetrachlorosilane, and the like. The innert organic solvent includes, for example, aliphatic hydrocarbons such as n-pentane, n-hexane, n-heptane and cyclohexane, aromatic hydrocarbons such as benzene, toluene, xylene, chlorobenzene, pyridine and o-dichlorobenzene, chlorinated hydrocarbons such as methylene chloride, chloroform, carbon tetrachloride, tetrachloroethylene and 1,2-dichloroethane, esters such as methyl acetate and ethyl acetate, amides such as N,N-dimethylformamide, N,N-dimethylacetamide and N-methylpyrrolidone, nitriles such as acetonitrile, ethers such as diethyl ether, tetrahydrofuran and dioxane, and the like. The reaction is carried out at a temperature of −20° to 100° C. using the dehydrating agent normally with a ratio of 0.5 to 10 moles, preferably with a ratio of 1 to 5 moles and using the amine compound represented by the formula [III] normally with a ratio of 0.1 to 10 moles, preferably with a ratio of 0.8 to 1.2 mole, each based on 1 mole of the carboxylic compound represented by the formula [II]. A reaction period is normally from 5 minutes to 100 hours, preferably from 30 minutes to 10 hours.

Production Method B: Production of an amide compound [I-2] which is represented by the formula [I] but $R^1$ is a hydrogen atom or an alkyl group of 1-4 carbons; $R^5$ is a halogen atom, an alkyl group of 1-8 carbons, a haloalkyl group of 1-8 carbons, a cycloalkyl group of 3-8 total carbons, an alkenyl group of 2-8 carbons, an alkynyl group of 2-8 carbons, an alkoxy group of 1-8 carbons, a haloalkoxy group of 1-8 carbons, an alkenyloxy group of 2-8 carbons, a haloalkenyloxy group of 2-8 carbons, an alkynyloxy group of 2-8 carbons, an alkylthio group of 1-8 carbons, a haloalkylthio group of 1-8 carbons, an alkenylthio group of 2-8 carbons, a haloalkenylthio group of 2-8 carbons, an alkynylthio group of 2-8 carbons, an alkoxyalkyl group of 2-8 total carbons, an alkylthioalkyl group of 2-8 carbons, a (haloalkylthio)alkyl group of 2-8 total carbons, an alkylsulfinyl group of 1-8 carbons, a haloalkylsulfinyl group of 1-8 carbons, an alkylsulfonyl group of 1-8 carbons, a haloalkylsulfonyl group of 1-8 carbons, an alkylsulfonyloxy group of 1-8 carbons, a haloalkylsulfonyloxy group of 1-8 carbons, an alkylamino group of 1-8 carbons, a haloalkylamino group of 1-8 carbons or a dialkylamino group of 2-16 total carbons; $R^6$ is a hydrogen atom, a halogen atom, an alkyl group of 1-3 carbons, a haloalkyl group of 1-3 carbons, a cycloalkyl group of 3-6 carbons, an alkenyl group of 2-6 carbons, an alkynyl group of 2-6 carbons, an alkoxy group of 1-3 carbons, a haloalkoxy group of 1-3 carbons, an alkenyloxy group of 2-6 carbons, a haloalkenyloxy group of 2-6 carbons, an alkynyloxy group of 2-6 carbons, an alkyl-thio group of 1-3 carbons, a haloalkylthio group of 1-3 carbons, an alkenylthio group of 2-6 carbons, a haloalkenylthio group of 2-6 carbons, an alkynylthio group of 2-6 carbons, an alkoxyalkyl group of 2-3 total carbons, an alkylsulfinyl group of 1-3 carbons, a haloalkylsulfinyl group of 1-3 carbons, an alkylsulfonyl group of 1-3 carbons, a haloalkylsulfonyl group of 1-3 carbons, an alkylsulfonyloxy group of 1-3 carbons or a haloalkylsulfonyloxy group of 1-3 carbons, provided that $R^5$ and $R^6$ may be linked at their ends, when they are adjacent each other, to form a saturated or unsaturated fiver- or six-membered ring which contains 0-2 oxygen or sulfur atoms therein and may be substituted with a halogen atom or an alkyl group of 1-4 carbons; and X is a sulfur atom.

The amide compound [I-2] is produced by the reaction of an amide compound represented by the formula [I-3],

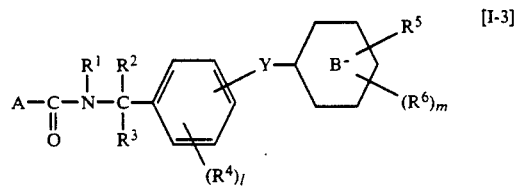

wherein A, $R^1$, $R^2$, $R^3$, $R^4$, $R^5$, $R^6$, the ring B, Y, l and m are the same meanings as defined for the compound [I-2], with phosphorus pentasulfide or a Lawesson's Reagent.

Solvent usable in this method are aromatic hydrocarbons such as benzene, toluene, xylene, monochlorobenzene, pyridine and quinoline, and the like, or mixtures thereof, and the reaction is carried out using 0.2 to 20 moles of phosphorus pentasulfide or 0.5 to 50 moles of the Lawesson's Reagent bassed on 1 mole of the amide compound represented by the formula [I-3], at a temperature of 0° to 250° C., preferably 20° to 150° C., and for a period of 0.5 to 50 hours.

Production method C: Production of an amide compound [I-4] which is represented by the formula [I] but $R^1$ is an alkyl group of 1-4 carbons, an alkylcarbonyl group of 1-8 total carbons or a group of the formula $—S(O)_nR^7$; $R^2$ and $R^3$ independently of one another are each a hydrogen atom or an alkyl group of 1-4 carbons; $R^5$ is a halogen atom, an alkyl group of 1-8 carbons, a haloalkyl group of 1-8 carbons, a cycloalkyl group of 3-8 total carbons, an alkenyl group of 2-8 carbons, an alkynyl group of 2-8 carbons, an alkoxy group of 1-8 carbons, a haloalkoxy group of 1-8 carbons, an alkenyloxy group of 2-8 carbons, a haloalkenyloxy group of 2-8 carbons, an alkynyloxy group of 2-8 carbons, an alkylthio group of 1-8 carbons, a haloalkylthio group of 1-8 carbons, an alkenylthio group of 2-8 carbons, a haloalkenhylthio group of 2-8 carbons, an alkynylthio group of 2-8 carbons, an alkoxyalkyl group of 2-8 total carbons, an alkylthioalkyl group of 2-8 total carbons, a (haloalkylthio)alkyl group of 2-8 total carbons, an alkylsulfinyl group of 1-8 carbons, a haloalkylsulfinyl group of 1-8 carbons, an alkylsulfonyl group of 1-8 carbons, a haloalkylsulfonyl group of 1-8 carbons, an alkylsulfonyloxy group of 1-8 carbons, a haloalkylsulfonyloxy group of 1-8 carbons, a dialkylamino group of 2-16 total carbons, an N-alkylformamidino group of 2-8 total carbons, an N-alkylacetamidino group of 3-8 total carbons, an N,N-dialkylformaidino group of 3-16 total carbons or an N,N-dialkylacetamidino group of 4–16 total carbons; $R^6$ is a hydrogen atom, a halogen atom, an alkyl group of 1–3 carbons, a haloalkyl group of 1–3 carbons, a cycloalkyl group of 3–6 carbons, an alkenyl group of 2–6 carbons, an alkynyl group of 2–6 carbons, an alkoxy group of 1–3 carbons, a haloalkoxy group of 1–3 carbons, an alkenyloxy group of 2–6 carbons, a haloalkenyloxy group of 2–6 carbons, an alkynyloxy group of 2–6 carbons, an alkylthio group of 1–3 carbons, a haloalkylthio group of 1–3 carbons, an alkenylthio group of 2–6 carbons, a haloalkenylthio group of 2–6 carbons, an alkynylthio group of 2–6 carbons, an alkoxyalkyl group of 2–3 total carbons, an alkylsulfinyl group of 1–3 carbons, a haloalkylsulfinyl group of 1–3 carbons, an alkylsulfonyl group of 1–3 carbons, a haloalkylsulfonyl group of 1–3 carbons, an alkylsulfonyloxy group of 1–3 carbons or a haloalkylsulfonyloxy group of 1–3 carbons, provided that $R^5$ and $R^6$ may be linked at their ends, when they are adjacent each other, to form a saturated or unsaturated five- or six-membered ring which contains 0–2 oxygen or sulfur atoms therein and may be substituted with a halogen atom or an alkyl group of 1–4 carbons; and X is an oxygen atom.

The amide compound [I-4] is produced by the reaction of an amide compound represented by the formula [I-5],

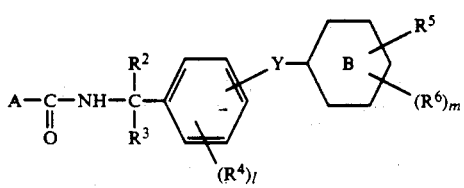

wherein A, $R^2$, $R^3$, $R^4$, $R^5$, $R^6$, the ring B, Y, l and m are the same meanings as defined for the compound [I-4], with a compound represented by the formula [IV],

  $R^1-D$  [IV]

wherein $R^1$ is an alkyl group of 1–4 carbons, an alkylcarbonyl group of 1–8 total carbons or a group of the formula $-S(O)_nR^7$ and D is leaving group such as a halogen atom.

Solvents usable in this method are ethers such as diethylether, tetrahydrofuran and dioxane, aroamtic hydrocarbons such as toluene, benzene, xylene, chlorobenzene and pyridine, hydrocarbons such as n-hexane, n-heptane and cyclohexane, halogenated hydrocarbons such as methylene chloride, chloroform, carbon tetrachloride and 1,2-dichloroethane, and the like or mixtures thereof, and the reaction is carried out in the presence of a base.

The base usable here includes, for example, organic bases such as triethylamine, pyridine and N,N-dimethylaminopyridine, alkali metal hydrides such as sodium hydride, and alkyllithium compounds such as n-butyllithium. A molar ratio used is 1 to 10 moles, preferably 1.1 to 2 moles, of the compound represented by the formula [IV] based on 1 mole of the amide compound represented by the formula [I-5]. The base is used with a ratio of 1 to 5 moles, preferably 1.1 to 2 moles, based on 1 mole of the amide compound represented by the formula [I-5]. A reaction temperature is −20° to 100° C., preferably 0° to 50° C., and a reaction period is from 10 minutes to 50 hours, preferably 1 to 24 hours.

The carboxylic compound represented by the above formula [II] can be prepared by the methods disclosed in, for example, Bull. Soc. Chim. Fr., 293 (1966), Khim. Farm. Zh., 4, 19 (1970), Org. Synth., IV, 351 (1963), Ann., 250, 257 (1889), Chem. Ber., 109, 268 (1976), Ann. Chim. (Rome), 55, 576 (1965), Chem. Ber., 112, 1712 (1979), Chem. Ber., 107, 1318 (1974), Chem. Ber., 109, 253 (1976), Aust. J. Chem., 36, 135 (1983), EP-A-27020 (1981), DE-A-2728523 (1979) and the like or by the analogous methods thereto.

The amine compound represented by the formula [III] can be prepared, for example, by the methods shown below.

Preparation Method a: Preparation of an amine compound [III-1] which is represented by the formula [III] but $R^1$, $R^2$ and $R^3$ are each a hydrogen atom; $R^5$ is a halogen atom, an alkyl group of 1–8 carbons, a haloalkyl group of 1–8 carbons, a cycloalkyl group of 3–8 total carbons, an alkoxy group of 1–8 carbons, a haloalkoxy group of 1–8 carbons, an alkylthio group of 1–8 carbons, a haloalkylthio group of 1–8 carbons, an alkoxyalkyl group of 2–8 total carbons, an alkylthioalkyl group of 2–8 total carbons, a (haloalkylthio)alkyl group of 2–8 total carbons, an alkylamino group of 1–8 carbons, a haloalkylamino group 1–8 carbons or a dialkylamino group of 2–16 total carbons; $R^6$ is a hydrogen atom, a halogen atom, an alkyl group of 1–3 carbons, a haloalkyl group of 1–3 carbons, a cycloalkyl group of 3–6 carbons, an alkoxy group of 1–3 carbons, a haloalkoxy group of 1–3 carbons, an alkylthio group of 1–3 carbons, a haloalkylthio group of 1–3 carbons or an alkoxyalkyl group of 2–3 total carbons, provided that $R^5$ and $R^6$ may be linked at their ends, when they are adjacent each other, to form a saturated five- or six-membered ring which contains 0–2 oxygen or sulfur atoms therein and may be substituted with a halogen atom or an alkyl group of 1–4 carbons; and Y is an oxygen atom, a sulfur atom, methylene group or a group represented by the formula $-NR^{20}-$; and $R^{20}$ is the same meanings as defined for the compound [I].

The amine compound [III-1] is prepared by reducing a nitrile compound represented by the formula [V],

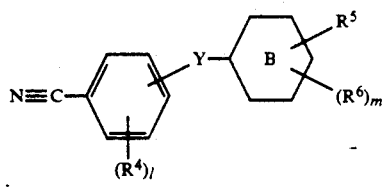

wherein $R^4$, $R^5$, $R^6$, the ring B, Y, l and m are the same meanings as defined for the compound [III-1].

The reducing reaction applicable here includes, for example, a method using a reducing agent such as lithium aluminum hydride, borane-tetrahydrofuran complex or sodium borohydride-sulfur, and catalytic hydrogenation using a catalyst such as platinum [IV] oxide, rhodium-aluminum oxide or Raney nickel, each disclosed in, e.g. J. Amer. Chem. Soc., 70, 3788 (1948), J. Amer. Chem. Soc., 82, 681 (1960), Can. J. Chem., 49, 2990 (1971), J. Org. Chem., 37, 335 (1972), J. Amer. Chem. Soc., 82, 2386 (1960), Org. Synth., III, 229 (1955) or the like, and the anlogous methods thereto.

Among the amine compounds [III-1], those represented by the formula [III-2] are novel:

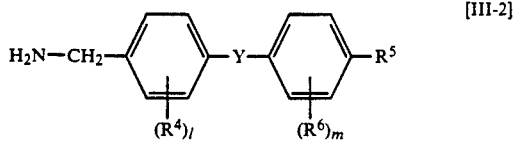

[III-2]

wherein $R^5$ is an alkylthio group of 1-8 carbons or a haloalkylthio group of 1-8 carbons; $R^4$ and $R^6$ independently of one another are each a hydrogen atom, a halogen atom or methyl group; Y is an oxygen atom, a sulfur atom or methylene group; and l and m are the same meanings as defined above.

The above reaction is carried out in a solvent including ethers such as diethyl ether, tetrahydrofuran, dioxane and 1,2-dimethoxyethane, aromatic hydrocarbons such as toluene, benzene and xylene, hydrocarbons such as n-hexane, n-heptane and cyclohexane, and mixtures thereof, at a temperature of $-20°$ to $200°$ C., preferably $0°$ to $150°$ C., and using a reducing agent including metal hydrogen complex compounds such as lithium aluminum hydride, aluminum hydride, sodium aluminum hydride, lithium trimethoxyaluminum hydride, sodium triethoxyaluminum hydride and sodium borohydride-sulfur, and borane compounds such as borane-tetrahydrofuran complex, normally with a ratio of 1 to 10 equivalents based on 1 mole of the nitrile compound represented by the formula [V]. A reaction period is normally from 5 minutes to 100 hours, preferably from 30 minutes to 10 hours.

Alternatively, when the reducing reaction is carried out by the catalytic hydrogenation, the following method is also applicable.

Thus, the nitrile compound represented by the formula [V] is subjected to the catalytic hydrogenation in a solvent including alcohols such as methanol and ethanol, esters such as ethyl acetate, and mixtures thereof, in the presence of a catalyst and under the condition of 1 to 5 atm in a hydrogen gas atmosphere to obtain the amine compound [III-1]. The catalyst usable here includes platinum [IV] oxide, Raney nickel, rhodium-aluminum oxide and the like. The catalyst is normally used in an amount of 0.0001 to 1 part by weight based on 1 part by weight of the nitrile compound represented by the formula [V]. A reaction temperature is $0°$ to $150°$ C., and a reaction period is normally from 10 minutes to 100 hours, preferably from 30 minutes to 10 hours.

Preparation Method b: Preparation of an amine compound [III-3] which is represented by the formula [III] but $R^1$ is a hydrogen atom or an alkyl group of 1-4 carbons; $R^2$ is a hydrogen atom; $R^5$ is a halogen atom, an alkyl group of 1-8 carbons, a haloalkyl group of 1-8 carbons, a cycloalkyl group of 3-8 total carbons, an alkoxy group of 1-8 carbons, a haloalkoxy group of 1-8 carbons, an alkylthio group of 1-8 carbons, a haloalkylthio group of 1-8 carbons, an alkoxyalkyl group of 2-8 total carbons, an alkylthioalkyl group of 2-8 total carbons, a (haloalkylthio)alkyl group of 2-8 total carbons, an alkylamino group of 1-8 carbons, a haloalkylamino group of 1-8 carbons or a dialkylamino group of 2-16 total carbons; $R^6$ is a hydrogen atom, a halogen atom, an alkyl group of 1-3 carbons, a haloalkyl group of 1-3 carbons, a cycloalkyl group of 3-6 carbons, an alkoxy group of 1-3 carbons, a haloalkoxy group of 1-3 carbons, an alkylthio group of 1-3 carbons, a haloalkylthio group of 1-3 carbons or an alkoxyalkyl group of 2-3 total carbons, provided that $R^5$ and $R^6$ may be linked at their ends, when they are adjacent each other, to form a saturated five- or six-membered ring which contains 0-2 oxygen or sulfur atoms therein and may be substituted with a halogen atom or an alkyl group of 1-4 carbons; and Y is an oxygen atom, a sulfur atom, methylene or a group represented by the formula $-NR^{20}-$; $R^{20}$ is the same meanings as defined for the compound [I].

The amine compound [III-3] is prepared by the reductive condensation of a carbonyl compound represented by the formula [VI],

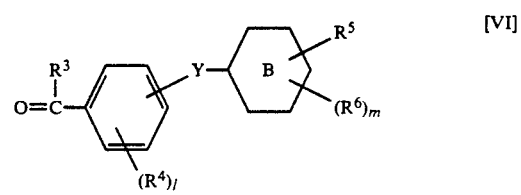

[VI]

wherein $R^3$, $R^4$, $R^5$, $R^6$, the ring B, Y, l and m are the same meanings as defined for the compound [III-3], with an amine compound represented by the formula [VII],

$R^1-NH_2$  [VII]

wherein $R^1$ is a hydrogen atom or an alkyl group of 1-4 carbons.

This reaction is carried out in the manner disclosed in, for example, Org. React., 4, 174 (1948), J. Amer. Chem. Soc., 61, 3566 (1939), J. Amer. Chem. Soc., 93, 2897 (1971), Org. React., 5, 323 (1949), and the like, or by the anlogous methods thereto.

Among the amine compounds [III-3], those represented by the formula [III-4] are novel:

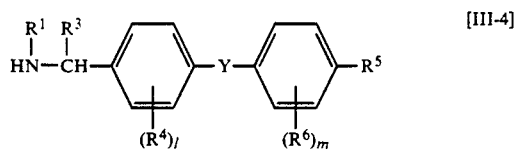

[III-4]

wherein $R^1$ and $R^3$ independently of one another are each a hydrogen atom or an alkyl group of 1-4 carbons; $R^5$ is an alkylthio group of 1-8 carbons or a haloalkylthio group of 1-8 carbons; $R^4$ and $R^6$ independently of one another are each a hydrogen atom, a halogen atom or methyl group; Y is an oxygen atom, a sulfur atom or methylene group; and l and m are the same meanings as defined above.

The reductive condensation reaction between the carbonyl compound represented by the formula [VI] and the amine compound represented by the formula [VII] proceeds through an intermediate imine compound represented by the formula [VIII],

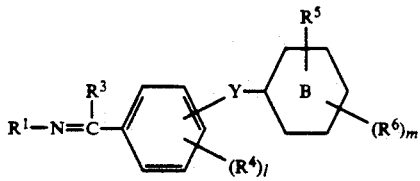

[VIII]

wherein $R^1$, $R^3$, $R^4$, $R^5$, $R^6$, the ring B, Y, l and m are the same meanings as defined for the compound [III-3]. This intermediate may be directly led to the amine compound [III-3] by continuing the reductive reaction without separation. If the imine compound represented by the formula [VIII] is intended for separation, a dehydrating condensation reaction is conducted in accordance with the usual manner. Thus, the reaction is carried out either without solvents or in a solvent including, for example, water, alcohols such as methanol and ethanol, aromatic hydrocarbons such as benzene, toluene and pyridine, ethers such as diethyl ether and tetrahydrofuran, halogenated hydrocarbons such as methylene chloride and chloroform, aliphatic hydrocarbons such as n-hexane and cyclohexane, and mixtures thereof, in the presence or absence of a base such as sodium hydroxide, potassium hydroxide, potassium carbonate and sodium carbonate or an acidic compound such as sulfuric acid, hydrochloric acid and p-toluenesulfonic acid, using normally 1 to 100 moles of the amine compound represented by the formula [VII] based on 1 mole of the carbonyl compound represented by the formula [VI], at a reaction temperature of $-20°$ to $150°$ C., preferably $0°$ to $120°$ C., and for a reaction period of from 5 minutes to 20 hours.

In preparing the amine compound [III-3] by the reduction of the imine compound represented by the formula [VIII], a reducing agent usable includes, for example, sodium borohydride, lithium aluminum hydride, sodium cyanoborohydride, lithium cyanoborohydride, borane-tetrahydrofuran complex and the like, and is normally used in an amount of 1 to 100 equivalents based on 1 mole of the imine compound represented by the formula [VIII]. Though a solvent used in this reaction should be selected depending on the kind of reducing agents, it includes, in general, water, alcohols such as methanol and ethanol, ethers such as diethyl ether and tetrahydrofuran, and the like or mixtures thereof. A reaction temperature is normally $-10°$ to $50°$ C., and a reaction period is 0.5 to 50 hours.

On the other hand, when the amine compound [III-3] is prepared from the carbonyl compound represented by the formula [VI] and the amine compound represented by the formula [VII] without separating the imine compound represented by the formula [VIII], the preparation can be performed by incorporating a reducing agent in the reaction system. The reducing agent usable here includes, for example, sodium borohydride, sodium cyanoborohydride, lithium cyanoborohydride and the like. In general, based on 1 mole of the carbonyl compound represented by the formula [VI], the reducing agent is used in an amount of 1 to 100 equivalents, and the amine compound represented by the formula [VII] is used in an amount of 1 to 50 moles. A solvent usable includes water, alcohols such as methanol and ethanol, ethers such as dioxane and tetrahydrofuran, and the like or mixtures thereof. A reaction temperature is $-10°$ to $150°$ C., and a reaction period is 0.5 to 50 hours.

When catalytic hydrogenation is applied to the reduction of the imine compound produced in the reaction system, the amine compound [III-3] can be prepared by subjecting the carbonyl compound represented by the formula [VI] to the reaction with the same amine compound used in the aforementioned preparation under the condition of 1 to 100 atm in a hydrogen gas atmosphere and using a catalyst. Raney nickel, platinum, platinum(IV) oxide, palladium black or the like can be used as the catalyst with a ratio of 0.0001 to 0.1 part by weight based on 1 part by weight of the carbonyl compound represented by the formula [VI]. A reaction temperature is $50°$ to $200°$ C., preferably $80°$ to $180°$ C., and a reaction period is 1 to 24 hours, preferably 2 to 12 hours.

Alternatively, the reduction of the imine compound produced in the reaction system can also be conducted by using formic acid, in which the carbonyl compound represented by the formula [VI] and either a formamide compound or a formate of an amine compound are subjected to a reaction together with formic acid. A reaction temperature is $100°$ to $250°$ C., preferably $120°$ to $200°$ C., and a reaction period is 1 to 50 hours, preferably 5 to 24 hours. Examples of the formamide compound usable herein are formamide, N-monoalkyl substituted formamides of 2-5total carbons including N-methylformamide, and the like, and examples of the formate of an amine compound are ammonium formate, monoalkylamine formates of 2-5 total carbons including ethylammonium formate, and the like. The formamide or formate compound is used in an amount of 3 to 10 moles, preferably 4 to 6 moles, based on 1 mole of the carbonyl compound represented by the formula [VI]. Formic acid is used in an-amount of 0.01 to 1 part by weight, preferably 0.05 to 0.1 part by weight based on 1 part by weight of the carbonyl compound represented by the formula [VI]. Further, the N-formyl derivative produced here can be hydrolyzed in the usual manner to obtain the amine compound [III-3].

Preparation Method c: Preparation of an amine compound [III-5] which is represented by the formula [III] but $R^1$ is a hydrogen atom; $R^2$ and $R^3$ independently of one another are each a hydrogen atom or an alkyl group of 1-4 carbons; $R^5$ is a halogen atom, an alkyl group of 1-8 carbons, a haloalkyl group of 1-8 carbons, a cycloalkyl group of 3-8 total carbons, an alkenyl group of 2-8 carbons, an alkynyl group of 2-8 carbons, an alkoxy group of 1-8 carbons, a haloalkoxy group of 1-8 carbons, an alkenyloxy group of 2-8 carbons, a haloalkenyloxy group of 2-8 carbons, an alkynyloxy group of 2-8 carbons, an alkylthio group of 1-8 carbons, a haloalkylthio group of 1-8 carbons, an alkenylthio group of 2-8 carbons, a haloalkenylthio group of 2-8 carbons, an alkynylthio group of 2-8 carbons, an alkoxyalkyl group of 2-8 total carbons, an alkylthioalkyl group of 2-8 total carbons, a (haloalkylthio)alkyl group of 2-8 total carbons, an alkylsulfinyl group of 1-8 carbons, a haloalkylsulfinyl group of 1-8 carbons, an alkylsulfonyl group of 1-8carbons, a haloalkylsulfonyl group of 1-8 carbons, an alkylsulfonyloxy group of 1-8 carbons, a haloalkylsulfonyloxy group of 1-8 carbons or a dialkylamino group of 2-16 total carbons; $R^6$ is a hydrogen atom, a halogen atom, an alkyl group of 1-3 carbons, a haloalkyl group of 1-3 carbons, a cycloalkyl group of 3-6 carbons, an alkenyl group of 2-6 carbons, an alkynyl group of 2-6 carbons, an alkoxy group of 1-3 carbons, a haloalkoxy group of 1-3 carbons, an alkenyloxy group of 2-6 carbons, a haloalkenyloxy group of 2-6 carbons, an alkynyloxy group of 2-6 carbons, an alkylthio group of 1-3 carbons, a haloalkylthio group of 1-3 carbons, an alkenylthio group of 2-6 carbons, a haloalkenylthio group of 2-6 carbons, an alkynylthio group of 2-6 carbons, an alkoxyalkyl group of 2-3 total carbons, an alkylsulfinyl group of 1-3 carbons, a haloalkylsulfinyl group of 1-3 carbons, an alkylsulfonyl group of 1-3 carbons, a haloalkylsulfonyl group of 1-3 carbons, an alkylsulfonyloxy group of 1-3 carbons, or a haloalkylsulfonyloxy group of 1-3 carbons, provided that $R^5$ and $R^6$ may be linked at their ends, when they are adjacent each other, to form a saturated or unsaturated five- or six-membered ring which contains 0-2 oxygen or sulfur atoms therein and may be substituted with a halogen atom or an alkyl group of 1-4 carbons; Y is an oxygen atom, a sulfur atom, sulfoxide, sulfonyl, methylene or a group represented by the formula of —$NR^{20}$—; and $R^{20}$ is an alkyl group of 1-4 carbons.

The amine compound [III-5] is prepared by subjecting a carboxylic compound represented by the formula [IX],

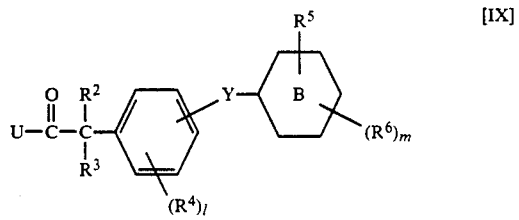

wherein $R^2$, $R^3$, $R^4$, $R^5$, $R^6$, the ring B, Y, l and m are the same meanings as defined for the compound [III-5], and U is amino or hydroxy group, or a chlorine atom, to a rearrangement reaction, for example, Hofmann reaction, Curtius rearrangement, Lossen rearrangement, Schmidt rearrangement or the like to obtain an isocyanate compound represented by the formula [X],

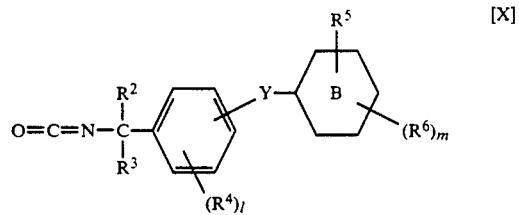

wherein $R^2$, $R^3$, $R^4$, $R^5$, $R^6$, the ring B, Y, l and m are the same meanings as defined for the compound [III-5], then hydrolyzing the product, with or without separation.

The rearrangement reaction is carried out in the manner disclosed in, for example, Org. React. 3, 267 (1946), Org. React, 3, 337 (1946), Chem. Rev., 33, 209 (1943), Org. React, 3, 307 (1946), J. Amer. Chem Soc., 71, 3352 (1949), J. Amer, Chem. Soc., 82, 2857 (1960), and the like, or by the analogous methods thereto.

Among the amine compounds [III-5], those represented by the formula [III-6] are novel;

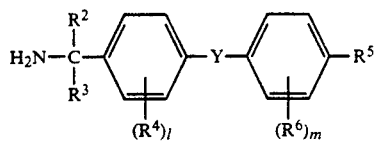

wherein $R^5$ is an alkylthio group of 1-8 carbons or haloalkylthio group of 1-8 carbons; $R^4$ and $R^6$ independently of one another are each a hydrogen atom, a halogen atom or methyl group; and $R^2$, $R^3$, Y, l and m are the same meanings as defined for the compound [III-5].

When U in the crboxylic compound represented by the formula [IX] is a chlorine atom, for example, Curtius rearrangement is applied, and the amine compound [III-5] is prepared, in general, by heating the carboxylic compound [XI] together with 1 to 20 equivalents of sodium azide based on 1 mole of the carboxylic compound represented by the formula [IX] in a solvent including aromatic hydrocarbons such as benzene, toluene and xylene, halogenated hydrocarbons, such as methylene chloride, chloroform and 1,2-dichloroethane, ethers such as diethyl ether and tetrahydrofuran, water and the like or mixtures thereof, then heating the resulting isocyanate compound represented by the formula [X] together with a mineral acid such as concentrated hydrochloric acid or an aqueous solution containing a base such as sodium hydroxide. A reaction temperature is 20° to 200° C., and a reaction period is 0.5 to 100 hours.

Preparation Method d: Preparation of an amine compound [III-7] which is represented by the formula [III] but $R^1$ is a hydrogen atom or an alkyl group of 1-4 carbons, and $R^2$ is a hydrogen atom.

The amine compound [III-7] is prepared by the reaction of a halogenated compound represented by the formula [XI],

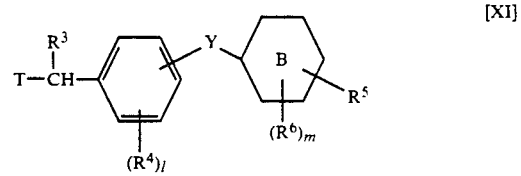

wherein $R^3$, $R^4$, $R^5$, $R^6$, the ring B, Y, l and m are the same meanings as defined for the compound [III-7], and T is a halogen atom, with an amine compound represented by the formula [VII].

This method is carried out normally in a solvent including alcohols such as methanol, ethanol and isopropanol, ethers such as diethyl ether, tetrahydrofuran and dioxane, aromatic hydrocarbons such as toluene, benzene, xylene and chlorobenzene, hydrocarbons such as n-hexane, n-heptane and cyclohexane, water, nitriles such as acetonitrile, polar solvents such as N,N-dimethylformamide, N,N-dimethylacetamide, N-methylpyrrolidone and dimethyl sulfoxide, and mixtures thereof, at a temperature of −20° to 100° C., preferably 0° to 50° C., and using the amine compound represented by the formula [VII] with a ratio of usually 1 to 100 moles, preferably 10 to 50 moles, based on 1 mole of the halogenated compound represented by the formula [XI]. A reaction period is 1 to 200 hours, preferably 10 to 100 hours. The amine compound represented by the formula [VII] may be subjected to the reaction in the form of a gaseous state, an aqueous solution or an alcoholic solution such as a methanol solution.

In order to prepare the amine compound [III-7] with higher yields, the following method is exemplified.

Thus, the halogenated compound represented by the formula [XI] is allowed to react with an alkali metal salt of cyclic imide including, for example, potassium succinimide, potassium phthalimide and sodium 2,3-diphenylmaleimide, in a solvent including ethers such as diethyl ether, tetrahydrofuran and dioxane, aromatic hydrocarbons such as toluene, benzene, xylene, chlorobenzene and pyridine, hydrocarbons such as n-hexane, n-heptane and cyclohexane, esters such as ethyl acetate and methyl acetate, nitriles such as acetonitrile, polar solvents such as N,N-dimethylformamide, N,N-dimethylacetamide, N-methylpyrrolidone and dimethyl sulfoxide, and mixtures thereof, at a temperature of $-20°$ to $100°$ C., preferably $0°$ to $50°$ C., using the alkali metal salt of cyclic imides usually with a ratio of 1 to 10 moles based on 1 mole of the halogenated compound represented by the formula [XI]. A reaction period is normally 1 to 100 hours, preferably 5 to 24 hours. The resulting N-substituted cyclic imide can then be subjected to a hydrolysis by either mineral acids such as hydrochloric acid or alkali metal hydroxides such as sodium hydroxide, or to a hydrazinolysis to obtain the amine compound [III-7]. A reaction solvent usable here includes alcohols such as methanol, ethanol and isopropanol, water, ethers such as diethyl ether, tetrahydrofuran and dioxane, and aromatic hydrocarbons such as toluene, benzene, xylene and chlorobenzen. The hydrolysis by means of the mineral acid as a catalyst is conducted using 0.0001 to 1 part by weight of the mineral acid based on 1 part by weight of the N-substituted cyclic imide, while the hydrolysis by means of the alkali metal hydroxide is conducted using 1 to 10 moles of the alkali metal hydroxide based on 1 mole of the N-substituted cyclic imide, and the hydrazinolysis is conducted using 1 to 10 moles of hydrazine based on 1 mole of the N-substituted cyclic imide. A reaction temperature is $0°$ to $140°$ C., preferably $50°$ to $100°$ C., and a reaction period is 1 to 100 hours, preferably 2 to 24 hours.

Preparation Method e: Preparation of an amine compound [III-8] which is represented by the formula [III] but $R^1$ is a hydrogen atom, and $R^2$ is a cyano group.

The amine compound [III-8] is prepared by subjecting a carbonyl compound represented by the formula [XII],

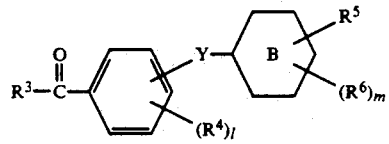
[XII]

wherein $R^3$, $R^4$, $R^5$, $R^6$, the ring B, Y, l and m are the same meanings as defined for the compound [III-8], to the reactions with ammonia and subsequently with hydrogen cyanide.

Among the amine compounds [III-8], those represented by the formula [III-9] are novel:

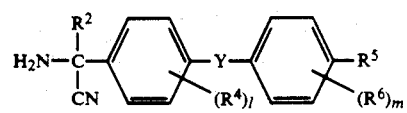
[III-9]

wherein $R^3$ is a hydrogen atom or an alkyl group of 1–4 carbons; $R^5$ is an alkylthio group of 1-8 carbons or a haloalkylthio group or 1-8 carbons; $R^4$ and $R^6$ independently of one another are each a hydrogen atom, a halogen atom or methyl group; Y is an oxygen atom, a sulfur atom, sulfinyl, sulfonyl or methylene group; and l and m are the same meanings as defined above.

Examples of a reaction solvent usable in this reaction are water and any mixtures of water and an organic solvent miscible with water including water/methanol, water/ethanol, water/tetrahydrofuran and the like. A reaction temperature is $-10°$ to $60°$ C., preferably $0°$ to $40°$ C. A reaction period is 1 to 24 hours, preferably 2 to 10 hours. Ammonia and hydrogen cyanide are used each with a ratio of 1 to 10 moles, preferably 1.1 to 2 moles, based on 1 mole of the carbonyl compound represented by the formula [XII]. Combinations of ammonium halides such as ammonium chloride and alkali cyanides such as sodium cyanide are also applicable in place of the combination of ammonia and hydrogen cyanide.

The aforementioned compounds represented by the formulas [V], [VI], [IX], [XI] and [XII] can be prepared in the usual manner or by the analogous methods thereto.

A diphenyl ether compound represented by the formula [XIII],

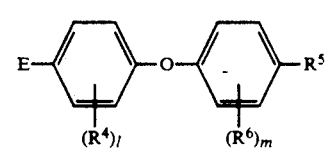
[XIII]

wherein $R^4$ and $R^6$ independently of one another are each a hydrogen atom, a halogen atom or methyl; $R^5$ is an alkylthio group of 1-8 carbons or a haloalkylthio group of 1-8 carbons; l and m are the same meanings as defined above; and E is cyano group or a group represented by the formula

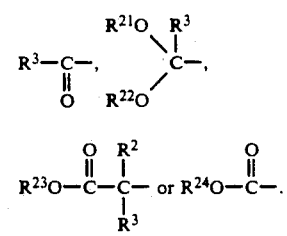

in which $R^3$ is the same meaning as defined above, $R^2$ is merely a hydrogen atom or an alkyl group of 1–4carbons among those defined for the formula [I], $R^{21}$, $R^{22}$, $R^{23}$ and $R^{24}$ independently of one another are each a lower alkyl group, but $R^{21}$ and $R^{22}$ may be linked at their ends to form a saturated five- or six-membered ring, is novel and is prepared, for example, in accordance with the following manner.

Preparation Method f: The diphenyl ether compound represented by the formula [XIII] is prepared in the presence of a base by the reaction of a compound represented by the formula [XIV],

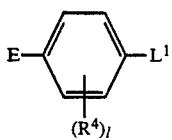

[XIV]

wherein E, $R^4$ and l are the same meanings as defined in the formula [XIII], and $L^1$ is a halogen atom or hydroxy group, with a compound represented by the formula [XV],

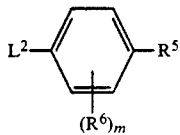

[XV]

wherein $R^5$, $R^6$ and m are the same meanings as defined in the formula [XIII], and $L^2$ is a halogen atom or hydroxy group, provided that when $L^1$ in the formula [XIV] is a halogen atom, $L^2$ in the formula [XV] is hydroxy group, and when $L^1$ is hydroxy group, $L^2$ is a halogen atom.

This reaction is carried out either without solvents or in a solvent including aromatic hydrocarbons such as toluene, benzene, xylene and pyridine, polar solvents such as N,N-dimethylformamide, N,N-dimethylacetamide, N-methylpyrrolidone, hexamethyl phosphoric triamide and dimethyl sulfoxide, and mixtures thereof, using 0.5 to 10 moles, preferably 0.8 to 2 moles, of the halobenzene compound based on 1 mole of the phenolic compound. A reaction temperature is 50° to 250° C., preferably 70° to 200° C., and a reaction period is 1 to 50 hours, preferably 2 to 24 hours. It is possible to use metallic copper or cuprous compounds such as copper(I) chloride and copper(I) iodide in an amount of 0.0001 to 0.1 part by weight based on 1 part by weight of the phenolic compound represented by the formula [XIV] or [XV].

A carbonyl compound represented by the formula [XIII-1] is novel and is prepared from an acetal compound represented by the formula [XIII-2],

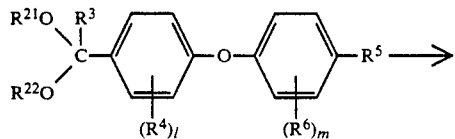

[XIII-2]

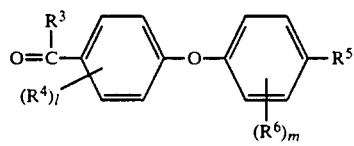

[XIII-1]

wherein $R^3$, $R^4$, $R^5$, $R^6$, $R^{21}$, $R^{22}$, l and m are the same meanings as defined in the formula [XIII].

The acetal compound represented by the formula [XIII-2] is subjected to a reaction in a solvent including ethers such as diethyl ether, tetrahydrofuran and dioxane, aromatic hydrocarbons such as toluene, benzene, xylene and chlorobenzene, hydrocarbons such as n-hexane, n-heptane and cyclohexane, halogenated hydrocarbons such as methylene chloride, chloroform, carbon tetrachloride and 1,2-dichloroethane, aliphatic ketones such as acetone and methyl ethyl ketone, water and mixtures thereof, under an acidic catalyst to obtain the carbonyl compound represented by the formula [XIII-1]. The acidic catalyst includes mineral acids such as hydrochloric acid and sulfuric acid, organic acids such as acetic acid, trifluoroacetic acid and p-toluenesulfonic acid, clay minerals such as montmorillonite, and mixtures thereof, and it can be used in an amount of 0.0001 to 0.1 part by weight, preferably 0.001 to 0.01 part by weight, based on 1 part by weight of the acetal compound represented by the formula [XIII-2]. A reaction temperature is 0° to 150° C., preferably 20° to 100° C., and a reaction period is from 10 minutes to 10 hours, preferably 1 to 5 hours.

Further, a carboxylic compound represented by the formula [XVI] is novel and can be prepared from a carboxylic acid represented by the formula [XVII],

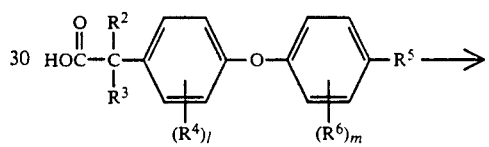

[XVII]

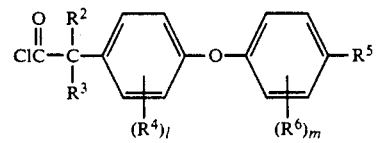

[XVI]

wherein $R^2$, $R^3$, $R^4$, $R^5$, $R^6$, l and m are the same meanings as defined in the formula [XIII].

This reaction is carried out by subjecting the carboxylic acid represented by the formula [XVII] to a reaction with a halogenation agent either in a solvent or without solvents, in which the solvent includes ethers such as diethyl ether, tetrahydrofuran and dioxane, aromatic hydrocarbons such as toluene, benzene, xylene and chlorobenzene, hydrocarbons such as n-hexane, n-heptane and cyclohexane, halogenated hydrocarbons such as methylene chloride, chloroform, carbon tetrachloride and 1,2-dichloroethane, and mixtures thereof. The halogenation agent includes phosphoryl chloride, thionyl chloride, phosphorus pentachloride, phosphorus trichloride, phosgene and the like, and it can be used with a ratio of 1 to 10 moles, preferably 1.1 to 5 moles, based on 1 mole of the carboxylic acid represented by the formula [XVII]. In order to accelerate the reaction, it is possible to use a catalyst such as zinc chloride, pyridine, iodine and triethylamine in an amount of 0.00001 to 0.01 part by weight, preferably 0.0001 to 0.001 part by weight, based on 1 part by weight of the carboxylic acid represented by the formula [XVII]. A reaction temperature is 0° to 200° C., preferably 50° to 150° C., and a reaction period is 1 to 100 hours, preferably 2 to 50 hours.

The carboxylic acid represented by the formula [XVII] is novel and can be prepared from an ester compound represented by the formula [XIII-3],

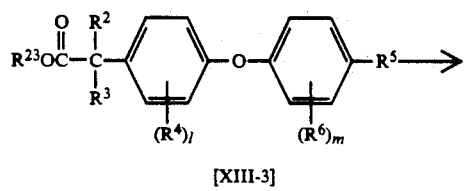

[XIII-3]

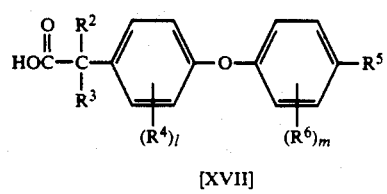

[XVII]

wherein $R^2$, $R^3$, $R^4$, $R^5$, $R^6$, $R^{23}$, l and m are the same meanings as defined in the formula [XIII].

The ester compound represented by the formula [XIII-3] is hydrolyzed in a solvent including ethers such as diethyl ether, tetrahydrofuran and dioxane, aromatic hydrocarbons such as toluene, benzene xylene and chlorobenzene, hydrocarbons such as n-hexane, n-heptane and cyclohexane, halogenated hydrocarbons such as methylene chloride, chloroform, carbon tetrachloride and 1,2-dichloroethane, water and mixtures thereof, in the coexistence of water and an acidic catalyst or a base to form the carboxylic acid [XVII]. The acidic catalyst includes mineral acids such as hydrochloric acid and sulfuric acid, while the base includes alkali hydroxides such as sodium hydroxide and potassium hydroxide, and alkali metal salts of weak acid such as potassium carbonate. When the acidic catalyst is applied, it can be used in an amount of 0.0001 to 0.1 part by weight, preferably 0.001 to 0.01 part by weight, based on 1 part by weight of the ester compound represented by the formula [XIII-3]. When the base is applied, it can be used with a ratio of 1 to 10 moles, preferably 1.1 to 2 moles, based on 1 mole of the ester compound represented by the formula [XIII-3]. A reaction temperature is 0° to 150° C., preferably 20° to 80° C., and a reaction period is 1 to 100 hours, preferably 2 to 24 hours.

An alcoholic compound represented by the formula [XVIII] is novel and can be prepared from the ester compound represented by the formula [XIII-3],

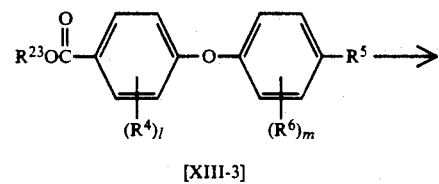

[XIII-3]

-continued

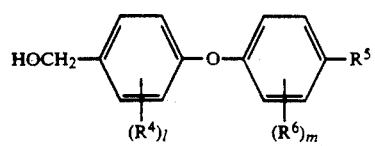

[XVIII]

wherein $R^4$, $R^5$, $R^6$, $R^{23}$, l and m are the same meanings as defined in the formula [XIII].

This reaction is performed by reducing the ester compound represented by the formula [XIII-3] in a solvent including ethers such as diethyl ether, tetrahydrofuran and dioxane, aromatic hydrocarbons such as toluene, benzene, xylene and chlorobenzene, and mixtures thereof. A reducing agent applicable here includes metal hydrogen complex compounds such as lithium aluminum hydride, lithium borohydride, aluminum hydride and lithium trimethoxyaluminum hydride, and it can be used with a ratio of 1 to 10 equivalents, preferably 1 to 2 equivalents, based on 1 mole of the ester compound represented by the formula [XIII-3]. A reaction temperature is −10° to 100° C., preferably 0° to 70° C., and a reaction period is from 10 minutes to 50 hours, preferably from 30 minutes to 24 hours.

A halogenated compound represented by the formula [XIX] is novel and can be prepared from an alcoholic compound represented by the formula [XVIII-1],

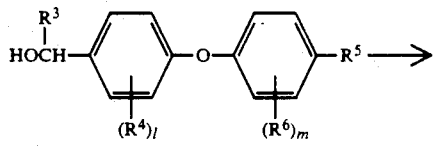

[XVIII-1]

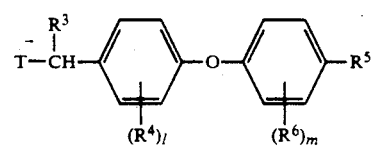

[XIX]

wherein $R^3$, $R^4$, $R^5$, $R^6$, l and m are the same meanings as defined in the formula [XIII], and T is the same meanings as defined in the formula [XI].

The alcoholic compound [XVIII-1] is subjected to a reaction with a halogenation agent either in a solvent or without solvents, in which the solvent includes ethers such as diethyl ether, tetrahydrofuran and dioxane, aromatic hydrocarbons such as toluene, benzene, xylene and chlorobenzene, hydrocarbons such as n-hexane, n-heptane and cyclohexane, halogenated hydrocarbons such as methylene chloride, chloroform, carbon tetrachloride and 1,2-dichloroethane, and mixtures thereof. The halogenation agent includes phosphoryl chloride, thionyl chloride, phosphorus pentachloride, phosphorus trichloride, phosgene and the like, and it can be used with a ratio of 1 to 50 moles, preferably 1.1 to 5 moles, based on 1 mole of the alcoholic compound represented by the formula [XVIII-1]. A reaction temperature is 0° to 200° C., preferably 50° to 150° C., and a reaction period is 1 to 100 hours, preferable 2 to 50 hours.

The alcoholic compound represented by the formula [XVIII-1] can be prepared from the carbonyl compound represented by the formula [XIII-1],

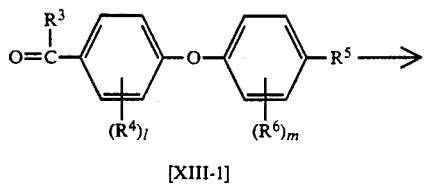

[XIII-1]

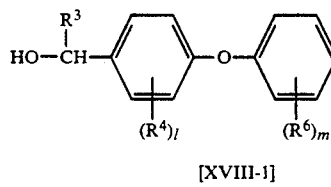

[XVIII-1]

wherein $R^3$, $R^4$, $R^5$, $R^6$, $l$ and $m$ are the same meanings as defined in the formula [XIII].

This reaction is performed by reducing the carbonyl compound represented by the formula [XIII-1] in a solvent including ethers such as diethyl ether, tetrahydrofuran and dioxane, aromatic hydrocarbons such as toluene, benzene, xylene and chlorobenzene, and mixtures thereof. A reducing agent applicable here includes metal hydrogen complex compounds such as lithium aluminum hydride, lithium borohydride, aluminum hydride and lithium trimethoxyaluminum hydride, and it can be used with a ratio of 1 to 10 equivalents, preferably 1 to 2 equivalents, based on 1 mole of the carbonyl compound represented by the formula [XIII-1]. A reaction temperature is $-10°$ to $100°$ C., preferably $0°$ to $70°$ C., and a reaction period is from 10 minutes to 50 hours, preferably from 30 minutes to 24 hours. The present compound can be obtained as a final product by conducting a usual aftertreatment subsequently to the completion of the reaction.

The present compounds have optical isomers originated from $R^2$ and $R^3$, and include also the mixtures of any isomers, each of which can be used as the active ingredient of insecticidall and/or acaricidal composition.

The compounds of the present invention are specifically shown in the following Table 1 to 5. However, these compounds are merely for exemplification, and not for limitation.

TABLE 1
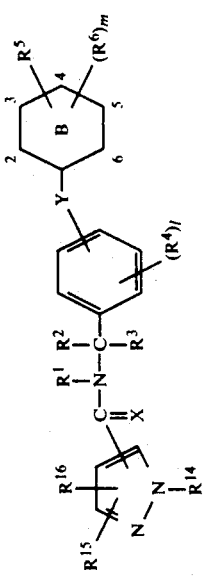
wherein the numbers 2-6 are to represent the positions of substitution.
| Compound No. | $R^{14}$ | $R^{15}$ | $R^{16}$ | X | $R^1$ | $R^2$ | $R^3$ | $(R^4)_l$ | Y | $R^5$ | $(R^6)_m$ |
|---|---|---|---|---|---|---|---|---|---|---|---|
| 1-1 | $CH_3$ | 3-$CH_3$ | 4-H | O | H | H | H | H | 4-O | 4-$CH_3$ | H |
| 1-2 | $CH_3$ | 3-$CH_3$ | 4-H | O | H | H | H | H | 4-O | 3-$CH_3$ | H |
| 1-3 | $CH_3$ | 3-$CH_3$ | 4-H | O | H | H | H | H | 4-O | 2-$CH_3$ | H |
| 1-4 | $CH_3$ | 3-$CH_3$ | 4-H | O | H | H | H | H | 4-O | 4-$C_2H_5$ | H |
| 1-5 | $CH_3$ | 3-$CH_3$ | 4-H | O | H | H | H | H | 4-O | 3-$C_2H_5$ | H |

-continued

| No. | | | | | | | | | | |
|---|---|---|---|---|---|---|---|---|---|---|
| 1-6 | CH₃ | 3-CH₃ | 4-H | O | H | H | H | 4-O | phenyl-4-n-C₃H₇ | H |
| 1-7 | CH₃ | 3-CH₃ | 4-H | O | H | H | H | 4-O | phenyl-3-n-C₃H₇ | H |
| 1-8 | CH₃ | 3-CH₃ | 4-H | O | H | H | H | 4-O | phenyl-4-i-C₃H₇ | H |
| 1-9 | CH₃ | 3-CH₃ | 4-H | O | H | H | H | 4-O | phenyl-3-i-C₃H₇ | H |
| 1-10 | CH₃ | 3-CH₃ | 4-H | O | H | H | H | 4-O | phenyl-4-n-C₄H₉ | H |
| 1-11 | CH₃ | 3-CH₃ | 4-H | O | H | H | H | 4-O | phenyl-3-n-C₄H₉ | H |
| 1-12 | CH₃ | 3-CH₃ | 4-H | O | H | H | H | 4-O | phenyl-4-i-C₄H₉ | H |
| 1-13 | CH₃ | 3-CH₃ | 4-H | O | H | H | H | 4-O | phenyl-3-i-C₄H₉ | H |
| 1-14 | CH₃ | 3-CH₃ | 4-H | O | H | H | H | 4-O | phenyl-4-sec-C₄H₉ | H |

-continued

| No. | | | | | | | | | 4-O | | |
|---|---|---|---|---|---|---|---|---|---|---|---|
| 1-15 | CH$_3$ | 3-CH$_3$ | 4-H | O | H | H | H | H | | ⬡–4-sec-C$_4$H$_9$ | H |
| 1-16 | CH$_3$ | 3-CH$_3$ | 4-H | O | H | H | H | H | 4-O | ⬡–4-n-C$_5$H$_{11}$ | H |
| 1-17 | CH$_3$ | 3-CH$_3$ | 4-H | O | H | H | H | H | 4-O | ⬡–3-n-C$_5$H$_{11}$ | H |
| 1-18 | CH$_3$ | 3-CH$_3$ | 4-H | O | H | H | H | H | 4-O | ⬡–4-i-C$_5$H$_{11}$ | H |
| 1-19 | CH$_3$ | 3-CH$_3$ | 4-H | O | H | H | H | H | 4-O | ⬡–3-i-C$_5$H$_{11}$ | H |
| 1-20 | CH$_3$ | 3-CH$_3$ | 4-H | O | H | H | H | H | 4-O | ⬡–4-sec-C$_5$H$_{11}$ | H |
| 1-21 | CH$_3$ | 3-CH$_3$ | 4-H | O | H | H | H | H | 4-O | ⬡–3-sec-C$_5$H$_{11}$ | H |
| 1-22 | CH$_3$ | 3-CH$_3$ | 4-H | O | H | H | H | H | 4-O | ⬡–4-neo-C$_5$H$_{11}$ | H |
| 1-23 | CH$_3$ | 3-CH$_3$ | 4-H | O | H | H | H | H | 4-O | ⬡–3-neo-C$_5$H$_{11}$ | H |

-continued

| | | | | | | | | | | |
|---|---|---|---|---|---|---|---|---|---|---|
| 1-24 | CH$_3$ | 3-CH$_3$ | 4-H | O | H | H | H | 4-O | phenyl, 4-n-C$_6$H$_{13}$ | H |
| 1-25 | CH$_3$ | 3-CH$_3$ | 4-H | O | H | H | H | 4-O | phenyl, 3-n-C$_6$H$_{13}$ | H |
| 1-26 | CH$_3$ | 3-CH$_3$ | 4-H | O | H | H | H | 4-O | phenyl, 4-n-C$_7$H$_{15}$ | H |
| 1-27 | CH$_3$ | 3-CH$_3$ | 4-H | O | H | H | H | 4-O | phenyl, 3-n-C$_7$H$_{15}$ | H |
| 1-28 | CH$_3$ | 3-CH$_3$ | 4-H | O | H | H | H | 4-O | phenyl, 4-n-C$_8$H$_{17}$ | H |
| 1-29 | CH$_3$ | 3-CH$_3$ | 4-H | O | H | H | H | 4-O | phenyl, 3-n-C$_8$H$_{17}$ | H |
| 1-30 | CH$_3$ | 3-CH$_3$ | 4-H | O | H | H | H | 4-O | phenyl, 4-CF$_2$H | H |
| 1-31 | CH$_3$ | 3-CH$_3$ | 4-H | O | H | H | H | 4-O | phenyl, 3-CF$_2$H | H |
| 1-32 | CH$_3$ | 3-CH$_3$ | 4-H | O | H | H | H | 4-O | phenyl, 4-CF$_3$ | H |

| No. | | | | | | | | | Ar | |
|---|---|---|---|---|---|---|---|---|---|---|
| 1-33 | CH₃ | 3-CH₃ | 4-H | O | H | H | H | 4-O | 3-CF₃ | H |
| 1-34 | CH₃ | 3-CH₃ | 4-H | O | H | H | H | 4-O | 4-CF₂CF₃ | H |
| 1-35 | CH₃ | 3-CH₃ | 4-H | O | H | H | H | 4-O | 4-CF₂CF₂CF₃ | H |
| 1-36 | CH₃ | 3-CH₃ | 4-H | O | H | H | H | 4-O | 4-CH₂CF₃ | H |
| 1-37 | CH₃ | 3-CH₃ | 4-H | O | H | H | H | 4-O | 2-Cl | H |
| 1-38 | CH₃ | 3-CH₃ | 4-H | O | H | H | H | 4-O | 3-Cl | H |
| 1-39 | CH₃ | 3-CH₃ | 4-H | O | H | H | H | 4-O | 4-Cl | H |
| 1-40 | CH₃ | 3-CH₃ | 4-H | O | H | H | H | 4-O | 3-F | H |
| 1-41 | CH₃ | 3-CH₃ | 4-H | O | H | H | H | 4-O | 4-F | H |

-continued

| | | | | | | | | | | |
|---|---|---|---|---|---|---|---|---|---|---|
| 1-42 | CH₃ | 3-CH₃ | 4-H | O | H | H | H | 4-O | Phenyl | 4-Br | H |
| 1-43 | CH₃ | 3-CH₃ | 4-H | O | H | H | H | 4-O | Phenyl | 3-Br | H |
| 1-44 | CH₃ | 3-CH₃ | 4-H | O | H | H | H | 4-O | Phenyl | 4-cyclopropyl | H |
| 1-45 | CH₃ | 3-CH₃ | 4-H | O | H | H | H | 4-O | Phenyl | 4-cyclopentyl | H |
| 1-46 | CH₃ | 3-CH₃ | 4-H | O | H | H | H | 4-O | Phenyl | 4-cyclohexyl | H |
| 1-47 | CH₃ | 3-CH₃ | 4-H | O | H | H | H | 4-O | Phenyl | 3-CH₂CH=CH₂ | H |
| 1-48 | CH₃ | 3-CH₃ | 4-H | O | H | H | H | 4-O | Phenyl | 4-CH₂CH=CH₂ | H |
| 1-49 | CH₃ | 3-CH₃ | 4-H | O | H | H | H | 4-O | Phenyl | 4-CH₂-C(CH₃)=CH₂ | H |
| 1-50 | CH₃ | 3-CH₃ | 4-H | O | H | H | H | 4-O | Phenyl | 4-C≡CH | H |

-continued

| | | | | | | | | | |
|---|---|---|---|---|---|---|---|---|---|
| 1-51 | CH₃ | 3-CH₃ | 4-H | O | H | H | H | 4-O | (phenyl) 4-CH₂—C≡CH | H |
| 1-52 | CH₃ | 3-CH₃ | 4-H | O | H | H | H | 4-O | (phenyl) 4-CH₂—C≡C—CH₃ | H |
| 1-53 | CH₃ | 3-CH₃ | 4-H | O | H | H | H | 4-O | (phenyl) 3-OCH₃ | H |
| 1-54 | CH₃ | 3-CH₃ | 4-H | O | H | H | H | 4-O | (phenyl) 4-OCH₃ | H |
| 1-55 | CH₃ | 3-CH₃ | 4-H | O | H | H | H | 4-O | (phenyl) 3-OC₂H₅ | H |
| 1-56 | CH₃ | 3-CH₃ | 4-H | O | H | H | H | 4-O | (phenyl) 4-OC₂H₅ | H |
| 1-57 | CH₃ | 3-CH₃ | 4-H | O | H | H | H | 4-O | (phenyl) 3-O-i-C₃H₇ | H |
| 1-58 | CH₃ | 3-CH₃ | 4-H | O | H | H | H | 4-O | (phenyl) 4-O-i-C₃H₇ | H |
| 1-59 | CH₃ | 3-CH₃ | 4-H | O | H | H | H | 4-O | (phenyl) 4-O-n-C₃H₇ | H |

-continued

| | | | | | | | | |
|---|---|---|---|---|---|---|---|---|
| 1-60 | $CH_3$ | 3-$CH_3$ | 4-H | O | H | H | H | 4-O | Ph(4-O-n-$C_4H_9$) | H |
| 1-61 | $CH_3$ | 3-$CH_3$ | 4-H | O | H | H | H | 4-O | Ph(4-O-n-$C_5H_{11}$) | H |
| 1-62 | $CH_3$ | 3-$CH_3$ | 4-H | O | H | H | H | 4-O | Ph(4-O-n-$C_6H_{13}$) | H |
| 1-63 | $CH_3$ | 3-$CH_3$ | 4-H | O | H | H | H | 4-O | Ph(3-$OCF_2H$) | H |
| 1-64 | $CH_3$ | 3-$CH_3$ | 4-H | O | H | H | H | 4-O | Ph(4-$OCF_2H$) | H |
| 1-65 | $CH_3$ | 3-$CH_3$ | 4-H | O | H | H | H | 4-O | Ph(3-$OCF_3$) | H |
| 1-66 | $CH_3$ | 3-$CH_3$ | 4-H | O | H | H | H | 4-O | Ph(3-$OCBrF_2$) | H |
| 1-67 | $CH_3$ | 3-$CH_3$ | 4-H | O | H | H | H | 4-O | Ph(4-$OCBrF_2$) | H |
| 1-68 | $CH_3$ | 3-$CH_3$ | 4-H | O | H | H | H | 4-O | Ph(4-$OCF_2CF_2H$) | H |

-continued

| | | | | | | | | | |
|---|---|---|---|---|---|---|---|---|---|
| 1-69 | CH₃ | 3-CH₃ | 4-H | O | H | H | H | 4-O | 3-OCF₂CF₂H | H |
| 1-70 | CH₃ | 3-CH₃ | 4-H | O | H | H | H | 4-O | 4-OCH₂CF₃ | H |
| 1-71 | CH₃ | 3-CH₃ | 4-H | O | H | H | H | 4-O | 3-OCH₂CF₃ | H |
| 1-72 | CH₃ | 3-CH₃ | 4-H | O | H | H | H | 4-O | 4-OCF₂CClFH | H |
| 1-73 | CH₃ | 3-CH₃ | 4-H | O | H | H | H | 4-O | 3-OCF₂CClFH | H |
| 1-74 | CH₃ | 3-CH₃ | 4-H | O | H | H | H | 4-O | 3-OCF₂CCl₂H | H |
| 1-75 | CH₃ | 3-CH₃ | 4-H | O | H | H | H | 4-O | 4-OCF₂CFHCF₃ | H |
| 1-76 | CH₃ | 3-CH₃ | 4-H | O | H | H | H | 4-O | 3-OCH₂CH₂F | H |
| 1-77 | CH₃ | 3-CH₃ | 4-H | O | H | H | H | 4-O | 4-OCH₂CH₂F | H |

-continued

| No. | | | | | | | | | |
|---|---|---|---|---|---|---|---|---|---|
| 1-78 | CH$_3$ | 3-CH$_3$ | 4-H | O | H | H | 4-O | phenyl, 3-OCH$_2$CH=CH$_2$ | H |
| 1-79 | CH$_3$ | 3-CH$_3$ | 4-H | O | H | H | 4-O | phenyl, 4-OCH$_2$CH=CH$_2$ | H |
| 1-80 | CH$_3$ | 3-CH$_3$ | 4-H | O | H | H | 4-O | phenyl, 4-OCHCH=CH$_2$ (CH$_3$) | H |
| 1-81 | CH$_3$ | 3-CH$_3$ | 4-H | O | H | H | 4-O | phenyl, 4-OCH$_2$C=CH$_2$ (CH$_3$) | H |
| 1-82 | CH$_3$ | 3-CH$_3$ | 4-H | O | H | H | 4-O | phenyl, 3-OCH$_2$C≡CH | H |
| 1-83 | CH$_3$ | 3-CH$_3$ | 4-H | O | H | H | 4-O | phenyl, 4-OCH$_2$C≡CH | H |
| 1-84 | CH$_3$ | 3-CH$_3$ | 4-H | O | H | H | 4-O | phenyl, 4-OCH$_2$C≡CCH$_3$ | H |
| 1-85 | CH$_3$ | 3-CH$_3$ | 4-H | O | H | H | 4-O | phenyl, 3-SCH$_3$ | H |
| 1-86 | CH$_3$ | 3-CH$_3$ | 4-H | O | H | H | 4-O | phenyl, 4-SCH$_3$ | H |

-continued

| | | | | | | | Ar | |
|---|---|---|---|---|---|---|---|---|
| 1-87 | CH₃ | 3-CH₃ | 4-H | O | H | H | 4-O | (phenyl) 3-SC₂H₅ | H |
| 1-88 | CH₃ | 3-CH₃ | 4-H | O | H | H | 4-O | (phenyl) 4-SC₂H₅ | H |
| 1-89 | CH₃ | 3-CH₃ | 4-H | O | H | H | 4-O | (phenyl) 3-S-n-C₃H₇ | H |
| 1-90 | CH₃ | 3-CH₃ | 4-H | O | H | H | 4-O | (phenyl) 4-S-n-C₃H₇ | H |
| 1-91 | CH₃ | 3-CH₃ | 4-H | O | H | H | 4-O | (phenyl) 3-S-i-C₃H₇ | H |
| 1-92 | CH₃ | 3-CH₃ | 4-H | O | H | H | 4-O | (phenyl) 4-S-i-C₃H₇ | H |
| 1-93 | CH₃ | 3-CH₃ | 4-H | O | H | H | 4-O | (phenyl) 3-S-n-C₄H₉ | H |
| 1-94 | CH₃ | 3-CH₃ | 4-H | O | H | H | 4-O | (phenyl) 4-S-n-C₄H₉ | H |
| 1-95 | CH₃ | 3-CH₃ | 4-H | O | H | H | 4-O | (phenyl) 3-S-i-C₄H₉ | H |

-continued

| No. | | | | | | | | | | |
|---|---|---|---|---|---|---|---|---|---|---|
| 1-96 | CH$_3$ | 3-CH$_3$ | 4-H | O | H | H | H | 4-O | 4-S-i-C$_4$H$_9$ | H |
| 1-97 | CH$_3$ | 3-CH$_3$ | 4-H | O | H | H | H | 4-O | 3-S-sec-C$_4$H$_9$ | H |
| 1-98 | CH$_3$ | 3-CH$_3$ | 4-H | O | H | H | H | 4-O | 4-S-sec-C$_4$H$_9$ | H |
| 1-99 | CH$_3$ | 3-CH$_3$ | 4-H | O | H | H | H | 4-O | 3-S-n-C$_5$H$_{11}$ | H |
| 1-100 | CH$_3$ | 3-CH$_3$ | 4-H | O | H | H | H | 4-O | 4-S-n-C$_5$H$_{11}$ | H |
| 1-101 | CH$_3$ | 3-CH$_3$ | 4-H | O | H | H | H | 4-O | 4-S—CHC$_2$H$_5$ (C$_2$H$_5$) | H |
| 1-102 | CH$_3$ | 3-CH$_3$ | 4-H | O | H | H | H | 4-O | 4-S—CHC$_3$H$_7$ (CH$_3$) | H |
| 1-103 | CH$_3$ | 3-CH$_3$ | 4-H | O | H | H | H | 4-O | 4-S—CH$_2$CHC$_2$H$_5$ (CH$_3$) | H |
| 1-104 | CH$_3$ | 3-CH$_3$ | 4-H | O | H | H | H | 4-O | 4-S—CH$_2$CH$_2$CH(CH$_3$)$_2$ | H |

-continued

| No. | | | | | | | | | Ar | |
|---|---|---|---|---|---|---|---|---|---|---|
| 1-105 | CH₃ | 3-CH₃ | 4-H | O | H | H | H | 4-O | 4-S—CH₂C(CH₃)₃ | H |
| 1-106 | CH₃ | 3-CH₃ | 4-H | O | H | H | H | 4-O | 4-S-tert-C₄H₉ | H |
| 1-107 | CH₃ | 3-CH₃ | 4-H | O | H | H | H | 4-O | 4-S-n-C₆H₁₃ | H |
| 1-108 | CH₃ | 3-CH₃ | 4-H | O | H | H | H | 4-O | 4-S-n-C₇H₁₅ | H |
| 1-109 | CH₃ | 3-CH₃ | 4-H | O | H | H | H | 4-O | 4-S-n-C₈H₁₇ | H |
| 1-110 | CH₃ | 3-CH₃ | 4-H | O | H | H | H | 4-O | 3-SCF₂H | H |
| 1-111 | CH₃ | 3-CH₃ | 4-H | O | H | H | H | 4-O | 4-S—CH₂—(CF₂)₃—CF₃ | H |
| 1-112 | CH₃ | 3-CH₃ | 4-H | O | H | H | H | 4-O | 3-SCF₃ | H |
| 1-113 | CH₃ | 3-CH₃ | 4-H | O | H | H | H | 4-O | 4-SCF₃ | H |

-continued

| | | | | | | | | |
|---|---|---|---|---|---|---|---|---|
| 1-114 | CH$_3$ | 3-CH$_3$ | 4-H | O | H | H | H | 4-O | H | Ph(3-SCH$_2$CH$_2$F) | H |
| 1-115 | CH$_3$ | 3-CH$_3$ | 4-H | O | H | H | H | 4-O | H | Ph(4-SCH$_2$CH$_2$F) | H |
| 1-116 | CH$_3$ | 3-CH$_3$ | 4-H | O | H | H | H | 4-O | H | Ph(3-SCH$_2$CF$_3$) | H |
| 1-117 | CH$_3$ | 3-CH$_3$ | 4-H | O | H | H | H | 4-O | H | Ph(4-SCH$_2$CF$_3$) | H |
| 1-118 | CH$_3$ | 3-CH$_3$ | 4-H | O | H | H | H | 4-O | H | Ph(3-SCF$_2$CF$_2$H) | H |
| 1-119 | CH$_3$ | 3-CH$_3$ | 4-H | O | H | H | H | 4-O | H | Ph(4-SCF$_2$CF$_2$H) | H |
| 1-120 | CH$_3$ | 3-CH$_3$ | 4-H | O | H | H | H | 4-O | H | Ph(3-SCF$_2$CClFH) | H |
| 1-121 | CH$_3$ | 3-CH$_3$ | 4-H | O | H | H | H | 4-O | H | Ph(4-SCF$_2$CClFH) | H |
| 1-122 | CH$_3$ | 3-CH$_3$ | 4-H | O | H | H | H | 4-O | H | Ph(4-SCF$_2$CCl$_2$H) | H |

| | | | | | | | Ar | |
|---|---|---|---|---|---|---|---|---|
| 1-123 | CH₃ | 3-CH₃ | 4-H | O | H | H | H | 4-O—⟨phenyl⟩-3-SCF₂CFHCF₃ | H |
| 1-124 | CH₃ | 3-CH₃ | 4-H | O | H | H | H | 4-O—⟨phenyl⟩-4-SCF₂CFHCF₃ | H |
| 1-125 | CH₃ | 3-CH₃ | 4-H | O | H | H | H | 4-O—⟨phenyl⟩-4-SCF₂CFHCF₂CF₃ | H |
| 1-126 | CH₃ | 3-CH₃ | 4-H | O | H | H | H | 4-O—⟨phenyl⟩-3-SCH₂CF₂CF₃ | H |
| 1-127 | CH₃ | 3-CH₃ | 4-H | O | H | H | H | 4-O—⟨phenyl⟩-4-SCH₂CF₂CF₃ | H |
| 1-128 | CH₃ | 3-CH₃ | 4-H | O | H | H | H | 4-O—⟨phenyl⟩-3-SCH₂CF₂CF₂CF₃ | H |
| 1-129 | CH₃ | 3-CH₃ | 4-H | O | H | H | H | 4-O—⟨phenyl⟩-4-SCH₂CF₂CF₂CF₃ | H |
| 1-130 | CH₃ | 3-CH₃ | 4-H | O | H | H | H | 4-O—⟨phenyl⟩-3-SCH₂CH=CH₂ | H |
| 1-131 | CH₃ | 3-CH₃ | 4-H | O | H | H | H | 4-O—⟨phenyl⟩-4-SCH₂CH=CH₂ | H |

| No. | | | | | | | | Ar | |
|---|---|---|---|---|---|---|---|---|---|
| 1-132 | CH₃ | 3-CH₃ | 4-H | O | H | H | 4-O | 4-SCHCH=CH₂ (CH₃) | H |
| 1-133 | CH₃ | 3-CH₃ | 4-H | O | H | H | 4-O | 4-SCH₂C=CH₂ (CH₃) | H |
| 1-134 | CH₃ | 3-CH₃ | 4-H | O | H | H | 4-O | 4-SCH₂CH=CHCH₃ | H |
| 1-135 | CH₃ | 3-CH₃ | 4-H | O | H | H | 4-O | 3-SCH₂C≡CH | H |
| 1-136 | CH₃ | 3-CH₃ | 4-H | O | H | H | 4-O | 4-SCH₂C≡CH | H |
| 1-137 | CH₃ | 3-CH₃ | 4-H | O | H | H | 4-O | 4-SCHC≡CH (CH₃) | H |
| 1-138 | CH₃ | 3-CH₃ | 4-H | O | H | H | 4-O | 4-SCH₂C≡CCH₃ | H |
| 1-139 | CH₃ | 3-CH₃ | 4-H | O | H | H | 4-O | 3-SCH₂CH=CH−C≡CH | H |
| 1-140 | CH₃ | 3-CH₃ | 4-H | O | H | H | 4-O | 4-SCH₂CH=CH−C≡CH | H |

-continued

| | | | | | | | | | | |
|---|---|---|---|---|---|---|---|---|---|---|
| 1-141 | CH₃ | 3-CH₃ | 4-H | O | H | H | H | 4-O | Ph(3-CH₂OCH₃) | H |
| 1-142 | CH₃ | 3-CH₃ | 4-H | O | H | H | H | 4-O | Ph(4-CH₂OCH₃) | H |
| 1-143 | CH₃ | 3-CH₃ | 4-H | O | H | H | H | 4-O | Ph(3-CH₂OC₂H₅) | H |
| 1-144 | CH₃ | 3-CH₃ | 4-H | O | H | H | H | 4-O | Ph(4-CH₂OC₂H₅) | H |
| 1-145 | CH₃ | 3-CH₃ | 4-H | O | H | H | H | 4-O | Ph(4-CH₂O-n-C₃H₇) | H |
| 1-146 | CH₃ | 3-CH₃ | 4-H | O | H | H | H | 4-O | Ph(4-CH₂O-i-C₃H₇) | H |
| 1-147 | CH₃ | 3-CH₃ | 4-H | O | H | H | H | 4-O | Ph(4-CH₂O-n-C₄H₉) | H |
| 1-148 | CH₃ | 3-CH₃ | 4-H | O | H | H | H | 4-O | Ph(4-CH₂O-n-C₅H₁₁) | H |
| 1-149 | CH₃ | 3-CH₃ | 4-H | O | H | H | H | 4-O | Ph(4-CH₂O-n-C₆H₁₃) | H |

-continued

| No. | | | | | | | | | | |
|---|---|---|---|---|---|---|---|---|---|---|
| 1-150 | CH$_3$ | 3-CH$_3$ | 4-H | O | H | H | H | 4-O | phenyl, 4-CH$_2$O-n-C$_7$H$_{15}$ | H |
| 1-151 | CH$_3$ | 3-CH$_3$ | 4-H | O | H | H | H | 4-O | phenyl, 3-S(O)CH$_3$ | H |
| 1-152 | CH$_3$ | 3-CH$_3$ | 4-H | O | H | H | H | 4-O | phenyl, 4-S(O)CH$_3$ | H |
| 1-153 | CH$_3$ | 3-CH$_3$ | 4-H | O | H | H | H | 4-O | phenyl, 3-S(O)C$_2$H$_5$ | H |
| 1-154 | CH$_3$ | 3-CH$_3$ | 4-H | O | H | H | H | 4-O | phenyl, 4-S(O)C$_2$H$_5$ | H |
| 1-155 | CH$_3$ | 3-CH$_3$ | 4-H | O | H | H | H | 4-O | phenyl, 4-S(O)-n-C$_3$H$_7$ | H |
| 1-156 | CH$_3$ | 3-CH$_3$ | 4-H | O | H | H | H | 4-O | phenyl, 4-S(O)-n-C$_4$H$_9$ | H |
| 1-157 | CH$_3$ | 3-CH$_3$ | 4-H | O | H | H | H | 4-O | phenyl, 4-S(O)-i-C$_3$H$_7$ | H |
| 1-158 | CH$_3$ | 3-CH$_3$ | 4-H | O | H | H | H | 4-O | phenyl, 3-S(O)CF$_2$H | H |

-continued

| | | | | | | | Ar substituent |
|---|---|---|---|---|---|---|---|
| 1-159 | CH$_3$ | 3-CH$_3$ | 4-H | O | H | H | H | 4-O | 4-S(O)CF$_2$H | H |
| 1-160 | CH$_3$ | 3-CH$_3$ | 4-H | O | H | H | H | 4-O | 3-S(O)CF$_3$ | H |
| 1-161 | CH$_3$ | 3-CH$_3$ | 4-H | O | H | H | H | 4-O | 4-S(O)CF$_3$ | H |
| 1-162 | CH$_3$ | 3-CH$_3$ | 4-H | O | H | H | H | 4-O | 4-S(O)CF$_2$CF$_2$H | H |
| 1-163 | CH$_3$ | 3-CH$_3$ | 4-H | O | H | H | H | 4-O | 3-S(O)CF$_2$CF$_2$H | H |
| 1-164 | CH$_3$ | 3-CH$_3$ | 4-H | O | H | H | H | 4-O | 3-S(O)CH$_2$CF$_3$ | H |
| 1-165 | CH$_3$ | 3-CH$_3$ | 4-H | O | H | H | H | 4-O | 4-S(O)CH$_2$CF$_3$ | H |
| 1-166 | CH$_3$ | 3-CH$_3$ | 4-H | O | H | H | H | 4-O | 4-S(O)CH$_2$CF$_2$CF$_3$ | H |
| 1-167 | CH$_3$ | 3-CH$_3$ | 4-H | O | H | H | H | 4-O | 4-S(O)CF$_2$CFHCF$_3$ | H |

-continued

| | | | | | | | | |
|---|---|---|---|---|---|---|---|---|
| 1-168 | CH₃ | 3-CH₃ | 4-H | O | H | H | H | 4-O | 3-S(O)₂CH₃ | H |
| 1-169 | CH₃ | 3-CH₃ | 4-H | O | H | H | H | 4-O | 4-S(O)₂CH₃ | H |
| 1-170 | CH₃ | 3-CH₃ | 4-H | O | H | H | H | 4-O | 3-S(O)₂C₂H₅ | H |
| 1-171 | CH₃ | 3-CH₃ | 4-H | O | H | H | H | 4-O | 4-S(O)₂C₂H₅ | H |
| 1-172 | CH₃ | 3-CH₃ | 4-H | O | H | H | H | 4-O | 3-S(O)₂CF₂H | H |
| 1-173 | CH₃ | 3-CH₃ | 4-H | O | H | H | H | 4-O | 4-S(O)₂CF₂H | H |
| 1-174 | CH₃ | 3-CH₃ | 4-H | O | H | H | H | 4-O | 3-S(O)CF₃ | H |
| 1-175 | CH₃ | 3-CH₃ | 4-H | O | H | H | H | 4-O | 4-S(O)CF₃ | H |
| 1-176 | CH₃ | 3-CH₃ | 4-H | O | H | H | H | 4-O | 3-S(O)₂CH₂CF₃ | H |

-continued

| | | | | | | | | Ar | |
|---|---|---|---|---|---|---|---|---|---|
| 1-177 | $CH_3$ | 3-$CH_3$ | 4-H | O | H | H | H | 4-O | 4-$S(O)_2CH_2CF_3$ phenyl | H |
| 1-178 | $CH_3$ | 3-$CH_3$ | 4-H | O | H | H | H | 4-O | 3-$S(O)_2CF_2CF_2H$ phenyl | H |
| 1-179 | $CH_3$ | 3-$CH_3$ | 4-H | O | H | H | H | 4-O | 4-$S(O)_2CF_2CF_2H$ phenyl | H |
| 1-180 | $CH_3$ | 3-$CH_3$ | 4-H | O | H | H | H | 4-O | 3-$OSO_2CH_3$ phenyl | H |
| 1-181 | $CH_3$ | 3-$CH_3$ | 4-H | O | H | H | H | 4-O | 4-$OSO_2CH_3$ phenyl | H |
| 1-182 | $CH_3$ | 3-$CH_3$ | 4-H | O | H | H | H | 4-O | 3-$OSO_2C_2H_5$ phenyl | H |
| 1-183 | $CH_3$ | 3-$CH_3$ | 4-H | O | H | H | H | 4-O | 4-$OSO_2C_2H_5$ phenyl | H |
| 1-184 | $CH_3$ | 3-$CH_3$ | 4-H | O | H | H | H | 4-O | 4-$OSO_2$-i-$C_3H_7$ phenyl | H |
| 1-185 | $CH_3$ | 3-$CH_3$ | 4-H | O | H | H | H | 4-O | 4-$OSO_2$-n-$C_3H_7$ phenyl | H |

| No. | | | | | | | | | | |
|---|---|---|---|---|---|---|---|---|---|---|
| 1-186 | $CH_3$ | 3-$CH_3$ | 4-H | O | H | H | H | 4-O | 4-$OSO_2$-n-$C_4H_9$ | H |
| 1-187 | $CH_3$ | 3-$CH_3$ | 4-H | O | H | H | H | 4-O | 3-$OSO_2CF_3$ | H |
| 1-188 | $CH_3$ | 3-$CH_3$ | 4-H | O | H | H | H | 4-O | 4-$OSO_2CF_3$ | H |
| 1-189 | $CH_3$ | 3-$CH_3$ | 4-H | O | H | H | H | 4-O | 3-$NHCH_3$ | H |
| 1-190 | $CH_3$ | 3-$CH_3$ | 4-H | O | H | H | H | 4-O | 4-$NHCH_3$ | H |
| 1-191 | $CH_3$ | 3-$CH_3$ | 4-H | O | H | H | H | 4-O | 3-$NHC_2H_5$ | H |
| 1-192 | $CH_3$ | 3-$CH_3$ | 4-H | O | H | H | H | 4-O | 4-$NHC_2H_5$ | H |
| 1-193 | $CH_3$ | 3-$CH_3$ | 4-H | O | H | H | H | 4-O | 4-NH-n-$C_3H_7$ | H |
| 1-194 | $CH_3$ | 3-$CH_3$ | 4-H | O | H | H | H | 4-O | 4-NH-i-$C_3H_7$ | H |

-continued

| No. | | | | | | | | | | |
|---|---|---|---|---|---|---|---|---|---|---|
| 1-195 | CH₃ | 3-CH₃ | 4-H | O | H | H | H | 4-O | phenyl, 4-NH-n-C₄H₉ | H |
| 1-196 | CH₃ | 3-CH₃ | 4-H | O | H | H | H | 4-O | phenyl, 4-NH-n-C₅H₁₁ | H |
| 1-197 | CH₃ | 3-CH₃ | 4-H | O | H | H | H | 4-O | phenyl, 3-NHCH₂CH₂F | H |
| 1-198 | CH₃ | 3-CH₃ | 4-H | O | H | H | H | 4-O | phenyl, 4-NHCH₂CH₂F | H |

| No. | | | | | | | | | | |
|---|---|---|---|---|---|---|---|---|---|---|
| 1-199 | CH$_3$ | 3-CH$_3$ | 4-H | O | H | H | H | 4-O | 3-NHCH$_2$CF$_3$-C$_6$H$_5$ | H |
| 1-200 | CH$_3$ | 3-CH$_3$ | 4-H | O | H | H | H | 4-O | 4-NHCH$_2$CF$_3$-C$_6$H$_5$ | H |
| 1-201 | CH$_3$ | 3-CH$_3$ | 4-H | O | H | H | H | 4-O | 3-N(CH$_3$)$_2$-C$_6$H$_5$ | H |
| 1-202 | CH$_3$ | 3-CH$_3$ | 4-H | O | H | H | H | 4-O | 4-N(CH$_3$)$_2$-C$_6$H$_5$ | H |
| 1-203 | CH$_3$ | 3-CH$_3$ | 4-H | O | H | H | H | 4-O | 3-N(CH$_3$)C$_2$H$_5$-C$_6$H$_5$ | H |
| 1-204 | CH$_3$ | 3-CH$_3$ | 4-H | O | H | H | H | 4-O | 4-N(CH$_3$)C$_2$H$_5$-C$_6$H$_5$ | H |
| 1-205 | CH$_3$ | 3-CH$_3$ | 4-H | O | H | H | H | 4-O | 4-N(C$_2$H$_5$)$_2$-C$_6$H$_5$ | H |
| 1-206 | CH$_3$ | 3-CH$_3$ | 4-H | O | H | H | H | 4-O | 3-N(C$_2$H$_5$)$_2$-C$_6$H$_5$ | H |
| 1-207 | CH$_3$ | 3-CH$_3$ | 4-H | O | H | H | H | 4-O | 4-N(CH$_3$)-n-C$_3$H$_7$-C$_6$H$_5$ | H |

| No. | | | | | | | | | Ar | |
|---|---|---|---|---|---|---|---|---|---|---|
| 1-208 | CH$_3$ | 3-CH$_3$ | 4-H | O | H | H | H | 4-O | 4-NHCH(=O) phenyl | H |
| 1-209 | CH$_3$ | 3-CH$_3$ | 4-H | O | H | H | H | 4-O | 4-NHCCH$_3$(=O) phenyl | H |
| 1-210 | CH$_3$ | 3-CH$_3$ | 4-H | O | H | H | H | 4-O | 4-NHCC$_2$H$_5$(=O) phenyl | H |
| 1-211 | CH$_3$ | 3-CH$_3$ | 4-H | O | H | H | H | 4-O | 3-NHCCH$_3$(=O) phenyl | H |
| 1-212 | CH$_3$ | 3-CH$_3$ | 4-H | O | H | H | H | 4-O | 3-NHCC$_2$H$_5$(=O) phenyl | H |
| 1-213 | CH$_3$ | 3-CH$_3$ | 4-H | O | H | H | H | 4-O | 3-N=CHCH$_3$ phenyl | H |
| 1-214 | CH$_3$ | 3-CH$_3$ | 4-H | O | H | H | H | 4-O | 4-N=CHC$_2$H$_5$ phenyl | H |
| 1-215 | CH$_3$ | 3-CH$_3$ | 4-H | O | H | H | H | 4-O | 3-N=CHC$_2$H$_5$ phenyl | H |
| 1-216 | CH$_3$ | 3-CH$_3$ | 4-H | O | H | H | H | 4-O | 4-N=CHCH$_3$ phenyl | H |

| | | | | | | | | |
|---|---|---|---|---|---|---|---|---|
| 1-217 | CH₃ | 3-CH₃ | 4-H | O | H | H | 4-O | Ph | 3-N=CH—NHCH₃ | H |
| 1-218 | CH₃ | 3-CH₃ | 4-H | O | H | H | 4-O | Ph | 4-N=CH—NHCH₃ | H |
| 1-219 | CH₃ | 3-CH₃ | 4-H | O | H | H | 4-O | Ph | 3-N=CH—NHC₂H₅ | H |
| 1-220 | CH₃ | 3-CH₃ | 4-H | O | H | H | 4-O | Ph | 4-N=CH—NHC₂H₅ | H |
| 1-221 | CH₃ | 3-CH₃ | 4-H | O | H | H | 4-O | Ph | 4-N=C(CH₃)—NHCH₃ | H |
| 1-222 | CH₃ | 3-CH₃ | 4-H | O | H | H | 4-O | Ph | 4-N=C(CH₃)—NHC₂H₅ | H |
| 1-223 | CH₃ | 3-CH₃ | 4-H | O | H | H | 4-O | Ph | 3-N=CH—N(CH₃)₂ | H |
| 1-224 | CH₃ | 3-CH₃ | 4-H | O | H | H | 4-O | Ph | 4-N=CH—N(CH₃)₂ | H |
| 1-225 | CH₃ | 3-CH₃ | 4-H | O | H | H | 4-O | Ph | 4-N=CH—N(C₂H₅)₂ | H |

| No. | | | | | | | | | | |
|---|---|---|---|---|---|---|---|---|---|---|
| 1-226 | CH₃ | 3-CH₃ | 4-H | O | H | H | H | 4-O | phenyl, 4-N=CH—N(CH₃)C₂H₅ | H |
| 1-227 | CH₃ | 3-CH₃ | 4-H | O | H | H | H | 4-O | phenyl, 3-N=C(CH₃)—N(CH₃)₂ | H |
| 1-228 | CH₃ | 3-CH₃ | 4-H | O | H | H | H | 4-O | phenyl, 4-N=C(CH₃)—N(C₂H₅)₂ | H |
| 1-229 | CH₃ | 3-CH₃ | 4-H | O | H | H | H | 4-O | phenyl, 4-N=C(CH₃)—N(CH₃)₂ | H |
| 1-230 | CH₃ | 3-CH₃ | 4-H | O | H | H | H | 4-O | phenyl, 3-N=C(CH₃)—N(C₂H₅)₂ | H |
| 1-231 | CH₃ | 3-CH₃ | 4-H | O | H | H | H | 4-O | phenyl, 4-N=C(CH₃)—N(CH₃)C₂H₅ | H |
| 1-232 | CH₃ | 3-CH₃ | 4-H | O | H | H | H | 4-O | phenyl, 4-NHSO₂CH₃ | H |
| 1-233 | CH₃ | 3-CH₃ | 4-H | O | H | H | H | 4-O | phenyl, 3-NHSO₂CH₃ | H |
| 1-234 | CH₃ | 3-CH₃ | 4-H | O | H | H | H | 4-O | phenyl, 4-NHSO₂C₂H₅ | H |

-continued

| | | | | | | | | Ar substituents | |
|---|---|---|---|---|---|---|---|---|---|
| 1-235 | CH$_3$ | 3-CH$_3$ | 4-H | O | H | H | H | 4-O | 4-NHSO$_2$-n-C$_3$H$_7$ | H |
| 1-236 | CH$_3$ | 3-CH$_3$ | 4-H | O | H | H | H | 4-O | 2-CH$_3$ | 3-CH$_3$ |
| 1-237 | CH$_3$ | 3-CH$_3$ | 4-H | O | H | H | H | 4-O | 2-CH$_3$ | 4-CH$_3$ |
| 1-238 | CH$_3$ | 3-CH$_3$ | 4-H | O | H | H | H | 4-O | 2-CH$_3$ | 5-CH$_3$ |
| 1-239 | CH$_3$ | 3-CH$_3$ | 4-H | O | H | H | H | 4-O | 2-CH$_3$ | 3,4-(CH$_3$)$_2$ |
| 1-240 | CH$_3$ | 3-CH$_3$ | 4-H | O | H | H | H | 4-O | 2-CH$_3$ | 4,5-(CH$_3$)$_2$ |
| 1-241 | CH$_3$ | 3-CH$_3$ | 4-H | O | H | H | H | 4-O | 2-CH$_3$ | 4,6-(CH$_3$)$_2$ |
| 1-242 | CH$_3$ | 3-CH$_3$ | 4-H | O | H | H | H | 4-O | 2-CH$_3$ | 4-C$_2$H$_5$ |
| 1-243 | CH$_3$ | 3-CH$_3$ | 4-H | O | H | H | H | 4-O | 2-CH$_3$ | 5-C$_2$H$_5$ |

-continued

| No. | | | | | | | | | Ar substituents |
|---|---|---|---|---|---|---|---|---|---|
| 1-244 | CH₃ | 3-CH₃ | 4-H | O | H | H | H | 4-O | 2-CH₃, 3,4,5-(CH₃)₃ |
| 1-245 | CH₃ | 3-CH₃ | 4-H | O | H | H | H | 4-O | 2-CH₃, 3-Cl |
| 1-246 | CH₃ | 3-CH₃ | 4-H | O | H | H | H | 4-O | 2-CH₃, 4-Cl |
| 1-247 | CH₃ | 3-CH₃ | 4-H | O | H | H | H | 4-O | 2-CH₃, 5-Cl |
| 1-248 | CH₃ | 3-CH₃ | 4-H | O | H | H | H | 4-O | 2-CH₃, 3-CH₃-4-Cl |
| 1-249 | CH₃ | 3-CH₃ | 4-H | O | H | H | H | 4-O | 2-CH₃, 3-Cl-4-CH₃ |
| 1-250 | CH₃ | 3-CH₃ | 4-H | O | H | H | H | 4-O | 2-CH₃, 3-CH₃-4-Br |
| 1-251 | CH₃ | 3-CH₃ | 4-H | O | H | H | H | 4-O | 2-CH₃, 3-CH₃-4-C₂H₅ |
| 1-252 | CH₃ | 3-CH₃ | 4-H | O | H | H | H | 4-O | 2-CH₃, 3-CH₃-4-n-C₃H₇ |

-continued

| No. | | | | | | | | | Ar | Ar' |
|---|---|---|---|---|---|---|---|---|---|---|
| 1-253 | CH$_3$ | 3-CH$_3$ | 4-H | O | H | H | H | 4-O | 2-CH$_3$-C$_6$H$_4$ | 4-n-C$_3$H$_7$ |
| 1-254 | CH$_3$ | 3-CH$_3$ | 4-H | O | H | H | H | 4-O | 4-n-C$_4$H$_9$-C$_6$H$_4$ | 2-CH$_3$ |
| 1-255 | CH$_3$ | 3-CH$_3$ | 4-H | O | H | H | H | 4-O | 4-n-C$_4$H$_9$-C$_6$H$_4$ | 2,3-(CH$_3$)$_2$ |
| 1-256 | CH$_3$ | 3-CH$_3$ | 4-H | O | H | H | H | 4-O | 4-n-C$_5$H$_{11}$-C$_6$H$_4$ | 2,3-(CH$_3$)$_2$ |
| 1-257 | CH$_3$ | 3-CH$_3$ | 4-H | O | H | H | H | 4-O | 2-CH$_3$-C$_6$H$_4$ | 3-Cl-4-C$_2$H$_5$ |
| 1-258 | CH$_3$ | 3-CH$_3$ | 4-H | O | H | H | H | 4-O | 2-CH$_3$-C$_6$H$_4$ | 3-Cl-4-n-C$_3$H$_7$ |
| 1-259 | CH$_3$ | 3-CH$_3$ | 4-H | O | H | H | H | 4-O | 2-CH$_3$-C$_6$H$_4$ | 4-CF$_3$ |
| 1-260 | CH$_3$ | 3-CH$_3$ | 4-H | O | H | H | H | 4-O | 2-CH$_3$-C$_6$H$_4$ | 4-cyclopropyl |
| 1-261 | CH$_3$ | 3-CH$_3$ | 4-H | O | H | H | H | 4-O | 2-CH$_3$-C$_6$H$_4$ | 4-CH$_2$—CH=CH$_2$ |

-continued

| No. | | | | | | | | | | |
|---|---|---|---|---|---|---|---|---|---|---|
| 1-262 | CH₃ | 3-CH₃ | 4-H | H | H | H | O | H | 2-CH₃ (phenyl) | 4-OCH₃ |
| 1-263 | CH₃ | 3-CH₃ | 4-H | H | H | H | O | H | 2-CH₃ (phenyl) | 4-OC₂H₅ |
| 1-264 | CH₃ | 3-CH₃ | 4-H | H | H | H | O | H | 2-CH₃ (phenyl) | 4-O-n-C₃H₇ |
| 1-265 | CH₃ | 3-CH₃ | 4-H | H | H | H | O | H | 2-CH₃ (phenyl) | 4-OCF₂H |
| 1-266 | CH₃ | 3-CH₃ | 4-H | H | H | H | O | H | 2-CH₃ (phenyl) | 4-OCF₂CF₂H |
| 1-267 | CH₃ | 3-CH₃ | 4-H | H | H | H | O | H | 2-CH₃ (phenyl) | 4-OCH₂—CH=CH₂ |
| 1-268 | CH₃ | 3-CH₃ | 4-H | H | H | H | O | H | 2-CH₃ (phenyl) | 4-OCH₂C≡CH |
| 1-269 | CH₃ | 3-CH₃ | 4-H | H | H | H | O | H | 2-CH₃ (phenyl) | 4-SCH₃ |
| 1-270 | CH₃ | 3-CH₃ | 4-H | H | H | H | O | H | 2-CH₃ (phenyl) | 5-SCH₃ |

| No. | | | | | | | | | Ar | | |
|---|---|---|---|---|---|---|---|---|---|---|---|
| 1-271 | CH₃ | 3-CH₃ | 4-H | O | H | H | H | 4-O | Ph | 2-CH₃ | 4-SC₂H₅ |
| 1-272 | CH₃ | 3-CH₃ | 4-H | O | H | H | H | 4-O | Ph | 2-CH₃ | 5-SC₂H₅ |
| 1-273 | CH₃ | 3-CH₃ | 4-H | O | H | H | H | 4-O | Ph | 2-CH₃ | 4-S-n-C₃H₇ |
| 1-274 | CH₃ | 3-CH₃ | 4-H | O | H | H | H | 4-O | Ph | 2-CH₃ | 5-S-n-C₃H₇ |
| 1-275 | CH₃ | 3-CH₃ | 4-H | O | H | H | H | 4-O | Ph | 4-S-n-C₄H₉ | 2-CH₃ |
| 1-276 | CH₃ | 3-CH₃ | 4-H | O | H | H | H | 4-O | Ph | 2-CH₃ | 4-S-i-C₃H₇ |
| 1-277 | CH₃ | 3-CH₃ | 4-H | O | H | H | H | 4-O | Ph | 4-S-n-C₅H₁₁ | 2-CH₃ |
| 1-278 | CH₃ | 3-CH₃ | 4-H | O | H | H | H | 4-O | Ph | 4-S-n-C₆H₁₃ | 2-CH₃ |
| 1-279 | CH₃ | 3-CH₃ | 4-H | O | H | H | H | 4-O | Ph | 2-CH₃ | 4-SCF₂H |

-continued

| | | | | | | | | Ar | |
|---|---|---|---|---|---|---|---|---|---|
| 1-280 | CH₃ | 3-CH₃ | 4-H | O | H | H | H | 4-O-(2-CH₃-phenyl) | 5-SCF₂H |
| 1-281 | CH₃ | 3-CH₃ | 4-H | O | H | H | H | 4-O-(2-CH₃-phenyl) | 4-SCF₃ |
| 1-282 | CH₃ | 3-CH₃ | 4-H | O | H | H | H | 4-O-(2-CH₃-phenyl) | 5-SCF₃ |
| 1-283 | CH₃ | 3-CH₃ | 4-H | O | H | H | H | 4-O-(2-CH₃-phenyl) | 4-SCF₂CF₂H |
| 1-284 | CH₃ | 3-CH₃ | 4-H | O | H | H | H | 4-O-(2-CH₃-phenyl) | 5-SCF₂CF₂H |
| 1-285 | CH₃ | 3-CH₃ | 4-H | O | H | H | H | 4-O-(2-CH₃-phenyl) | 4-SCH₂CF₃ |
| 1-286 | CH₃ | 3-CH₃ | 4-H | O | H | H | H | 4-O-(2-CH₃-phenyl) | 5-SCH₂CF₃ |
| 1-287 | CH₃ | 3-CH₃ | 4-H | O | H | H | H | 4-O-(2-CH₃-phenyl) | 4-SCH₂CH₂F |
| 1-288 | CH₃ | 3-CH₃ | 4-H | O | H | H | H | 4-O-(2-CH₃-phenyl) | 5-SCH₂CH₂F |

| No. | | | | | | | | | Ar |
|---|---|---|---|---|---|---|---|---|---|
| 1-289 | CH₃ | 3-CH₃ | 4-H | O | H | H | H | 4-O | 2-Cl, 4-CH₃ |
| 1-290 | CH₃ | 3-CH₃ | 4-H | O | H | H | H | 4-O | 2-Cl, 4-SCH₃ |
| 1-291 | CH₃ | 3-CH₃ | 4-H | O | H | H | H | 4-O | 2-Br, 4-CH₃ |
| 1-292 | CH₃ | 3-CH₃ | 4-H | O | H | H | H | 4-O | 2-Cl, 4-C₂H₅ |
| 1-293 | CH₃ | 3-CH₃ | 4-H | O | H | H | H | 4-O | 2-Cl, 4-n-C₃H₇ |
| 1-294 | CH₃ | 3-CH₃ | 4-H | O | H | H | H | 4-O | 2-Cl, 4-SC₂H₅ |
| 1-295 | CH₃ | 3-CH₃ | 4-H | O | H | H | H | 4-O | 2-Br, 4-C₂H₅ |
| 1-296 | CH₃ | 3-CH₃ | 4-H | O | H | H | H | 4-O | 2-Br, 4-SCH₃ |
| 1-297 | CH₃ | 3-CH₃ | 4-H | O | H | H | H | 4-O | 2-Br, 4-SC₂H₅ |

-continued

| | | | | | | | | Ar substituents | |
|---|---|---|---|---|---|---|---|---|---|
| 1-298 | CH₃ | 3-CH₃ | 4-H | O | H | H | H | 4-O | 2-CH₃ / 4-CH₂—C≡CH |
| 1-299 | CH₃ | 3-CH₃ | 4-H | O | H | H | H | 4-O | 2-CH₃ / 4-S—CH₂—CH=CH₂ |
| 1-300 | CH₃ | 3-CH₃ | 4-H | O | H | H | H | 4-O | 2-CH₃ / 4-S—CH₂—C≡CH |
| 1-301 | CH₃ | 3-CH₃ | 4-H | O | H | H | H | 4-O | 2-CH₃ / 4-CH₂OCH₃ |
| 1-302 | CH₃ | 3-CH₃ | 4-H | O | H | H | H | 4-O | 4-CH₂CH₂OC₂H₅ / 2-CH₃ |
| 1-303 | CH₃ | 3-CH₃ | 4-H | O | H | H | H | 4-O | 2-CH₃ / 4-S(O)CH₃ |
| 1-304 | CH₃ | 3-CH₃ | 4-H | O | H | H | H | 4-O | 2-CH₃ / 4-S(O)C₂H₅ |
| 1-305 | CH₃ | 3-CH₃ | 4-H | O | H | H | H | 4-O | 2-CH₃ / 4-S(O)CF₂H |
| 1-306 | CH₃ | | | O | H | H | H | 4-O | 4-S(O)CF₂CF₂H |

| No. | | | | | | | | | | | |
|---|---|---|---|---|---|---|---|---|---|---|---|
| 1-307 | CH$_3$ | 3-CH$_3$ | 4-H | O | H | H | H | H | 4-O | 2-CH$_3$-C$_6$H$_4$ | 4-S(O)CH$_2$CF$_3$ |
| 1-308 | CH$_3$ | 3-CH$_3$ | 4-H | O | H | H | H | H | 4-O | 2-CH$_3$-C$_6$H$_4$ | 4-S(O)$_2$CH$_3$ |
| 1-309 | CH$_3$ | 3-CH$_3$ | 4-H | O | H | H | H | H | 4-O | 2-CH$_3$-C$_6$H$_4$ | 4-S(O)$_2$C$_2$H$_5$ |
| 1-310 | CH$_3$ | 3-CH$_3$ | 4-H | O | H | H | H | H | 4-O | 2-CH$_3$-C$_6$H$_4$ | 4-S(O)$_2$CF$_2$H |
| 1-311 | CH$_3$ | 3-CH$_3$ | 4-H | O | H | H | H | H | 4-O | 2-CH$_3$-C$_6$H$_4$ | 4-S(O)$_2$CF$_2$CF$_2$H |
| 1-312 | CH$_3$ | 3-CH$_3$ | 4-H | O | H | H | H | H | 4-O | 2-CH$_3$-C$_6$H$_4$ | 4-S(O)$_2$CH$_2$CF$_3$ |
| 1-313 | CH$_3$ | 3-CH$_3$ | 4-H | O | H | H | H | H | 4-O | 2-CH$_3$-C$_6$H$_4$ | 4-OSO$_2$CH$_3$ |
| 1-314 | CH$_3$ | 3-CH$_3$ | 4-H | O | H | H | H | H | 4-O | 2-CH$_3$-C$_6$H$_4$ | 4-OSO$_2$C$_2$H$_5$ |
| 1-315 | CH$_3$ | 3-CH$_3$ | 4-H | O | H | H | H | H | 4-O | 2-CH$_3$-C$_6$H$_4$ | 4-OSO$_2$CF$_3$ |

-continued

| No. | | | | | | | | | Ar | sub1 | sub2 |
|---|---|---|---|---|---|---|---|---|---|---|---|
| 1-316 | CH₃ | 3-CH₃ | 4-H | O | H | H | H | 4-O | phenyl | 2-CH₃ | 3,5-(CH₃)₂ |
| 1-317 | CH₃ | 3-CH₃ | 4-H | O | H | H | H | 4-O | phenyl | 2-CH₃ | 3,6-(CH₃)₂ |
| 1-318 | CH₃ | 3-CH₃ | 4-H | O | H | H | H | 4-O | phenyl | 3-CH₃ | 4-CH₃ |
| 1-319 | CH₃ | 3-CH₃ | 4-H | O | H | H | H | 4-O | phenyl | 3-CH₃ | 5-CH₃ |
| 1-320 | CH₃ | 3-CH₃ | 4-H | O | H | H | H | 4-O | phenyl | 3-CH₃ | 4-C₂H₅ |
| 1-321 | CH₃ | 3-CH₃ | 4-H | O | H | H | H | 4-O | phenyl | 3-CH₃ | 5-C₂H₅ |
| 1-322 | CH₃ | 3-CH₃ | 4-H | O | H | H | H | 4-O | phenyl | 2-Cl | 3-Cl |
| 1-323 | CH₃ | 3-CH₃ | 4-H | O | H | H | H | 4-O | phenyl | 2-Cl | 4-Cl |
| 1-324 | CH₃ | 3-CH₃ | 4-H | O | H | H | H | 4-O | phenyl | 2-Cl | 4-Br |

| No. | | | | | | | | | Ar | |
|---|---|---|---|---|---|---|---|---|---|---|
| 1-325 | CH₃ | 3-CH₃ | 4-H | O | H | H | H | 4-O | 2-Cl | 5-Cl |
| 1-326 | CH₃ | 3-CH₃ | 4-H | O | H | H | H | 4-O | 2-Br | 4-Cl |
| 1-327 | CH₃ | 3-CH₃ | 4-H | O | H | H | H | 4-O | 3-Cl | 4-Cl |
| 1-328 | CH₃ | 3-CH₃ | 4-H | O | H | H | H | 4-O | 3-Cl | 5-Cl |
| 1-329 | CH₃ | 3-CH₃ | 4-H | O | H | H | H | 4-O | 2-Cl | 3,6-Cl₂ |
| 1-330 | CH₃ | 3-CH₃ | 4-H | O | H | H | H | 4-O | 2-Cl | 4,6-Cl₂ |
| 1-331 | CH₃ | 3-CH₃ | 4-H | O | H | H | H | 4-O | 3-F | 4-SCH₃ |
| 1-332 | CH₃ | 3-CH₃ | 4-H | O | H | H | H | 4-O | 3-Cl | 4-SCH₃ |
| 1-333 | CH₃ | 3-CH₃ | 4-H | O | H | H | H | 4-O | 3-Br | 4-SCH₃ |

| No. | | | | | | | | | Ar substituents | |
|---|---|---|---|---|---|---|---|---|---|---|
| 1-334 | CH$_3$ | 3-CH$_3$ | 4-H | O | H | H | H | 4-O | 3-F | 4-SC$_2$H$_5$ |
| 1-335 | CH$_3$ | 3-CH$_3$ | 4-H | O | H | H | H | 4-O | 3-Cl | 4-SC$_2$H$_5$ |
| 1-336 | CH$_3$ | 3-CH$_3$ | 4-H | O | H | H | H | 4-O | 3-Br | 4-SC$_2$H$_5$ |
| 1-337 | CH$_3$ | 3-CH$_3$ | 4-H | O | H | H | H | 4-O | 3-F | 4-SCF$_2$H |
| 1-338 | CH$_3$ | 3-CH$_3$ | 4-H | O | H | H | H | 4-O | 3-Cl | 4-SCF$_2$H |
| 1-339 | CH$_3$ | 3-CH$_3$ | 4-H | O | H | H | H | 4-O | 3-Br | 4-SCF$_2$H |
| 1-340 | CH$_3$ | 3-CH$_3$ | 4-H | O | H | H | H | 4-O | 3-Cl | 4-SCF$_3$ |
| 1-341 | CH$_3$ | 3-CH$_3$ | 4-H | O | H | H | H | 4-O | 3-Br | 3-SCF$_3$ |
| 1-342 | CH$_3$ | 3-CH$_3$ | 4-H | O | H | H | H | 4-O | 3-Cl | 4-SCF$_2$CF$_2$H |

-continued

| | | | | | | | | | | Ar substituents |
|---|---|---|---|---|---|---|---|---|---|---|
| 1-343 | CH₃ | 3-CH₃ | 4-H | O | H | H | H | 4-O | (phenyl) 3-F | 4-SCF₂CF₂H |
| 1-344 | CH₃ | 3-CH₃ | 4-H | O | H | H | H | 4-O | 3-Br | 3-SCF₂CF₂H |
| 1-345 | CH₃ | 3-CH₃ | 4-H | O | H | H | H | 4-O | 3-Cl | 4-SCH₂CF₃ |
| 1-346 | CH₃ | 3-CH₃ | 4-H | O | H | H | H | 4-O | 3-Br | 4-SCH₂CF₃ |
| 1-347 | CH₃ | 3-CH₃ | 4-H | O | H | H | H | 4-O | 3-Cl | 4-SCH₂CH₂F |
| 1-348 | CH₃ | 3-CH₃ | 4-H | O | H | H | H | 4-O | 3-F | 4-SCH₂CH₂F |
| 1-349 | CH₃ | 3-CH₃ | 4-H | O | H | H | H | 4-O | 3-CH₃ | 4-SCH₃ |
| 1-350 | CH₃ | 3-CH₃ | 4-H | O | H | H | H | 4-O | 3-CH₃ | 4-SC₂H₅ |
| 1-351 | CH₃ | 3-CH₃ | 4-H | O | H | H | H | 4-O | 3-CH₃ | 4-SCF₂H |

| No. | | | | | | | | | | Ar |
|---|---|---|---|---|---|---|---|---|---|---|
| 1-352 | CH₃ | 3-CH₃ | 4-H | O | H | H | H | 4-O | H | 3-CH₃, 4-SCH₂CH₂F |
| 1-353 | CH₃ | 3-CH₃ | 4-H | O | H | H | H | 4-O | H | 3-CH₃, 4-SCF₃ |
| 1-354 | CH₃ | 3-CH₃ | 4-H | O | H | H | H | 4-O | H | 3-CH₃, 4-SCF₂CF₂H |
| 1-355 | CH₃ | 3-CH₃ | 4-H | O | H | H | H | 4-O | H | 3-CH₃, 4-SCH₂CF₃ |
| 1-356 | CH₃ | 3-CH₃ | 4-H | O | H | H | H | 4-O | H | 4-SCH₃, 2,5-Cl₂ |
| 1-357 | CH₃ | 3-CH₃ | 4-H | O | H | H | H | 4-O | H | 4-SCH₃, 2-Cl-5-CH₃ |
| 1-358 | CH₃ | 3-CH₃ | 4-H | O | H | H | H | 4-O | H | 4-SCH₃, 2-CH₃-5-Cl |
| 1-359 | CH₃ | 3-CH₃ | 4-H | O | H | H | H | 4-O | H | 4-SCH₃, 2-F-5-CH₃ |
| 1-360 | CH₃ | 3-CH₃ | 4-H | O | H | H | H | 4-O | H | 4-SCH₃, 2-CH₃-5-F |

| No. | | | | | | | | Ar | |
|---|---|---|---|---|---|---|---|---|---|
| 1-361 | CH₃ | 3-CH₃ | 4-H | O | H | H | H | 4-O — 4-SC₂H₅ | 2,5-Cl₂ |
| 1-362 | CH₃ | 3-CH₃ | 4-H | O | H | H | H | 4-O — 4-SC₂H₅ | 2-Cl-5-CH₃ |
| 1-363 | CH₃ | 3-CH₃ | 4-H | O | H | H | H | 4-O — 4-SC₂H₅ | 2-CH₃-5-Cl |
| 1-364 | CH₃ | 3-CH₃ | 4-H | O | H | H | H | 4-O — 4-SC₂H₅ | 2-F-5-CH₃ |
| 1-365 | CH₃ | 3-CH₃ | 4-H | O | H | H | H | 4-O — 4-SC₂H₅ | 2-CH₃-5-F |
| 1-366 | CH₃ | 3-CH₃ | 4-H | O | H | H | H | 4-O — 4-SCH₃ | 2,3-Cl₂ |
| 1-367 | CH₃ | 3-CH₃ | 4-H | O | H | H | H | 4-O — 4-SC₂H₅ | 2,3-Cl₂ |
| 1-368 | CH₃ | 3-CH₃ | 4-H | O | H | H | H | 4-O — 4-SCF₂H | 2,3-Cl₂ |
| 1-369 | CH₃ | 3-CH₃ | 4-H | O | H | H | H | 4-O — 4-SCF₂H | 2,5-Cl₂ |

-continued

| No. | | | | | | | | | | Ar substituents |
|---|---|---|---|---|---|---|---|---|---|---|
| 1-370 | CH₃ | 3-CH₃ | 4-H | O | H | H | H | H | 4-O | 4-SCF₂H, 2-Cl-5-CH₃ |
| 1-371 | CH₃ | 3-CH₃ | 4-H | O | H | H | H | H | 4-O | 4-SCF₂H, 2-CH₃-5-F |
| 1-372 | CH₃ | 3-CH₃ | 4-H | O | H | H | H | H | 4-O | 4-SCF₂H, 2-F-5-CH₃ |
| 1-373 | CH₃ | 3-CH₃ | 4-H | O | H | H | H | H | 4-O | 4-SCF₂H, 2-CH₃-6-F |
| 1-374 | CH₃ | 3-CH₃ | 4-H | O | H | H | H | H | 4-O | 4-SCF₂CF₂H, 2,3-Cl₂ |
| 1-375 | CH₃ | 3-CH₃ | 4-H | O | H | H | H | H | 4-O | 4-SCF₂CF₂H, 2,5-Cl₂ |
| 1-376 | CH₃ | 3-CH₃ | 4-H | O | H | H | H | H | 4-O | 4-SCF₂CF₂H, 2-Cl-5-CH₃ |
| 1-377 | CH₃ | 3-CH₃ | 4-H | O | H | H | H | H | 4-O | 4-SCF₂CF₂H, 2-CH₃-5-Cl |
| 1-378 | CH₃ | 3-CH₃ | 4-H | O | H | H | H | H | 4-O | 4-SCH₂CF₃, 2,3-Cl₂ |

-continued

| No. | | | | | | | | | Ar substituents |
|---|---|---|---|---|---|---|---|---|---|
| 1-379 | $CH_3$ | 3-$CH_3$ | 4-H | O | H | H | H | 4-O | 4-$SCH_2CF_3$, 2,5-$Cl_2$ |
| 1-380 | $CH_3$ | 3-$CH_3$ | 4-H | O | H | H | H | 4-O | 4-$SCH_2CF_3$, 2-Cl-5-$CH_3$ |
| 1-381 | $CH_3$ | 3-$CH_3$ | 4-H | O | H | H | H | 4-O | 4-$SCH_2CF_3$, 2-$CH_3$-5-Cl |
| 1-382 | $CH_3$ | 3-$CH_3$ | 4-H | O | H | H | H | 4-O | 4-$SCH_2CH_2F$, 2,3-$Cl_2$ |
| 1-383 | $CH_3$ | 3-$CH_3$ | 4-H | O | H | H | H | 4-O | 4-$SCH_2CH_2F$, 2,5-$Cl_2$ |
| 1-384 | $CH_3$ | 3-$CH_3$ | 4-H | O | H | H | H | 4-O | 4-$SCH_2CH_2F$, 2-Cl-5-$CH_3$ |
| 1-385 | $CH_3$ | 3-$CH_3$ | 4-H | O | H | H | H | 4-O | 4-$SCH_2CH_2F$, 2-$CH_3$-5-Cl |
| 1-386 | $CH_3$ | 3-$CH_3$ | 4-H | O | H | H | H | 4-O | 3-$C_2H_5$, 4-$SCH_3$ |
| 1-387 | $CH_3$ | 3-$CH_3$ | 4-H | O | H | H | H | 4-O | 3-$C_2H_5$, 4-$SC_2H_5$ |

-continued

| No. | | | | | | | | | Phenyl subst. 1 | Phenyl subst. 2 |
|---|---|---|---|---|---|---|---|---|---|---|
| 1-388 | $CH_3$ | 3-$CH_3$ | 4-H | O | H | H | H | 4-O | 3-$C_2H_5$ | 4-$SCF_2H$ |
| 1-389 | $CH_3$ | 3-$CH_3$ | 4-H | O | H | H | H | 4-O | 3-$C_2H_5$ | 4-$SCH_2CF_3$ |
| 1-390 | $CH_3$ | 3-$CH_3$ | 4-H | O | H | H | H | 4-O | 3-$C_2H_5$ | 4-$SCF_2CF_2H$ |
| 1-391 | $CH_3$ | 3-$CH_3$ | 4-H | O | H | H | H | 4-O | 4-$SCH_3$ | 2,3-$(CH_3)_2$ |
| 1-392 | $CH_3$ | 3-$CH_3$ | 4-H | O | H | H | H | 4-O | 4-$SC_2H_5$ | 2,3-$(CH_3)_2$ |
| 1-393 | $CH_3$ | 3-$CH_3$ | 4-H | O | H | H | H | 4-O | 4-$SCF_2H$ | 2,3-$(CH_3)_2$ |
| 1-394 | $CH_3$ | 3-$CH_3$ | 4-H | O | H | H | H | 4-O | 4-$SCH_2CF_3$ | 2,3-$(CH_3)_2$ |
| 1-395 | $CH_3$ | 3-$CH_3$ | 4-H | O | H | H | H | 4-O | 4-$SCH_2CH_2F$ | 2,3-$(CH_3)_2$ |
| 1-396 | $CH_3$ | 3-$CH_3$ | 4-H | O | H | H | H | 4-O | 4-$SCF_2CF_2H$ | 2,3-$(CH_3)_2$ |

| | | | | | | | | |
|---|---|---|---|---|---|---|---|---|
| 1-397 | CH₃ | 3-CH₃ | 4-H | O | H | H | H | 4-O | Ph(4-SCH₃)(2,3,5-(CH₃)₃) |
| 1-398 | CH₃ | 3-CH₃ | 4-H | O | H | H | H | 4-O | Ph(4-SC₂H₅)(2,3,5-(CH₃)₃) |
| 1-399 | CH₃ | 3-CH₃ | 4-H | O | H | H | H | 4-O | Ph(4-SCF₂H)(2,3,5-(CH₃)₃) |
| 1-400 | CH₃ | 3-CH₃ | 4-H | O | H | H | H | 4-O | Ph(4-SCH₂CF₃)(2,3,5-(CH₃)₃) |
| 1-401 | CH₃ | 3-CH₃ | 4-H | O | H | H | H | 4-O | Ph(4-SCH₂CH₂F)(2,3,5-(CH₃)₃) |
| 1-402 | CH₃ | 3-CH₃ | 4-H | O | H | H | H | 4-O | Ph(4-SCF₂CF₂H)(2,3,5-(CH₃)₃) |
| 1-403 | CH₃ | 3-CH₃ | 4-H | O | H | H | H | 4-O | Ph(4-SCH₃)(3,5-(CH₃)₂) |
| 1-404 | CH₃ | 3-CH₃ | 4-H | O | H | H | H | 4-O | Ph(4-SC₂H₅)(3,5-(CH₃)₂) |

| # | | | | | | | | | |
|---|---|---|---|---|---|---|---|---|---|
| 1-405 | CH₃ | 3-CH₃ | 4-H | O | H | H | H | 4-O | Ph(4-SCF₂H, 3,5-(CH₃)₂) |
| 1-406 | CH₃ | 3-CH₃ | 4-H | O | H | H | H | 4-O | Ph(4-SCH₂CF₃, 3,5-(CH₃)₂) |
| 1-407 | CH₃ | 3-CH₃ | 4-H | O | H | H | H | 4-O | Ph(4-SCF₂CF₂H, 3,5-(CH₃)₂) |
| 1-408 | CH₃ | 3-CH₃ | 4-H | O | H | H | H | 4-O | Ph(4-SCH₃, 2,5-(CH₃)₂) |
| 1-409 | CH₃ | 3-CH₃ | 4-H | O | H | H | H | 4-O | Ph(4-SC₂H₅, 2,5-(CH₃)₂) |
| 1-410 | CH₃ | 3-CH₃ | 4-H | O | H | H | H | 4-O | Ph(4-SCF₂H, 2,5-(CH₃)₂) |
| 1-411 | CH₃ | 3-CH₃ | 4-H | O | H | H | H | 4-O | Ph(4-SCH₂CF₃, 2,5-(CH₃)₂) |
| 1-412 | CH₃ | 3-CH₃ | 4-H | O | H | H | H | 4-O | Ph(4-SCF₂CF₂H, 2,5-(CH₃)₂) |
| 1-413 | CH₃ | 3-CH₃ | 4-H | O | H | H | H | 4-O | Ph(3-Cl, 4-S(O)CH₃) |

-continued
| | | | | | | | | | |
|---|---|---|---|---|---|---|---|---|---|
| 1-414 | CH₃ | 3-CH₃ | 4-H | O | H | H | H | 4-O |  3-Br | 4-S(O)CH₃ |
| 1-415 | CH₃ | 3-CH₃ | 4-H | O | H | H | H | 4-O |  3-F | 4-S(O)CH₃ |
| 1-416 | CH₃ | 3-CH₃ | 4-H | O | H | H | H | 4-O |  3-Cl | 4-S(O)C₂H₅ |
| 1-417 | CH₃ | 3-CH₃ | 4-H | O | H | H | H | 4-O |  3-Br | 4-S(O)C₂H₅ |
| 1-418 | CH₃ | 3-CH₃ | 4-H | O | H | H | H | 4-O |  3-F | 4-S(O)C₂H₅ |
| 1-419 | CH₃ | 3-CH₃ | 4-H | O | H | H | H | 4-O |  4-S(O)CH₃ | 2,5-Cl₂ |
| 1-420 | CH₃ | 3-CH₃ | 4-H | O | H | H | H | 4-O | 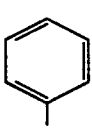 4-S(O)CH₃ | 2,3-Cl₂ |
| 1-421 | CH₃ | 3-CH₃ | 4-H | O | H | H | H | 4-O |  4-S(O)CH₃ | 2-Cl-5-CH₃ |
| 1-422 | CH₃ | 3-CH₃ | 4-H | O | H | H | H | 4-O | 4-S(O)CH₃ | 2-F-5-CH₃ |

-continued

| | | | | | | | | Ar substituents |
|---|---|---|---|---|---|---|---|---|
| 1-423 | CH₃ | 3-CH₃ | 4-H | O | H | H | H | 4-O | 4-S(O)CH₃ | 2-CH₃-5-Cl |
| 1-424 | CH₃ | 3-CH₃ | 4-H | O | H | H | H | 4-O | 4-S(O)CH₃ | 2-CH₃-5-F |
| 1-425 | CH₃ | 3-CH₃ | 4-H | O | H | H | H | 4-O | 4-S(O)C₂H₅ | 2,5-Cl₂ |
| 1-426 | CH₃ | 3-CH₃ | 4-H | O | H | H | H | 4-O | 4-S(O)C₂H₅ | 2,5-(CH₃)₂ |
| 1-427 | CH₃ | 3-CH₃ | 4-H | O | H | H | H | 4-O | 4-S(O)C₂H₅ | 2-Cl-5-CH₃ |
| 1-428 | CH₃ | 3-CH₃ | 4-H | O | H | H | H | 4-O | 4-S(O)C₂H₅ | 2-CH₃-5-Cl |
| 1-429 | CH₃ | 3-CH₃ | 4-H | O | H | H | H | 4-O | 4-S(O)C₂H₅ | 2-F-5-CH₃ |
| 1-430 | CH₃ | 3-CH₃ | 4-H | O | H | H | H | 4-O | 4-S(O)C₂H₅ | 2-CH₃-5-F |
| 1-431 | CH₃ | 3-CH₃ | 4-H | O | H | H | H | 4-O | | 3,4-(O—CH₂—O)- |

-continued

| No. | | | | | | | | | | |
|---|---|---|---|---|---|---|---|---|---|---|
| 1-432 | $CH_3$ | 3-$CH_3$ | 4-H | O | H | H | H | 4-O | Ph | 3,4-(O—$CF_2$—O)— |
| 1-433 | $CH_3$ | 3-$CH_3$ | 4-H | O | H | H | H | 4-O | Ph | 3,4-(O—$CH_2$—$CH_2$—O)— |
| 1-434 | $CH_3$ | 3-$CH_3$ | 4-H | O | H | H | H | 4-O | Ph | 3,4-(O—$CF_2$—$CF_2$—O)— |
| 1-435 | $CH_3$ | 3-$CH_3$ | 4-H | O | H | H | H | 4-O | Ph | 3,4-($CH_2$—$CH_2$—$CH_2$)— |
| 1-436 | $CH_3$ | 3-$CH_3$ | 4-H | O | H | H | H | 4-O | Ph | 3,4-($CH_2$—$CH_2$—$CH_2$—$CH_2$)— |
| 1-437 | $CH_3$ | 3-$CH_3$ | 4-H | O | H | H | H | 4-O | Ph | 3,4-(O—$CH_2$—$CH_2$)— |
| 1-438 | $CH_3$ | 3-$CH_3$ | 4-H | O | H | H | H | 4-O | Ph | 3,4-($CH_2$—$CH_2$—O)— |
| 1-439 | $CH_3$ | 3-$CH_3$ | 4-H | O | H | H | H | 4-O | Ph | 3,4-($CH_2$—$CH_2$—S)— |
| 1-440 | $CH_3$ | 3-$CH_3$ | 4-H | O | H | H | H | 4-O | Ph | 3,4-($CH_2$—O—$CH_2$)— |

-continued

| No. | | | | | | | | | | Ring | Substituent |
|---|---|---|---|---|---|---|---|---|---|---|---|
| 1-441 | CH₃ | 3-CH₃ | 4-H | O | H | H | H | H | 4-O | phenyl | 3,4-(CH₂—CH(CH₃)—O) |
| 1-442 | CH₃ | 3-CH₃ | 4-H | O | H | H | H | H | 4-O | phenyl | 3,4-(CH₂—CH(CH₃)—S) |
| 1-443 | CH₃ | 3-CH₃ | 4-H | O | H | H | H | H | 4-O | phenyl | 3,4-(CH₂—CH₂—CH(CH₃)—S) |
| 1-444 | CH₃ | 3-CH₃ | 4-H | O | H | H | H | H | 4-O | phenyl | 3,4-(CH₂—C(CH₃)₂—O) |
| 1-445 | CH₃ | 3-CH₃ | 4-H | O | H | H | H | H | 4-O | phenyl | 3,4-(CH₂—C(CH₃)₂—S) |
| 1-446 | CH₃ | 3-CH₃ | 4-H | O | H | H | H | H | 4-O | phenyl | 2-F, 4-Cl |
| 1-447 | CH₃ | 3-CH₃ | 4-H | O | H | H | H | H | 4-O | phenyl | 2-F, 4-F |
| 1-448 | CH₃ | 3-CH₃ | 4-H | O | H | H | H | H | 4-O | phenyl | 2-F, 4-Br |
| 1-449 | CH₃ | 3-CH₃ | 4-H | O | H | H | H | H | 4-O | phenyl | 3-F, 5-F |

-continued

| | | | | | | | | Ar | |
|---|---|---|---|---|---|---|---|---|---|
| 1-450 | $CH_3$ | $3\text{-}CH_3$ | 4-H | O | H | H | H | 4-$CH_3$ | 3,5-$Cl_2$ |
| 1-451 | $CH_3$ | $3\text{-}CH_3$ | 4-H | O | H | H | H | 4-$CH_3$ | 3,5-$Br_2$ |
| 1-452 | $CH_3$ | $3\text{-}CH_3$ | 4-H | O | H | H | H | 4-$C_2H_5$ | 3,5-$Cl_2$ |
| 1-453 | $CH_3$ | $3\text{-}CH_3$ | 4-H | O | H | H | H | 3-F | 4-$CH_3$ |
| 1-454 | $CH_3$ | $3\text{-}CH_3$ | 4-H | O | H | H | H | 3-F | 4-$C_2H_5$ |
| 1-455 | $CH_3$ | $3\text{-}CH_3$ | 4-H | O | H | H | H | 4-Cl | 3,5-$(CH_3)_2$ |
| 1-456 | $CH_3$ | $3\text{-}CH_3$ | 4-H | O | H | H | H | 4-Br | 3,5-$(CH_3)_2$ |
| 1-457 | $CH_3$ | $3\text{-}CH_3$ | 4-H | O | H | H | H | 4-Br | 2,6-$(CH_3)_2$ |
| 1-458 | $CH_3$ | $3\text{-}CH_3$ | 4-H | O | H | H | H | 6-$CH_3$ | 2,4-$Cl_2$ |

-continued

| | | | | | | | | | Ring subst. 1 | Ring subst. 2 |
|---|---|---|---|---|---|---|---|---|---|---|
| 1-459 | CH₃ | 3-CH₃ | 4-H | O | H | H | H | 4-O | 2-Cl | 4-Br-6-CH₆ |
| 1-460 | CH₃ | 3-CH₃ | 4-H | O | H | H | H | 4-O | 3-CH₃ | 4-Cl |
| 1-461 | CH₃ | 3-CH₃ | 4-H | O | H | H | H | 4-O | 3-CH₃ | 4-Br |
| 1-462 | CH₃ | 3-CH₃ | 4-H | O | H | H | H | 4-O | 3-CH₃ | 4-F |
| 1-463 | CH₃ | 3-CH₃ | 4-H | O | H | H | H | 4-O | 3-Cl | 4-CH₃ |
| 1-464 | CH₃ | 3-CH₃ | 4-H | O | H | H | H | 4-O | 3-Cl | 4-C₂H₅ |
| 1-465 | CH₃ | 3-CH₃ | 4-H | O | H | H | H | 4-O | 3-Br | 4-CH₃ |
| 1-466 | CH₃ | 3-CH₃ | 4-H | O | H | H | H | 4-O | 3-Br | 4-C₂H₅ |
| 1-467 | CH₃ | 3-CH₃ | 4-H | O | H | H | H | 4-O | 2-Cl | 4,5-(CH₃)₂ |

-continued

| No. | | | | | | | | | Ph subst. | extra subst. |
|---|---|---|---|---|---|---|---|---|---|---|
| 1-468 | CH$_3$ | 3-CH$_3$ | 4-H | O | H | H | H | 4-O | 4-Br | 3,5-(CH$_3$)$_2$ |
| 1-469 | CH$_3$ | 3-CH$_3$ | 4-H | O | H | H | H | 4-O | 4-Cl | 3,5-(CH$_3$)$_2$ |
| 1-470 | CH$_3$ | 3-CH$_3$ | 4-H | O | H | H | H | 4-O | 4-CH$_3$ | 2,5-Cl$_2$ |
| 1-471 | CH$_3$ | 3-CH$_3$ | 4-H | O | H | H | H | 4-O | 4-C$_2$H$_5$ | 2,5-Cl$_2$ |
| 1-472 | CH$_3$ | 3-CH$_3$ | 4-H | O | H | H | H | 4-O | 3-Br | 4-Br |
| 1-473 | CH$_3$ | 3-CH$_3$ | 4-H | O | H | H | H | 4-O | 3-Br | 5-Br |
| 1-474 | CH$_3$ | 3-CH$_3$ | 4-H | O | H | H | H | 4-O | 2-Br | 3,6-Br$_2$ |
| 1-475 | CH$_3$ | 3-CH$_3$ | 4-H | O | H | H | H | 4-O | 2-Br | 4,6-Br$_2$ |
| 1-476 | CH$_3$ | 3-CH$_3$ | 4-H | O | H | H | H | 4-O | 2-Br | 3,4-Br$_2$ |

-continued

| No. | | | | | | | | | | Ar | |
|---|---|---|---|---|---|---|---|---|---|---|---|
| 1-477 | CH₃ | 3-CH₃ | 4-H | O | H | H | H | H | 4-O | 2-Br | 3,5-Br₂ |
| 1-478 | CH₃ | 3-CH₃ | 4-H | O | H | H | H | H | 4-O | 2-Cl | 3,4-Cl₂ |
| 1-479 | CH₃ | 3-CH₃ | 4-H | O | H | H | H | H | 4-O | 2-Cl | 3,5-Cl₂ |
| 1-480 | CH₃ | 3-CH₃ | 4-H | O | H | H | H | H | 4-O | 2-Cl | 4,5-Cl₂ |
| 1-481 | CH₃ | 3-CH₃ | 4-H | O | H | H | H | H | 4-O | 2-Br | 4,5-Br₂ |
| 1-482 | CH₃ | 3-CH₃ | 4-H | O | H | H | H | H | 4-O | 2-Cl | 4-F |
| 1-483 | CH₃ | 3-CH₃ | 4-H | O | H | H | H | H | 4-O | 3-Cl | 4-F |
| 1-484 | CH₃ | 3-CH₃ | 4-H | O | H | H | H | H | 4-O | 2-F | 3,5,6-F₃ |
| 1-485 | CH₃ | 3-CH₃ | 4-H | O | H | H | H | H | 4-O | 2-Cl | 3,4,5,6-Cl₄ |

-continued

| No. | | | | | | | | | Ph | | |
|---|---|---|---|---|---|---|---|---|---|---|---|
| 1-486 | CH$_3$ | 3-CH$_3$ | 4-H | O | H | H | H | 4-O | Ph | 3-CH$_3$ | 4-Br |
| 1-487 | CH$_3$ | 3-CH$_3$ | 4-H | O | H | H | H | 4-O | Ph | 2-Cl | 5-CH$_3$ |
| 1-488 | CH$_3$ | 3-CH$_3$ | 4-H | O | H | H | H | 4-O | Ph | 2-Cl | 6-CH$_3$ |
| 1-489 | CH$_3$ | 3-CH$_3$ | 4-H | O | H | H | H | 4-O | Ph | 4-CH$_2$CH$_2$OC$_2$H$_5$ | 2,3-(CH$_3$)$_2$ |
| 1-490 | CH$_3$ | 3-CH$_3$ | 4-H | O | H | H | H | 4-O | Ph | 4-n-C$_5$H$_{11}$ | 2-Cl |
| 1-491 | CH$_3$ | 3-CH$_3$ | 4-H | O | H | H | H | 4-O | Ph | 4-CH$_2$CH$_2$OC$_2$H$_5$ | 2-Cl |
| 1-492 | CH$_3$ | 3-CH$_3$ | 4-H | O | H | H | H | 4-O | Ph | | 3,4-(-CH=CH-CH=CH-) |
| 1-493 | CH$_3$ | 3-CH$_3$ | 4-H | O | H | H | H | 4-O | Ph | | 3,4-(-CH=CH-C(Cl)=CH-) |
| 1-494 | CH$_3$ | 3-CH$_3$ | 4-H | O | H | H | H | 4-O | Ph | 3-CH$_3$ | 4-OCF$_2$CF$_2$H |

-continued

| No. | | | | | | | | | Ring | Subst. 1 | Subst. 2 |
|---|---|---|---|---|---|---|---|---|---|---|---|
| 1-495 | CH₃ | 3-CH₃ | 4-H | O | H | H | H | 4-O | phenyl | 3-CH₃ | 4-OCH₂CF₃ |
| 1-496 | CH₃ | 3-CH₃ | 4-H | O | H | H | H | 4-O | phenyl | 3-CH₃ | 4-OCH₂CH₂F |
| 1-497 | CH₃ | 3-CH₃ | 4-H | O | H | H | H | 4-O | phenyl | 3-Cl | 4-OCF₃ |
| 1-498 | CH₃ | 3-CH₃ | 4-H | O | H | H | H | 4-O | phenyl | 3-Cl | 4-OCH₂CF₃ |
| 1-499 | CH₃ | 3-CH₃ | 4-H | O | H | H | H | 4-O | cyclohexyl | 3-C₂H₅ | H |
| 1-500 | CH₃ | 3-CH₃ | 4-H | O | H | H | H | 4-O | cyclohexyl | 4-tert-C₄H₉ | H |
| 1-501 | CH₃ | 3-CH₃ | 4-H | O | H | H | H | 4-O | cyclohexyl | 3-CH₃ | H |
| 1-502 | CH₃ | 3-CH₃ | 4-H | O | H | H | H | 4-O | cyclohexyl | 2-OCH₃ | H |
| 1-503 | CH₃ | 3-CH₃ | 4-H | O | H | H | H | 4-O | cyclohexyl | 2-OC₂H₅ | H |

-continued

| | | | | | | | | | | |
|---|---|---|---|---|---|---|---|---|---|---|
| 1-504 | CH₃ | 3-CH₃ | 4-H | O | H | H | H | 4-O | ⬡(H) | 2-O-n-C₃H₇ | H |
| 1-505 | CH₃ | 3-CH₃ | 4-H | O | H | H | H | 4-O | ⬡(H) | 2-OCF₂CF₂H | /H |
| 1-506 | CH₃ | 3-CH₃ | 4-H | O | H | H | H | 4-O | ⬡(N) | 4-CF₃ | H |
| 1-507 | CH₃ | 3-CH₃ | 4-H | O | H | H | H | 4-O | ⬡(N) | 2-Cl | 4-CF₃ |
| 1-508 | CH₃ | 3-CH₃ | 4-H | O | H | H | H | 3-O | ⬡ | 4-SCH₃ | H |
| 1-509 | CH₃ | 3-CH₃ | 4-H | O | H | H | H | 3-O | ⬡ | 4-SC₂H₅ | H |
| 1-510 | CH₃ | 3-CH₃ | 4-H | O | H | H | H | 3-O | ⬡ | 4-SCH₃ | 3-Cl |
| 1-511 | CH₃ | 3-CH₃ | 4-H | O | H | H | H | 3-O | ⬡ | 4-SCH₃ | 2,5-Cl₂ |
| 1-512 | CH₃ | 3-CH₃ | 4-H | O | H | H | 2-F | 4-O | ⬡ | 4-SCH₃ | H |

-continued

| No. | | | | | | | | | Ar | |
|---|---|---|---|---|---|---|---|---|---|---|
| 1-513 | CH$_3$ | 3-CH$_3$ | 4-H | O | H | H | 2-F | 4-O | 4-SC$_2$H$_5$ | H |
| 1-514 | CH$_3$ | 3-CH$_3$ | 4-H | O | H | H | 2-F | 4-O | 4-SCF$_2$H | H |
| 1-515 | CH$_3$ | 3-CH$_3$ | 4-H | O | H | H | 2-F | 4-O | 4-SCH$_3$ | 3-Cl |
| 1-516 | CH$_3$ | 3-CH$_3$ | 4-H | O | H | H | 2,5-F$_2$ | 4-O | 4-SCH$_3$ | H |
| 1-517 | CH$_3$ | 3-CH$_3$ | 4-H | O | H | H | 3-CH$_3$ | 4-O | 4-SCH$_3$ | H |
| 1-518 | CH$_3$ | 3-CH$_3$ | 4-H | O | H | CH$_3$ | H | 4-O | 4-SCH$_3$ | H |
| 1-519 | CH$_3$ | 3-CH$_3$ | 4-H | O | H | C$_2$H$_5$ | H | 4-O | 4-SCH$_3$ | H |
| 1-520 | CH$_3$ | 3-CH$_3$ | 4-H | O | H | i-C$_3$H$_7$ | H | 4-O | 4-SCH$_3$ | H |
| 1-521 | CH$_3$ | 3-CH$_3$ | 4-H | O | H | CN | H | 4-O | 4-SC$_2$H$_5$ | H |

| No. | | | | | | | | | |
|---|---|---|---|---|---|---|---|---|---|
| 1-522 | CH₃ | 3-CH₃ | 4-H | O | H | CH₃ | 4-O | 4-SCH₃-C₆H₄ | H |
| 1-523 | CH₃ | 3-CH₃ | 4-H | O | CH₃ | H | 4-O | 4-SCH₃-C₆H₄ | H |
| 1-524 | CH₃ | 3-CH₃ | 4-H | O | C₂H₅ | H | 4-O | 4-SCH₃-C₆H₄ | H |
| 1-525 | CH₃ | 3-CH₃ | 4-H | S | H | H | 4-O | 4-SCH₃-C₆H₄ | H |
| 1-526 | CH₃ | 3-CH₃ | 4-H | S | H | H | 4-O | 4-SCH₃-C₆H₄ | 3-Cl |
| 1-527 | CH₃ | 3-C₂H₅ | 4-H | O | H | H | 4-O | 4-SCH₃-C₆H₄ | H |
| 1-528 | CH₃ | 3-C₂H₅ | 4-H | O | H | H | 4-O | 4-SCH₃-C₆H₄ | 3-Cl |
| 1-529 | CH₃ | 3-C₂H₅ | 4-H | O | H | H | 4-O | 4-SCH₃-C₆H₄ | 2,5-Cl₂ |
| 1-530 | CH₃ | 3-C₂H₅ | 4-H | O | H | H | 4-O | 4-SCH₃-C₆H₄ | 3-Br |

-continued
| No. | | | | | | | | | | | |
|---|---|---|---|---|---|---|---|---|---|---|---|
| 1-531 | CH₃ | 3-i-C₃H₇ | 4-H | O | H | H | H | 4-O |  4-SCH₃ | | H |
| 1-532 | CH₃ | △ 3- | 4-H | O | H | H | H | 4-O | 4-SCH₃ | | H |
| 1-533 | CH₃ | ⬡ 3- | H | O | H | H | H | 4-O | 4-SCH₃ | | H |
| 1-534 | CH₃ | ⬡ 3- | H | O | H | H | H | 4-O | 4-OCF₂CF₂H | | H |
| 1-535 | C₂H₅ | 3-CH₃ | H | O | H | H | H | 4-O | 4-SCH₃ | | H |
| 1-536 | i-C₃H₇ | 3-CH₃ | H | O | H | H | H | 4-O | 4-SCH₃ | | H |
| 1-537 | △ | 3-CH₃ | H | O | H | H | H | 4-O | 4-SCH₃ | | H |
| 1-538 | CF₃CH₂ | 3-CH₃ | H | O | H | H | H | 4-O | 4-SCH₃ | | H |
| 1-539 | CH₃ | 3-CH₃ | 4-Cl | O | H | H | H | 4-O | 4-CH₃ | | H |

| No. | | | | | | | | | |
|---|---|---|---|---|---|---|---|---|---|
| 1-540 | CH₃ | 3-CH₃ | 4-CH₃ | H | H | O | H | 4-O-C₆H₄(4-CH₃) | H |
| 1-541 | CH₃ | 3-CH₃ | 4-Cl | H | H | O | H | 4-O-C₆H₄(4-C₂H₅) | H |
| 1-542 | CH₃ | 3-CH₃ | 4-CH₃ | H | H | O | H | 4-O-C₆H₄(4-C₂H₅) | H |
| 1-543 | CH₃ | 3-CH₃ | 4-Cl | H | H | O | H | 4-O-C₆H₄(4-OC₂H₅) | H |
| 1-544 | CH₃ | 3-CH₃ | 4-CH₃ | H | H | O | H | 4-O-C₆H₄(4-OC₂H₅) | H |
| 1-545 | CH₃ | 3-CH₃ | 4-Cl | H | H | O | H | 4-O-C₆H₄(4-SCH₃) | H |
| 1-546 | CH₃ | 3-CH₃ | 4-CH₃ | H | H | O | H | 4-O-C₆H₄(4-SCH₃) | H |
| 1-547 | CH₃ | 3-CH₃ | 4-Cl | H | H | O | H | 4-O-C₆H₄(4-OCF₂CF₂H) | H |
| 1-548 | CH₃ | 3-CH₃ | 4-Cl | H | H | O | H | 4-O-C₆H₄(4-SCF₂CF₂H) | H |

-continued

| No. | | | | | | | | | | Ar | |
|---|---|---|---|---|---|---|---|---|---|---|---|
| 1-549 | CH₃ | 3-CH₃ | 4-Cl | O | H | H | H | H | 4-O | 4-NHC₂H₅ | H |
| 1-550 | CH₃ | 3-CH₃ | 4-Cl | O | H | H | H | H | 4-O | 4-n-C₃H₇ | H |
| 1-551 | CH₃ | 3-CH₃ | 4-Cl | O | H | H | H | H | 4-O | 4-n-C₄H₉ | H |
| 1-552 | CH₃ | 3-CH₃ | 4-Cl | O | H | H | H | H | 4-O | 4-OCH₃ | H |
| 1-553 | CH₃ | 3-CH₃ | 4-Cl | O | H | H | H | H | 4-O | 4-O-n-C₃H₇ | H |
| 1-554 | CH₃ | 3-CH₃ | 4-Br | O | H | H | H | H | 4-O | 4-OCF₂CF₂H | H |
| 1-555 | CH₃ | 3-CH₃ | 4-Br | O | H | H | H | H | 4-O | 4-SCH₃ | H |
| 1-556 | CH₃ | 3-CH₃ | 4-C₂H₅ | O | H | H | H | H | 4-O | 4-OCF₂CF₂H | H |
| 1-557 | CH₃ | 3-CH₃ | 4-Cl | O | H | H | H | H | 4-O | 4-i-C₃H₇ | H |

| No. | | | | | | | | | | |
|---|---|---|---|---|---|---|---|---|---|---|
| 1-558 | CH₃ | 3-CH₃ | 4-Cl | O | H | H | H | 4-O | 4-cyclopropyl-phenyl | H |
| 1-559 | CH₃ | 3-CH₃ | 4-Cl | O | H | H | H | 4-O | 3-CH₃-phenyl | H |
| 1-560 | CH₃ | 3-CH₃ | 4-Cl | O | H | H | H | 4-O | 3-C₂H₅-phenyl | H |
| 1-561 | CH₃ | 3-CH₃ | 4-Cl | O | H | H | H | 4-O | 4-n-C₆H₁₃-phenyl | H |
| 1-562 | CH₃ | 3-CH₃ | 4-Cl | O | H | H | H | 4-O | 4-O-n-C₆H₁₃-phenyl | H |
| 1-563 | CH₃ | 3-CH₃ | 4-Cl | O | H | H | H | 4-O | 3-OCH₃-phenyl | H |
| 1-564 | CH₃ | 3-CH₃ | 4-Cl | O | H | H | H | 4-O | 3-OC₂H₅-phenyl | H |
| 1-565 | CH₃ | 3-CH₃ | H | O | H | H | H | 4-S | 4-OCH₃-phenyl | H |
| 1-566 | CH₃ | 3-CH₃ | 4-Cl | O | H | H | H | 4-O | 2-CH₃-phenyl | H |

| | | | | | | | | | | |
|---|---|---|---|---|---|---|---|---|---|---|
| 1-567 | CH₃ | 3-CH₃ | 4-Cl | O | H | H | H | 4-O | 4-CF₃-C₆H₄ | H |
| 1-568 | CH₃ | 3-CH₃ | 4-Cl | O | H | H | H | 4-S | 4-OCH₃-C₆H₄ | H |
| 1-569 | CH₃ | 3-CH₃ | H | O | H | H | H | 4-S | 3-OCH₃-C₆H₄ | H |
| 1-570 | CH₃ | 3-CH₃ | 4-Cl | O | H | H | H | 4-S | 3-OC₂H₅-C₆H₄ | H |
| 1-571 | CH₃ | 3-CH₃ | 4-Cl | O | H | H | H | 4-O | 4-CH₂—CH=CH₂-C₆H₄ | H |
| 1-572 | CH₃ | 3-CH₃ | 4-Cl | O | H | H | H | 4-O | 4-O—CH₂—CH=CH₂-C₆H₄ | H |
| 1-573 | CH₃ | 3-CH₃ | 4-Cl | O | H | H | H | 4-O | 4-O—CH₂—C≡CH-C₆H₄ | H |
| 1-574 | CH₃ | 3-CH₃ | 4-Cl | O | H | H | H | 4-O | 4-S—CH₂—CH=CH₂-C₆H₄ | H |
| 1-575 | CH₃ | 3-CH₃ | 4-Cl | O | H | H | H | 4-O | 4-S(O)CH₃-C₆H₄ | H |

-continued

| No. | | | | | | | | | | |
|---|---|---|---|---|---|---|---|---|---|---|
| 1-576 | CH₃ | 3-CH₃ | 4-Cl | O | H | H | H | 4-O | 4-S(O)₂CH₃ | H |
| 1-577 | CH₃ | 3-CH₃ | 4-Cl | O | H | H | H | 4-O | 4-OSO₂CF₃ | H |
| 1-578 | CH₃ | 3-CH₃ | 4-Cl | O | H | H | H | 4-O | 4-N(CH₃)₂ | H |
| 1-579 | CH₃ | 3-CH₃ | 4-Cl | O | H | H | H | 4-O | 3-Cl | 4-CH₃ |
| 1-580 | CH₃ | 3-CH₃ | 4-Cl | O | H | H | H | 4-O | 3,4-(O—CH₂—O) | |
| 1-581 | CH₃ | 3-CH₃ | 4-Cl | O | H | H | H | 4-O | 3,4-(O—CF₂—O) | |
| 1-582 | CH₃ | 3-CH₃ | 4-Cl | O | H | H | H | 4-O | 3-Cl | 4-C₂H₅ |
| 1-583 | CH₃ | 3-CH₃ | 4-Cl | O | H | H | H | 4-O | 3-Cl | 4-OC₂H₅ |
| 1-584 | CH₃ | 3-CH₃ | 4-Cl | O | H | H | H | 4-CH₂ | 4-OC₂H₅ | H |

| No. | | | | | | | | | | |
|---|---|---|---|---|---|---|---|---|---|---|
| 1-585 | $CH_3$ | 3-$CH_3$ | 4-Cl | O | H | H | H | 4-NH | Ph, 4-$OC_2H_5$ | H |
| 1-586 | $CH_3$ | 3-$CH_3$ | 4-Cl | O | H | H | H | 4-$NCH_3$ | Ph, 4-$OC_2H_5$ | H |
| 1-587 | $CH_3$ | 3-$CH_3$ | 4-Cl | O | H | H | H | 4-$SO_2$ | Ph, 4-$OC_2H_5$ | H |
| 1-588 | $CH_3$ | 3-$CH_3$ | 4-Cl | O | $CH_3$ | H | H | 4-O | Ph, 4-$OCF_2CF_2H$ | H |
| 1-589 | $CH_3$ | 4-H | 5-$CH_3$ | O | H | H | H | 4-O | Ph, 4-$OC_2H_5$ | H |
| 1-590 | $CH_3$ | 4-H | 5-$CH_3$ | O | H | H | H | 4-O | Ph, 4-$CH_3$ | H |
| 1-591 | $CH_3$ | 4-Cl | 5-$CH_3$ | O | H | H | H | 4-O | Ph, 4-$OCF_2CF_2H$ | H |
| 1-592 | $CH_3$ | 4-H | 5-$CH_3$ | O | H | H | H | 4-O | Ph, 3-F | 5-F |
| 1-593 | $CH_3$ | 3-$CH_3$ | 4-Cl | O | H | H | H | 4-O | Ph, 4-$C_2H_5$ | H |

-continued

| | | | | | | | | | | |
|---|---|---|---|---|---|---|---|---|---|---|
| 1-594 | CH$_3$ | 4-H | 5-CH$_3$ | O | H | H | H | 4-O | Ar-4-n-C$_3$H$_7$ | H |
| 1-595 | CH$_3$ | 4-H | 5-CH$_3$ | O | H | H | H | 4-O | Ar-4-n-C$_4$H$_9$ | H |
| 1-596 | CH$_3$ | 4-H | 5-CH$_3$ | O | H | H | H | 4-O | Ar-4-SCH$_3$ | H |
| 1-597 | CH$_3$ | 4-H | 5-CH$_3$ | O | H | H | H | 4-O | Ar-4-SC$_2$H$_5$ | H |
| 1-598 | CH$_3$ | 4-H | 5-CH$_3$ | O | H | H | H | 4-O | Ar-4-SCF$_2$CCl$_2$H | H |
| 1-599 | CH$_3$ | 4-H | 5-CH$_3$ | O | H | H | H | 4-O | Ar-4-SCH$_2$CF$_3$ | H |
| 1-600 | CH$_3$ | 4-H | 5-CH$_3$ | O | H | H | H | 4-O | Ar-4-SCF$_2$CF$_2$H | H |

| No. | | | | | | | | | | |
|---|---|---|---|---|---|---|---|---|---|---|
| 1-601 | CH₃ | 4-H | 5-CH₃ | O | H | H | H | 4-O | ⌬ | 4-S-n-C₃H₇ | H |
| 1-602 | CH₃ | 4-H | 5-CH₃ | O | H | H | H | 4-O | ⌬ | 4-SC₂H₅ | 3-Cl |
| 1-603 | CH₃ | 4-H | 5-CH₃ | O | H | H | H | 4-O | ⌬ | 4-SCH₃ | 2,5-Cl₂ |
| 1-604 | CH₃ | 4-H | 5-CH₃ | O | H | H | H | 4-O | ⌬ | 4-SCH₃ | 2-CH₃-5-Cl |
| 1-605 | CH₃ | 4-H | 5-CH₃ | O | H | H | CH₃ | 4-O | ⌬ | 4-SC₂H₅ | 3-Br |
| 1-606 | CH₃ | 4-H | 5-CH₃ | O | H | H | H | 4-O | ⌬ | 4-SC₂H₅ | 3-F |
| 1-607 | CH₃ | 3-CH₃ | 4-Cl | O | H | CH₃ | H | 4-O | ⌬ | 4-OC₂H₅ | H |
| 1-608 | CH₃ | 3-CH₃ | 4-Cl | O | H | C₂H₅ | H | 4-O | ⌬ | 4-OC₂H₅ | H |
| 1-609 | CH₃ | 3-CH₃ | 4-Cl | O | H | CH₃ | CH₃ | 4-O | ⌬ | 4-OC₂H₅ | H |

| No. | | | | | | | | | Ring | |
|---|---|---|---|---|---|---|---|---|---|---|
| 1-610 | CH₃ | 3-CH₃ | 4-Cl | O | H | H | H | 2-F | 4-O | phenyl, 4-OC₂H₅ | H |
| 1-611 | CH₃ | 3-CH₃ | 4-Cl | O | H | H | 3-Cl | 4-O | phenyl, 4-OC₂H₅ | H |
| 1-612 | CH₃ | 3-CH₃ | 4-Cl | O | H | H | 3-CH₃ | 4-O | phenyl, 4-OC₂H₅ | H |
| 1-613 | CH₃ | 3-CH₃ | 4-Cl | O | H | H | H | 4-O | phenyl, 3-Cl | H |
| 1-614 | CH₃ | 3-CH₃ | 4-Cl | O | H | H | H | 4-O | cyclohexyl, 4-CH₃ | H |
| 1-615 | CH₃ | 3-CH₃ | 4-Cl | O | H | H | H | 4-O | cyclohexyl, 4-tert-C₄H₉ | H |
| 1-616 | CH₃ | 3-CH₃ | 4-Cl | O | H | H | H | 4-O | pyridyl, 4-CF₃ | H |
| 1-617 | CH₃ | 3-CH₃ | 4-Cl | O | H | H | H | 4-O | pyridyl, 2-Cl | 4-CF₃ |
| 1-618 | CH₃ | 3-CH₃ | 4-Cl | O | H | H | H | 4-O | phenyl | 3,4-(CH=CH—CH=CH—) |

-continued

| No. | | | | | | | | | Ar | |
|---|---|---|---|---|---|---|---|---|---|---|
| 1-619 | CH₃ | 3-CH₃ | 4-Cl | O | H | H | H | 4-O | (phenyl) | 3,4-(CH₂-C(CH₃)₂-O) |
| 1-620 | CH₃ | 3-CH₃ | 4-Cl | O | H | H | H | 4-O | 4-OCF₂CCl₂H (phenyl) | H |
| 1-621 | CH₃ | 3-CH₃ | 4-Cl | O | H | H | H | 4-O | 4-N(C₂H₅)₂ (phenyl) | H |
| 1-622 | CH₃ | 3-CH₃ | 4-Cl | O | H | H | H | 4-O | 4-CH₂CH₂OCH₃ (phenyl) | H |
| 1-623 | CH₃ | 3-CH₃ | 4-Cl | O | H | H | H | 4-O | 4-NHC(O)CH₃ (phenyl) | H |
| 1-624 | CH₃ | 3-CH₃ | 4-Cl | O | H | H | H | 4-O | 4-NHC(O)C₂H₅ (phenyl) | H |
| 1-625 | CH₃ | 3-CH₃ | 4-Cl | O | H | H | H | 4-O | 4-N=CHC₂H₅ (phenyl) | H |
| 1-626 | CH₃ | 3-CH₃ | 4-Cl | O | H | H | H | 4-O | 4-N=CH—N(CH₃)₂ (phenyl) | H |
| 1-627 | CH₃ | 3-CH₃ | 4-Cl | O | H | H | H | 4-O | 4-N=C(CH₃)—N(CH₃)₂ (phenyl) | H |

-continued

| No. | | | | | | | | | | Ring | Substituent | |
|---|---|---|---|---|---|---|---|---|---|---|---|---|
| 1-628 | CH$_3$ | 3-CH$_3$ | 4-Cl | O | H | H | H | 4-O | ⌬ | 4-N=C(CH$_3$)—NHCH$_3$ | H |
| 1-629 | CH$_3$ | 3-CH$_3$ | 4-Cl | O | H | H | H | 4-O | ⌬ | 4-NHSO$_2$CH$_3$ | H |
| 1-630 | CH$_3$ | 3-CH$_3$ | 4-Cl | O | H | H | H | 4-O | ⌬ | 4-NHSO$_2$C$_2$H$_5$ | H |
| 1-631 | CH$_3$ | 3-CH$_3$ | 5-OCH$_3$ | O | H | H | H | 4-O | ⌬ | 4-OC$_2$H$_5$ | H |
| 1-632 | CH$_3$ | 3-CH$_3$ | 5-O-i-C$_3$H$_7$ | O | H | H | H | 4-O | ⌬ | 4-OC$_2$H$_5$ | H |
| 1-633 | CH$_3$ | 3-CH$_3$ | 5-OCH$_2$CF$_3$ | O | H | H | H | 4-O | ⌬ | 4-OC$_2$H$_5$ | H |
| 1-634 | CH$_3$ | 3-CH$_3$ | 5-O-⌬ | O | H | H | H | 4-O | ⌬ | 4-OC$_2$H$_5$ | H |
| 1-635 | CH$_3$ | 3-CH$_3$ | 4-Cl | O | H | H | H | 4-O | ⌬(H) | 2-OC$_2$H$_5$ | H |
| 1-636 | CH$_3$ | 3-CH$_3$ | 4-Cl | O | H | H | H | 4-O | ⌬(H) | 2-O-n-C$_3$H$_7$ | H |

| | | | | | | | -continued | | |
|---|---|---|---|---|---|---|---|---|---|
| 1-637 | CH₃ | 3-OCH₃ | 4-Br | O | H | H | H | 4-O | 4-SC₂H₅ | H |
| 1-638 | CH₃ | 3-OCH₃ | 4-H | O | H | H | H | 4-O | 4-SC₂H₅ | H |
| 1-639 | CH₃ | 3-OC₂H₅ | 4-H | O | H | H | H | 4-O | 4-SC₂H₅ | H |
| 1-640 | CH₃ | 3-O-i-C₃H₇ | 4-H | O | H | H | H | 4-O | 4-SC₂H₅ | H |
| 1-641 | CH₃ | 3-OCH₃ | 4-H | O | H | H | H | 4-O | 3-Cl | 4-SCH₃ |
| 1-642 | CH₃ | 3-OCH₃ | 4-H | O | H | H | H | 4-O | 4-SCH₃ | 2,5-Cl₂ |
| 1-643 | CH₃ | 3-OCH₃ | 4-CH₃ | O | H | H | H | 4-O | 4-SCH₃ | H |
| 1-644 | CH₃ | 3-OCH₃ | 4-H | O | H | H | H | 4-O | 4-OC₂H₅ | H |
| 1-645 | CH₃ | 3-CH₃ | 5-CH₃ | O | H | H | H | 4-O | 4-OC₂H₅ | H |

-continued
| No. | | | | | | | | | | | |
|---|---|---|---|---|---|---|---|---|---|---|---|
| 1-646 | CH$_3$ | 3-C$_2$H$_5$ | 4-Cl | O | H | H | H | 4-O |  | 4-OC$_2$H$_5$ | H |
| 1-647 | CH$_3$ | 3-i-C$_3$H$_7$ | 4-Cl | O | H | H | H | 4-O |  | 4-OC$_2$H$_5$ | H |
| 1-648 | CH$_3$ | ▷ | 4-Cl | O | H | H | H | 4-O | | 4-OC$_2$H$_5$ | H |
| 1-649 | CH$_3$ | 3-<phenyl> | 4-Cl | O | H | H | H | 4-O | | 4-OC$_2$H$_5$ | H |
| 1-650 | CH$_3$ | 3-<3-F-phenyl> | 4-Cl | O | H | H | H | 4-O | | 4-OC$_2$H$_5$ | H |
| 1-651 | CH$_3$ | 3-<4-F-phenyl> | 4-Cl | O | H | H | H | 4-O |  | 4-OC$_2$H$_5$ | H |
| 1-652 | C$_2$H$_5$ | 3-CH$_3$ | 4-Cl | O | H | H | H | 4-O |  | 4-OC$_2$H$_5$ | H |
| 1-653 | i-C$_3$H$_7$ | 3-CH$_3$ | 4-Cl | O | H | H | H | 4-O | | 4-OC$_2$H$_5$ | H |

-continued

| | | | | | | | | | |
|---|---|---|---|---|---|---|---|---|---|
| 1-654 | ▽ | 3-CH₃ | 4-Cl | O | H | H | H | 4-O | Ph(4-OC₂H₅) | H |
| 1-655 | CF₂CH₂ | 3-CH₃ | 4-Cl | O | H | H | H | 4-O | Ph(4-OC₂H₅) | H |
| 1-656 | CH₃ | 3-CH₃ | 4-Cl | O | H | H | H | 4-O | Ph(4-OCF₂H) | H |
| 1-657 | CH₃ | 3-CH₃ | 4-Br | O | H | H | H | 4-O | Ph(4-SCH₃) | H |
| 1-658 | CH₃ | 3-CH₃ | 4-Cl | O | H | H | H | 4-S | Ph(3-CH₃) | H |
| 1-659 | CH₃ | 3-CH₃ | 4-H | O | H | H | H | 4-S | Ph(3-CH₃) | H |
| 1-660 | CH₃ | 3-CH₃ | 5-CH₃ | O | H | H | H | 4-O | Ph(4-OCF₂CF₂H) | H |
| 1-661 | CH₃ | 3-CH₃ | 5-CH₃ | O | H | H | H | 4-O | Ph(4-SCH₃) | H |
| 1-662 | CH₃ | 3-CH₃ | 4-Cl | O | H | H | H | 4-S | Ph(3-OCH₃) | H |

| No. | | | | | | | | | | |
|---|---|---|---|---|---|---|---|---|---|---|
| 1-663 | CH₃ | 3-CH₃ | 5-Cl | O | H | H | H | 4-O | 4-OCF₂CF₂H | H |
| 1-664 | CH₃ | 3-CH₃ | 4-Cl | O | H | H | H | 4-O | 4-SCH₃ | H |
| 1-665 | CH₃ | 4-H | 5-CH₃ | O | H | H | H | 4-O | 4-OCF₂CF₂H | H |
| 1-666 | CH₃ | 4-Br | 5-CH₃ | O | H | H | H | 4-O | 4-OCF₂CF₂H | H |
| 1-667 | CH₃ | 4-Cl | 5-CH₃ | O | H | H | H | 4-O | 4-OCF₂CF₂H | H |
| 1-668 | CH₃ | 3-CH₃ | 4-CH₃ | O | H | H | H | 4-O | 4-OCF₂CF₂H | H |
| 1-669 | CH₃ | 3-CH₃ | 4-Cl | O | H | H | H | 4-O | 2-CH₃ | 3-CH₃ |
| 1-670 | CH₃ | 3-CH₃ | 4-Cl | O | H | H | H | 4-O | 3-CH₃ | 4-CH₃ |
| 1-671 | CH₃ | 3-CH₃ | 4-Cl | O | H | H | H | 4-O | 3-CH₃ | 5-CH₃ |

-continued

| No. | | | | | | | | | Ar | |
|---|---|---|---|---|---|---|---|---|---|---|
| 1-672 | CH₃ | 3-CH₃ | 4-Cl | O | H | H | H | 4-O | phenyl | 2-CH₃, 6-CH₃ |
| 1-673 | CH₃ | 3-CH₃ | 4-Cl | O | H | H | H | 4-O | phenyl | 3,4-(CH₂―CH₂―CH₂) |
| 1-674 | CH₃ | 3-CH₃ | 4-Cl | O | H | H | H | 4-O | phenyl | 2-CH₃, 4,5-(CH₃)₂ |
| 1-675 | CH₃ | 3-CH₃ | 4-Cl | O | H | H | H | 4-O | phenyl | 2-CH₃, 3,6-(CH₃)₂ |
| 1-676 | CH₃ | 3-CH₃ | 4-Cl | O | H | H | H | 4-O | phenyl | 2-CH₃, 4,6-(CH₃)₂ |
| 1-677 | CH₃ | 3-CH₃ | 4-Cl | O | H | H | H | 4-O | phenyl | 2-CH₃, 3,5-(CH₃)₂ |
| 1-678 | CH₃ | 3-CH₃ | 4-Cl | O | H | H | H | 4-O | phenyl | 2-CH₃, 4-CH₃ |
| 1-679 | CH₃ | 3-CH₃ | 4-Cl | O | H | H | H | 4-O | phenyl | 2-CH₃, 5-CH₃ |
| 1-680 | CH₃ | 3-CH₃ | 5-CH₃ | O | H | H | H | 4-O | phenyl | 3-Cl, 4-CH₃ |

| No. | | | | | | | | | | Aryl substituents |
|---|---|---|---|---|---|---|---|---|---|---|
| 1-681 | CH₃ | 3-CH₃ | 4-Cl | O | H | H | H | 4-O | 3-Cl | 4-Cl |
| 1-682 | CH₃ | 3-CH₃ | 4-Cl | O | H | H | H | 4-O | 3-Cl | 5-Cl |
| 1-683 | CH₃ | 3-CH₃ | 4-Cl | O | H | H | H | 4-O | 2-Cl | 5-Cl |
| 1-684 | CH₃ | 3-CH₃ | 4-Cl | O | H | H | H | 4-O | 2-Cl | 4-Cl |
| 1-685 | CH₃ | 3-CH₃ | 4-Cl | O | H | H | H | 4-O | 3-Cl | 4-F |
| 1-686 | CH₃ | 3-CH₃ | 4-Cl | O | H | H | H | 4-O | 2-Cl | 4-Br |
| 1-687 | CH₃ | 3-CH₃ | 4-Cl | O | H | H | H | 4-O | 3-F | 4-CH₃ |
| 1-688 | CH₃ | 3-CH₃ | 4-Cl | O | H | H | H | 4-O | 3-Br | 4-CH₃ |
| 1-689 | CH₃ | 3-CH₃ | 4-Cl | O | H | H | H | 4-O | 3-CH₃ | 4-Cl |

| No. | R | R' | R'' | X | Y | Y' | Y'' | Z | Ar substituents |
|---|---|---|---|---|---|---|---|---|---|
| 1-690 | CH₃ | 3-CH₃ | 4-Cl | O | H | H | H | 4-O | 2-CH₃, 4-Cl |
| 1-691 | CH₃ | 3-CH₃ | 4-Cl | O | H | H | H | 4-O | 2-Cl, 5-CH₃ |
| 1-692 | CH₃ | 3-CH₃ | 4-Cl | O | H | H | H | 4-O | 4-Cl, 3,5-(CH₃)₂ |
| 1-693 | CH₃ | 3-CH₃ | 4-Cl | O | H | H | H | 4-O | 2-Cl, 4,5-(CH₃)₂ |
| 1-694 | CH₃ | 3-CH₃ | 4-Cl | O | H | H | H | 4-O | 2-CH₃, 4-Cl |
| 1-695 | CH₃ | 3-CH₃ | 4-Cl | O | H | H | H | 4-O | 3,4-(O—CH₂—O) |
| 1-696 | CH₃ | 3-CH₃ | 4-Cl | O | H | H | H | 4-O | 4-SC₂H₅, H |
| 1-697 | CH₃ | 3-CH₃ | 4-Cl | O | H | H | H | 4-O | 3-SCH₃, H |
| 1-698 | CH₃ | 3-CH₃ | 4-Cl | O | H | H | H | 4-O | 3-SC₂H₅, H |

-continued

| No. | | | | | | | | | Ar1 | Ar2 |
|---|---|---|---|---|---|---|---|---|---|---|
| 1-699 | CH3 | 3-CH3 | 4-Cl | O | H | H | H | 4-O | 2-CH3 | 4-SCH3 |
| 1-700 | CH3 | 3-CH3 | 4-Cl | O | H | H | H | 4-O | 2-CH3 | 3-CH3, 4-SCH3 |
| 1-701 | CH3 | 3-CH3 | 4-Cl | O | H | H | H | 4-O | 3-C2H5 | 4-SCH3 |
| 1-702 | CH3 | 3-CH3 | 4-Cl | O | H | H | H | 4-O | 4-SCH3 | 2,6-(CH3)2 |
| 1-703 | CH3 | 3-CH3 | 4-Cl | O | H | H | H | 4-O | 3-CH3 | 4-SCH3 |
| 1-704 | CH3 | 3-CH3 | 4-Cl | O | H | H | H | 4-O | 3-F | 4-SCH3 |
| 1-705 | CH3 | 3-CH3 | 4-Cl | O | H | H | H | 4-O | 4-SCH3 | 2,3,5-(CH3)3 |
| 1-706 | CH3 | 3-CH3 | 4-Cl | O | H | H | H | 4-O | 4-SCH3 | 3,5-(CH3)2 |
| 1-707 | CH3 | 3-CH3 | 4-Cl | O | H | H | H | 4-O | 3-OCH3 | 4-SCH3 |

| No. | | | | | | | | | Ar1 | Ar2 |
|---|---|---|---|---|---|---|---|---|---|---|
| 1-708 | CH₃ | 3-CH₃ | 4-Cl | O | H | H | H | 4-O | 3-Cl | 4-SCH₃ |
| 1-709 | CH₃ | 3-CH₃ | 4-Cl | O | H | H | H | 4-O | 4-SCH₃ | 2,5-(CH₃)₂ |
| 1-710 | CH₃ | 4-H | 5-CH₃ | O | H | H | H | 4-O | 3-Cl | 4-CH₃ |
| 1-711 | CH₃ | 3-CH₃ | 4-Cl | O | H | H | H | 4-O | 3-Br | 4-SCH₃ |
| 1-712 | CH₃ | 3-CH₃ | 4-Cl | O | H | H | H | 4-O | 4-SCF₂H | H |
| 1-713 | CH₃ | 3-CH₃ | 4-Cl | O | H | H | H | 4-O | 4-SCF₃ | H |
| 1-714 | CH₃ | 3-CH₃ | 4-Cl | O | H | H | H | 4-O | 4-OCF₃ | H |
| 1-715 | CH₃ | 3-CH₃ | 4-Cl | O | H | H | H | 4-O | 2-Cl | 4-CF₃ |
| 1-716 | CH₃ | 3-CH₃ | 4-Cl | O | H | H | H | 4-O | 4-F | H |

-continued

| No. | | | | | | | | | Ar | |
|---|---|---|---|---|---|---|---|---|---|---|
| I-717 | CH$_3$ | 3-CH$_3$ | 4-Cl | O | H | H | H | 4-O | 4-Cl-C$_6$H$_4$ | H |
| I-718 | CH$_3$ | 3-CH$_3$ | 4-Cl | O | H | H | H | 4-O | 4-Br-C$_6$H$_4$ | H |
| I-719 | CH$_3$ | 3-CH$_3$ | 4-Cl | O | H | H | H | 4-O | 3-Cl-C$_6$H$_4$ | H |
| I-720 | CH$_3$ | 3-CH$_3$ | 4-Cl | O | H | H | H | 4-O | 2-Cl-C$_6$H$_4$ | H |
| I-721 | CH$_3$ | 3-CH$_3$ | 4-Cl | O | H | H | H | 4-O | 4-S-n-C$_3$H$_7$-C$_6$H$_4$ | H |
| I-722 | CH$_3$ | 3-CH$_3$ | 4-Cl | O | H | H | H | 4-O | 4-S-n-C$_4$H$_9$-C$_6$H$_4$ | H |
| I-723 | CH$_3$ | 3-CH$_3$ | 4-Cl | O | H | H | H | 4-O | 4-S-i-C$_3$H$_7$-C$_6$H$_4$ | H |
| I-724 | CH$_3$ | 3-CH$_3$ | 4-Cl | O | H | H | H | 4-O | 2-Br-C$_6$H$_4$ | 4-CH$_3$ |
| I-725 | CH$_3$ | 3-CH$_3$ | 4-Cl | O | H | H | H | 4-O | 2-F-C$_6$H$_4$ | 4-F |

-continued

| No. | | | | | | | | | | Ar | |
|---|---|---|---|---|---|---|---|---|---|---|---|
| 1-726 | CH₃ | 3-CH₃ | 4-Cl | O | H | H | H | 4-O | H | Ph(3-Cl) | 5-OCH₃ |
| 1-727 | CH₃ | 3-CH₃ | 4-Cl | O | H | H | H | 4-O | H | Ph | 3,4-(CH=CH—CH=CH) |
| 1-728 | CH₃ | 3-CH₃ | 4-Cl | O | H | H | H | 4-O | H | Ph(3-OCH₃) | 5-OCH₃ |
| 1-729 | CH₃ | 3-CH₃ | 4-Cl | O | H | H | H | 4-O | H | Ph(2-CH₃) | 4-Cl |
| 1-730 | CH₃ | 3-CH₃ | 4-Br | O | H | H | H | 4-O | H | Ph(4-SC₂H₅) | H |
| 1-731 | CH₃ | 3-CH₃ | 4-Br | O | H | H | H | 4-O | H | Ph(3-Cl) | 4-CH₃ |
| 1-732 | CH₃ | 3-CH₃ | 4-CH₃ | O | H | H | H | 4-O | H | Ph(4-SC₂H₅) | H |
| 1-733 | CH₃ | 4-H | 5-CH₃ | O | H | H | H | 4-O | H | Ph(4-SCF₂H) | H |
| 1-734 | CH₃ | 4-H | 5-CH₃ | O | H | H | H | 4-O | H | Ph(4-SCF₃) | H |

| No. | | | | | | | | | | Ar |
|---|---|---|---|---|---|---|---|---|---|---|
| 1-735 | CH₃ | 4-H | 5-CH₃ | O | H | H | H | 4-O | H | 4-OCH₃ phenyl |
| 1-736 | CH₃ | 3-CH₃ | 4-Cl | O | H | H | H | 4-O | H | 4-SCF₂H phenyl |
| 1-737 | CH₃ | 3-CH₃ | 4-Cl | O | H | H | H | 4-O | H | 4-SCF₃ phenyl |
| 1-738 | CH₃ | 3-CH₃ | 4-Cl | O | H | H | H | 4-O | H | 4-OCF₃ phenyl |
| 1-739 | CH₃ | 3-CH₃ | 4-H | O | H | H | H | 4-O | H | 4-SCF₂H phenyl |
| 1-740 | CH₃ | 3-CH₃ | 4-Cl | O | H | H | H | 4-O | H | 4-OCF₃ phenyl |
| 1-741 | CH₃ | 3-CH₃ | 4-Cl | O | CH₃ | H | H | 4-O | H | 4-SCH₃ phenyl |
| 1-742 | CH₃ | 4-CH₃ | 5-CH₃ | O | H | H | H | 4-O | H | 4-SCH₃ phenyl |
| 1-743 | CH₃ | 3-CH₃ | 4-Cl | O | H | H | H | 4-O | H | 4-C₂H₅ cyclohexyl |

| No. | | | | | | | | Ring | Ring sub. | |
|---|---|---|---|---|---|---|---|---|---|---|
| 1-744 | CH₃ | 3-CH₃ | 4-H | O | H | H | H | (cyclohexane, H) | 4-CH₃ | H |
| 1-745 | CH₃ | 3-CH₃ | 4-Cl | O | H | H | H | (cyclohexane, H) | 4-C₂H₅ | H |
| 1-746 | CH₃ | 4-H | 5-CH₃ | O | H | H | H | (cyclohexane, H) | 4-CH₃ | H |
| 1-747 | CH₃ | 4-H | 5-CH₃ | O | H | H | H | (cyclohexane, H) | 4-C₂H₅ | H |
| 1-748 | CH₃ | 4-Cl | 5-CH₃ | O | H | H | H | (phenyl) | 4-SCH₃ | H |
| 1-749 | CH₃ | 4-Br | 5-CH₃ | O | H | H | H | (phenyl) | 4-SCH₃ | H |
| 1-750 | CH₃ | 4-H | 5-CH₃ | O | H | H | H | (phenyl) | 3-Cl | 4-CH₃ |
| 1-751 | CH₃ | 3-CH₃ | 4-Cl | O | H | CN | H | (phenyl) | 4-SCH₃ | H |
| 1-752 | CH₃ | 4-H | 5-CH₃ | O | H | CN | H | (phenyl) | 4-SCH₃ | H |

| No. | | | | | | | | | |
|---|---|---|---|---|---|---|---|---|---|
| 1-753 | CH₃ | 3-CH₃ | 4-H | O | H | H | H | 4-O—(C₆H₄-4-SCH₃) | H |
| 1-754 | CH₃ | 4-Cl | 5-CH₃ | O | H | CN | H | 4-O—(C₆H₄-4-SCH₃) | H |
| 1-755 | CH₃ | 3-OCH₃ | 4-H | O | H | CN | H | 4-O—(C₆H₄-4-SCH₃) | H |
| 1-756 | CH₃ | 4-H | 5-OCH₃ | O | H | H | H | 4-O—(C₆H₄-4-SCH₃) | H |
| 1-757 | CH₃ | 3-OC₂H₅ | 4-H | O | H | H | H | 4-O—(C₆H₄-4-SCH₃) | H |
| 1-758 | CH₃ | 4-H | 5-OC₂H₅ | O | H | H | H | 4-O—(C₆H₄-4-SCH₃) | H |
| 1-759 | CH₃ | 3-O-i-C₃H₇ | 4-H | O | H | H | H | 4-O—(C₆H₄-4-SCH₃) | H |
| 1-760 | CH₃ | 4-H | 5-O-i-C₃H₇ | O | H | H | H | 4-O—(C₆H₄-4-SCH₃) | H |
| 1-761 | CH₃ | 3-CH₃ | 4-Cl | O | H | H | H | 4-O—(C₆H₄-2-Cl) | 3-Cl |

-continued

| No. | | | | | | | | | Ar | |
|---|---|---|---|---|---|---|---|---|---|---|
| 1-762 | CH₃ | 4-Cl | 5-OCH₃ | O | H | H | H | 4-O | Ph(4-SCH₃) | H |
| 1-763 | CH₃ | 3-OCH₃ | 4-Br | O | H | H | H | 4-O | Ph(4-SCH₃) | H |
| 1-764 | CH₃ | 3-CH₃ | 4-Cl | O | H | H | H | 4-O | Ph(4-Cl) | 3-C₂H₅ |
| 1-765 | CH₃ | 4-CH₃ | 5-OCH₃ | O | H | H | H | 4-O | Ph(4-SCH₃) | H |
| 1-766 | CH₃ | 3-OCH₃ | 4-CH₃ | O | H | H | H | 4-O | Ph(4-SCH₃) | H |
| 1-767 | CH₃ | 3-CH₃ | 4-Cl | O | H | H | H | 4-O | Ph(3-OCH₃) | 4-OCH₃ |
| 1-768 | CH₃ | 3-CH₃ | 4-Cl | O | H | H | H | 4-O | Ph(3-OCH₃) | 4-OC₂H₅ |
| 1-769 | CH₃ | 3-OCH₃ | 4-H | O | H | H | H | 4-O | Ph(3-Cl) | 4-CH₃ |
| 1-770 | CH₃ | 3-CH₃ | 4-Cl | O | H | CH₃ | H | 4-O | Ph(4-SCH₃) | H |

| No. | | | | | | | | | Ar | |
|---|---|---|---|---|---|---|---|---|---|---|
| 1-771 | CH₃ | 3-CH₃ | 4-Br | O | H | CH₃ | H | H | 4-O | 4-SCH₃-C₆H₄ | H |
| 1-772 | CH₃ | 4-H | 4-CH₃ | O | H | CH₃ | H | H | 4-O | 4-SCH₃-C₆H₄ | H |
| 1-773 | CH₃ | 3-OCH₃ | 4-H | O | H | CH₃ | H | H | 4-O | 4-SCH₃-C₆H₄ | H |
| 1-774 | CH₃ | 3-OCH₃ | 4-Br | O | H | CH₃ | H | H | 4-O | 4-SCH₃-C₆H₄ | H |
| 1-775 | CH₃ | 3-CH₃ | 4-Br | O | H | C₂H₅ | H | H | 4-O | 4-SCH₃-C₆H₄ | H |
| 1-776 | CH₃ | 3-OCH₃ | 4-H | O | H | C₂H₅ | H | H | 4-O | 4-SCH₃-C₆H₄ | H |
| 1-777 | CH₃ | 3-OCH₃ | 4-Br | O | H | C₂H₅ | H | H | 4-O | 4-SCH₃-C₆H₄ | H |
| 1-778 | CH₃ | 4-H | 5-CH₃ | O | H | C₂H₅ | H | H | 4-O | 4-SCH₃-C₆H₄ | H |
| 1-779 | CH₃ | 3-CH₃ | 4-Cl | O | H | C₂H₅ | H | H | 4-O | 4-SCH₃-C₆H₄ | H |

-continued

| No. | | | | | | | | | | Phenyl substituents |
|---|---|---|---|---|---|---|---|---|---|---|
| 1-780 | $CH_3$ | 3-$CH_3$ | 4-Br | O | H | H | H | 4-O | H | 3-Cl, 4-$SCH_3$ |
| 1-781 | $CH_3$ | 4-H | 5-$CH_3$ | O | H | H | H | 4-O | H | 3-Cl, 4-$SCH_3$ |
| 1-782 | $CH_3$ | 3-$CH_3$ | 4-Cl | O | H | H | H | 4-O | H | 3-Cl, 4-$SC_2H_5$ |
| 1-783 | $CH_3$ | 3-$OCH_3$ | 4-H | O | H | H | H | 4-O | H | 3-Cl, 4-$SC_2H_5$ |
| 1-784 | $CH_3$ | 3-$C_2H_5$ | 4-Cl | O | H | H | H | 4-O | H | 4-$SCH_3$, H |
| 1-785 | $CH_3$ | 3-$C_2H_5$ | 4-Cl | S | H | H | H | 4-O | H | 4-$SCH_3$, H |
| 1-786 | $CH_3$ | 3-$C_2H_5$ | 4-Cl | O | H | $CH_3$ | H | 4-O | H | 4-$SC_2H_5$, H |
| 1-787 | $CH_3$ | 3-$C_2H_5$ | 4-Cl | O | H | CN | H | 4-O | H | 4-$SC_2H_5$, H |
| 1-788 | $CH_3$ | 3-$C_2H_5$ | 4-Cl | O | H | H | H | 4-O | H | 3-Cl, 4-$SCH_3$ |

| No. | | | | | | | | | | |
|---|---|---|---|---|---|---|---|---|---|---|
| 1-789 | $CH_3$ | 3-$C_2H_5$ | 4-Cl | O | H | i-$C_3H_7$ | H | 4-O | [phenyl] | 4-$SC_2H_5$ | H |
| 1-790 | $CH_3$ | 3-$CH_3$ | 4-Cl | O | H | H | H | 4-O | [phenyl] | 4-$SCH_3$ | 2,5-$Cl_2$ |

TABLE 2
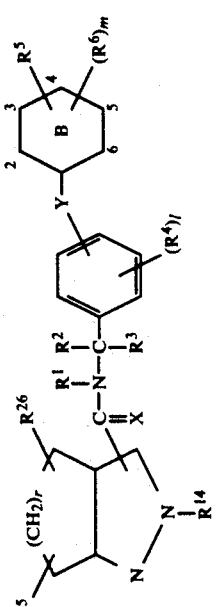
| Compound No. | R¹⁴ | (structure) | X | R¹ | R² | R³ | (R⁴)$_l$ | Y | B | R⁵ | (R⁶)$_m$ |
|---|---|---|---|---|---|---|---|---|---|---|---|
| 2-1 | CH₃ | cyclopentyl | O | H | H | H | H | 4-O | phenyl | 4-CH₃ | H |
| 2-2 | CH₃ | cyclopentyl | O | H | H | H | H | 4-O | phenyl | 2-CH₃ | H |
| 2-3 | CH₃ | cyclopentyl | O | H | H | H | H | 4-O | phenyl | 3-CH₃ | H |
| 2-4 | CH₃ | cyclopentyl | O | H | H | H | H | 4-O | phenyl | 2-CH₃ | 6-CH₃ |
| 2-5 | CH₃ | cyclopentyl | O | H | H | H | H | 4-O | phenyl | 2-CH₃ | 3,5-(CH₃)₂ |
| 2-6 | CH₃ | cyclopentyl | O | H | H | H | H | 4-O | phenyl | 2-CH₃ | 4,6-(CH₃)₂ |

-continued

| No. | | | | | | | | | | | |
|---|---|---|---|---|---|---|---|---|---|---|---|
| 2-7 | CH₃ | (cyclopentyl) | O | H | H | H | H | 4-O | (phenyl) | 2-CH₃ | 3,6-(CH₃)₂ |
| 2-8 | CH₃ | (cyclopentyl) | O | H | H | H | H | 4-O | (phenyl) | 3-CH₃ | 4-CH₃ |
| 2-9 | CH₃ | (cyclopentyl) | O | H | H | H | H | 4-O | (phenyl) | 3-CH₃ | 5-CH₃ |
| 2-10 | CH₃ | (cyclopentyl) | O | H | H | H | H | 4-O | (phenyl) | 2-CH₃ | 3-CH₃ |
| 2-11 | CH₃ | (cyclopentyl) | O | H | H | H | H | 4-O | (phenyl) | 3-F | 4-CH₃ |
| 2-12 | CH₃ | (cyclopentyl) | O | H | H | H | H | 4-O | (phenyl) | 2-F | H |
| 2-13 | CH₃ | (cyclopentyl) | O | H | H | H | H | 4-O | (phenyl) | 3-n-C₃H₇ | H |
| 2-14 | CH₃ | (cyclopentyl) | O | H | H | H | H | 4-O | (phenyl) | 4-n-C₃H₇ | H |
| 2-15 | CH₃ | (cyclopentyl) | O | H | H | H | H | 4-O | (phenyl) | 4-n-C₄H₉ | H |

-continued

| | 2-16 | 2-17 | 2-18 | 2-19 | 2-20 | 2-21 | 2-22 | 2-23 | 2-24 |
|---|---|---|---|---|---|---|---|---|---|
| | CH₃ | CH₃ | CH₃ | CH₃ | CH₃ | CH₃ | CH₃ | CH₃ | CH₃ |
| (cyclopentyl) | ⬠ | ⬠ | ⬠ | ⬠ | ⬠ | ⬠ | ⬠ | ⬠ | ⬠ |
| | O | O | O | O | O | O | O | O | O |
| | H | H | H | H | H | H | H | H | H |
| | H | H | H | H | H | H | H | H | H |
| | H | H | H | H | H | H | H | H | H |
| | H | H | H | H | H | H | H | H | H |
| | 4-O | 4-O | 4-O | 4-O | 4-O | 4-O | 4-O | 4-O | 4-O |
| (phenyl) | ⬡ | ⬡ | ⬡ | ⬡ | ⬡ | ⬡ | ⬡ | ⬡ | ⬡ |
| | 4-i-C₃H₇ | 4-n-C₆H₁₃ | 4-tert-C₄H₉ | 2-Cl | 3-Cl | 2-Cl | 3-Cl | 3-Cl | 3-Cl |
| | H | H | H | H | H | 4-Cl | H | 4-Cl | 5-Cl |

-continued

| No. | | | | | | | | | | |
|---|---|---|---|---|---|---|---|---|---|---|
| 2-25 | CH₃ | (cyclopentyl) | O | H | H | H | H | 4-O | (phenyl) 2-Cl | 4-Cl |
| 2-26 | CH₃ | (cyclopentyl) | O | H | H | H | H | 4-O | (phenyl) 2-Cl | 3-Cl |
| 2-27 | CH₃ | (cyclopentyl) | O | H | H | H | H | 4-O | (phenyl) 2-Cl | 5-Cl |
| 2-28 | CH₃ | (cyclopentyl) | O | H | H | H | H | 4-O | (phenyl) 2-Cl | 3,6-Cl₂ |
| 2-29 | CH₃ | (cyclopentyl) | O | H | H | H | H | 4-O | (phenyl) 2-Cl | 4,6-Cl₂ |
| 2-30 | CH₃ | (cyclopentyl) | O | H | H | H | H | 4-O | (phenyl) 3-CF₃ | H |
| 2-31 | CH₃ | (cyclopentyl) | O | H | H | H | H | 4-O | (phenyl) 4-OCF₃ | H |
| 2-32 | CH₃ | (cyclopentyl) | O | H | H | H | H | 4-O | (phenyl) 4-OCF₂CF₂H | H |
| 2-33 | CH₃ | (cyclopentyl) | O | H | H | H | H | 4-O | (phenyl) 3-CF₃ | 5-Cl |

| | | | | | | | |
|---|---|---|---|---|---|---|---|
| 2-34 | CH₃ | [cyclopentyl] | O | H | H | H | H | 4-O | [phenyl]-4-OCF₂H | H |
| 2-35 | CH₃ | [cyclopentyl] | O | H | H | H | H | 4-O | [phenyl]-4-SCF₃ | H |
| 2-36 | CH₃ | [cyclopentyl] | O | H | H | H | H | 4-O | [phenyl]-4-SCF₂H | H |
| 2-37 | CH₃ | [cyclopentyl] | O | H | H | H | H | 4-O | [phenyl]-4-SCF₂CF₂H | H |
| 2-38 | CH₃ | [cyclopentyl] | O | H | H | H | H | 4-O | [phenyl]-4-SCF₃ | H |
| 2-39 | CH₃ | [cyclopentyl] | O | H | H | H | H | 4-O | [phenyl]-4-SC₂H₅ | H |
| 2-40 | CH₃ | [cyclopentyl] | O | H | H | H | H | 4-O | [phenyl]-4-SOCH₃ | H |
| 2-41 | CH₃ | [cyclopentyl] | O | H | H | H | H | 4-O | [phenyl]-4-SO₂CH₃ | H |
| 2-42 | CH₃ | [cyclopentyl] | O | H | H | H | H | 4-O | [phenyl]-4-S-n-C₃H₇ | H |

-continued
| No. | | | | | | | | | | |
|---|---|---|---|---|---|---|---|---|---|---|
| 2-43 | CH$_3$ |  | O | H | H | H | 4-O |  | 4-S-n-C$_4$H$_7$ | H |
| 2-44 | CH$_3$ |  | O | H | H | H | 4-O |  | 4-S-i-C$_3$H$_7$ | H |
| 2-45 | CH$_3$ |  | O | H | H | H | 4-O |  | 3-Cl | 4-SCH$_3$ |
| 2-46 | CH$_3$ |  | O | H | H | H | 4-O |  | 2-CH$_3$ | 4-SCH$_3$ |
| 2-47 | CH$_3$ |  | O | H | H | H | 4-O |  | 4-SCH$_3$ | 2,3-(CH$_3$)$_2$ |
| 2-48 | CH$_3$ |  | O | H | H | H | 4-O |  | 3-C$_2$H$_5$ | 4-SCH$_3$ |
| 2-49 | CH$_3$ |  | O | H | H | H | 4-O |  | 3-CH$_3$ | 4-SCH$_3$ |
| 2-50 | CH$_3$ | | O | H | H | H | 4-O | | 4-SCH$_3$ | 2-CH$_3$-3-SCH$_3$-5-CH$_3$ |
| 2-51 | CH$_3$ | | O | H | H | H | 4-O | | 3-CH$_3$ | 4-SCH$_3$-5-CH$_3$ |

-continued

| | | | | | | | | |
|---|---|---|---|---|---|---|---|---|
| 2-52 | CH₃ | (cyclopentyl) | O | H | H | H | 4-O | (phenyl) 2-CH₃ | 4-SCH₃-5-CH₃ |
| 2-53 | CH₃ | (cyclopentyl) | O | H | H | H | 4-O | (phenyl) 3-F | 4-SCH₃ |
| 2-54 | CH₃ | (cyclopentyl) | O | H | H | H | 4-O | (phenyl) 3-Cl | 4-SC₂H₅ |
| 2-55 | CH₃ | (cyclopentyl) | O | H | H | H | 4-O | (phenyl) 3-Br | 4-SCH₃ |
| 2-56 | CH₃ | (cyclopentyl) | O | H | H | H | 4-O | (phenyl) 3-OCH₃ | 4-SCH₃ |
| 2-57 | CH₃ | (cyclopentyl) | O | H | H | H | 4-O | (phenyl) 3-CH₃ | 4-SOCH₃ |
| 2-58 | CH₃ | (cyclopentyl) | O | H | H | H | 4-O | (phenyl) 3-CH₃ | 4-SO₂CH₃ |
| 2-59 | CH₃ | (cyclopentyl) | O | H | H | H | 4-O | (phenyl) 2-Cl | 4-SCH₃-5-Cl |
| 2-60 | CH₃ | (cyclopentyl) | O | H | H | H | 4-O | (phenyl) 3,4-(O—CH₂—O-) | |

-continued

| No. | | | | | | | | | | | |
|---|---|---|---|---|---|---|---|---|---|---|---|
| 2-61 | CH₃ | cyclopentyl | O | H | H | H | H | 4-O | phenyl | 3,4-(O—CF₂—O) | 4-OCH₃ |
| 2-62 | CH₃ | cyclopentyl | O | H | H | H | H | 4-O | phenyl | 3-OCH₃ | H |
| 2-63 | CH₃ | cyclopentyl | O | H | H | H | H | 4-O | phenyl | 3-SCH₃ | H |
| 2-64 | CH₃ | cyclopentyl | O | H | H | H | H | 4-O | phenyl | 4-NHC₂H₅ | H |
| 2-65 | CH₃ | cyclopentyl | O | H | H | H | H | 4-O | phenyl | 4-cyclopropyl | H |
| 2-66 | CH₃ | cyclopentyl | O | H | H | H | H | 4-O | phenyl | 4-CH₂—CH=CH₂ | H |
| 2-67 | CH₃ | cyclopentyl | O | H | H | H | H | 4-O | phenyl | 4-S—CH₂—CH=CH₂ | H |
| 2-68 | CH₃ | cyclopentyl | O | H | H | H | H | 4-O | phenyl | 4-OSO₂CF₃ | H |
| 2-69 | CH₃ | cyclopentyl | O | H | H | H | H | 4-O | phenyl | 4-N(CH₃)₂ | H |

-continued
| | | | | | | | | | |
|---|---|---|---|---|---|---|---|---|---|
| 2-70 | CH₃ |  | O | H | H | H | H | 4-O |  4-NHCCH₃ (C=O) | H |
| 2-71 | CH₃ |  | O | H | H | H | H | 4-O |  3,4-(CH=CH—CH=CH–) | — |
| 2-72 | CH₃ |  | O | H | H | H | H | 4-O |  3-F | 5-F |
| 2-73 | CH₃ |  | O | H | H | H | H | 4-O |  3-Cl | 4-CH₃-5-Cl |
| 2-74 | CH₃ |  | O | H | H | H | H | 4-O | 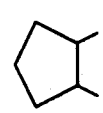 3-Br | 4-CH₃-5-Br |
| 2-75 | CH₃ | 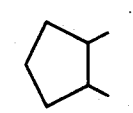 | O | H | H | H | H | 4-O |  3-C₂H₅ | H |
| 2-76 | CH₃ | 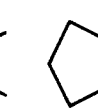 | O | H | H | H | H | 4-O | 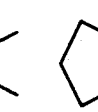 3-CH₃ | 4-Cl-5-CH₃ |
| 2-77 | CH₃ | 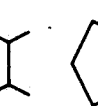 | O | H | H | H | H | 4-O | 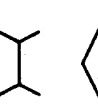 2-CH₃ | 4-Br-6-CH₃ |
| 2-78 | CH₃ | 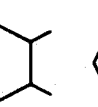 | O | H | H | H | H | 4-O | 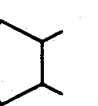 2-Cl | 4-Cl-6-CH₃ |

| No. | R | | | | | | Ar | | Sub |
|---|---|---|---|---|---|---|---|---|---|
| 2-79 | CH₃ (cyclopentyl) | O | H | H | H | 4-O | phenyl | 3-CH₃ | 4-Cl |
| 2-80 | CH₃ (cyclopentyl) | O | H | H | H | 4-O | phenyl | 2-Cl | 4,5-(CH₃)₂ |
| 2-81 | CH₃ (cyclopentyl) | O | H | H | H | 4-O | phenyl | 3-CH₃ | 4-Br-5-CH₃ |
| 2-82 | CH₃ (cyclopentyl) | O | H | H | H | 4-O | phenyl | 3-Br | 4-Br |
| 2-83 | CH₃ (cyclopentyl) | O | H | H | H | 4-O | phenyl | 3-Br | 5-Br |
| 2-84 | CH₃ (cyclopentyl) | O | H | H | H | 4-O | phenyl | 2-Br | 3,6-Br₂ |
| 2-85 | CH₃ (cyclopentyl) | O | H | H | H | 4-O | phenyl | 2-Br | 4,6-Br₂ |
| 2-86 | CH₃ (cyclopentyl) | O | H | H | H | 4-O | phenyl | 2-Br | 3,4-Br₂ |
| 2-87 | CH₃ (cyclopentyl) | O | H | H | H | 4-O | phenyl | 2-Br | 3,5-Br₂ |

-continued

| | | | | | | | | |
|---|---|---|---|---|---|---|---|---|
| 2-88 | 2-89 | 2-90 | 2-91 | 2-92 | 2-93 | 2-94 | 2-95 | 2-96 |
| CH$_3$ | CH$_3$ | CH$_3$ | CH$_3$ | CH$_3$ | CH$_3$ | CH$_3$ | CH$_3$ | CH$_3$ |
| cyclopentyl | cyclopentyl | cyclopentyl | cyclopentyl | cyclopentyl | cyclopentyl | cyclopentyl | cyclopentyl | cyclopentyl |
| O | O | O | O | O | O | O | O | O |
| H | H | H | H | H | H | H | H | H |
| H | H | H | H | H | H | H | H | H |
| H | H | H | H | H | H | H | H | H |
| H | H | H | H | H | H | H | H | H |
| 4-O | 4-O | 4-O | 4-O | 4-O | 4-O | 4-O | 4-O | 4-O |
| phenyl (4-C$_2$H$_5$) | phenyl (4-F) | phenyl (4-I) | phenyl (3-Cl) | phenyl (2-Cl) | phenyl (3-CH$_3$) | phenyl (2-CH$_3$) | phenyl (2-Cl) | phenyl (2-Cl) |
| H | H | H | 4-F | 3,4,5,6-Cl$_4$ | 4-Br | 4-Cl | 5-CH$_3$ | 6-CH$_3$ |

-continued

| | | | | | | | |
|---|---|---|---|---|---|---|---|
| 2-97 | CH₃ | (cyclopentyl) | O | H | H | H | 4-O | (phenyl) 2-Br | 4-CH₃ |
| 2-98 | CH₃ | (cyclopentyl) | O | H | H | H | 4-O | (phenyl) 3-Cl | 4-CH₃ |
| 2-99 | CH₃ | (cyclopentyl) | O | H | H | H | 4-O | (phenyl) 3-Br | 4-CH₃ |
| 2-100 | CH₃ | (cyclopentyl) | O | H | H | H | 4-O | (phenyl) 3-Cl | 4-C₂H₅ |
| 2-101 | CH₃ | (cyclopentyl) | O | H | H | H | 4-O | (phenyl) 3,4-(CH₂—C(CH₃)₂—O—) | |
| 2-102 | CH₃ | (cyclopentyl) | O | H | H | H | 4-O | (phenyl) 4-CH₂CH₂OCH₃ | H |
| 2-103 | CH₃ | (cyclopentyl) | O | H | H | H | 4-O | (phenyl) 4-N(C₂H₅)₂ | H |
| 2-104 | CH₃ | (cyclopentyl) | O | H | H | H | 4-O | (phenyl) 4-N=CHC₂H₅ | H |
| 2-105 | CH₃ | (cyclopentyl) | O | H | H | H | 4-O | (phenyl) 4-N=CH—N(CH₃)₂ | H |

-continued

| No. | | | | | | | | | | |
|---|---|---|---|---|---|---|---|---|---|---|
| 2-106 | CH₃ | cyclopentane | O | H | H | H | H | 4-O | 4-N=C(CH₃)-N(CH₃)₂-phenyl | H |
| 2-107 | CH₃ | cyclopentane | O | H | H | H | H | 4-O | 4-N=C(CH₃)-NHCH₃-phenyl | H |
| 2-108 | CH₃ | cyclopentane | O | H | H | H | H | 4-O | 3-Br-phenyl | 4-C₂H₅ |
| 2-109 | CH₃ | cyclopentane | O | H | H | H | H | 4-O | 2-Br-phenyl | 4-CH₃-6-Br |
| 2-110 | CH₃ | cyclopentane | O | H | H | H | H | 4-O | 2-OCH₃-phenyl | H |
| 2-111 | CH₃ | cyclopentane | O | H | H | H | H | 4-O | 3-OCH₃-phenyl | H |
| 2-112 | CH₃ | cyclopentane | O | H | H | H | H | 4-O | 4-OCH₃-phenyl | H |
| 2-113 | CH₃ | cyclopentane | O | H | H | H | H | 4-O | 4-OC₂H₅-phenyl | H |
| 2-114 | CH₃ | cyclopentane | O | H | H | H | H | 4-O | 4-O-n-C₃H₇-phenyl | H |

| No. | | | | | | | | | | | |
|---|---|---|---|---|---|---|---|---|---|---|---|
| 2-115 | CH₃ | cyclopentyl | O | H | H | H | H | 4-O | Ph | 3-OCH₃ | H |
| 2-116 | CH₃ | cyclopentyl | O | H | H | H | H | 4-O | Ph | 4-O-n-C₆H₁₃ | H |
| 2-117 | CH₃ | cyclopentyl | O | H | H | H | H | 4-O | Ph | 4-O—CH₂—CH=CH₂ | H |
| 2-118 | CH₃ | cyclopentyl | O | H | H | H | H | 4-O | Ph | 4-O—CH₂—C≡CH | H |
| 2-119 | CH₃ | cyclopentyl | O | H | H | H | H | 4-O | cyclohexyl | 2-OC₂H₅ | H |
| 2-120 | CH₃ | cyclopentyl | O | H | H | H | H | 4-O | Ph | 3-OCH₃ | 5-OCH₃ |
| 2-121 | CH₃ | cyclopentyl | O | H | H | H | H | 4-O | Ph | 3-Cl | 4-OCH₃ |
| 2-122 | CH₃ | cyclopentyl | O | H | H | H | H | 4-O | Ph | 3-OCH₃ | 4,5-(OCH₃)₂ |
| 2-123 | CH₃ | cyclopentyl | O | H | H | H | H | 4-O | Ph | 2-Cl | 5-OCH₃ |

| | | | | | | | | Phenyl substituent | |
|---|---|---|---|---|---|---|---|---|---|
| 2-124 | CH₃ | ⬠ | O | H | H | H | 4-O | ⬡ | 2-CF₃ | H |
| 2-125 | CH₃ | ⬠ | O | H | H | H | 4-O | ⬡ | 3-CF₃ | H |
| 2-126 | CH₃ | ⬠ | O | H | H | H | 4-O | ⬡ | 4-CF₃ | H |
| 2-127 | CH₃ | ⬠ | O | H | H | H | 4-O | ⬡ | 2-Cl | 4-CF₃ |
| 2-128 | CH₃ | ⬠ | O | H | H | H | 4-O | ⬡ | 2-Cl | 3,4-Cl₂ |
| 2-129 | CH₃ | ⬠ | O | H | H | H | 4-O | ⬡ | 2-Cl | 3,5-Cl₂ |
| 2-130 | CH₃ | ⬠ | O | H | H | H | 4-O | ⬡ | 2-Br | H |
| 2-131 | CH₃ | ⬠ | O | H | H | H | 4-O | ⬡ | 3-Br | H |
| 2-132 | CH₃ | ⬠ | O | H | H | H | 4-O | ⬡ | 4-Br | H |

-continued

| No. | | | | | | | | | | | |
|---|---|---|---|---|---|---|---|---|---|---|---|
| 2-133 | CH₃ | cyclopentyl | O | H | H | H | H | 4-O | phenyl, 2-Br | 4-Br |
| 2-134 | CH₃ | cyclopentyl | O | H | H | H | H | 4-O | phenyl, 2-Br | 3-Br |
| 2-135 | CH₃ | cyclopentyl | O | H | H | H | H | 4-O | phenyl, 2-Br | 5-Br |
| 2-136 | CH₃ | cyclopentyl | O | H | H | H | H | 4-O | phenyl, 4-NHSO₂CH₃ | H |
| 2-137 | CH₃ | cyclopentyl | O | H | H | H | H | 4-O | phenyl, 4-NHSO₂C₂H₅ | H |
| 2-138 | CH₃ | cyclopentyl | O | H | H | H | H | 4-O | phenyl, 2,3-(CH₂—CH₂—CH₂—CH₂) | |
| 2-139 | CH₃ | cyclopentyl | O | H | H | H | H | 4-O | cyclohexyl, 4-CH₃ | H |
| 2-140 | CH₃ | cyclopentyl | O | H | H | H | H | 4-O | cyclohexyl, 4-tert-C₄H₉ | H |
| 2-141 | CH₃ | cyclopentyl | O | H | H | H | H | 4-O | pyridyl, 4-CF₃ | H |

| No. | Ring A | R₁ | X | R₂ | R₃ | R₄ | R₅ | Y | Ring B | Sub |
|---|---|---|---|---|---|---|---|---|---|---|
| 2-142 | cyclopentyl | CH₃ | O | H | H | H | H | 4-O | pyridyl | 5-CF₃, H |
| 2-143 | cyclopentyl | CH₃ | O | H | H | H | H | 4-O | pyridyl | 4-CF₃, 6-Cl |
| 2-144 | cyclopentyl | CH₃ | O | H | H | H | H | 3-O | phenyl | 4-SCH₃, H |
| 2-145 | cyclopentyl | CH₃ | O | H | H | H | H | 4-S | phenyl | 4-SCH₃, H |
| 2-146 | cyclopentyl | CH₃ | O | CH₃ | H | H | H | 4-O | phenyl | 3-Cl, 4-SCH₃ |
| 2-147 | cyclopentyl | CH₃ | O | CH₃ | H | H | H | 4-O | phenyl | 3-Cl, 4-CH₃ |
| 2-148 | cyclopentyl | CH₃ | O | C₂H₅ | H | H | H | 4-O | phenyl | 2-Cl, 4-SCH₃-5-Cl |
| 2-149 | cyclopentyl | CH₃ | O | C₂H₅ | H | H | H | 4-O | phenyl | 4-SCH₃, H |
| 2-150 | cyclopentyl | CH₃ | O | H | H | H | 2-CH₃ | 4-O | phenyl | 4-SCH₃, H |

| No. | Cyclopentyl | | | | | | | Phenyl sub | |
|---|---|---|---|---|---|---|---|---|---|
| 2-151 |  | CH₃ | O | H | H | H | 2-F,3-F | 4-O | 3-Br | 4-CH₃ |
| 2-152 |  | CH₃ | O | H | CN | H | H | 4-O | 4-SCF₃ | H |
| 2-153 |  | CH₃ | O | H | CH₃ | H | H | 4-O | 3-Cl | 4-SCH₃ |
| 2-154 |  | CH₃ | O | H | C₂H₅ | H | H | 4-O | 3-F | 4-SCH₃ |
| 2-155 |  | CH₃ | O | H | CH₃ | H | H | 4-O | 3-Br | 4-SCH₃ |
| 2-156 |  | C₂H₅ | O | H | CH₃ | CH₃ | H | 4-O | 4-SCF₂H | H |
| 2-157 |  | CH₃ | O | H | H | H | H | 4-O | 4-CH₃ | H |
| 2-158 |  | CH₃ | O | H | H | H | H | 4-O | 4-OC₂H₅ | H |
| 2-159 |  | CH₃ | O | H | H | H | H | 4-O | 4-S-n-C₄H₉ | H |

| 2-160 | 2-161 | 2-162 | 2-163 | 2-164 | 2-165 | 2-166 | 2-167 | 2-168 |
|---|---|---|---|---|---|---|---|---|
| CH₃ | CH₃ | CH₃ | CH₃ | CH₃ | CH₃ | CH₃ | CH₃ | CH₃ |
|  |  |  |  |  |  |  |  |  |
| O | O | O | O | O | O | O | O | O |
| H | H | H | H | H | H | H | H | H |
| H | H | H | H | H | H | H | H | H |
| H | H | H | H | H | H | H | H | H |
| 4-O | 4-O | 4-O | 4-O | 4-O | 4-O | 4-O | 4-O | 4-O |
|  |  |  |  |  |  |  |  |  |
| 4-OCF₂CF₂H | 4-SCF₃ | 3-Cl | 3-CH₃ | 4-CH₃ | 4-Cl | 4-n-C₄H₉ | 4-i-C₃H₇ | 4-tert-C₄H₉ |
| H | H | 4-CH₃ | H | H | H | H | H | H |

-continued

| No. | | | | | | | | | |
|---|---|---|---|---|---|---|---|---|---|
| 2-169 | CH₃ (cyclopentyl-CH₃) | CH₃ | O | H | H | H | H | 4-O | 2-Cl | 4-Cl |
| 2-170 | CH₃ (cyclopentyl-CH₃) | CH₃ | O | H | H | H | H | 4-O | 4-O-n-C₃H₇ | H |
| 2-171 | CH₃ (cyclopentyl-CH₃) | CH₃ | O | H | H | H | H | 4-O | 4-O—CH₂—CH=CH₂ | H |
| 2-172 | CH₃ (cyclopentyl-CH₃) | CH₃ | O | H | H | H | H | 4-O | 4-O—CH₂—C≡CH | H |
| 2-173 | CH₃ (cyclopentyl-CH₃) | CH₃ | O | H | H | H | H | 4-O | 2-Cl | 4-CF₃ |
| 2-174 | CH₃ (cyclopentyl-CH₃) | CH₃ | O | H | H | H | H | 4-O | 3-Br | 4-Br |
| 2-175 | CH₃ (cyclopentyl-CH₃) | CH₃ | O | H | H | H | H | 4-O | 4-NHC(O)CH₃ | H |
| 2-176 | CH₃ (cyclopentyl-CH₃) | CH₃ | O | H | H | H | H | 4-O | 4-N=CH—N(CH₃)₂ | H |
| 2-177 | CH₃ (cyclopentyl-CH₃) | CH₃ | O | H | H | H | H | 4-O | 4-NHSO₂CH₃ | H |

| No. | Structure | R | | | H | H | H | Position | Ar | Extra |
|---|---|---|---|---|---|---|---|---|---|---|
| 2-178 | cyclopentyl-CH3 | CH3 | O | H | H | H | H | 4-O | phenyl, 2,3-(CH2-CH2-CH2-CH2-) | H |
| 2-179 | cyclopentyl-CH3 | CH3 | O | H | H | H | H | 4-O | pyridyl, 4-CF3 | H |
| 2-180 | cyclopentyl-CH3 | CH3 | O | H | H | H | H | 4-O | pyridyl, 4-CF3 | 6-Cl |
| 2-181 | cyclopentyl-CH3 | CH3 | O | H | H | H | H | 4-O | phenyl, 4-SCF2CF2H | H |
| 2-182 | cyclopentyl-CH3 | CH3 | O | H | H | H | H | 4-O | phenyl, 4-SC2H5 | H |
| 2-183 | cyclopentyl-CH3 | CH3 | O | H | H | H | H | 4-O | phenyl, 4-SOCH3 | H |
| 2-184 | cyclopentyl-CH3 | CH3 | O | H | H | H | H | 4-O | phenyl, 3-Cl | 4-SCH3 |
| 2-185 | cyclopentyl-CH3 | CH3 | O | H | H | H | H | 4-O | phenyl, 3-CH3 | 4-SCH3 |
| 2-186 | cyclopentyl-CH3 | CH3 | O | H | H | H | H | 4-O | phenyl, 3-F | 4-SCH3 |

| | | | | | | | | |
|---|---|---|---|---|---|---|---|---|
| 2-187 | CH₃ [cyclopentane-CH₃,CH₃] | CH₃ | O | H | H | H | 4-O | [phenyl] 2-Cl | 4-SCH₃-5-Cl |
| 2-188 | CH₃ [cyclopentane-CH₃,CH₃] | CH₃ | O | H | H | H | 4-O | [phenyl] 4-OCF₃ | H |
| 2-189 | CH₃ [cyclopentane-CH₃,CH₃] | CH₃ | O | H | H | H | 4-O | [phenyl] 3-CH₃ | 4-Cl |
| 2-190 | CH₃ [cyclopentane-CH₃,CH₃] | CH₃ | O | H | H | H | 4-O | [phenyl] 3-CH₃ | H |
| 2-191 | CH₃ [cyclopentane-CH₃,CH₃] | CH₃ | O | H | H | H | 4-O | [cyclohexyl] 4-CH₃ | H |
| 2-192 | CH₃ [cyclopentane-CH₃,CH₃] | CH₃ | O | H | H | H | 4-O | [phenyl] 4-Cl | H |
| 2-193 | CH₃ [cyclopentane-CH₃,CH₃] | CH₃ | O | H | H | H | 4-O | [phenyl] 4-n-C₄H₉ | H |
| 2-194 | CH₃ [cyclopentane-CH₃,CH₃] | CH₃ | O | H | H | H | 4-O | [phenyl] 4-i-C₃H₇ | H |

| | | | | | | | |
|---|---|---|---|---|---|---|---|
| 2-195 | CH₃ | ![cyclopentyl-CH₃] | O | H | H | H | H | 4-O | ![phenyl] | 4-tert-C₄H₉ | H |
| 2-196 | CH₃ | ![cyclopentyl-CH₃] | O | H | H | H | H | 4-O | ![phenyl] | 4-SCH₃ | H |
| 2-197 | CH₃ | ![cyclopentyl-CH₃] | O | H | H | H | H | 4-O | ![phenyl] | 4-O-n-C₃H₇ | H |
| 2-198 | CH₃ | ![cyclopentyl-CH₃] | O | H | H | H | H | 4-O | ![phenyl] | 4-OCH₂—CH=CH₂ | H |
| 2-199 | CH₃ | ![cyclopentyl-CH₃] | O | H | H | H | H | 4-O | ![phenyl] | 2-Cl | 4-CF₃ |
| 2-200 | CH₃ | ![cyclopentyl-CH₃] | O | H | H | H | H | 4-O | ![phenyl] | 3-Br | 4-Br |
| 2-201 | CH₃ | ![cyclopentyl-CH₃] | O | H | H | H | H | 4-O | ![phenyl] | 4-NHC(=O)CH₃ | H |

| No. | | | | | | | | | |
|---|---|---|---|---|---|---|---|---|---|
| 2-202 | CH₃ | [CH₃-cyclopentyl] | O | H | H | H | 4-O | [phenyl] | 4-N=CH—N(CH₃)₂ | H |
| 2-203 | CH₃ | [CH₃-cyclopentyl] | O | H | H | H | 4-O | [phenyl] | 2,3-(CH₂—CH₂—CH₂—CH₂—) | H |
| 2-204 | CH₃ | [CH₃-cyclopentyl] | O | H | H | H | 4-O | [pyridyl] | 4-CF₃ | H |
| 2-205 | CH₃ | [CH₃-cyclopentyl] | O | H | H | H | 4-O | [pyridyl] | 4-CF₃ | 6-Cl |
| 2-206 | CH₃ | [CH₃-cyclopentyl] | O | H | H | H | 4-O | [phenyl] | 4-SCF₂CF₂H | H |
| 2-207 | CH₃ | [CH₃-cyclopentyl] | O | H | H | H | 4-O | [phenyl] | 4-SC₂H₅ | H |
| 2-208 | CH₃ | [CH₃-cyclopentyl] | O | H | H | H | 4-O | [phenyl] | 4-SO₂CH₃ | H |

| | | | | | | | |
|---|---|---|---|---|---|---|---|
| 2-209 | CH₃ | ![cyclopentane with CH₃] | O | H | H | H | 4-O | ![phenyl] 3-Cl | 4-SCH₃ |
| 2-210 | CH₃ | ![cyclopentane with CH₃] | O | H | H | H | 4-O | ![phenyl] 3-CH₃ | 4-SCH₃ |
| 2-211 | CH₃ | ![cyclopentane with CH₃] | O | H | H | H | 4-O | ![phenyl] 3-F | 4-SCH₃ |
| 2-212 | CH₃ | ![cyclopentane with CH₃] | O | H | H | H | 4-O | ![phenyl] 3-Br | 4-SCH₃ |
| 2-213 | CH₃ | ![cyclopentane with CH₃] | O | H | H | H | 4-O | ![phenyl] 4-SCF₃ | H |
| 2-214 | CH₃ | ![cyclopentane with CH₃] | O | H | H | H | 4-O | ![phenyl] 4-SCF₂H | H |
| 2-215 | CH₃ | ![cyclopentane with CH₃] | O | H | H | H | 4-O | ![phenyl] 3-Cl | 4-CH₃ |

| No. | | | | | | | | | |
|---|---|---|---|---|---|---|---|---|---|
| 2-216 | CH₃ | (2,4-dimethylcyclopentyl, 1-CH₃) | O | H | H | H | 4-O | phenyl | 3-CH₃ | 4-Br |
| 2-217 | CH₃ | (2,3-dimethylcyclohexyl, 1-CH₃) | O | H | H | H | 4-O | phenyl | 4-CH₃ | H |
| 2-218 | CH₃ | (2,3-dimethylcyclohexyl, 1-CH₃) | O | H | H | H | 4-O | phenyl | 4-OC₂H₅ | H |
| 2-219 | CH₃ | (2,3-dimethylcyclohexyl, 1-CH₃) | O | H | H | H | 4-O | phenyl | 4-SCH₃ | H |
| 2-220 | CH₃ | (2,3-dimethylcyclohexyl, 1-CH₃) | O | H | H | H | 4-O | phenyl | 4-OCF₂CF₂H | H |
| 2-221 | CH₃ | (2,3-dimethylcyclohexyl, 1-CH₃) | O | H | H | H | 4-O | phenyl | 4-SCF₃ | H |
| 2-222 | CH₃ | (2,3-dimethylcyclohexyl, 1-CH₃) | O | H | H | H | 4-O | phenyl | 3-Cl | 4-CH₃ |

-continued

| | | | | | | Ar substituent |
|---|---|---|---|---|---|---|
| 2-223 | [cyclohexyl-CH3, CH3] | O | H | H | H | H | 4-O / 3-CH3 phenyl / H |
| 2-224 | [cyclohexyl-CH3, CH3] | O | H | H | H | H | 4-O / 4-O-CH2-C≡CH phenyl / H |
| 2-225 | [cyclohexyl-CH3, CH3] | O | H | H | H | H | 4-O / 4-CH3 phenyl / H |
| 2-226 | [cyclohexyl-CH3, CH3] | O | H | H | H | H | 4-O / 2-Cl phenyl / 4-Cl |
| 2-227 | [cyclohexyl-CH3, CH3] | O | H | H | H | H | 4-O / 3-Cl phenyl / 4-Cl |
| 2-228 | [cyclohexyl-CH3, CH3] | O | H | H | H | H | 4-O / 2-Cl phenyl / 4-CF3 |
| 2-229 | [cyclohexyl-CH3, CH3] | O | H | H | H | H | 4-O / 4-N=CH—N(CH3)2 phenyl / H |

| No. | | | | | | | | | |
|---|---|---|---|---|---|---|---|---|---|
| 2-230 | CH₃ | ![cyclohexane-CH₃] | O | H | H | H | 4-O | ![phenyl]-4-NHSO₂CH₃ | H |
| 2-231 | CH₃ | ![cyclohexane-CH₃] | O | H | H | H | 4-O | ![pyridyl]-4-CF₃ | H |
| 2-232 | CH₃ | ![cyclohexane-CH₃] | O | H | H | H | 4-O | ![pyridyl]-4-CF₃ | 6-Cl |
| 2-233 | CH₃ | ![cyclohexane-CH₃] | O | H | H | H | 4-O | ![phenyl]-4-SCF₂CF₂H | H |
| 2-234 | CH₃ | ![cyclohexane-CH₃] | O | H | H | H | 4-O | ![phenyl]-4-SC₂H₅ | H |
| 2-235 | CH₃ | ![cyclohexane-CH₃] | O | H | H | H | 4-O | ![phenyl]-4-SO₂CH₃ | H |
| 2-236 | CH₃ | ![cyclohexane-CH₃] | O | H | H | H | 4-O | ![phenyl]-3-Br | 4-SCH₃ |

-continued

| | | | | | | | | | |
|---|---|---|---|---|---|---|---|---|---|
| 2-237 | CH₃ | ![cyclohexane with CH₃] | O | H | H | H | H | 4-O | ![phenyl]  3-CH₃ | 4-SCH₃-5-CH₃ |
| 2-238 | CH₃ | ![cyclohexane with CH₃] | O | H | H | H | H | 4-O | ![phenyl]  4-OCF₃ | H |
| 2-239 | CH₃ | ![cyclohexane with CH₃] | O | H | H | H | H | 4-O | ![phenyl]  3-CH₃ | 4-Cl |
| 2-240 | CH₃ | ![cyclohexane with CH₃] | O | H | H | H | H | 4-O | ![phenyl]  4-tert-C₄H₉ | H |
| 2-241 | CH₃ | ![cyclohexane with CH₃] | O | H | H | H | H | 4-O | ![phenyl]  4-F | H |
| 2-242 | CH₃ | ![cyclohexane with CH₃] | O | H | H | H | H | 4-O | ![phenyl]  4-OCF₂H | H |
| 2-243 | CH₃ | ![cyclohexane with CH₃] | O | H | H | H | H | 4-O | ![phenyl]  4-I | H |

| | | | | | | | |
|---|---|---|---|---|---|---|---|
| 2-244 | CH₃ | ⬡ | O | H | H | H | 4-O | ⬡ 4-CH₃ | H |
| 2-245 | CH₃ | ⬡ | O | H | H | H | 4-O | ⬡ 4-OC₂H₅ | H |
| 2-246 | CH₃ | ⬡ | O | H | H | H | 4-O | ⬡ 4-SCH₃ | H |
| 2-247 | CH₃ | ⬡ | O | H | H | H | 4-O | ⬡ 4-OCF₂CF₂H | H |
| 2-248 | CH₃ | ⬡ | O | H | H | H | 4-O | ⬡ 4-SCF₃ | H |
| 2-249 | CH₃ | ⬡ | O | H | H | H | 4-O | ⬡ 3-Cl | 4-CH₃ |
| 2-250 | CH₃ | ⬡ | O | H | H | H | 4-O | ⬡ 3-CH₃ | H |

-continued

| | | | | | | | Ar substituent |
|---|---|---|---|---|---|---|---|
| 2-251 | CH₃ | cyclohexyl | O | H | H | H | 4-O- / phenyl (4-CH₃) / H |
| 2-252 | CH₃ | cyclohexyl | O | H | H | H | 4-O- / phenyl (2-Cl) / 4-Cl |
| 2-253 | CH₃ | cyclohexyl | O | H | H | H | 4-O- / phenyl (4-O—CH₂—CH=CH₂) / H |
| 2-254 | CH₃ | cyclohexyl | O | H | H | H | 4-O- / phenyl (3-Br) / 4-Br |
| 2-255 | CH₃ | cyclohexyl | O | H | H | H | 4-O- / phenyl (2-Cl) / 4-CF₃ |
| 2-256 | CH₃ | cyclohexyl | O | H | H | H | 4-O- / phenyl (4-N=CH—N(H)CH₃) / H |
| 2-257 | CH₃ | cyclohexyl | O | H | H | H | 4-O- / phenyl (4-NHSO₂CH₃) / H |

-continued

| No. | | | | | | | | | | | |
|---|---|---|---|---|---|---|---|---|---|---|---|
| 2-258 | CH₃ | cyclohexane | O | H | H | H | H | 4-O | pyridine (N) | 4-CF₃ | H |
| 2-259 | CH₃ | cyclohexane | O | H | H | H | H | 4-O | pyridine (N) | 4-CF₃ | 6-Cl |
| 2-260 | CH₃ | cyclohexane | O | H | H | H | H | 4-O | phenyl | 4-SCF₂CF₂H | H |
| 2-261 | CH₃ | cyclohexane | O | H | H | H | H | 4-O | phenyl | 4-SC₂H₅ | H |
| 2-262 | CH₃ | cyclohexane | O | H | H | H | H | 4-O | phenyl | 4-SOCH₃ | H |
| 2-263 | CH₃ | cyclohexane | O | H | H | H | H | 4-O | phenyl | 3-Cl | 4-SCH₃ |
| 2-264 | CH₃ | cyclohexane | O | H | H | H | H | 4-O | phenyl | 3-CH₃ | 4-SCH₃ |

-continued

| No. | | | | | | | | | Phenyl subst. | Add'l subst. |
|---|---|---|---|---|---|---|---|---|---|---|
| 2-265 | CH₃ | cyclohexyl | O | H | H | H | H | 4-O | 3-Br | 4-SCH₃ |
| 2-266 | CH₃ | cyclohexyl | O | H | H | H | H | 4-O | 4-OCF₃ | H |
| 2-267 | CH₃ | cyclohexyl | O | H | H | H | H | 4-O | 3-CH₃ | 4-Cl |
| 2-268 | CH₃ | cyclohexyl | O | H | H | H | H | 4-O | 4-i-C₃H₇ | H |
| 2-269 | CH₃ | cyclohexyl | O | H | H | H | H | 4-O | 4-Br | H |
| 2-270 | CH₃ | cyclohexyl | O | H | H | H | H | 4-O | 4-OCF₂H | H |
| 2-271 | CH₃ | cyclopentyl | O | H | H | H | H | 4-O | 3-Cl | 4-SC₂H₅ |
| 2-272 | CH₃ | cyclopentyl | O | H | H | H | H | 4-O | 2-Cl | 4-SC₂H₅-5-Cl |

-continued

| No. | R | | | | | | | Ar | R' |
|---|---|---|---|---|---|---|---|---|---|
| 2-273 | CH₃ | cyclopentyl | O | H | H | H | 4-O | 3-Br-phenyl | 4-SC₂H₅ |
| 2-274 | CH₃ | cyclopentyl | O | H | H | H | 4-O | 3-F-phenyl | 4-SC₂H₅ |
| 2-275 | CH₃ | cyclopentyl | O | H | H | H | 4-O | 3-Cl-phenyl | 4-S-n-C₃H₇ |
| 2-276 | CH₃ | cyclopentyl | O | H | H | H | 4-O | 4-SCH₃-phenyl | H |
| 2-277 | CH₃ | cyclopentyl | O | H | H | H | 4-O | 3-Cl-phenyl | 4-n-C₄H₉ |
| 2-278 | C₂H₅ | cyclopentyl | O | H | H | H | 4-O | 4-OC₂H₅-phenyl | H |
| 2-279 | i-C₃H₇ | cyclopentyl | O | H | H | H | 4-O | 4-OC₂H₅-phenyl | H |
| 2-280 | cyclopropyl | cyclopentyl | O | H | H | H | 4-O | 4-OC₂H₅-phenyl | H |
| 2-281 | CF₃CH₂ | cyclopentyl | O | H | H | H | 4-O | 4-OC₂H₅-phenyl | H |

-continued

| | 2-282 | 2-283 | 2-284 | 2-285 | 2-286 | 2-287 | 2-288 | 2-289 | 2-290 |
|---|---|---|---|---|---|---|---|---|---|
| | CH₃ | CH₃ | CH₃ | CH₃ | CH₃ | CH₃ | CH₃ | CH₃ | CH₃ |
| | cyclopentyl | cyclopentyl | cyclopentyl | cyclopentyl | cyclopentyl | cyclopentyl | cyclopentyl | cyclopentyl | cyclopentyl |
| | O | O | O | O | O | O | O | O | O |
| | H | H | H | H | H | H | CH₃ | H | H |
| | H | H | H | H | H | H | H | CH₃ | C₂H₅ |
| | H | H | H | H | H | H | H | H | H |
| | H | H | H | H | H | H | H | H | H |
| Ar | 4-OCH₃-C₆H₄ | 3-OCH₃-C₆H₄ | 4-OC₂H₅-C₆H₄ | 4-OC₂H₅-C₆H₄ | 4-OC₂H₅-C₆H₄ | 4-OC₂H₅-C₆H₄ | 4-OCF₂CF₂H-C₆H₄ | 4-OC₂H₅-C₆H₄ | 4-OC₂H₅-C₆H₄ |
| | 4-S | 4-S | 4-CH₂ | 4-NH | 4-NCH₃ | 4-SO₂ | 4-O | 4-O | 4-O |
| | H | H | H | H | H | H | H | H | H |

-continued

| No. | | | | | | | | | | | |
|---|---|---|---|---|---|---|---|---|---|---|---|
| 2-291 | CH₃ | cyclopentyl | O | H | CH₃ | CH₃ | H | 4-O | phenyl | 4-OC₂H₅ | H |
| 2-292 | CH₃ | cyclopentyl | O | H | H | H | 2-F | 4-O | phenyl | 4-OC₂H₅ | H |
| 2-293 | CH₃ | cyclopentyl | O | H | H | H | 3-Cl | 4-O | phenyl | 4-OC₂H₅ | H |
| 2-294 | CH₃ | cyclopentyl | O | H | H | H | 3-CH₃ | 4-O | phenyl | 4-OC₂H₅ | H |
| 2-295 | CH₃ | cyclopentyl | O | H | H | H | H | 4-O | phenyl | 4-Cl | H |
| 2-296 | CH₃ | cyclopentyl | O | H | H | H | H | 4-O | phenyl | 4-OCF₂CCl₂H | H |
| 2-297 | CH₃ | cyclopentyl | O | H | H | H | H | 4-O | cyclohexyl | 4-O-n-C₃H₇ | H |
| 2-298 | CH₃ | cyclopentyl | O | H | H | H | H | 4-S | phenyl | 3-CH₃ | H |
| 2-299 | CH₃ | cyclopentyl | O | H | H | H | H | 4-O | phenyl | 3-CH₃ | 4-Cl |

-continued
| | | | | | | | | | | |
|---|---|---|---|---|---|---|---|---|---|---|
| 2-300 | CH₃ |  | O | H | H | H | H | 4-O | 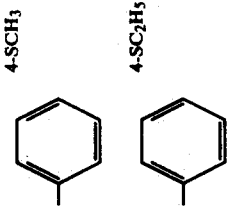 4-SCH₃ | H |
| 2-301 | CH₃ | 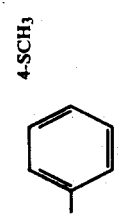 | O | H | CH₃ | H | H | 4-O | 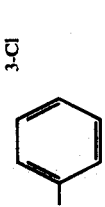 4-SCH₃ | H |
| 2-302 | CH₃ |  | O | H | H | H | H | 4-O¹ |  4-SCH₃ | H |
| 2-303 | CH₃ | 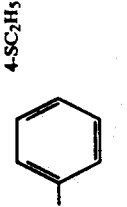 | O | H | H | H | H | 4-O | 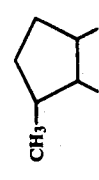 4-SC₂H₅ | H |
| 2-304 | CH₃ | 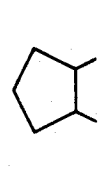 | O | H | CN | H' | H | 4-O | 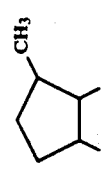 3-Cl | 4-SCH₃ |
| 2-305 | CH₃ | 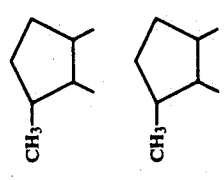 | O | H | CH₃ | H | H | 4-O | 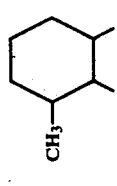 4-SC₂H₅ | H |
¹wherein R²⁵ and R²⁶ are, respectively, a hydrogen atom or an alkyl group of 1–4 carbons; r is an integer of 1 or 2; the numbers 2–6 are to represent the positions of substitution.

TABLE 3

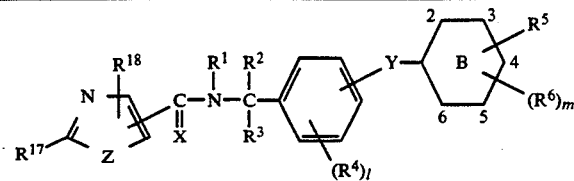

wherein the numbers 2–6 are to represent the positions of substitution.

| Compound No. | $R^{17}$ | $R^{18}$ | Z | X | $R^1$ | $R^2$ | $R^3$ | $(R^4)_l$ | Y | $R^5$ | $(R^6)_m$ |
|---|---|---|---|---|---|---|---|---|---|---|---|
| 3-1 | $CH_3$ | 4-$CH_3$ | O | O | H | H | H | H | 4-O | 2-$CH_3$ | H |
| 3-2 | $CH_3$ | 4-$CH_3$ | O | O | H | H | H | H | 4-O | 3-$CH_3$ | H |
| 3-3 | $CH_3$ | 4-$CH_3$ | O | O | H | H | H | H | 4-O | 4-$CH_3$ | H |
| 3-4 | $CH_3$ | 4-$CH_3$ | O | O | H | H | H | H | 4-O | 4-$C_2H_5$ | H |
| 3-5 | $CH_3$ | 4-$CH_3$ | O | O | H | H | H | H | 4-O | 3-$C_2H_5$ | H |
| 3-6 | $CH_3$ | 4-$CH_3$ | O | O | H | H | H | H | 4-O | 4-n-$C_4H_9$ | H |
| 3-7 | $CH_3$ | 4-$CH_3$ | O | O | H | H | H | H | 4-O | 4-n-$C_6H_{13}$ | H |
| 3-8 | $CH_3$ | 4-$CH_3$ | O | O | H | H | H | H | 4-O | 4-$CF_3$ | H |
| 3-9 | $CH_3$ | 4-$CH_3$ | O | O | H | H | H | H | 4-O | 4-$CH_2$—CH=$CH_2$ | H |
| 3-10 | $CH_3$ | 4-$CH_3$ | O | O | H | H | H | H | 4-O | 4-$CH_2$—C≡CH | H |
| 3-11 | $CH_3$ | 4-$CH_3$ | O | O | H | H | H | H | 4-O | 4-$OCH_3$ | H |

TABLE 3-continued

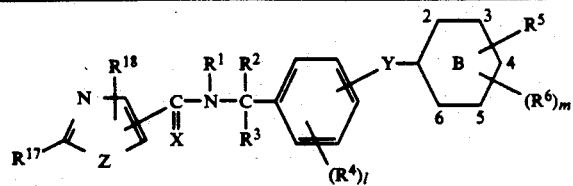

wherein the numbers 2–6 are to represent the positions of substitution.

| Compound No. | $R^{17}$ | $R^{18}$ | Z | X | $R^1$ | $R^2$ | $R^3$ | $(R^4)l$ | Y | B | $R^5$ | $(R^6)_m$ |
|---|---|---|---|---|---|---|---|---|---|---|---|---|
| 3-12 | $CH_3$ | 4-$CH_3$ | O | O | H | H | H | H | 4-O | phenyl | 4-$OC_2H_5$ | H |
| 3-13 | $CH_3$ | 4-$CH_3$ | O | O | H | H | H | H | 4-O | phenyl | 4-O-n-$C_3H_7$ | H |
| 3-14 | $CH_3$ | 4-$CH_3$ | O | O | H | H | H | H | 4-O | phenyl | 4-O-n-$C_6H_{13}$ | H |
| 3-15 | $CH_3$ | 4-$CH_3$ | O | O | H | H | H | H | 4-O | phenyl | 4-$OCF_2H$ | H |
| 3-16 | $CH_3$ | 4-$CH_3$ | O | O | H | H | H | H | 4-O | phenyl | 4-$OCF_3$ | H |
| 3-17 | $CH_3$ | 4-$CH_3$ | O | O | H | H | H | H | 4-O | phenyl | 4-$OCF_2CF_2H$ | H |
| 3-18 | $CH_3$ | 4-$CH_3$ | O | O | H | H | H | H | 4-O | phenyl | 4-$OCH_2CF_3$ | H |
| 3-19 | $CH_3$ | 4-$CH_3$ | O | O | H | H | H | H | 4-O | phenyl | 4-$OCH_2CH_2F$ | H |
| 3-20 | $CH_3$ | 4-$CH_3$ | O | O | H | H | H | H | 4-O | phenyl | 4-O—$CH_2$—CH=$CH_2$ | H |
| 3-21 | $CH_3$ | 4-$CH_3$ | O | O | H | H | H | H | 4-O | phenyl | 4-O—$CH_2$—C≡CH | H |
| 3-22 | $CH_3$ | 4-$CH_3$ | O | O | H | H | H | H | 4-O | phenyl | 4-$SCH_3$ | H |

TABLE 3-continued

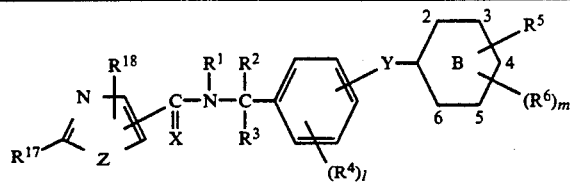

wherein the numbers 2-6 are to represent the positions of substitution.

| Compound No. | $R^{17}$ | $R^{18}$ | Z | X | $R^1$ | $R^2$ | $R^3$ | $(R^4)l$ | Y | B | $R^5$ | $(R^6)_m$ |
|---|---|---|---|---|---|---|---|---|---|---|---|---|
| 3-23 | $CH_3$ | 4-$CH_3$ | O | O | H | H | H | H | 4-O | phenyl | 4-$SC_2H_5$ | H |
| 3-24 | $CH_3$ | 4-$CH_3$ | O | O | H | H | H | H | 4-O | phenyl | 4-S-n-$C_3H_7$ | H |
| 3-25 | $CH_3$ | 4-$CH_3$ | O | O | H | H | H | H | 4-O | phenyl | 4-S-i-$C_3H_7$ | H |
| 3-26 | $CH_3$ | 4-$CH_3$ | O | O | H | H | H | H | 4-O | phenyl | 4-$SCF_2H$ | H |
| 3-27 | $CH_3$ | 4-$CH_3$ | O | O | H | H | H | H | 4-O | phenyl | 4-$SCF_3$ | H |
| 3-28 | $CH_3$ | 4-$CH_3$ | O | O | H | H | H | H | 4-O | phenyl | 4-$SCH_2CH_2F$ | H |
| 3-29 | $CH_3$ | 4-$CH_3$ | O | O | H | H | H | H | 4-O | phenyl | 4-$SCH_2CF_3$ | H |
| 3-30 | $CH_3$ | 4-$CH_3$ | O | O | H | H | H | H | 4-O | phenyl | 4-$SCF_2CF_2H$ | H |
| 3-31 | $CH_3$ | 4-$CH_3$ | O | O | H | H | H | H | 4-O | phenyl | 4-$NHC_2H_5$ | H |
| 3-32 | $CH_3$ | 4-$CH_3$ | O | O | H | H | H | H | 4-O | phenyl | 4-$S(O)CH_3$ | H |
| 3-33 | $CH_3$ | 4-$CH_3$ | O | O | H | H | H | H | 4-O | phenyl | 4-$S(O)C_2H_5$ | H |

TABLE 3-continued

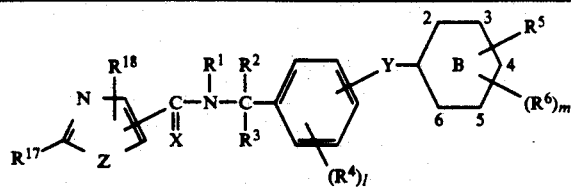

wherein the numbers 2-6 are to represent the positions of substitution.

| Compound No. | $R^{17}$ | $R^{18}$ | Z | X | $R^1$ | $R^2$ | $R^3$ | $(R^4)_l$ | Y | B | $R^5$ | $(R^6)_m$ |
|---|---|---|---|---|---|---|---|---|---|---|---|---|
| 3-34 | $CH_3$ | 4-$CH_3$ | O | O | H | H | H | H | 4-O | phenyl | 4-$S(O)_2CH_3$ | H |
| 3-35 | $CH_3$ | 4-$CH_3$ | O | O | H | H | H | H | 4-O | phenyl | 4-Cl | H |
| 3-36 | $CH_3$ | 4-$CH_3$ | O | O | H | H | H | H | 4-O | phenyl | 3-Cl | H |
| 3-37 | $CH_3$ | 4-$CH_3$ | O | O | H | H | H | H | 4-O | phenyl | 2-Cl | H |
| 3-38 | $CH_3$ | 4-$CH_3$ | O | O | H | H | H | H | 4-O | phenyl | 2-Cl | 3-Cl |
| 3-39 | $CH_3$ | 4-$CH_3$ | O | O | H | H | H | H | 4-O | phenyl | 2-Cl | 4-F |
| 3-40 | $CH_3$ | 4-$CH_3$ | O | O | H | H | H | H | 4-O | phenyl | 2-F | 4-Cl |
| 3-41 | $CH_3$ | 4-$CH_3$ | O | O | H | H | H | H | 4-O | phenyl | 2-F | 4-Br |
| 3-42 | $CH_3$ | 4-$CH_3$ | O | O | H | H | H | H | 4-O | phenyl | 2-Cl | 3,4-$Cl_2$ |
| 3-43 | $CH_3$ | 4-$CH_3$ | O | O | H | H | H | H | 4-O | phenyl | 2-Cl | 4,5-$Cl_2$ |
| 3-44 | $CH_3$ | 4-$CH_3$ | O | O | H | H | H | H | 4-O | phenyl | 4-$SCH_3$ | 3-Cl |

TABLE 3-continued

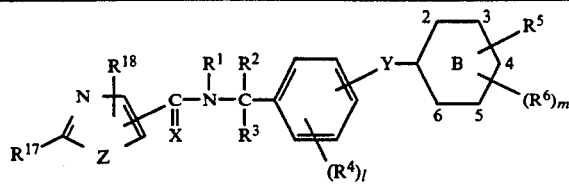

wherein the numbers 2-6 are to represent the positions of substitution.

| Compound No. | $R^{17}$ | $R^{18}$ | Z | X | $R^1$ | $R^2$ | $R^3$ | $(R^4)l$ | Y | B | $R^5$ | $(R^6)_m$ |
|---|---|---|---|---|---|---|---|---|---|---|---|---|
| 3-45 | $CH_3$ | 4-$CH_3$ | O | O | H | H | H | H | 4-O | phenyl | 4-$SCH_3$ | 2-Cl |
| 3-46 | $CH_3$ | 4-$CH_3$ | O | O | H | H | H | H | 4-O | phenyl | 4-$SCH_3$ | 2,3-$Cl_2$ |
| 3-47 | $CH_3$ | 4-$CH_3$ | O | O | H | H | H | H | 4-O | phenyl | 4-$SCH_3$ | 3-$CH_3$ |
| 3-48 | $CH_3$ | 4-$CH_3$ | O | O | H | H | H | H | 4-O | phenyl | 4-$SCH_3$ | 2,5-$Cl_2$ |
| 3-49 | $CH_3$ | 4-$CH_3$ | O | O | H | H | H | H | 4-O | phenyl | 4-$SCH_3$ | 2-$CH_3$-5-Cl |
| 3-50 | $CH_3$ | 4-$CH_3$ | O | O | H | H | H | H | 4-O | phenyl | 4-$SCH_3$ | 2-Cl-5-$CH_3$ |
| 3-51 | $CH_3$ | 4-$CH_3$ | O | O | H | H | H | H | 4-O | phenyl | 4-$SCH_3$ | 3-F |
| 3-52 | $CH_3$ | 4-$CH_3$ | O | O | H | H | H | H | 4-O | phenyl | 4-$SCH_3$ | 3-Br |
| 3-53 | $CH_3$ | 4-$CH_3$ | O | O | H | H | H | H | 4-O | phenyl | 4-$SCH_3$ | 3,5-$(CH_3)_2$ |
| 3-54 | $CH_3$ | 4-$CH_3$ | O | O | H | H | H | H | 4-O | phenyl | 4-$SCH_3$ | 2,5-$(CH_3)_2$ |
| 3-55 | $CH_3$ | 4-$CH_3$ | O | O | H | H | H | H | 4-O | phenyl | 4-$SC_2H_5$ | 3-Cl |

TABLE 3-continued

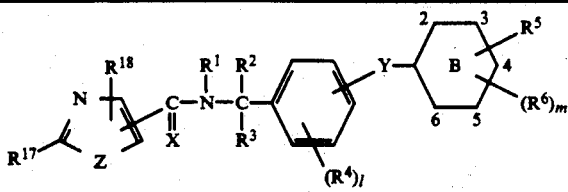

wherein the numbers 2–6 are to represent the positions of substitution.

| Compound No. | $R^{17}$ | $R^{18}$ | Z | X | $R^1$ | $R^2$ | $R^3$ | $(R^4)l$ | Y | $R^5$ | $(R^6)_m$ |
|---|---|---|---|---|---|---|---|---|---|---|---|
| 3-56 | $CH_3$ | 4-$CH_3$ | O | O | H | H | H | H | 4-O | 4-$SC_2H_5$ | 2,5-$Cl_2$ |
| 3-57 | $CH_3$ | 4-$CH_3$ | O | O | H | H | H | H | 4-O | 4-$SCF_2H$ | 3-Cl |
| 3-58 | $CH_3$ | 4-$CH_3$ | O | O | H | H | H | H | 4-O | 4-$SCF_3$ | 3-Cl |
| 3-59 | $CH_3$ | 4-$CH_3$ | O | O | H | H | H | H | 4-O | 4-$SCF_2CF_2H$ | 3-Cl |
| 3-60 | $CH_3$ | 4-$CH_3$ | O | O | H | H | H | H | 4-O | 3-Cl | 4-$CH_3$ |
| 3-61 | $CH_3$ | 4-$CH_3$ | O | O | H | H | H | H | 4-O | 3-Cl | 4-$C_2H_5$ |
| 3-62 | $CH_3$ | 4-$CH_3$ | O | O | H | H | H | H | 4-O | 3-$CH_3$ | 4-Cl |
| 3-63 | $CH_3$ | 4-$CH_3$ | O | O | H | H | H | H | 4-O | 3-$CH_3$ | 4-Br |
| 3-64 | $CH_3$ | 4-$CH_3$ | O | O | H | H | H | H | 4-O | 4-$CH_2CH_2OCH_3$ | 2-$CH_3$ |
| 3-65 | $CH_3$ | 4-$CH_3$ | O | O | H | H | H | H | 4-O | 4-$CH_2CH_2OCH_3$ | 2-$C_2H_5$ |
| 3-66 | $CH_3$ | 4-$CH_3$ | O | O | H | H | H | H | 4-O | 4-$CH_2CH_2OC_2H_5$ | 2,3-$(CH_3)_2$ |

TABLE 3-continued

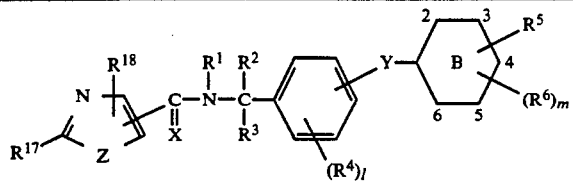

wherein the numbers 2-6 are to represent the positions of substitution.

| Compound No. | R17 | R18 | Z | X | R1 | R2 | R3 | (R4)l | Y | B | R5 | (R6)m |
|---|---|---|---|---|---|---|---|---|---|---|---|---|
| 3-67 | CH3 | 4-CH3 | O | O | H | H | H | H | 4-O | cyclohexyl-H | 4-CH3 | H |
| 3-68 | CH3 | 4-CH3 | O | O | H | H | H | H | 4-O | cyclohexyl-H | 4-C2H5 | H |
| 3-69 | CH3 | 4-CH3 | O | O | H | H | H | H | 4-O | cyclohexyl-H | 2-OCH3 | H |
| 3-70 | CH3 | 4-CH3 | O | O | H | H | H | H | 4-O | cyclohexyl-H | 2-O-n-C3H7 | H |
| 3-71 | CH3 | 4-CH3 | O | O | H | H | H | H | 4-O | cyclohexyl-H | 2-OC2H5 | H |
| 3-72 | CH3 | 4-CH3 | O | O | H | H | H | H | 4-O | pyridyl | 4-CF3 | H |
| 3-73 | CH3 | 4-CH3 | O | O | H | H | H | H | 4-O | pyridyl | 2-Cl | 4-CF3 |
| 3-74 | CH3 | 4-CH3 | O | O | H | H | H | H | 3-O | phenyl | 4-OC2H5 | H |
| 3-75 | CH3 | 4-CH3 | O | O | H | H | H | H | 3-O | phenyl | 4-OCF2CF2H | H |
| 3-76 | CH3 | 4-CH3 | O | O | H | H | H | H | 3-O | phenyl | 4-SCH3 | H |
| 3-77 | CH3 | 4-CH3 | O | O | H | H | H | H | 3-O | phenyl | 4-SC2H5 | H |

TABLE 3-continued

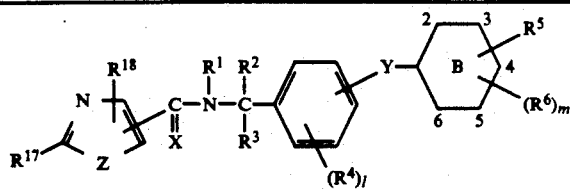

wherein the numbers 2-6 are to represent the positions of substitution.

| Compound No. | $R^{17}$ | $R^{18}$ | Z | X | $R^1$ | $R^2$ | $R^3$ | $(R^4)l$ | Y | $R^5$ | $(R^6)_m$ |
|---|---|---|---|---|---|---|---|---|---|---|---|
| 3-78 | $CH_3$ | 4-$CH_3$ | O | O | H | H | H | H | 4-S | 4-$SCH_3$ | H |
| 3-79 | $CH_3$ | 4-$CH_3$ | O | O | H | H | H | H | 4-$CH_2$ | 4-$OC_2H_5$ | H |
| 3-80 | $CH_3$ | 4-$CH_3$ | O | O | H | H | H | H | 4-$CH_2$ | 4-$SCH_3$ | H |
| 3-81 | $CH_3$ | 4-$CH_3$ | O | O | H | H | H | H | 4-SO | 4-$SCH_3$ | H |
| 3-82 | $CH_3$ | 4-$CH_3$ | O | O | H | H | H | H | 4-$SO_2$ | 4-$SCH_3$ | H |
| 3-83 | $CH_3$ | 4-$CH_3$ | O | O | H | H | H | 2-F | 4-O | 4-$SCH_3$ | H |
| 3-84 | $CH_3$ | 4-$CH_3$ | O | O | H | H | H | 3-Cl | 4-O | 4-$SCH_3$ | H |
| 3-85 | $CH_3$ | 4-$CH_3$ | O | O | H | H | H | 3-$CH_3$ | 4-O | 4-$OC_2H_5$ | H |
| 3-86 | $CH_3$ | 4-$CH_3$ | O | O | H | $CH_3$ | H | H | 4-O | 4-$OC_2H_5$ | H |
| 3-87 | $CH_3$ | 4-$CH_3$ | O | O | H | $C_2H_5$ | H | H | 4-O | 4-$OC_2H_5$ | H |
| 3-88 | $CH_3$ | 4-$CH_3$ | O | O | H | i-$C_3H_7$ | H | H | 4-O | 4-$OC_2H_5$ | H |

TABLE 3-continued

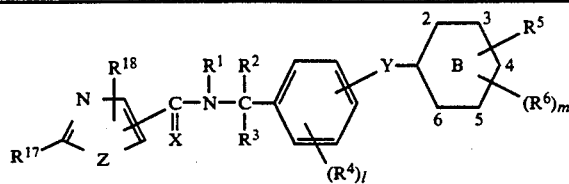

wherein the numbers 2–6 are to represent the positions of substitution.

| Compound No. | $R^{17}$ | $R^{18}$ | Z | X | $R^1$ | $R^2$ | $R^3$ | $(R^4)_l$ | Y | B | $R^5$ | $(R^6)_m$ |
|---|---|---|---|---|---|---|---|---|---|---|---|---|
| 3-89 | $CH_3$ | 4-$CH_3$ | O | O | H | $CH_3$ | H | H | 4-O | phenyl | 4-$SCH_3$ | H |
| 3-90 | $CH_3$ | 4-$CH_3$ | O | O | H | $CH_3$ | H | H | 4-O | phenyl | 4-$SCH_3$ | 3-Cl |
| 3-91 | $CH_3$ | 4-$CH_3$ | O | O | H | $CH_3$ | H | H | 4-O | phenyl | 4-$SCH_3$ | 2,5-$Cl_2$ |
| 3-92 | $CH_3$ | 4-$CH_3$ | O | O | H | $C_2H_5$ | H | H | 4-O | phenyl | 4-$SCH_3$ | H |
| 3-93 | $CH_3$ | 4-$CH_3$ | O | O | H | $C_2H_5$ | H | H | 4-O | phenyl | 4-$SCH_3$ | 3-Cl |
| 3-94 | $CH_3$ | 4-$CH_3$ | O | O | H | $C_2H_5$ | H | H | 4-O | phenyl | 4-$SCH_3$ | 2,5-$Cl_2$ |
| 3-95 | $CH_3$ | 4-$CH_3$ | O | O | H | $C_2H_5$ | H | H | 4-O | phenyl | 4-$SC_2H_5$ | H |
| 3-96 | $CH_3$ | 4-$CH_3$ | O | O | H | $CH_3$ | $CH_3$ | H | 4-O | phenyl | 4-$SCH_3$ | H |
| 3-97 | $CH_3$ | 4-$CH_3$ | O | O | H | CN | H | H | 4-O | phenyl | 4-$SCH_3$ | H |
| 3-98 | $CH_3$ | 4-$CH_3$ | O | O | $CH_3$ | H | H | H | 4-O | phenyl | 4-$OC_2H_5$ | H |
| 3-99 | $CH_3$ | 4-$CH_3$ | O | O | $C_2H_5$ | H | H | H | 4-O | phenyl | 4-$OC_2H_5$ | H |

TABLE 3-continued

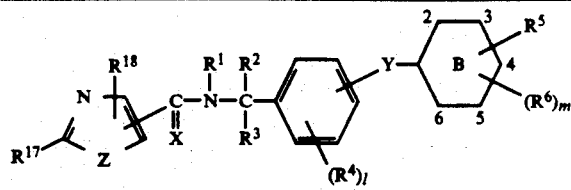

wherein the numbers 2-6 are to represent the positions of substitution.

| Compound No. | $R^{17}$ | $R^{18}$ | Z | X | $R^1$ | $R^2$ | $R^3$ | $(R^4)l$ | Y | $R^5$ | $(R^6)_m$ |
|---|---|---|---|---|---|---|---|---|---|---|---|
| 3-100 | $CH_3$ | 4-$CH_3$ | O | O | i-$C_3H_7$ | H | $CH_3$ | H | 4-O | 4-$OC_2H_5$ | H |
| 3-101 | $CH_3$ | 4-$CH_3$ | O | S | H | H | H | H | 4-O | 4-$OC_2H_5$ | H |
| 3-102 | $CH_3$ | 4-$C_2H_5$ | O | O | H | H | H | H | 4-O | 4-$SCH_3$ | H |
| 3-103 | $C_2H_5$ | 4-$CH_3$ | O | O | H | H | H | H | 4-O | 4-$SCH_3$ | H |
| 3-104 | i-$C_3H_7$ | 4-$CH_3$ | O | O | H | H | H | H | 4-O | 4-$SCH_3$ | H |
| 3-105 | ◁ | 4-$CH_3$ | O | O | H | H | H | H | 4-O | 4-$SCH_3$ | H |
| 3-106 | $CF_3$ | 4-$CH_3$ | O | O | H | H | H | H | 4-O | 4-$SCH_3$ | H |
| 3-107 | $CH_3$ | 4-$CH_3$ | S | O | H | H | H | H | 4-O | 4-$SCH_3$ | H |
| 3-108 | $CH_3$ | 4-$CH_3$ | S | O | H | H | H | H | 4-O | 4-$OC_2H_5$ | H |
| 3-109 | $CH_3$ | 4-$CH_3$ | S | O | H | H | H | H | 4-O | 4-n-$C_4H_9$ | H |
| 3-110 | $CH_3$ | 4-$CH_3$ | S | O | H | H | H | H | 4-O | 4-$CH_3$ | 3-Cl |

TABLE 3-continued

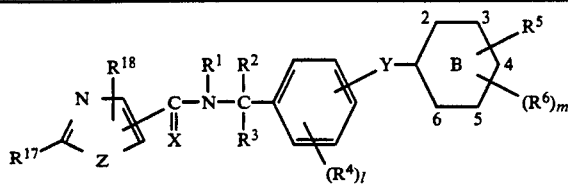

wherein the numbers 2-6 are to represent the positions of substitution.

| Compound No. | $R^{17}$ | $R^{18}$ | Z | X | $R^1$ | $R^2$ | $R^3$ | $(R^4)l$ | Y | B | $R^5$ | $(R^6)_m$ |
|---|---|---|---|---|---|---|---|---|---|---|---|---|
| 3-111 | $CH_3$ | 4-$CH_3$ | S | O | H | H | H | H | 4-O | phenyl | 4-$SC_2H_5$ | H |
| 3-112 | $CH_3$ | 4-$CH_3$ | S | O | H | H | H | H | 4-O | phenyl | 4-$SCH_3$ | 3-Cl |
| 3-113 | $CH_3$ | 4-$CH_3$ | S | O | H | H | H | H | 4-O | phenyl | 4-$SCH_3$ | 2,5-$Cl_2$ |
| 3-114 | $CH_3$ | 4-$CH_3$ | S | O | H | H | H | H | 4-O | phenyl | 4-$SC_2H_5$ | 3-Cl |
| 3-115 | H | 4-$CH_3$ | O | O | H | H | H | H | 4-O | phenyl | 4-$OCF_2CF_2H$ | H |
| 3-116 | $CH_3$ | H | O | O | H | H | H | H | 4-O | phenyl | 4-$OC_2H_5$ | H |
| 3-117 | $CH_3$ | H | O | O | H | H | H | H | 4-O | phenyl | 4-$OCF_2CF_2H$ | H |
| 3-118 | $CH_3$ | 4-$CH_3$ | S | O | H | H | H | H | 4-O | cyclohexyl | 4-$CH_3$ | H |
| 3-119 | $CH_3$ | 4-$CH_3$ | S | O | H | H | H | H | 4-O | cyclohexyl | 4-$C_2H_5$ | H |
| 3-120 | $CH_3$ | 4-$CH_3$ | S | O | H | H | $CH_3$ | H | 4-O | cyclohexyl | 2-O-n-$C_3H_7$ | H |
| 3-121 | $CH_3$ | 5-$CH_3$ | O | O | H | H | H | H | 4-O | phenyl | 4-$SCH_3$ | H |

TABLE 3-continued

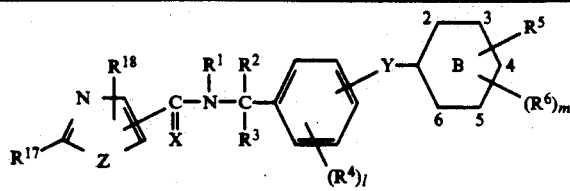

wherein the numbers 2-6 are to represent the positions of substitution.

| Compound No. | $R^{17}$ | $R^{18}$ | Z | X | $R^1$ | $R^2$ | $R^3$ | $(R^4)_l$ | Y | $R^5$ | $(R^6)_m$ |
|---|---|---|---|---|---|---|---|---|---|---|---|
| 3-122 | $CH_3$ | 4-$CH_3$ | O | O | H | H | H | H | 4-O | 4-cyclopropyl-phenyl | H |
| 3-123 | $CH_3$ | 4-$CH_3$ | O | O | H | H | H | H | 4-O | 3-$C_2H_5$-phenyl | H |
| 3-124 | $CH_3$ | 4-$CH_3$ | O | O | H | H | H | H | 4-O | 4-S—$CH_2CH=CH_2$-phenyl | H |
| 3-125 | $CH_3$ | 4-$CH_3$ | O | O | H | H | H | H | 4-O | 4-$N(CH_3)_2$-phenyl | H |
| 3-126 | $CH_3$ | 4-$CH_3$ | O | O | H | H | H | H | 4-O | 3,4-(O—$CH_2$—O)-phenyl | H |
| 3-127 | $CH_3$ | 4-$CH_3$ | O | O | H | H | H | H | 4-O | 3,4-(O—$CF_2$—O)-phenyl | H |
| 3-128 | $CH_3$ | 4-$CH_3$ | O | O | H | H | H | H | 4-N$CH_3$ | 4-$SCH_3$-phenyl | H |
| 3-129 | $CH_3$ | 4-$CH_3$ | O | O | H | H | H | H | 4-O | 4-NHCOCH$_3$-phenyl | H |
| 3-130 | $CH_3$ | 4-$CH_3$ | O | O | H | H | $CH_3$ | H | 4-O | 4-N=CHC$_2$H$_5$-phenyl | H |
| 3-131 | $CH_3$ | 4-$CH_3$ | O | O | H | H | H | H | 4-O | 4-N=CH—N(CH$_3$)$_2$-phenyl | H |
| 3-132 | $CH_3$ | 4-$CH_3$ | O | O | H | H | H | H | 4-O | 4-NHSO$_2$CH$_3$-phenyl | H |

TABLE 3-continued

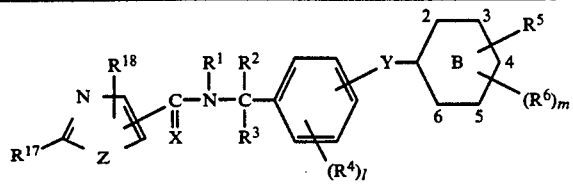

wherein the numbers 2-6 are to represent the positions of substitution.

| Compound No. | $R^{17}$ | $R^{18}$ | Z | X | $R^1$ | $R^2$ | $R^3$ | $(R^4)_l$ | Y | $R^5$ | $(R^6)_m$ |
|---|---|---|---|---|---|---|---|---|---|---|---|
| 3-133 | $CH_3$ | 4-$CH_3$ | O | O | H | H | H | H | 4-O | 3,4-(CH$_2$—CH(CH$_3$)—S-) | |
| 3-134 | $CH_3$ | 4-$CH_3$ | O | O | H | H | H | H | 4-O | 3,4-(CH$_2$—CH(CH$_3$)—O-) | |
| 3-135 | $CH_3$ | 4-$CH_3$ | O | O | H | H | H | H | 4-O | 3,4-(O—CH$_2$—CH$_2$—O-) | |
| 3-136 | $CH_3$ | 4-$CH_3$ | O | O | H | H | H | H | 4-O | 3,4-(O—CF$_2$—CF$_2$—O-) | |
| 3-137 | $CH_3$ | 4-$CH_3$ | O | O | H | H | H | H | 4-O | 3,4-(CH=CH—CH=CH-) | |
| 3-138 | $CH_3$ | 4-$CH_3$ | O | O | H | $CH_3$ | H | H | 4-O | 4-$SCH_3$ | 3-Cl |
| 3-139 | $CH_3$ | 4-$CH_3$ | O | O | H | $CH_3$ | H | H | 4-O | 4-$SCH_3$ | 2,5-$Cl_2$ |
| 3-140 | $CH_3$ | 4-$CH_3$ | O | O | H | $C_2H_5$ | H | H | 4-O | 4-$SCH_3$ | 3-Cl |
| 3-141 | $CH_3$ | 4-$CH_3$ | S | O | H | H | H | H | 4-O | 4-$OCF_2CF_2H$ | H |
| 3-142 | $CH_3$ | 4-$CH_3$ | O | O | H | H | H | H | 4-O | 3,4-(CH$_2$—CH$_2$—CH$_2$-) | |
| 3-143 | $CH_3$ | 4-$CH_3$ | O | O | H | H | H | H | 4-O | 4-n-$C_3H_7$ | H |

TABLE 3-continued

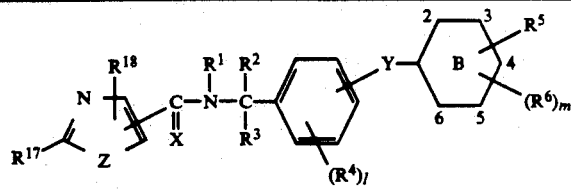

wherein the numbers 2–6 are to represent the positions of substitution.

| Compound No. | $R^{17}$ | $R^{18}$ | Z | X | $R^1$ | $R^2$ | $R^3$ | $(R^4)l$ | Y | B $R^5$ | $(R^6)_m$ |
|---|---|---|---|---|---|---|---|---|---|---|---|
| 3-144 | $CH_3$ | 4-$CH_3$ | S | O | H | $CH_3$ | H | H | 4-O | 4-$SCH_3$ | H |
| 3-145 | $CH_3$ | 4-$CH_3$ | S | O | H | $C_2H_5$ | H | H | 4-O | 4-$SCH_3$ | H |
| 3-146 | $CH_3$ | 4-$CH_3$ | O | O | H | H | H | H | 4-O | 3-Cl | 4-$SC_2H_5$ |

TABLE 4

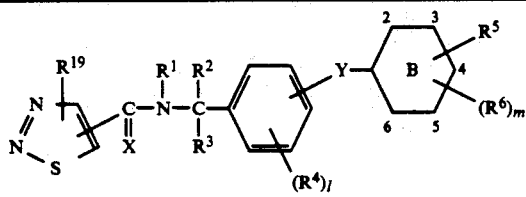

l wherein the numbers 2–6 are to represent the positions of substitutioin.

| Compound No. | $R^{19}$ | X | $R^1$ | $R^2$ | $R^3$ | $(R^4)l$ | Y | B $R^5$ | $(R^6)m$ |
|---|---|---|---|---|---|---|---|---|---|
| 4-1 | 4-$CH_3$ | O | H | H | H | H | 4-O | 4-$OCF_2CF_2H$ | H |
| 4-2 | 4-$CH_3$ | O | H | H | H | H | 4-O | 4-$SCH_3$ | H |
| 4-3 | 4-$CH_3$ | O | H | H | H | H | 4-O | 2-$CH_3$ | H |
| 4-4 | 4-$CH_3$ | O | H | H | H | H | 4-O | 4-$CH_3$ | H |

TABLE 4-continued

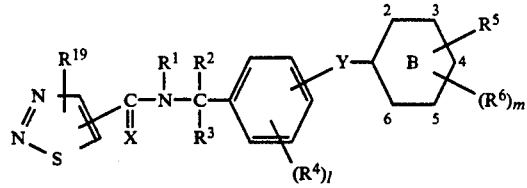

1 wherein the numbers 2-6 are to represent the positions of substitutioin.

| Compound No. | R¹⁹ | X | R¹ | R² | R³ | (R⁴)l | Y | B | R⁵ | (R⁶)m |
|---|---|---|---|---|---|---|---|---|---|---|
| 4-5 | 4-CH₃ | O | H | H | H | H | 4-O | phenyl | 4-C₂H₅ | H |
| 4-6 | 4-CH₃ | O | H | H | H | H | 4-O | phenyl | 4-n-C₃H₇ | H |
| 4-7 | 4-CH₃ | O | H | H | H | H | 4-O | phenyl | 4-Cl | H |
| 4-8 | 4-CH₃ | O | H | H | H | H | 4-O | phenyl | 2-Cl | 5-Cl |
| 4-9 | 4-CH₃ | O | H | H | H | H | 4-O | phenyl | 2-Cl | 4,5-Cl₂ |
| 4-10 | 4-CH₃ | O | H | H | H | H | 4-O | phenyl | 4-SC₂H₅ | H |
| 4-11 | 4-CH₃ | O | H | H | H | H | 4-O | phenyl | 4-OC₂H₅ | H |
| 4-12 | 4-CH₃ | O | H | H | H | H | 4-O | phenyl | 4-OCH₃ | H |
| 4-13 | 4-CH₃ | O | H | H | H | H | 4-O | phenyl | 4-SCF₂H | H |
| 4-14 | 4-CH₃ | O | H | H | H | H | 4-O | phenyl | 4-SCF₃ | H |
| 4-15 | 4-CH₃ | O | H | H | H | H | 4-O | phenyl | 4-SCF₂CF₂H | H |

TABLE 4-continued

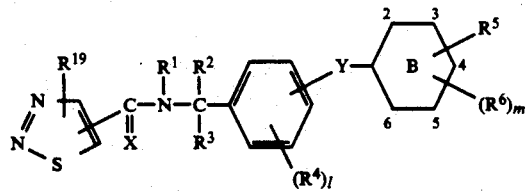

1 wherein the numbers 2–6 are to represent the positions of substitutioin.

| Compound No. | R¹⁹ | X | R¹ | R² | R³ | (R⁴)l | Y | B | R⁵ | (R⁶)m |
|---|---|---|---|---|---|---|---|---|---|---|
| 4-16 | 4-CH₃ | O | H | H | H | H | 4-O | phenyl | 4-SCH₂CH₂F | H |
| 4-17 | 4-CH₃ | O | H | H | H | H | 4-O | phenyl | 4-SCH₂CF₃ | H |
| 4-18 | 4-C₂H₅ | O | H | H | H | H | 4-O | phenyl | 4-SCH₃ | H |
| 4-19 | 4-H | O | H | H | H | H | 4-O | phenyl | 4-SCH₃ | H |
| 4-20 | 4-CH₃ | S | H | H | H | H | 4-O | phenyl | 4-SCH₃ | H |
| 4-21 | 4-CH₃ | O | CH₃ | H | H | H | 4-O | phenyl | 4-SCH₃ | H |
| 4-22 | 4-CH₃ | O | C₂H₅ | H | H | H | 4-O | phenyl | 4-SCH₃ | H |
| 4-23 | 4-CH₃ | O | i-C₃H₇ | H | H | H | 4-O | phenyl | 4-SCH₃ | H |
| 4-24 | 4-CH₃ | O | H | CH₃ | H | H | 4-O | phenyl | 4-OCF₂CF₂H | H |
| 4-25 | 4-CH₃ | O | H | CN | H | H | 4-O | phenyl | 4-OCF₂CF₂H | H |

TABLE 4-continued

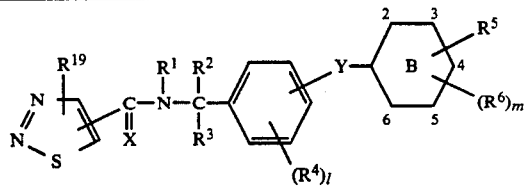

1 wherein the numbers 2-6 are to represent the positions of substitutioin.

| Compound No. | R[19] | X | R[1] | R[2] | R[3] | (R[4])l | Y | B | R[5] | (R[6])m |
|---|---|---|---|---|---|---|---|---|---|---|
| 4-26 | 4-$CH_3$ | O | H | $C_2H_5$ | H | H | 4-O | phenyl | 4-$OCF_2CF_2H$ | H |
| 4-27 | 4-$CH_3$ | O | H | i-$C_3H_7$ | H | H | 4-O | phenyl | 4-$OCF_2CF_2H$ | H |
| 4-28 | 4-$CH_3$ | O | H | $CH_3$ | $CH_3$ | H | 4-O | phenyl | 4-$OCF_2CF_2H$ | H |
| 4-29 | 4-$CH_3$ | O | H | H | H | 2-F | 4-O | phenyl | 4-$SCH_3$ | H |
| 4-30 | 4-$CH_3$ | O | H | H | H | 3-Cl | 4-O | phenyl | 4-$SCH_3$ | H |
| 4-31 | 4-$CH_3$ | O | H | H | H | 3-$CH_3$ | 4-O | phenyl | 4-$SCH_3$ | H |
| 4-32 | 4-$CH_3$ | O | H | H | H | H | 4-S | phenyl | 4-$SCH_3$ | H |
| 4-33 | 4-$CH_3$ | O | H | H | H | H | 3-O | phenyl | 4-$SCH_3$ | H |
| 4-34 | 4-$CH_3$ | O | H | H | H | H | 4-SO | phenyl | 4-$SCH_3$ | H |
| 4-35 | 4-$CH_3$ | O | H | H | H | H | 4-$SO_2$ | phenyl | 4-$SCH_3$ | H |
| 4-36 | 4-$CH_3$ | O | H | H | H | H | 4-$CH_2$ | phenyl | 4-$SCH_3$ | H |

TABLE 4-continued
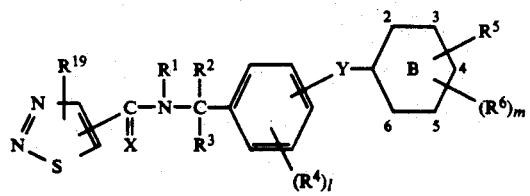
1 wherein the numbers 2-6 are to represent the positions of substitution.
| Compound No. | R19 | X | R1 | R2 | R3 | (R4)l | Y | B | R5 | (R6)m |
|---|---|---|---|---|---|---|---|---|---|---|
| 4-37 | 4-CH3 | O | H | H | H | H | 4-O | cyclohexyl (H) | 4-CH3 | H |
| 4-38 | 4-CH3 | O | H | H | H | H | 4-O | cyclohexyl (H) | 4-C2H5 | H |
| 4-39 | 4-CH3 | O | H | H | H | H | 4-O | cyclohexyl (H) | 2-O-n-C3H7 | H |
| 4-40 | 4-CH3 | O | H | H | H | H | 4-O | pyridyl | 4-CF3 | H |
| 4-41 | 4-CH3 | O | H | H | H | H | 4-O | pyridyl | 2-Cl | 4-CF3 |
| 4-42 | 4-CH3 | O | H | H | H | H | 4-O | phenyl | 4-SCH3 | 3-Cl |
| 4-43 | 4-CH3 | O | H | H | H | H | 4-O | phenyl | 4-SCH3 | 2,5-Cl2 |
| 4-44 | 4-CH3 | O | H | H | H | H | 4-O | phenyl | 4-S-n-C3H7 | H |
| 4-45 | 4-CH3 | O | H | H | H | H | 4-O | phenyl | 4-n-C4H9 | H |
| 4-46 | 4-CH3 | O | H | H | H | H | 4-O | phenyl | 4-O-n-C6H13 | H |

TABLE 4-continued

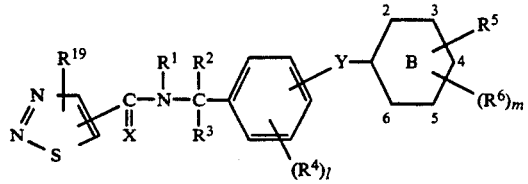

1 wherein the numbers 2-6 are to represent the positions of substitutioin.

| Compound No. | R[19] | X | R[1] | R[2] | R[3] | (R[4])l | Y | B | R[5] | (R[6])m |
|---|---|---|---|---|---|---|---|---|---|---|
| 4-47 | 4-CH$_3$ | O | H | H | H | H | 4-O | phenyl | 4-S-i-C$_3$H$_7$ | H |
| 4-48 | 4-CH$_3$ | O | H | H | H | H | 4-O | phenyl | 4-S-n-C$_4$H$_9$ | H |
| 4-49 | 4-CH$_3$ | O | H | H | H | H | 4-O | phenyl | 4-S-n-C$_6$H$_{13}$ | H |
| 4-50 | 4-CH$_3$ | O | H | H | H | H | 4-O | phenyl | 4-NHC$_2$H$_5$ | H |
| 4-51 | 4-CH$_3$ | O | H | H | H | H | 4-O | phenyl | 4-SC$_2$H$_5$ | 3-Cl |
| 4-52 | 4-CH$_3$ | O | H | CH$_3$ | CH$_3$ | H | 4-O | phenyl | 4-SCH$_3$ | H |
| 4-53 | 4-CH$_3$ | O | H | CH$_3$ | H | H | 4-O | phenyl | 4-SCH$_3$ | H |
| 4-54 | 4-CH$_3$ | O | H | C$_2$H$_5$ | H | H | 4-O | phenyl | 4-SCH$_3$ | H |
| 4-55 | 4-CH$_3$ | O | H | i-C$_3$H$_7$ | H | H | 4-O | phenyl | 4-SCH$_3$ | H |
| 4-56 | 4-CH$_3$ | O | CH$_3$ | H | H | H | 4-O | phenyl | 4-SCH$_3$ | H |
| 4-57 | 4-CH$_3$ | O | H | CN | H | H | 4-O | phenyl | 4-SCH$_3$ | H |

TABLE 4-continued

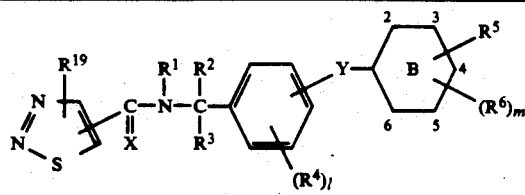

wherein the numbers 2-6 are to represent the positions of substitutioin.

| Compound No. | $R^{19}$ | X | $R^1$ | $R^2$ | $R^3$ | $(R^4)l$ | Y | B | $R^5$ | $(R^6)m$ |
|---|---|---|---|---|---|---|---|---|---|---|
| 4-58 | 4-$CH_3$ | S | H | H | H | H | 4-O | phenyl | 4-$OC_2H_5$ | H |
| 4-59 | 5-$CH_3$ | O | H | H | H | H | 4-O | phenyl | 4-$SCH_3$ | H |

TABLE 5

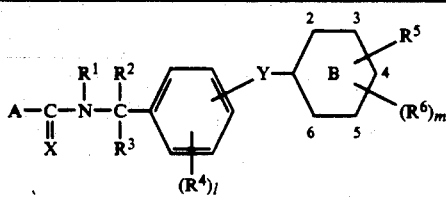

wherein the numbers 2-6 are to represent the positions of substitutioin.

$G^1$ to $G^8$ in Table 5 are, respectively, as follows;

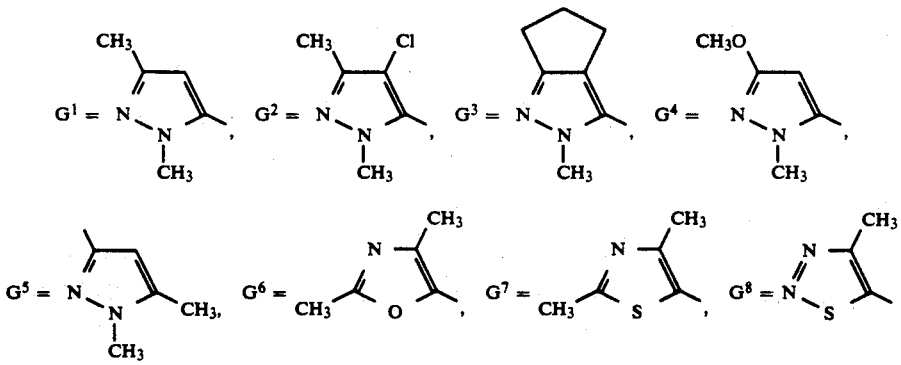

| Compound No. | A | X | $R^1$ | $R^2$ | $R^3$ | $(R^4)l$ | Y | B | $R^5$ | $(R^6)m$ |
|---|---|---|---|---|---|---|---|---|---|---|
| 5-1 | $G^1$ | O | $-S-N(CH_3)-CO_2CH_3$ | H | H | H | 4-O | phenyl | 4-$SCH_3$ | H |
| 5-2 | $G^1$ | O | $-S-N(CH_3)-CO_2C_2H_5$ | H | H | H | 4-O | phenyl | 4-$SCH_3$ | H |

TABLE 5-continued

| | | | | | | | | | |
|---|---|---|---|---|---|---|---|---|---|
| 5-3 | G¹ | O | —S—N(CH₃)—CO₂-n-C₄H₉ | H | H | H | 4-O | 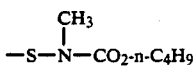 | 4-SCH₃ | H |
| 5-4 | G¹ | O | —S—N(CH₃)—CO₂—CH₂CH₂OCH₃ | H | H | H | 4-O | 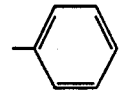 | 4-SCH₃ | H |
| 5-5 | G¹ | O | —S—N(CH₃)—CO₂—CH₂CH₂F | H | H | H | 4-O | 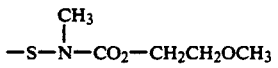 | 4-SCH₃ | H |
| 5-6 | G¹ | O | —S—N(CH₃)—CO₂—CH₂CF₃ | H | H | H | 4-O | 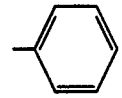 | 4-SCH₃ | H |
| 5-7 | G¹ | O | —S—N(CH₃)—CO₂—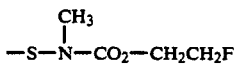 | H | H | H | 4-O | 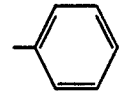 | 4-SCH₃ | H |
| 5-8 | G¹ | O | —S—N(CH₂C₆H₅)—CO₂CH₃ | H | H | H | 4-O | 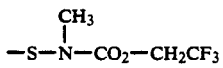 | 4-SCH₃ | H |
| 5-9 | G¹ | O | —S—N(CH₃)—C₂H₄CO₂C₂H₅ | H | H | H | 4-O | 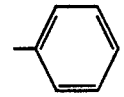 | 4-SCH₃ | H |
| 5-10 | G¹ | O | —S—N(CH(CH₃)₂)—C₂H₄CO₂C₂H₅ | H | H | H | 4-O | 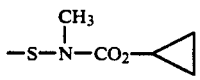 | 4-SCH₃ | H |
| 5-11 | G¹ | O | —S—N(C₆H₅)—C₂H₄CO₂C₂H₅ | H | H | H | 4-O | 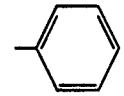 | 4-SCH₃ | H |
| 5-12 | G¹ | O | —S—N(CH₃)—C₂H₄CO₂-n-C₄H₉ | H | H | H | 4-O | 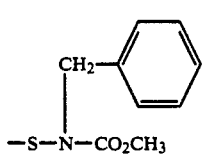 | 4-SCH₃ | H |
| 5-13 | G¹ | O | —S—N(n-C₄H₉)₂ | H | H | H | 4-O | 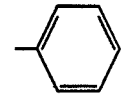 | 4-SCH₃ | H |
| 5-14 | G¹ | O | —S—N(piperidinyl) | H | H | H | 4-O | 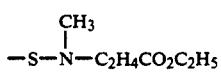 | 4-SCH₃ | H |
| 5-15 | G¹ | O | —S—N(morpholinyl) | H | H | H | 4-O | 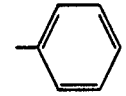 | 4-SCH₃ | H |

TABLE 5-continued
| | | | | | | | | | |
|---|---|---|---|---|---|---|---|---|---|
| 5-16 | G¹ | O | —S(O)—N(n-C₄H₉)₂ | H | H | H | 4-O |  4-SCH₃ | H |
| 5-17 | G¹ | O | —S(O)₂—N(n-C₄H₉)₂ | H | H | H | 4-O | 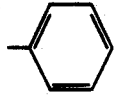 4-SCH₃ | H |
| 5-18 | G¹ | O | —S-n-C₄H₉ | H | H | H | 4-O |  4-SCH₃ | H |
| 5-19 | G¹ | O | —S—⟨C₆H₄⟩—Cl | H | H | H | 4-O |  4-SCH₃ | H |
| 5-20 | G¹ | O | —S—CH₂—⟨C₆H₅⟩ | H | H | H | 4-O | 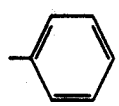 4-SCH₃ | H |
| 5-21 | G¹ | O | —C(O)—CH₃ | H | H | H | 4-O | 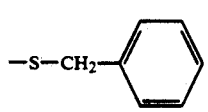 4-SCH₃ | H |
| 5-22 | G¹ | O | —C(O)—C₂H₅ | H | H | H | 4-O | 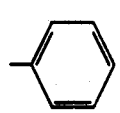 4-SCH₃ | H |
| 5-23 | G¹ | O | —C(O)-n-C₄H₉ | H | H | H | 4-O | 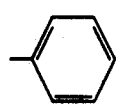 4-SCH₃ | H |
| 5-24 | G¹ | O | —C(O)-n-C₆H₁₃ | H | H | H | 4-O | 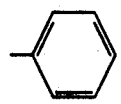 4-SCH₃ | H |
| 5-25 | G² | O | —S—N(CH₃)—CO₂C₂H₅ | H | H | H | 4-O | 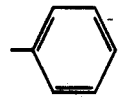 4-SCH₃ | H |
| 5-26 | G³ | O | —S—N(CH₃)—CO₂C₂H₅ | H | H | H | 4-O | 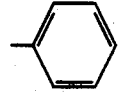 4-SCH₃ | H |
| 5-27 | G⁴ | O | —S—N(CH₃)—CO₂C₂H₅ | H | H | H | 4-O | 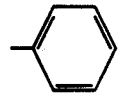 4-SCH₃ | H |
| 5-28 | G⁵ | O | —S—N(CH₃)—CO₂C₂H₅ | H | H | H | 4-O | 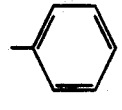 4-SCH₃ | H |

TABLE 5-continued

| | | | | | | | | | | |
|---|---|---|---|---|---|---|---|---|---|---|
| 5-29 | G⁶ | O | CH₃<br>−S−N−CO₂C₂H₅ | H | H | H | 4-O | 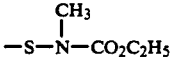 | 4-SCH₃ | H |
| 5-30 | G⁷ | O | CH₃<br>−S−N−CO₂C₂H₅ | H | H | H | 4-O | 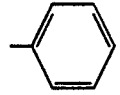 | 4-SCH₃ | H |
| 5-31 | G⁸ | O | CH₃<br>−S−N−CO₂C₂H₅ | H | H | H | 4-O | 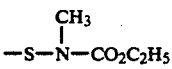 | 4-SCH₃ | H |
| 5-32 | G¹ | O | CH₃<br>−S−N−CO₂C₂H₅ | H | H | H | 4-O | 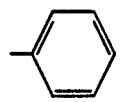 | 4-SC₂H₅ | H |
| 5-33 | G¹ | O | CH₃<br>−S−N−CO₂C₂H₅ | H | H | H | 4-O | 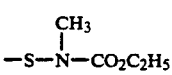 | 4-S-n-C₃H₇ | H |
| 5-34 | G¹ | O | CH₃<br>−S−N−CO₂C₂H₅ | H | H | H | 4-O | 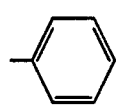 | 4-SCF₂H | H |
| 5-35 | G¹ | O | CH₃<br>−S−N−CO₂C₂H₅ | H | H | H | 4-O | 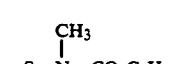 | 4-SCF₃ | H |
| 5-36 | G¹ | O | CH₃<br>−S−N−CO₂C₂H₅ | H | H | H | 4-O | 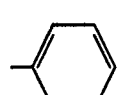 | 4-SCF₂CF₂H | H |
| 5-37 | G¹ | O | CH₃<br>−S−N−CO₂C₂H₅ | H | H | H | 4-O | 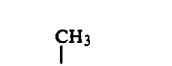 | 3-Cl | 4-SCH₃ |
| 5-38 | G¹ | O | CH₃<br>−S−N−CO₂C₂H₅ | H | H | H | 4-O | 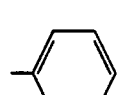 | 4-SCH₃ | 2,5-Cl₂ |
| 5-39 | G¹ | O | CH₃<br>−S−N−CO₂C₂H₅ | H | H | H | 4-O | 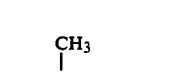 | 3-Br | 4-SCH₃ |
| 5-40 | G¹ | O | CH₃<br>−S−N−CO₂C₂H₅ | H | H | H | 4-O | 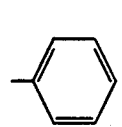 | 3-F | 4-SCH₃ |
| 5-41 | G¹ | O | CH₃<br>−S−N−CO₂C₂H₅ | CH₃ | H | H | 4-O | 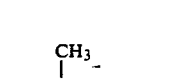 | 4-SCH₃ | H |

TABLE 5-continued

| No. | | | | | | | | | |
|---|---|---|---|---|---|---|---|---|---|
| 5-42 | G¹ | O | —S—N(CH₃)—CO₂C₂H₅ | CH₃ | H | H | 4-O | 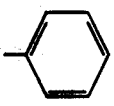 | 4-SC₂H₅ | H |
| 5-43 | G¹ | O | —S—N(CH₃)—CO₂C₂H₅ | C₂H₅ | H | H | 4-O | 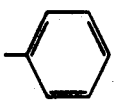 | 4-SCH₃ | H |
| 5-44 | G¹ | O | —S—N(CH₃)—CO₂C₂H₅ | C₂H₅ | H | H | 4-O | 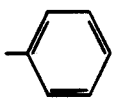 | 4-SC₂H₅ | H |
| 5-45 | G² | O | —S—N(CH(CH₃)₂)—C₂H₄CO₂C₂H₅ | H | H | H | 4-O | 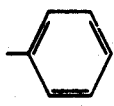 | 4-SCH₃ | H |
| 5-46 | G² | O | —S—N(CH(CH₃)₂)—C₂H₄CO₂C₂H₅ | H | H | H | 4-O | 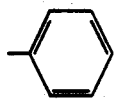 | 4-SC₂H₅ | H |
| 5-47 | G² | O | —S—N(CH(CH₃)₂)—C₂H₄CO₂C₂H₅ | H | H | H | 4-O | 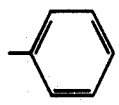 | 3-Cl | 4-SCH₃ |
| 5-48 | G² | O | —S—N(CH(CH₃)₂)—C₂H₄CO₂C₂H₅ | H | H | H | 4-O | 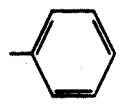 | 3-Cl | 4-SC₂H₅ |
| 5-49 | G² | O | —S—N(CH(CH₃)₂)—C₂H₄CO₂C₂H₅ | H | H | H | 4-O | 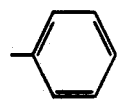 | 4-SCH₃ | 2,5-Cl₂ |
| 5-50 | G³ | O | —S—N(CH(CH₃)₂)—C₂H₄CO₂C₂H₅ | H | H | H | 4-O | 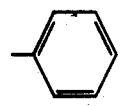 | 4-SCH₃ | H |
| 5-51 | G³ | O | —S—N(CH(CH₃)₂)—C₂H₄CO₂C₂H₅ | H | H | H | 4-O | 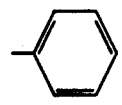 | 4-SC₂H₅ | H |
| 5-52 | G² | O | —S—N(morpholino) | H | H | H | 4-O | 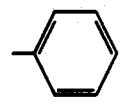 | 4-SCH₃ | H |
| 5-53 | G² | O | —S—N-(n-C₄H₉)₂ | H | H | H | 4-O | 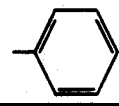 | 4-SCH₃ | H |

When the compound of the present invention is used as an active ingredient of the insecticidal, acaricidal composition, it may be used as it is without any addition of other ingredients, but usually, it is used in the formulations such as oil formulations, emulsifiable concentrates, wettable powders, flowable formulations, granules, dusts, aerosols and poisonous baits by mixing it with solid carriers, liquid carriers, gaseous carriers, baits or the like, and if necessary, by adding thereto surface active agents and/or other adjuvants for the formulation.

These formulations usually contain the present compound as the active ingredient in an amount of from 0.01% to 95% by weight.

The solid carriers usable in the formulations include, for example, clays (such as kaolin clay, diatomaceous earth, synthetic hydrated silicon dioxide, bentonite, Fubasami clay and acid clay), talcs, ceramics, other inorganic minerals (such as sericite, quartz, sulfur, activated carbon, calcium carbonate and hydrated silica), chemical fertilizers (such as ammonium sulfate, ammonium phosphate, ammonium nitrate, urea fertilizer and ammonium chloride), and the like, each in the form of fine powders or granules. The liquid carriers include, for example, water, alcohols (such as methanol and ethanol), ketones (such as acetone and methyl ethyl ketone), aromatic hydrocarbons (such as benzene, toluene, xylene, ethylbenzene and methylnaphthalene), aliphatic hydrocarbons (such as hexane, cyclohexane, kerosene and gas oil), esters (such as ethyl acetate and butyl acetate), nitriles (such as acetonitrile and isobutyronitrile), ethers (such as diisopropyl ether and dioxane), acid amides (such as N,N-dimethylformamide and N,N-dimethylacetamide), halogenated hydrocarbons (such as dichloromethane, trichloroethane and carbon tetrachloride), dimethyl sulfoxide, vegetable oils such as soybean oil and cotton seed oil, and the like. The gaseous carriers, i.e. propellants, include, for example, Flon gas, butane gas, LPG (liquified petroleum gas), dimethyl ether, carbon dioxide gas, and the like.

The surface active agents usable for the emulsification, dispersion, wetting and the like include, for example, anionic surface active agents such as the salts of alkyl sulfates, the salts of alkyl(aryl)sulfonic acids, the salts of dialkyl sulfosuccinates, the salts of polyoxyethylene alkylaryl ether phosphates and naphthalenesulfonic acid/formaldehyde condensates, and nonionic surface active agents such as polyoxyethylene alkyl ethers, polyoxyethylene polyoxypropylene block copolymers, sorbitan fatty acid esters and polyoxyethylene sorbitan fatty acid esters.

As to the adjuvants for the formulation, the stickers and dispersing agents include, for example, casein, gelatin, polysaccharides (such as starch powder, gum arabic, cellulose derivatives and alginic acid), lignin derivatives, bentonite, saccharides, synthetic water-soluble polymers (such as polyvinyl alcohol, polyvinyl pyrrolidone and polyacrylic acids) and the like. The stabilizers include, for example, PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters, and the like.

The substrates for the poisonous baits include, for example, bait components such as grain powders, vegetable essential oils, saccharides and crystalline cellulose, antioxidants such as dibutylhydroxytoluene and nordihydroguaiaretic acid, preservatives such as dehydroacetic acid, mis-eating inhibitors such as red pepper powders, attractive perfumes such as cheese perfume and onion perfume, and the like.

The flowable formulations (suspension in water or emulsion in water) are prepared, in general, by finely dispersing 1 to 75% of the active compound into water containing 0.5 to 15% of a dispersing agent, 0.1 to 10% of a dispersing auxiliary (such as protective colloids and compounds capable of giving thixotropy) and 0 to 10% of a suitable adjuvant (such as deforming agents, anticorrosives, stabilizers, spreaders, penetration auxiliaries, antifreezing agents, antibacterial agents and antimolding agents). It is also possible to prepare the suspension in oil by using an oil scarcely dissolving the active compound in place of the water. The protective colloids include, for example, gelatin, casein, gums, cellulose ethers, polyvinyl alcohol and the like, and the compounds capable of giving thixotropy include, for example, bentonite, aluminum magnesium silicate, xanthan gum, polyacrylic acid and the like.

The formulations thus obtained can be used directly or after diluted with a diluent such as water. Alternatively, they can be used as a mixture with any other agent such as insecticides, acaricides, nematocides, soil-pest controlling agents, insect pest controlling agents, fungicides, herbicides, plant growth regulators, synergists, fertilizers and soil improvers, and also can be used simultaneously with any of these agents without mixing.

When the compound of the present invention is used as the active ingredient of the insecticidal, acaricidal compositions for agricultural use, the dosage rate of the active ingredient is usually from 1 g to 1000 g per 10 ares. The emulsifiable concentrates, wettable powders, flowable formulations and the like may be diluted with water at the usage, and their application concentration is from 10 ppm to 1000 ppm as the concentration of the active ingredient. The granules, dusts and the like are normally applied as they are without any dilution. When the insecticidal, acaricidal compositions are use for the household use or public hygiene, the emulsifiable concentrates, wettable powders, flowable formulations and the like are applied by diluting them with water to a concentration of the active ingredient of from 0.1 ppm to 1000 ppm, while the oil formulations, aerosols, misting agents, poisonous baits and the like are applied as they are.

Since the dosage rate and the application concentration possibly vary with any situations such as the kind of formulations, the seasons, place and manner of the application, the kind of pests, and the degree of damage, they may be increased or decreased irrespective of the above-mentioned ranges.

The present invention will more fully be described by referring production examples, as well as formulation examples and test examples, which are, however, not to limit the present invention.

First, the production examples will be illustrated.

PRODUCTION EXAMPLE 1

Preparation of the Compound (1-547)

To a stirred mixture of 4-[4-(1,1,2,2-tetrafluoroethoxy)phenoxy]benzylamine (359 mg, 1.14 mM), triethylamine (136 mg, 1.35 mM) and toluene (20 ml) was added dropwise a solution (10 ml) of 4-chloro-1,3-dimethylpyrazole-5-carbonyl chloride (200 mg, 1.04 mM) in toluene at 0°–10° C., and the mixture was stirred for 3 h at room temperature. The mixture was poured into ice water, and the mixture was extracted with toluene. The extract was washed with saturated sodium hydrogen carbonate solution, saturated ammonium chloride solution and brine, dried with magnesium sulfate, and concentrated in vacuo. The residue was chromatographed over silica gel to give N-{4-[1,1,2,2,-tetrafluoroethoxy)-phenoxy]benzyl}-4-chloro-1,3-dimethylpyrazole-5-carboxamide (420 mg, 86%) as colorless crystals, m.p. 101.3° C.

PRODUCTION EXAMPLE 2

Preparation of the Compound (4-2)

In the same manner, 4-methyl-1,2,3-thiadiazole-5-carbonyl chloride (200 mg, 1.23 mM), 4-(4-methylthiophenoxy)benzylamine (302 mg, 1.23 mM) and triethylamine (137 mg, 1.35 mM) yielded N-[4-(4-methylthiophenoxy)benzyl]-4-methyl-1,2,3-thiadiazole-5-carboxamide (297 mg, 65%) as a colorless oil, $n_D^{22.6}$ 1.6212.

PRODUCTION EXAMPLE 3

Preparation of the Compound (3-23)

To a stirred mixture of 2,4-dimethyl-1,3-oxazole-5-carboxylic acid (155 mg, 1.1 mM) and dichloromethane (20 ml) was added 1,3-dicyclohexylcarbodiimide (227 mg, 1.1 mM) at 0°-10° C., and the mixture was stirred for 30 min at the same temperature. To this was added dropwise a solution (10 ml) of 4-(4-ethylthiophenoxy)benzylamine (285 mg, 1.1 mM) in dichloromethane, and the mixture was stirred for 12 h at room temperature. The mixture was poured into ice water, and the mixture was extracted with dichloromethane. The extract was washed with saturated ammonium chloride solution and brine, dried with magnesium sulfate, and concentrated in vacuo. The residue was chromatographed over silica gel to give N-[4-(4-ethylthiophenoxy)benzyl]-2,4-dimethyl-1,3-oxazole-5-carboxamide (164 mg, 39%) as colorless crystals, m.p. 60.0°-64.5° C.

PRODUCTION EXAMPLE 4

Preparation of the Compound (3-17)

To a stirred mixture of 4-[4-(1,1,2,2-tetrafluoroethoxy)phenoxy]benzylamine (378 mg, 1.2 mM) and dry tetrahydrofurane (20 ml) was added 2,4-dimethyl-5-(1-imidazolylcarbonyl)-1,3-oxazole (229 mg, 1.2 mM) at 0°-10° C., and the mixture was stirred for 1 h at room temperature, and the mixture was concentrated in vacuo. To the residue was added water, and the mixture was extracted with ethyl acetate. The extract was washed with water(x2), dried with magnesium sulfate and concentrated in vacuo.

The residue was chromatographed over silica gel to give N-{4-[4-(1,1,2,2-tetrafluoroethoxy)phenoxy]-benzyl}-2,4-dimethyl-1,3-oxazole-5-carboxamide (399 mg, 68%) as a colorless oil, $n_D^{24.8}$ 1.5310.

PRODUCTION EXAMPLE 5

Preparation of the Compound (3-109)

In the same manner, 4-(4-n-butylphenoxy)benzylamine (307 mg, 1.2 mM) and 2,4-dimethyl-5-(1-imidazolylcarbonyl)-1,3-thiazole (249 mg, 1.2 mM) yielded N-[4-(4-n-butylphenoxy)benzyl]-2,4-dimethyl-1,3-thiazole-5-carboxamide (336 mg, 71%) as colorless crystals, m.p. 77°-79° C.

PRODUCTION EXAMPLE 6

Preparation of the Compound (2-196)

To a stirred mixture of 4-(4-methylthiophenoxy)benzylamine (124 mg, 0.505 mM), triethylamine (61 mg, 0.60 mM) and toluene (20 ml) was added dropwise a solution (10 ml) of 2,5-dimethylcyclopenta[1,2-c]pyrazole-3-carbonyl chloride(100 mg, 0.503 mM) in toluene at 0°-10° C., and the mixture was stirred for 3 h at the room temperature. The mixture was poured into ice water, and the mixture was extracted with toluene. The extract was washed with saturated sodium hydrogen carbonate solution, water, saturated ammonium chloride solution and brine, dried with magnesium sulfate, and concentrated in vacuo. The residue was chromatographed over silica gel to give N-[4-(4-methylthiophenoxy)benzyl]-2,5-dimethylcyclopenta[1,2-c]pyrazole-3-carboxamide (138 mg, 67%) as colorless crystals, m.p. 138.0° C.

PRODUCTION EXAMPLE 7

Preparation of the Compound (3-108)

To a stirred mixture of 2,4-dimethyl-1,3-thiazole-5-carboxylic acid (156 mg, 0.993 mM) and chloroform (20 ml) was added 1-ethyl-3-(3-dimethylaminopropyl)carbodiimde (190 mg, 0.393 mM) at 0°-10° C., and the mixture was stirred for 30 min at the same temperature. To this was added a solution (10 ml) of 4-(4-ethoxyphenoxy)benzylamine (242 mg, 0.993 mM) in chloroform at 0°-10° C., and the mixture was stirred for 12 h at the room temperature. The mixture was poured into ice water, and the mixture was extracted with chloroform. The extract was washed with saturated ammonium chloride solution and brine, dried with magnesium sulfate, and concentrated in vacuo. The residue was chromatographed over silica gel to give N-[4-(4-ethoxyphenoxy)benzyl]-2,4-dimethyl-1,3-thiazole-5-carboxamide (171 mg, 45%) as colorless crystals, m.p. 99°-101° C.

PRODUCTION EXAMPLE 8

Preparation of the Compound (1-711)

In the same manner, 4-chloro-1,3-dimethylpyrazole-5-carboxylic acid (182 mg, 1.04 mM), 1-ethyl-3-(3-dimethylaminopropyl)carbodiimide (200 mg, 1.04 mM) and 4-(3-bromo-4-methylthiophenoxy)benzylamine (304 mg, 1.04 mM) yielded N-[4-(3-bromo-4-methylthiophenoxy)benzyl]-4-chloro-1,3-dimethylpyrazole-5-carboxamide (219 mg, 47%) as colorless crystals, m.p. 117°-119° C.

PRODUCTION EXAMPLE 9

Preparation of the Compound (5-53)

To a stirred mixture of N̄-[4-(4-methylthiophenoxy)benzyl]-4-chloro-1,3-dimethylpyrazole-5-carboxamide (300 mg, 0.746 mM), 4-(N,N-dimethylamino)pyridine (119 mg, 0.970 mM) and dry pyridine (5 ml) was added dropwise N,N-di-n-butylaminosulfenyl chloride (190 mg, 0.970 mM) at 0°-10° C., and the mixture was stirred for 4 h at the room temperature. The mixture was poured into ice water, and the mixture was extracted with dichloromethane. The extract was washed with saturated ammonium chloride solution(x2) and brine, dried with sodium sulfate, and concentrated in vacuo. The residue was chromatographed over silica gel to give N-(N,N-di-n-butylaminosulfenyl)-N-[4-(4-methylthiophenoxy)benzyl]4-chloro-1,3-dimethylpyrazole-5-carboxamide (217 mg, 52%) as a colorless oil, $n_D^{23.3}$ 1.5748.

PRODUCTION EXAMPLE 10

Preparation of 4-(3-bromo-4-methylthiophenoxy)benzylamine

To a stirred mixture of lithium aluminum hydride (2.37 g, 62.5 mM) and dry tetrahydrofurane (200 ml) was added dropwise a solution(50 ml) of 4-(3-bromo-4-methylthiophenoxy)benzonitrile (10 g, 31 mM) in dry tetrahydrofurane at 0°-10° C., and the mixture was stirred for 1 day at the room temperature. To this was added tetrahydrofurane (100 ml) and added dropwise water (10 ml) at 0°-10° C. To the mixture was added sodium sulfate (100 g), and the mixture was stirred for 30 min at room temperature. The mixture was filtered through celite, and the filtrate was concentrated in vacuo to give 4-(3-bromo-4-methylthiohenoxy)benzylamine (9.82 g, 97%) as colorless crystals, m.p. 75.3° C.

PRODUCTION EXAMPLE 11

4-(3,5-dimethyl-4-methylthiophenoxy)benzonitrile

To a stirred mixture of sodium hydride (1.22 g, 50.9 mM) and dry N,N-dimethylformamide (200 ml) was added a solution (50 ml) of 3,5-dimethyl-4-(methylthio)-phenol (9.34 g, 55.5 mM) in dry N,N-dimethylformamide at room temperature, and the mixture was stirred for 30 min at the same temperature. To this was added 4-chlorobenzonitrile (6.37 g, 46.3 mM) and copper(I) chloride (0.5 g), and the mixture was stirred for 12 h at 140°-150° C. The mixture was cooled to the room temperature and this was poured into ice water (500 ml). The mixture was extracted with toluene, and the extract was washed with 5N aq NaOH, water, saturated ammonium chloride solution, water and brine, dried with magnesium sulfate, and concentrated in vacuo. The residue was chromatographed over silica gel to give 4-(3,5-dimethyl-4-methylthiophenoxy)benzonitrile (13.03 g, 87%) as colorless crystals, m.p. 71.8° C.

PRODUCTION EXAMPLE 12

Preparation of 4-(4-methylthiophenoxy)propiophenone

To a stirred mixture of sodium hydride (1.57 g, 65.3 mM) and dry N,N-dimethylformamide (200 ml) was added dropwise a solution (50 ml) of 4-(methylthio)-phenol (71.3 mM) in dry N,N-dimethylformamide at room temperature, and the mixture was stirred for 30 min at the same temperature. To this was added 4-bromoacetophenone dimethylacetal (15.4 g, 59.4 mM) and copper(I) chloride (0.5 g) and the mixture was stirred for 12 h at 140°-150° C. The mixture was cooled to room temperature and poured into water, and the mixture was extracted with toluene. The extract was washed with 5N-NaOH, water, saturated ammonium chloride solution, water and brine, and this was dried with magnesium sulfate and concentrated in vacuo. The residue was chromatographed over alumina to give 4-(4-methylthiophenoxy)propiophenone dimethylacetal (10.8 g, 57%). To this (5.00 g, 15.7 mM) was added methanol (200 ml), water (50 ml) and 2N-H$_2$SO$_4$, and the mixture was stirred for 5 h under reflux. The mixture was concentrated in vacuo, and the residue was diluted with water. The mixture was extracted with ether, and the extract was washed with saturated sodium hydrogen carbonate solution, water and brine, dried with sodium sulfate and concentrated in vacuo.

The residue was chromatographed over silica gel to give 4-(4-methylthiophenoxy)propiophenone (2.60 g, 61%) as colorless crystals, m.p. 69.4° C.

PRODUCTION EXAMPLE 13

Preparation of Ethyl 4-(4-methylthiophenoxy)benzoate

The mixture of 4-bromothioanisole (10.0 g, 49.2 mM), ethyl 4-hydroxybenzoate (8.17 g, 49.2 mM), potassium carbonate (6.80 g, 49.2 mM), copper (0.5 g) and xylene (300 ml) was stirred for 24 h under reflux. The mixture was cooled to the room temperature and poured into water. The mixture was filtered through celite, and the toluene solution was washed with water and brine, dried with magnesium sulfate, and concentrated in vacuo. The residue was chromatographed over silica gel to give ethyl 4-(4-methylthiophenoxy)benzoate (4.86 g, 36%) as colorless crystals, m.p. 46.4° C.

PRODUCTION EXAMPLE 14

Preparation of 4-(4-methylthiophenoxy)benzyl alcohol

To a stirred mixture of lithium aluminum hydride (0.55 g, 14.6 mM) and dry tetrahydrofurane (100 ml) was added a solution (30 ml) of ethyl 4-(4-methylthiophenoxy)benzoate (4.00 g, 14.6 mM) in dry tetrahydrofurane at 0°-10° C., and the mixture was stirred for 12 h at room temperature. To this was added 10% HCl (200 ml) and the mixture was extracted with toluene. The extract was washed with saturated sodium hydrogen carbonate solution and brine, dried with magnesium sulfate, and concentrated in vacuo. The residue was chromatographed over silica gel to give 4-(4-methylthiophenoxy)benzyl alcohol (3.13 g, 87%) as colorless crystals, m.p. 103.3° C.

PRODUCTION EXAMPLE 15

Preparation of 4-(4-methylthiophenoxy)benzyl bromide

To a stirred mixture of phosphorus tribromide (1.20 g, 4.43 mM) and dry ether (100 ml) was added a solution (20 ml) of 4-(4-methylthiophenoxy)benzyl alcohol (3.00 g, 12.1 mM) in dry ether at the room temperature, and the mixture was stirred for 12 h at the same temperature. The mixture was poured into ice water, and the mixture was extracted with ether. The extract was washed with saturated sodium hydrogen carbonate solution and brine, dried with magnesium sulfate, and concentrated in vacuo to give 4-(4-methylthiophenoxy)benzyl bromide (2.39 g, 64%) as colorless crystals, m.p.32.9° C.

PRODUCTION EXAMPLE 16

Preparation of 4-(4-methylthiophenoxy)benzylamine

To a stirred mixture of 28% aq NH$_3$ (40 ml) and methanol (200 ml) was added dropwise a solution (20 ml) of 4-(4-methylthiophenoxy)benzylbromide (5.00 g, 16.2 mM) in methanol at room temperature, and the mixture was stirred for 4 days at the same temperature. To the mixture was added water (100 ml), and the mixture was concentrated in vacuo. The residue was diluted with chloroform, and the mixture was washed with water and brine, dried with sodium sulfate, and concentrated in vacuo. The residue was chromatographed over alumina to give 4-(4-methylthiophenoxy)-benzylamine (2.11 g, 53%) as colorless crystals, m.p. 61.8° C.

PRODUCTION EXAMPLE 17

Preparation of 4-(4-methylthiophenoxy)benzylamine

To a stirred mixture of potassium phthalimide (3.60 g, 19.4 mM) and dry N,N-dimethylformamide (200 ml) was added dropwise a solution of 4-(4-methylthiophenoxy)benzylbromide (5.00 g, 16.2 mM) in dry N,N-dimethylformamide at room temperature, the mixture was stirred for 5 h at the same temperature. The mixture was poured into water, and the mixture was extracted with toluene. The extract was washed with 5N NaOH, water and brine, dried with magnesium sulfate, and concentrated in vacuo. The residue was diluted with methanol (200 ml), and to the mixture was added dropwise hydrazine monohydrate (1.10 g, 21.1 mM). The mixture was stirred for 6 h under reflux, and this was cooled to the room temperature and concentrated in vacuo. The residue was diluted with chloroform and the mixture was filtered through celite. The filtrate was washed with 5N NaOH(x3) and brine(x2), dried with potassium carbonate, and concentrated in vacuo to give 4-(4-methylthiophenoxy)benzylamine (3.02 g, 76%) as colorless crystals, m.p. 61.8° C.

PRODUCTION EXAMPLE 18

Preparation of 1-[4-(4-methylthiophenoxy)phenyl]propylamine

A mixture of 4-(4-methylthiopheoxy)propiophenone (9.00 g, 33 mM), ammonium acetate (50.9 g, 660 mM), NaBH$_3$CN (2.10 g, 33 mM) and dry methanol (300 ml) was stirred for 3 days at room temperature under nitrogen. To the mixture was added c.HCl until pH <2, and concentrated in vacuo. To the residue was added water (200 ml) and ether (200 ml), and the mixture was stirred for 10 min. To the separated aqueous phase was added solid KOH until pH >10, and the mixture was saturated with NaCl. The mixture was extracted with ether, and the extract was dried with sodium sulfate and concentrated in vacuo to give 1-[4-(4-methylthiophenoxy)-phenyl]propylamine (7.60 g, 84%) as a colorless oil, $n_D^{24.0}$ 1.6027.

In Table 6, there are shown some compounds of the present invention prepared according to the process or substantially the same procedure in the Production Examples 1 to 9. The compound numbers are according to those described in Table 1 to 5.

TABLE 6

| Compound | Physical Property |
|---|---|
| 1-1 | $n_D^{22.1}$ 1.5819 |
| 1-2 | $n_D^{22.2}$ 1.5779 |
| 1-3 | $n_D^{23.0}$ 1.5698 |
| 1-4 | $n_D^{24.4}$ 1.5686 |
| 1-5 | $n_D^{22.0}$ 1.5647 |
| 1-6 | $n_D^{24.8}$ 1.5702 |
| 1-8 | $n_D^{25.2}$ 1.5805 |
| 1-10 | $n_D^{22.5}$ 1.5766 |
| 1-24 | $n_D^{21.7}$ 1.5635 |
| 1-44 | $n_D^{24.5}$ 1.5819 |
| 1-53 | $n_D^{22.2}$ 1.5916 |
| 1-54 | $n_D^{19.3}$ 1.5859 |
| 1-55 | $n_D^{22.1}$ 1.5830 |
| 1-56 | $n_D^{18.9}$ 1.5769 |
| 1-59 | $n_D^{18.5}$ 1.5764 |
| 1-62 | $n_D^{24.3}$ 1.5648 |
| 1-68 | $n_D^{22.8}$ 1.5378 |
| 1-86 | mp 88–90° C. |
| 1-88 | $n_D^{26.2}$ 1.6071 |
| 1-90 | $n_D^{22.0}$ 1.6045 |
| 1-92 | mp 99.1° C. |
| 1-94 | $n_D^{22.0}$ 1.5890 |
| 1-113 | $n_D^{49.5}$ 1.5655 |
| 1-119 | $n_D^{24.9}$ 1.5620*1 |
| 1-192 | $n_D^{25.1}$ 1.5884 |
| 1-331 | $n_D^{26.5}$ 1.6017 |
| 1-332 | resinoid |
| 1-333 | mp 84.1° C. |
| 1-335 | $n_D^{22.9}$ 1.6007 |
| 1-356 | $n_D^{23.8}$ 1.6292 |
| 1-460 | mp 116.0° C. |
| 1-463 | $n_D^{19.9}$ 1.5829*2 |
| 1-518 | $n_D^{26.3}$ 1.6095 |
| 1-519 | mp 116.7° C. |
| 1-539 | mp 73.0° C. |
| 1-540 | $n_D^{22.5}$ 1.5870 |
| 1-541 | $n_D^{24.6}$ 1.5715 |
| 1-542 | $n_D^{22.5}$ 1.5711 |
| 1-543 | mp 71.8° C. |
| 1-544 | $n_D^{19.2}$ 1.5798 |
| 1-545 | mp 118.8° C. |
| 1-546 | mp 151.1° C. |
| 1-547 | mp 101.3° C. |
| 1-548 | $n_D^{24.3}$ 1.5656 |
| 1-549 | $n_D^{25.5}$ 1.5919 |
| 1-550 | $n_D^{21.5}$ 1.5739*3 |

TABLE 6-continued

| Compound | Physical Property |
|---|---|
| 1-551 | mp 99.3° C. |
| 1-552 | $n_D^{19.7}$ 1.5892 |
| 1-553 | $n_D^{19.8}$ 1.5797 |
| 1-554 | mp 99.0° C. |
| 1-555 | mp 137.3° C. |
| 1-556 | $n_D^{24.1}$ 1.5415 |
| 1-557 | $n_D^{25.0}$ 1.5840 |
| 1-558 | $n_D^{24.3}$ 1.5848 |
| 1-559 | $n_D^{22.3}$ 1.5810 |
| 1-560 | $n_D^{21.9}$ 1.5682 |
| 1-561 | $n_D^{22.3}$ 1.5669 |
| 1-562 | $n_D^{24.9}$ 1.5672 |
| 1-563 | $n_D^{21.7}$ 1.5871 |
| 1-564 | $n_D^{22.0}$ 1.5782 |
| 1-565 | $n_D^{24.4}$ 1.6070 |
| 1-566 | mp 81.3° C. |
| 1-567 | $n_D^{26.0}$ 1.5766 |
| 1-568 | $n_D^{24.4}$ 1.5990 |
| 1-569 | $n_D^{24.5}$ 1.5903 |
| 1-571 | $n_D^{24.0}$ 1.5718 |
| 1-572 | $n_D^{24.2}$ 1.5753 |
| 1-573 | $n_D^{21.9}$ 1.5766 |
| 1-574 | $n_D^{24.0}$ 1.6049 |
| 1-575 | $n_D^{24.4}$ 1.6091*4 |
| 1-576 | $n_D^{22.3}$ 1.5999*5 |
| 1-577 | $n_D^{22.1}$ 1.5716 |
| 1-578 | $n_D^{24.2}$ 1.5849 |
| 1-579 | m.p. 109.3° C. |
| 1-580 | $n_D^{24.3}$ 1.5814 |
| 1-581 | $n_D^{24.5}$ 1.5376 |
| 1-582 | $n_D^{24.0}$ 1.5691 |
| 1-583 | $n_D^{24.1}$ 1.5775 |
| 1-584 | $n_D^{24.0}$ 1.5877 |
| 1-585 | $n_D^{24.1}$ 1.5698 |
| 1-586 | $n_D^{24.4}$ 1.5744 |
| 1-587 | $n_D^{22.4}$ 1.5915 |
| 1-588 | $n_D^{23.7}$ 1.5466 |
| 1-589 | $n_D^{25.5}$ 1.5778 |
| 1-590 | $n_D^{25.3}$ 1.5826 |
| 1-591 | m.p. 150.6° C. |
| 1-592 | $n_D^{23.8}$ 1.5768 |
| 1-593 | $n_D^{23.9}$ 1.5841 |
| 1-594 | $n_D^{23.3}$ 1.5875 |
| 1-595 | $n_D^{23.6}$ 1.5897 |
| 1-596 | $n_D^{25.1}$ 1.6105*6 |
| 1-597 | $n_D^{29.5}$ 1.6087 |
| 1-602 | $n_D^{22.9}$ 1.6004 |
| 1-603 | $n_D^{23.4}$ 1.6297 |
| 1-607 | $n_D^{23.6}$ 1.5866 |
| 1-608 | $n_D^{24.2}$ 1.5835 |
| 1-609 | $n_D^{24.2}$ 1.5799 |
| 1-610 | $n_D^{24.0}$ 1.5801 |
| 1-611 | $n_D^{23.9}$ 1.5831 |
| 1-612 | $n_D^{23.5}$ 1.5792 |
| 1-613 | $n_D^{24.2}$ 1.5756 |
| 1-614 | $n_D^{24.4}$ 1.5568 |
| 1-615 | $n_D^{24.3}$ 1.5470 |
| 1-616 | $n_D^{23.5}$ 1.5741 |
| 1-617 | $n_D^{23.6}$ 1.5777 |
| 1-618 | $n_D^{25.0}$ 1.5896 |
| 1-619 | $n_D^{25.1}$ 1.5789 |
| 1-620 | $n_D^{22.4}$ 1.5570 |
| 1-621 | $n_D^{23.5}$ 1.5872 |
| 1-622 | $n_D^{23.1}$ 1.5761 |
| 1-623 | resinoid |
| 1-624 | resinoid |
| 1-625 | $n_D^{24.7}$ 1.5673 |
| 1-626 | $n_D^{22.5}$ 1.5915 |
| 1-627 | $n_D^{23.6}$ 1.5963 |
| 1-628 | $n_D^{23.5}$ 1.5954 |
| 1-629 | resinoid |
| 1-630 | $n_D^{25.1}$ 1.6125 |
| 1-631 | $n_D^{24.6}$ 1.5757 |
| 1-632 | $n_D^{24.3}$ 1.5688 |
| 1-633 | $n_D^{24.5}$ 1.5621 |
| 1-635 | $n_D^{24.1}$ 1.5575 |
| 1-636 | $n_D^{24.2}$ 1.5551 |
| 1-638 | $n_D^{33.7}$ 1.6023 |
| 1-641 | mp 146.3° C. |
| 1-646 | $n_D^{24.1}$ 1.5805 |
| 1-647 | $n_D^{24.0}$ 1.5799 |

TABLE 6-continued

| Compound | Physical Property |
|---|---|
| 1-648 | $n_D^{24.7}$ 1.5811 |
| 1-649 | resinoid |
| 1-650 | resinoid |
| 1-651 | resinoid |
| 1-652 | $n_D^{25.9}$ 1.5827 |
| 1-653 | $n_D^{26.1}$ 1.5809 |
| 1-654 | $n_D^{24.8}$ 1.5800 |
| 1-655 | $n_D^{27.1}$ 1.5515 |
| 1-656 | $n_D^{24.1}$ 1.5415 |
| 1-657 | mp 137.3° C. |
| 1-658 | $n_D^{19.9}$ 1.6187 |
| 1-659 | $n_D^{19.9}$ 1.5793 |
| 1-660 | mp 119–121° C. |
| 1-661 | $n_D^{22.9}$ 1.5966 |
| 1-662 | mp 102–104° C. |
| 1-663 | viscous liquid |
| 1-664 | resinoid |
| 1-665 | mp 103–104° C. |
| 1-666 | mp 151.7° C. |
| 1-667 | mp 150.6° C. |
| 1-668 | mp 127.7° C. |
| 1-669 | mp 89.0° C. |
| 1-670 | $n_D^{25.2}$ 1.5873 |
| 1-671 | mp 81.9° C. |
| 1-672 | mp 107.9° C. |
| 1-673 | mp 83.5° C. |
| 1-674 | $n_D^{21.9}$ 1.5869 |
| 1-675 | mp 90.0° C. |
| 1-676 | mp 109.5° C. |
| 1-677 | mp 122.5° C. |
| 1-678 | mp 104.5° C. |
| 1-679 | mp 106.8° C. |
| 1-680 | mp 121.2° C. |
| 1-681 | mp 87.1° C. |
| 1-682 | $n_D^{23.0}$ 1.5922 |
| 1-683 | $n_D^{24.1}$ 1.5973 |
| 1-684 | mp 129.5° C. |
| 1-685 | $n_D^{23.0}$ 1.5740 |
| 1-686 | $n_D^{21.1}$ 1.5922 |
| 1-687 | $n_D^{23.1}$ 1.5818 |
| 1-688 | mp 70.5° C. |
| 1-689 | mp 112.5° C. |
| 1-690 | mp 144–146° C. |
| 1-691 | mp 90.1° C. |
| 1-692 | mp 106.4° C. |
| 1-693 | $n_D^{23.3}$ 1.5848 |
| 1-694 | mp 142.7° C. |
| 1-695 | $n_D^{24.2}$ 1.5899 |
| 1-696 | mp 76–77.5° C. |
| 1-697 | $n_D^{21.7}$ 1.6140 |
| 1-698 | $n_D^{21.8}$ 1.6076 |
| 1-699 | mp 148–149° C. |
| 1-700 | mp 127.2° C. |
| 1-701 | mp 99–101° C. |
| 1-702 | mp 126.2° C. |
| 1-703 | mp 96.5° C. |
| 1-704 | mp 74–77° C. |
| 1-705 | mp 96.8° C. |
| 1-706 | mp 103.1° C. |
| 1-707 | mp 98.1° C. |
| 1-708 | mp 106.3° C. |
| 1-709 | mp 117.0° C. |
| 1-710 | $n_D^{36.5}$ 1.5920 |
| 1-711 | mp 117–119° C. |
| 1-712 | mp 87–91° C. |
| 1-713 | mp 115–119° C. |
| 1-714 | mp 105.5–107° C. |
| 1-715 | mp 152.7° C. |
| 1-716 | mp 117.1° C. |
| 1-717 | mp 107.2° C. |
| 1-718 | mp 96.3° C. |
| 1-719 | mp 77.6° C. |
| 1-720 | $n_D^{23.0}$ 1.5950 |
| 1-721 | mp 57.7° C. |
| 1-722 | $n_D^{35.5}$ 1.5911 |
| 1-723 | mp 96.8° C. |
| 1-724 | mp 70.0° C. |
| 1-725 | mp 95.0° C. |
| 1-726 | $n_D^{26.5}$ 1.5922 |
| 1-727 | mp 116.2° C. |
| 1-728 | mp 86.5° C. |
| 1-729 | mp 142.7° C. |
| 1-730 | mp 87.0° C. |
| 1-731 | mp 105.7° C. |
| 1-732 | mp 81.6° C. |
| 1-733 | mp 87.7° C. |
| 1-734 | mp 83–87° C. |
| 1-735 | $n_D^{23.7}$ 1.5641 |
| 1-736 | mp 87–91° C. |
| 1-737 | mp 115–119° C. |
| 1-738 | mp 105.5–107° C. |
| 1-739 | mp 84–88° C. |
| 1-740 | $n_D^{23.7}$ 1.5454 |
| 1-741 | $n_D^{25.7}$ 1.6021 |
| 1-742 | mp 114–116° C. |
| 1-743 | $n_D^{23.1}$ 1.5553 |
| 1-744 | mp 138.0° C. |
| 1-745 | mp 78.0° C. |
| 1-746 | mp 102.9° C. |
| 1-747 | mp 83.5° C. |
| 1-748 | mp 137.8° C. |
| 1-749 | mp 148.5° C. |
| 1-750 | $n_D^{25.2}$ 1.5827 |
| 1-751 | mp 116.6° C. |
| 1-752 | $n_D^{25.6}$ 1.5992 |
| 1-753 | $n_D^{25.3}$ 1.5970 |
| 1-754 | mp 136.5° C. |
| 1-755 | $n_D^{25.7}$ 1.6131 |
| 1-756 | $n_D^{23.1}$ 1.6042 |
| 1-757 | $n_D^{23.0}$ 1.6051 |
| 1-758 | $n_D^{23.8}$ 1.6038 |
| 1-759 | $n_D^{23.6}$ 1.5836 |
| 1-760 | $n_D^{23.1}$ 1.5912 |
| 1-761 | $n_D^{23.6}$ 1.5842 |
| 1-762 | mp 114–117° C. |
| 1-763 | mp 98–99° C. |
| 1-764 | mp 119.5° C. |
| 1-765 | $n_D^{24.1}$ 1.6025 |
| 1-766 | mp 104–106° C. |
| 1-767 | mp 112.0° C. |
| 1-768 | mp 99.2° C. |
| 1-769 | $n_D^{27.4}$ 1.5898 |
| 1-770 | mp 106.8° C. |
| 1-771 | mp 117.0° C. |
| 1-772 | $n_D^{24.3}$ 1.6068 |
| 1-773 | $n_D^{26.1}$ 1.6042 |
| 1-774 | $n_D^{23.5}$ 1.6121 |
| 1-775 | mp 120.9° C. |
| 1-776 | $n_D^{26.1}$ 1.5928 |
| 1-777 | $n_D^{24.2}$ 1.5989 |
| 1-778 | $n_D^{24.2}$ 1.5826 |
| 1-779 | mp 124.0° C. |
| 1-780 | mp 98.6° C. |
| 1-781 | $n_D^{21.0}$ 1.6205 |
| 1-782 | $n_D^{22.9}$ 1.6039 |
| 1-783 | $n_D^{22.8}$ 1.6079 |
| 1-790 | mp 144–147° C. |
| 2-1 | mp 90.2° C. |
| 2-3 | $n_D^{23.2}$ 1.5975 |
| 2-14 | $n_D^{24.0}$ 1.5865 |
| 2-15 | $n_D^{23.2}$ 1.5975 |
| 2-16 | $n_D^{24.5}$ 1.6004 |
| 2-17 | $n_D^{22.1}$ 1.5800 |
| 2-32 | mp 122.2° C. |
| 2-34 | $n_D^{23.9}$ 1.5581 |
| 2-35 | mp 117.3° C. |
| 2-37 | $n_D^{22.4}$ 1.5783 |
| 2-38 | mp 145.8° C. |
| 2-39 | $n_D^{24.0}$ 1.6183 |
| 2-40 | $n_D^{23.9}$ 1.6254 |
| 2-41 | $n_D^{22.5}$ 1.6164 |
| 2-45 | $n_D^{21.0}$ 1.6285 |
| 2-59 | mp 158–160° C. |
| 2-60 | $n_D^{24.0}$ 1.5982 |
| 2-64 | $n_D^{23.0}$ 1.6050 |
| 2-65 | $n_D^{23.5}$ 1.6003 |
| 2-66 | $n_D^{22.2}$ 1.5880 |
| 2-67 | $n_D^{25.1}$ 1.6214 |
| 2-68 | $n_D^{22.8}$ 1.5881 |
| 2-69 | $n_D^{24.0}$ 1.6014 |
| 2-71 | $n_D^{22.9}$ 1.6064 |
| 2-72 | $n_D^{24.2}$ 1.5993 |

TABLE 6-continued

| Compound | Physical Property |
|---|---|
| 2-75 | $n_D^{23.0}$ 1.5812 |
| 2-88 | $n_D^{23.1}$ 1.5851 |
| 2-98 | mp 124.3° C. |
| 2-100 | $n_D^{22.0}$ 1.5856 |
| 2-101 | $n_D^{21.5}$ 1.5950 |
| 2-102 | $n_D^{19.1}$ 1.5926 |
| 2-103 | $n_D^{22.2}$ 1.6037 |
| 2-104 | $n_D^{20.9}$ 1.5839 |
| 2-105 | $n_D^{22.3}$ 1.6079 |
| 2-106 | $n_D^{24.9}$ 1.6127 |
| 2-107 | $n_D^{22.7}$ 1.6121 |
| 2-111 | $n_D^{24.2}$ 1.6037 |
| 2-112 | $n_D^{22.1}$ 1.6057 |
| 2-113 | mp 124.7° C. |
| 2-114 | $n_D^{23.7}$ 1.5962 |
| 2-115 | $n_D^{22.9}$ 1.5947 |
| 2-116 | $n_D^{23.5}$ 1.5834 |
| 2-117 | $n_D^{24.6}$ 1.5918 |
| 2-118 | $n_D^{21.7}$ 1.5935 |
| 2-119 | $n_D^{19.7}$ 1.5742 |
| 2-121 | $n_D^{25.6}$ 1.5941 |
| 2-136 | $n_D^{25.0}$ 1.6289 |
| 2-139 | mp 103.4° C. |
| 2-140 | $n_D^{24.0}$ 1.5903 |
| 2-141 | $n_D^{23.8}$ 1.5907 |
| 2-143 | $n_D^{23.6}$ 1.5943 |
| 2-196 | mp 138.0° C. |
| 2-246 | mp 137.3° C. |
| 2-278 | $n_D^{25.0}$ 1.5990 |
| 2-279 | $n_D^{23.9}$ 1.5976 |
| 2-280 | $n_D^{22.3}$ 1.5865 |
| 2-281 | $n_D^{24.3}$ 1.5682 |
| 2-282 | $n_D^{24.0}$ 1.6235 |
| 2-283 | $n_D^{21.9}$ 1.6068 |
| 2-284 | $n_D^{22.0}$ 1.6046 |
| 2-285 | $n_D^{21.9}$ 1.5860 |
| 2-286 | $n_D^{23.8}$ 1.5911 |
| 2-287 | $n_D^{24.5}$ 1.6078 |
| 2-288 | $n_D^{25.6}$ 1.5631 |
| 2-289 | $n_D^{19.8}$ 1.6032 |
| 2-290 | $n_D^{24.4}$ 1.6009 |
| 2-291 | $n_D^{20.6}$ 1.5966 |
| 2-292 | $n_D^{25.2}$ 1.5960 |
| 2-293 | $n_D^{20.1}$ 1.5977 |
| 2-294 | $n_D^{21.3}$ 1.5959 |
| 2-295 | mp 117.1° C. |
| 2-296 | $n_D^{24.5}$ 1.5937 |
| 2-297 | $n_D^{22.9}$ 1.5722 |
| 2 298 | $n_D^{24.1}$ 1.6352 |
| 2-299 | mp 154.7° C. |
| 2-301 | mp 153.7° C. |
| 3-6 | mp 65-68° C. |
| 3-12 | $n_D^{25.2}$ 1.5771 |
| 3-17 | $n_D^{24.8}$ 1.5310 |
| 3-22 | mp 75-79° C. |
| 3-23 | mp 60-64.5° C. |
| 3-44 | $n_D^{22.0}$ 1.6161 |
| 3-48 | $n_D^{21.0}$ 1.5995 |
| 3-60 | mp 141-143° C. |
| 3-67 | mp 132-134° C. |
| 3-68 | mp 114-118° C. |
| 3-89 | $n_D^{25.5}$ 1.5945 |
| 3-92 | $n_D^{26.6}$ 1.5875 |
| 3-107 | mp 94-98° C. |
| 3-108 | mp 99-101° C. |
| 3-109 | mp 77-79° C. |
| 3-110 | mp 68-71° C. |
| 3-111 | mp 93,1° C. |
| 3-112 | $n_D^{21.5}$ 1.6300 |
| 3-113 | mp 144-149° C. |
| 3-114 | $n_D^{22.8}$ 1.6180 |
| 3-118 | $n_D^{22.1}$ 1.5679 |
| 3-119 | $n_D^{22.2}$ 1.5648 |
| 3-141 | viscous liquid |
| 3-142 | mp 129.5-130.5° C. |
| 3-143 | $n_D^{24.1}$ 1.5423 |
| 3-144 | $n_D^{25.7}$ 1.6143 |
| 3-145 | mp 105.8° C. |
| 3-146 | $n_D^{22.8}$ 1.5922 |
| 4-1 | $n_D^{22.7}$ 1.5565 |
| 4-2 | $n_D^{22.6}$ 1.6212 |
| 4-10 | $n_D^{25.6}$ 1.6258 |
| 4-11 | $n_D^{24.5}$ 1.5956 |
| 4-15 | $n_D^{22.3}$ 1.5833 |
| 4-42 | $n_D^{25.0}$ 1.6245 |
| 4-53 | $n_D^{24.5}$ 1.6019 |
| 5-3 | $n_D^{24.5}$ 1.5976 |
| 5-10 | $n_D^{26.5}$ 1.6014 |
| 5-25 | $n_D^{25.1}$ 1.5911 |
| 5-52 | $n_D^{24.1}$ 1.5902 |
| 5-53 | $n_D^{23.3}$ 1.5748 |

*[1] This compound was allowed to stand at the room temperature for one week for solidification. mp 78–82° C.
*[2] This compound was allowed to stand at the room temperature for one week for solidification. mp 99–100° C.
*[3] This compound was allowed to stand at the room temperature for one week for solidification. mp 78.0° C.
*[4] This compound was allowed to stand at the room temperature for one week for solidification. mp 137.2° C.
*[5] This compound was allowed to stand at the room temperature for one week for solidification. mp 163.8° C.
*[6] This compound was allowed to stand at the room temperature for one week for solidification. mp 87.7° C.

Then, the formulation examples will be illustrated. All parts are by weight. The compounds of the present invention employed herein are shown with reference to the compound numbers in Table 1 to 5

FORMULATION EXAMPLE 1

Emulsifiable Concentrate

Each 10 parts portion of the Compounds described in Table 1 to 5 was dissolved into a mixture of 35 parts of xylene and 35 parts of dimethylformamide. To the resulting solution were added 14 parts of polyoxyethylene styrylphenyl ether and 6 parts of calcium dodecylbenzenesulfonate. After blending by full agitation, a 10% emulsifiable concentrate of each Compound was obtained.

FORMULATION EXAMPLE 2

Wettable Powder

Each 20 parts portion of the solid Compounds described in Table 1 to 5 was added to a mixture of 4 parts of sodium lauryl sulfate, 2 parts of calcium lignisulfonate, 20 parts of finely powdered synthetic hydrous silicon oxide, and 54 parts of diatomaceous earth, and the resulting mixture was blended by agitation using a juice-mixer, thereby to obtain a 20% wettable powder of each Compound.

FORMULATION EXAMPLE 3

Dust Formulation

Each 1 part portion of the Compounds described in Table 1 to 5 was dissolved in an adequate amount of acetone. To the resulting solution were added 5 parts of finely powdered synthetic hydrous silicon oxide, 0.3 part of PAP, and 93.7 parts of clay, and the mixture was blended by agitation in a juice-mixer. Removal of the acetone by evaporation left a 1% dust formulation of each Compound.

FORMULATION EXAMPLE 4

Flowable Formulation

Each 20 parts portion of the Compounds described in Table 1 to 5 and 1.5 parts of sorbitan trioleate were mixed with 28.5 parts of an aqueous solution containing 2 parts of polyvinyl alcohol. The mixture was finely particulated (up to not more than 3 μ particle diameter)

using a sand grinder. Thereto were added 40 parts of an aqueous solution containing 0.05 part of xanthan gum and 0.1 part of aluminum magnesium silicate, and then 10 parts of propylene glycol. The mixture was blended by agitation, to obtain a 20% flowable formulation of each Compound.

FORMULATION EXAMPLE 5

Oil Formulation

Each 0.1 part portion of the Compounds described in Table 1 to 5 was dissolved into a mixture of 5 parts of xylene and 5 parts of trichloroethane. Blending of the solution with 89.9 parts of deodorized kerosene yielded a 0.1% oil formulation of each Compound.

Then, test examples will be illustrated. The compounds of the present invention employed herein are shown with reference to the numbers of the compounds in Table 1 to 5, and the compounds employed for the comparison are shown by symbolic letters of the compounds in Table 7.

plant by the mites was observed. The efficacy was judged according to the following criteria:
—: Almost no damage was observed,
+: Slight damage was observed,
++: Similar degree of damage as that of the untreated was observed.

The results are shown in Table 8.

TABLE 8

| Test Compound | effect |
|---|---|
| 1-1 | — |
| 1-2 | — |
| 1-3 | — |
| 1-4 | — |
| 1-5 | — |
| 1-6 | — |
| 1-8 | — |
| 1-10 | — |
| 1-24 | — |
| 1-44 | — |
| 1-53 | — |
| 1-54 | — |
| 1-55 | — |

TABLE 7

| Symbolic letter of the compound | Structural formula | remarks |
|---|---|---|
| A | (pyrazole with CH₃, N-N-CH₃, O-phenyl, CH=NOCH₂-C₆H₄-COC(CH₃)₃) | Compound No. 60 described in EP No. 234045A₂ |
| B | (pyrazole with CH₃, Cl, N-N-CH₃, C(=O)-NH-CH₂-C₆H₄-C(CH₃)₃) | Compound No. 36 described in EP No. 289879-A |
| C | (cyclopentane-fused pyrazole, N-N-CH₃, CONH-CH₂-C₆H₄-C(CH₃)₃) | Compound described in EP No. 307801-A |
| D | (pyrazole with CH₃, Cl, N-N-CH₃, CONH-CH₂-C₆H₄-O-C₆H₅) | Compound No. 36 described in EP No. 289879-A |

TEST EXAMPLE 1

Test Against Carmine Mites (*Tetranychus cinnabarinus*)

Potted vineless kidney beans plants 7 days after sowing (at the stage of primordial leaves) were parasitized by 10 female adult carmine mites per leaf, and placed in an incubator at a temperature of 25° C. After 6 days, an emulsifiable concentrate of a test compound formulated according to the Formulating Example 1 was diluted with water to 500 ppm concentration of the active ingredient, and the diluted emulsion was sprayed to the potted plants on a turn table in an amount of 15 ml per pot. At the same time, 2 ml of the emulsion was treated on the pot soil. After 8 days, the damaged level of each

| | |
|---|---|
| 1-56 | — |
| 1-59 | — |
| 1-62 | — |
| 1-68 | — |
| 1-86 | — |
| 1-88 | — |
| 1-90 | — |
| 1-92 | — |
| 1-94 | — |
| 1-113 | — |
| 1-119 | — |
| 1-192 | — |
| 1-331 | — |
| 1-332 | — |
| 1-333 | — |
| 1-335 | — |
| 1-356 | — |
| 1-340 | — |

TABLE 8-continued

| Test Compound | effect |
|---|---|
| 1-463 | — |
| 1-518 | — |
| 1-519 | — |
| 1-539 | — |
| 1-540 | — |
| 1-541 | — |
| 1-542 | — |
| 1-543 | — |
| 1-544 | — |
| 1-545 | — |
| 1-546 | — |
| 1-547 | — |
| 1-548 | — |
| 1-549 | — |
| 1-550 | — |
| 1-551 | — |
| 1-552 | — |
| 1-553 | — |
| 1-554 | — |
| 1-555 | — |
| 1-556 | — |
| 1-557 | — |
| 1-558 | — |
| 1-559 | — |
| 1-560 | — |
| 1-561 | — |
| 1-563 | — |
| 1-564 | — |
| 1-565 | — |
| 1-566 | — |
| 1-567 | — |
| 1-568 | — |
| 1-569 | — |
| 1-571 | — |
| 1-572 | — |
| 1-573 | — |
| 1-574 | — |
| 1-575 | — |
| 1-576 | — |
| 1-577 | — |
| 1-578 | — |
| 1-579 | — |
| 1-580 | — |
| 1-581 | — |
| 1-582 | — |
| 1-583 | — |
| 1-584 | — |
| 1-585 | — |
| 1-587 | — |
| 1-589 | — |
| 1-590 | — |
| 1-592 | — |
| 1-593 | — |
| 1-594 | — |
| 1-595 | — |
| 1-596 | — |
| 1-597 | — |
| 1-602 | — |
| 1-607 | — |
| 1-608 | — |
| 1-609 | — |
| 1-610 | — |
| 1-611 | — |
| 1-612 | — |
| 1-613 | — |
| 1-614 | — |
| 1-615 | — |
| 1-616 | — |
| 1-617 | — |
| 1-618 | — |
| 1-619 | — |
| 1-620 | — |
| 1-621 | — |
| 1-622 | — |
| 1-623 | — |
| 1-624 | — |
| 1-625 | — |
| 1-626 | — |
| 1-627 | — |
| 1-628 | — |
| 1-629 | — |
| 1-630 | — |
| 1-631 | — |
| 1-632 | — |
| 1-633 | — |
| 1-635 | — |
| 1-636 | — |
| 1-638 | — |
| 1-641 | — |
| 1-656 | — |
| 1-657 | — |
| 1-658 | — |
| 1-659 | — |
| 1-660 | — |
| 1-661 | — |
| 1-662 | — |
| 1-663 | — |
| 1-664 | — |
| 1-665 | — |
| 1-666 | — |
| 1-668 | — |
| 1-669 | — |
| 1-670 | — |
| 1-673 | — |
| 1-674 | — |
| 1-680 | — |
| 1-681 | — |
| 1-682 | — |
| 1-683 | — |
| 1-684 | — |
| 1-685 | — |
| 1-686 | — |
| 1-687 | — |
| 1-688 | — |
| 1-693 | — |
| 1-695 | — |
| 1-696 | — |
| 1-697 | — |
| 1-698 | — |
| 1-699 | — |
| 1-700 | — |
| 1-701 | — |
| 1-703 | — |
| 1-704 | — |
| 1-705 | — |
| 1-706 | — |
| 1-707 | — |
| 1-708 | — |
| 1-710 | — |
| 1-711 | — |
| 1-712 | — |
| 1-713 | — |
| 1-714 | — |
| 1-715 | — |
| 1-716 | — |
| 1-717 | — |
| 1-718 | — |
| 1-719 | — |
| 1-720 | — |
| 1-721 | — |
| 1-722 | — |
| 1-723 | — |
| 1-724 | — |
| 1-730 | — |
| 1-731 | — |
| 1-732 | — |
| 1-733 | — |
| 1-734 | — |
| 1-735 | — |
| 1-736 | — |
| 1-737 | — |
| 1-738 | — |
| 1-739 | — |
| 1-740 | — |
| 1-741 | — |
| 1-743 | — |
| 1-744 | — |
| 1-745 | — |
| 1-746 | — |
| 1-753 | — |
| 1-756 | — |
| 1-757 | — |

TABLE 8-continued

| Test Compound | effect |
|---|---|
| 1-758 | — |
| 1-759 | — |
| 1-761 | — |
| 1-763 | — |
| 1-766 | — |
| 1-769 | — |
| 1-770 | — |
| 1-771 | — |
| 1-773 | — |
| 1-774 | — |
| 1-776 | — |
| 1-777 | — |
| 1-778 | — |
| 1-779 | — |
| 1-780 | — |
| 1-781 | — |
| 1-782 | — |
| 1-783 | — |
| 2-1 | — |
| 2-3 | — |
| 2-32 | — |
| 2-35 | — |
| 2-38 | — |
| 2-39 | — |
| 2-45 | — |
| 2-59 | — |
| 2-98 | — |
| 2-139 | — |
| 2-246 | — |
| 2-295 | — |
| 2-299 | — |
| 2-301 | — |
| 3-6 | — |
| 3-17 | — |
| 3-22 | — |
| 3-23 | — |
| 3-44 | — |
| 3-48 | — |
| 3-67 | — |
| 3-68 | — |
| 3-89 | — |
| 3-92 | — |
| 3-107 | — |
| 3-108 | — |
| 3-109 | — |
| 3-111 | — |
| 3-112 | — |
| 3-113 | — |
| 3-114 | — |
| 3-118 | — |
| 3-119 | — |
| 3-141 | — |
| 3-143 | — |
| 3-144 | — |
| 3-145 | — |
| 3-146 | — |
| 4-1 | — |
| 4-2 | — |
| 4-10 | — |
| 4-11 | — |
| 4-15 | — |
| 4-53 | — |
| 5-3 | — |
| 5-10 | — |
| 5-25 | — |
| 5-52 | — |
| 5-53 | — |

TEST EXAMPLE 2

Insecticidal Test Against Common Mosquitos (*Culex pipiens pallens*)

A test compound was formulated to an emulsifiable concentrate in accordance with the Formulation Example 1, and the concentrate was diluted with water by 200 times. Then, 2 ml of the resulting emulsion was added in 98 ml of ion-exchanged water to obtain a liquid having an active ingredient concentration of 10 ppm. Into the resulting liquid, 20 larvae of common mosquitos in mature instar were released, and the mortality at one day later was investigated.

The insecticidal activity was judged with the following criteria:
 a: Mortality rate of not less than 90%.
 b: Mortality rate between not less than 10% and less than 90%.
 c: Mortality rate of less than 10%.

The results are shown in Table 9.

TABLE 9

| Test Compound | Mortality |
|---|---|
| 1-1 | a |
| 1-2 | a |
| 1-10 | a |
| 1-68 | a |
| 1-86 | a |
| 1-88 | a |
| 1-119 | a |
| 1-331 | a |
| 1-332 | a |
| 1-333 | a |
| 1-356 | a |
| 1-463 | a |
| 1-518 | a |
| 1-539 | a |
| 1-541 | a |
| 1-543 | a |
| 1-545 | a |
| 1-546 | a |
| 1-547 | a |
| 1-548 | a |
| 1-549 | a |
| 1-551 | a |
| 1-552 | a |
| 1-553 | a |
| 1-554 | a |
| 1-555 | a |
| 1-556 | a |
| 1-557 | a |
| 1-559 | a |
| 1-560 | a |
| 1-564 | a |
| 1-565 | a |
| 1-567 | a |
| 1-575 | a |
| 1-576 | a |
| 1-579 | a |
| 1-580 | a |
| 1-588 | a |
| 1-591 | a |
| 1-593 | a |
| 1-594 | a |
| 1-596 | a |
| 1-597 | a |
| 1-613 | a |
| 1-614 | a |
| 1-638 | a |
| 1-641 | a |
| 1-657 | a |
| 1-660 | a |
| 1-661 | a |
| 1-664 | a |
| 1-665 | a |
| 1-668 | a |
| 1-669 | a |
| 1-670 | a |
| 1-673 | a |
| 1-680 | a |
| 1-681 | a |
| 1-684 | a |
| 1-685 | a |
| 1-686 | a |
| 1-687 | a |
| 1-688 | a |
| 1-689 | a |
| 1-693 | a |
| 1-695 | a |
| 1-696 | a |
| 1-697 | a |

TABLE 9-continued

| Test Compound | Mortality |
|---|---|
| 1-698 | a |
| 1-701 | a |
| 1-703 | a |
| 1-704 | a |
| 1-707 | a |
| 1-708 | a |
| 1-710 | a |
| 1-711 | a |
| 1-712 | a |
| 1-713 | a |
| 1-714 | a |
| 1-716 | a |
| 1-717 | a |
| 1-718 | a |
| 1-719 | a |
| 1-720 | a |
| 1-721 | a |
| 1-722 | a |
| 1-723 | a |
| 1-724 | a |
| 1-725 | a |
| 1-730 | a |
| 1-732 | a |
| 1-733 | a |
| 1-734 | a |
| 1-735 | a |
| 1-736 | a |
| 1-737 | a |
| 1-738 | a |
| 1-739 | a |
| 1-740 | a |
| 1-741 | a |
| 1-744 | a |
| 1-753 | a |
| 1-755 | a |
| 1-757 | a |
| 1-759 | a |
| 1-761 | a |
| 1-763 | a |
| 1-764 | a |
| 1-766 | a |
| 1-769 | a |
| 1-770 | a |
| 1-771 | a |
| 1-773 | a |
| 1-774 | a |
| 1-775 | a |
| 1-776 | a |
| 1-777 | a |
| 1-780 | a |
| 1-782 | a |
| 1-783 | a |
| 1-790 | a |
| 2-1 | a |
| 2-3 | a |
| 2-14 | a |
| 2-15 | a |
| 2-16 | a |
| 2-17 | a |
| 2-32 | a |
| 2-34 | a |
| 2-35 | a |
| 2-37 | a |
| 2-38 | a |
| 2-39 | a |
| 2-40 | a |
| 2-41 | a |
| 2-45 | a |
| 2-59 | a |
| 2-60 | a |
| 2-64 | a |
| 2-65 | a |
| 2-66 | a |
| 2-67 | a |
| 2-68 | a |
| 2-69 | a |
| 2-71 | a |
| 2-72 | a |
| 2-75 | a |
| 2-88 | a |
| 2-98 | a |
| 2-100 | a |
| 2-101 | a |
| 2-102 | a |
| 2-103 | a |
| 2-104 | a |
| 2-105 | a |
| 2-106 | a |
| 2-107 | a |
| 2-111 | a |
| 2-112 | a |
| 2-113 | a |
| 2-114 | a |
| 2-115 | a |
| 2-116 | a |
| 2-117 | a |
| 2-118 | a |
| 2-119 | a |
| 2-121 | a |
| 2-136 | a |
| 2-139 | a |
| 2-140 | a |
| 2-141 | a |
| 2-143 | a |
| 2-153 | a |
| 2-196 | a |
| 2-246 | a |
| 2-278 | a |
| 2-279 | a |
| 2-280 | a |
| 2-281 | a |
| 2-282 | a |
| 2-283 | a |
| 2-284 | a |
| 2-285 | a |
| 2-286 | a |
| 2-287 | a |
| 2-288 | a |
| 2-289 | a |
| 2-290 | a |
| 2-291 | a |
| 2-292 | a |
| 2-293 | a |
| 2-294 | a |
| 2-295 | a |
| 2-296 | a |
| 2-297 | a |
| 2-298 | a |
| 3-22 | a |
| 3-23 | a |
| 3-44 | a |
| 3-48 | a |
| 3-51 | a |
| 3-52 | a |
| 3-60 | a |
| 3-67 | a |
| 3-89 | a |
| 3-92 | a |
| 3-107 | a |
| 3-110 | a |
| 3-111 | a |
| 3-112 | a |
| 3-113 | a |
| 3-141 | a |
| 3-142 | a |
| 3-144 | a |
| 3-146 | a |
| 4-2 | a |
| 5-2 | a |
| 5-3 | a |
| 5-9 | a |
| 5-10 | a |
| 5-15 | a |
| 5-21 | a |
| 5-25 | a |
| 5-37 | a |
| 5-38 | a |
| 5-39 | a |
| 5-40 | a |
| 5-45 | a |
| 5-47 | a |
| 5-48 | a |

TABLE 9-continued

| Test Compound | Mortality |
| --- | --- |
| 5-49 | a |
| 5-52 | a |
| 5-53 | a |
| B | c |
| C | c |

TEST EXAMPLES 3

Insecticidal Test Against Diamondback Moths (*Plutella xylostella*)

An emulsifiable concentrate of a test compound formulated according to the Formulating Example 1 was diluted with water to make an emulsion (corresponding to 50 ppm concentration). Two of radish shoots (5–6 days after sowing) were immersed into the emulsion for 30 minutes, then air-dried, and placed in a cage in which a lot number of wild, adult diamondback moths of 1–3 day age after emergence have been released, to allow them to lay eggs. At the time of 100–150 eggs laid on each shoot, the shoots were taken out of the cage, and placed in a polyethylene cup of 5.5 cm diameter. The mortality of the larvae after hatching was observed. (two replications)

The mortalities were shown in 3 degrees as mentioned below:
a: 100%,
b: not less than 70%, but less than 100%,
c: less than 70%.

The results are shown in Table 10.

TABLE 10

| Test Compound | Mortality |
| --- | --- |
| 1-10 | a |
| 1-86 | a |
| 1-88 | a |
| 1-90 | a |
| 1-92 | a |
| 1-94 | a |
| 1-119 | a |
| 1-331 | a |
| 1-332 | a |
| 1-333 | a |
| 1-335 | a |
| 1-463 | a |
| 1-518 | a |
| 1-519 | a |
| 1-539 | a |
| 1-543 | a |
| 1-545 | a |
| 1-547 | a |
| 1-548 | a |
| 1-550 | a |
| 1-551 | a |
| 1-552 | a |
| 1-557 | a |
| 1-575 | a |
| 1-579 | a |
| 1-596 | a |
| 1-597 | a |
| 1-614 | a |
| 1-638 | a |
| 1-670 | a |
| 1-673 | a |
| 1-687 | a |
| 1-688 | a |
| 1-689 | a |
| 1-692 | a |
| 1-697 | a |
| 1-704 | a |
| 1-708 | a |
| 1-709 | a |
| 1-711 | a |
| 1-712 | a |
| 1-713 | a |
| 1-714 | a |
| 1-716 | a |
| 1-717 | a |
| 1-718 | a |
| 1-721 | a |
| 1-722 | a |
| 1-723 | a |
| 1-724 | a |
| 1-729 | a |
| 1-730 | a |
| 1-732 | a |
| 1-733 | a |
| 1-734 | a |
| 1-736 | a |
| 1-737 | a |
| 1-738 | a |
| 1-739 | a |
| 1-741 | a |
| 1-743 | a |
| 1-755 | a |
| 1-757 | a |
| 1-759 | a |
| 1-763 | a |
| 1-766 | a |
| 1-770 | a |
| 1-771 | a |
| 1-773 | a |
| 1-774 | a |
| 2-32 | a |
| 2-35 | a |
| 2-38 | a |
| 2-39 | a |
| 2-98 | a |
| 2-295 | a |
| 3-22 | a |
| 3-23 | a |
| 3-107 | a |
| 3-110 | a |
| 3-111 | a |
| 5-25 | a |
| 5-52 | a |
| 5-53 | a |
| A | c |
| B | c |
| C | c |
| D | c |

TEST EXAMPLE 4

Insecticidal Test Against Tobacco Cutworms (*Spodoptera litura*)

A test compound was formulated to an emulsifiable concentrate in accordance with the Formulation Example 1, and the concentrate was diluted with water by 200 times to obtain an emulsion containing 500 ppm of the test compound. On the other hand, 13 g of an artificial diet for tobacco cutworm was prepared in a polyethylene cup having a diameter of 11 cm, and was impregnated with 2 ml of the emulsion obtained above. Ten fourth instar larvae of tobacco cutworms were released therein, and six days later, the mortality was determined (two replications). The damaged level of the artificial diet was also investigated in parallel. The damaged level was judged with the following criteria:

—: Almost no damage was observed.
+: Damage was observed.
++: Damage was heavy, and the artificial diet scarcely remained.

The results are shown in Table 11.

TABLE 11

| Test Compound | Mortality | Damage of diet |
|---|---|---|
| 1-68 | 100 | — |
| 1-86 | 100 | — |
| 1-88 | 100 | — |
| 1-119 | 100 | — |
| 1-331 | 100 | — |
| 1-333 | 100 | — |
| 1-463 | 100 | — |
| 1-518 | 100 | — |
| 1-519 | 100 | — |
| 1-539 | 100 | — |
| 1-541 | 100 | — |
| 1-545 | 100 | — |
| 1-546 | 100 | — |
| 1-548 | 100 | — |
| 1-550 | 100 | — |
| 1-551 | 100 | — |
| 1-554 | 100 | — |
| 1-555 | 100 | — |
| 1-556 | 100 | — |
| 1-559 | 100 | — |
| 1-560 | 100 | — |
| 1-567 | 100 | — |
| 1-575 | 100 | — |
| 1-576 | 100 | — |
| 1-579 | 100 | — |
| 1-580 | 100 | — |
| 1-596 | 100 | — |
| 1-597 | 100 | — |
| 1-614 | 100 | — |
| 1-638 | 100 | — |
| 1-665 | 100 | — |
| 1-668 | 100 | — |
| 1-669 | 100 | — |
| 1-673 | 100 | — |
| 1-674 | 100 | — |
| 1-687 | 100 | — |
| 1-688 | 100 | — |
| 1-689 | 100 | — |
| 1-691 | 100 | — |
| 1-693 | 100 | — |
| 1-695 | 100 | — |
| 1-696 | 100 | — |
| 1-697 | 100 | — |
| 1-698 | 100 | — |
| 1-701 | 100 | — |
| 1-703 | 100 | — |
| 1-704 | 100 | — |
| 1-708 | 100 | — |
| 1-711 | 100 | — |
| 1-712 | 100 | — |
| 1-713 | 100 | — |
| 1-714 | 100 | — |
| 1-717 | 100 | — |
| 1-721 | 100 | — |
| 1-722 | 100 | — |
| 1-723 | 100 | — |
| 1-730 | 100 | — |
| 1-732 | 100 | — |
| 1-733 | 100 | — |
| 1-734 | 100 | — |
| 1-745 | 100 | — |
| 1-736 | 100 | — |
| 1-737 | 100 | — |
| 1-738 | 100 | — |
| 1-739 | 100 | — |
| 1-740 | 100 | — |
| 1-741 | 100 | — |
| 1-751 | 100 | — |
| 1-753 | 100 | — |
| 1-755 | 100 | — |
| 1-757 | 100 | — |
| 1-759 | 100 | — |
| 1-763 | 100 | — |
| 1-766 | 100 | — |
| 1-770 | 100 | — |
| 1-771 | 100 | — |
| 1-773 | 100 | — |
| 1-774 | 100 | — |
| 1-775 | 100 | — |
| 1-776 | 100 | — |
| 1-777 | 100 | — |
| 1-778 | 100 | — |
| 1-779 | 100 | — |
| 1-780 | 100 | — |
| 1-782 | 100 | — |
| 1-783 | 100 | — |
| 1-790 | 100 | — |
| 1-335 | 100 | — |
| 2-32 | 100 | — |
| 2-35 | 100 | — |
| 2-38 | 100 | — |
| 2-39 | 100 | — |
| 2-45 | 100 | — |
| 2-98 | 100 | — |
| 2-196 | 100 | — |
| 2-246 | 100 | — |
| 2-295 | 100 | — |
| 3-22 | 100 | — |
| 3-23 | 100 | — |
| 3-111 | 100 | — |
| 3-146 | 100 | — |
| 4-2 | 100 | — |
| 5-25 | 100 | — |
| A | 95 | + |
| B | 50 | + |
| C | 0 | ++ |
| D | 10 | ++ |

TEST EXAMPLE 5

Insecticidal Test Against Houseflies (*Musca clomestica*)

A filter paper was taken into a polyethylene cup (a diameter of 5.5 cm) at the bottom. The emulsifiable concentrate of a test compound which was prepared in accordance with the Formulation Example 1 was diluted with water by 200 times to obtain an emulsion containing 500 ppm of the test compound, and 0.7 ml of the emulsion was dropped on the filter paper. Further, about 30 mg of sugar was placed there as a bait. Ten adult females of housefly were released in the cup which was then capped. One day later, the mortality was determined.

The results are shown in Table 12.

TABLE 12

| Test Compound | Mortality |
|---|---|
| 1-1 | 100 |
| 1-86 | 100 |
| 1-119 | 100 |
| 1-332 | 100 |
| 1-333 | 100 |
| 1-518 | 100 |
| 1-519 | 100 |
| 1-539 | 100 |
| 1-545 | 100 |
| 1-546 | 100 |
| 1-548 | 100 |
| 1-575 | 100 |
| 1-596 | 100 |
| 1-597 | 100 |
| 1-669 | 100 |
| 1-688 | 100 |
| 1-696 | 100 |
| 1-700 | 100 |
| 1-703 | 100 |
| 1-708 | 100 |
| 1-711 | 100 |
| 1-712 | 100 |
| 1-714 | 100 |
| 1-716 | 100 |
| 1-717 | 100 |
| 1-718 | 100 |
| 1-721 | 100 |
| 1-722 | 100 |
| 1-723 | 100 |
| 1-730 | 100 |

TABLE 12-continued

| Test Compound | Mortality |
|---|---|
| 1-732 | 100 |
| 1-734 | 100 |
| 1-736 | 100 |
| 1-738 | 100 |
| 1-739 | 100 |
| 1-740 | 100 |
| 1-759 | 100 |
| 1-770 | 100 |
| 1-771 | 100 |
| 1-773 | 100 |
| 1-774 | 100 |
| 1-780 | 100 |
| 1-782 | 100 |
| 1-783 | 100 |
| 2-1 | 100 |
| 2-35 | 100 |
| 2-39 | 100 |
| 3-22 | 100 |
| 3-111 | 100 |
| 3-144 | 100 |
| 3-146 | 100 |
| 4-15 | 100 |
| 5-25 | 100 |
| 5-52 | 100 |
| 5-53 | 100 |
| A | 0 |
| B | 0 |
| C | 0 |

What is claimed is:

1. An amide compound represented by the formula of $$A-\underset{\underset{X}{\|}}{C}-\underset{\underset{R^3}{|}}{N}-\underset{\underset{R^3}{|}}{C}-\underset{(R^4)_l}{\text{[benzene ring]}}-Y-\underset{(R^6)_m}{\text{[ring B with }R^5\text{]}}$$

wherein
$R^1$ is a hydrogen atom or an alkyl group of 1-4 carbons,
$R^2$ is a hydrogen atom, an alkyl group of 1-4 carbons or a cyano group;
$R^3$ is a hydrogen atom or an alkyl group of 1-4 carbons;
$R^4$ is a hydrogen atom, a halogen atom or an alkyl group of 1-4 carbons;
$R^5$ is a halogen atom, an alkyl group of 1-8 carbons, a haloalkyl group of 1-8 carbons, a cycloalkyl group of 3-8 total carbons, an alkenyl group of 2-8 carbons, an alkynyl group of 2-8 carbons, an alkoxy group of 1-8 carbons, a haloalkoxy group of 1-8 carbons, an alkenyloxy group of 2-8 carbons, a haloalkenyloxy group of 2-8 carbons, an alkynyloxy group of 2-8 carbons, an alkylthio group of 1-8 carbons, a haloalkylthio group of 1-8 carbons, an alkenylthio group of 2-8 carbons, a haloalkenylthio group of 2-8 carbons, an alkynylthio group of 2-8 carbons, an alkoxyalkyl group of 2-8 total carbons, an alkylthioalkyl group of 2-8 total carbons, a (haloalkylthio)alkyl group of 2-8 total carbons, an alkylsulfinyl group of 1-8 carbons, a haloalkylsulfinyl group of 1-8 carbons, an alkylsulfonyl group of 1-8 carbons, a haloalkylsulfonyl group of 1-8 carbons, an alkylsulfonyloxy group of 1-8 carbons, a haloalkylsulfonyloxy group of 1-8 carbons, an alkylamino group of 1-8 carbons, a haloalkylamino group of 1-8 carbons, a dialkylamino group of 2-16 total carbons, an alkanoylamino group of 1-8 carbons, an alkylimino group of 1-8 carbons, an N-alkylformamidino group of 2-8 total carbons, an N-alkylacetamidino group of 3-8 total carbons, an N,N-dialkylformamidino group of 3-16 total carbons, an N,N-dialkylacetamidino group of 4-16 carbons or an alkylsulfonylamido group of 1-8 carbons;

$R^6$ is a hydrogen atom, a halogen atom, an alkyl group of 1-3 carbons, a haloalkyl group of 1-3 carbons, a cycloalkyl group of 3-6 carbons, an alkenyl group of 2-6 carbons, an alkynyl group of 2-6 carbons, an alkoxy group of 1-3 carbons, a haloalkoxy group of 1-3 carbons, an alkenyloxy group of 2-6 carbons, a haloalkenyloxy group of 2-6 carbons, an alkynyloxy group of 2-6 carbons, an alkylthio group of 1-3 carbons, a haloalkylthio group of 1-3 carbons, an alkenylthio group of 2-6 carbons, a haloalkenylthio group of 2-6 carbons, an alkynylthio group of 2-6 carbons, an alkoxyalkyl group of 2-3 total carbons, an alkylsulfinyl group of 1-3 carbons, a haloalkylsulfinyl group of 1-3 carbons, an alkylsulfonyl group of 1-3 carbons, a haloalkylsulfonyl group of 1-3 carbons, an alkylsulfonyloxy group of 1-3 carbons or a haloalkylsulfonyloxy group of 1-3 carbons, provided that $R^5$ and $R^6$ may be linked at their ends, when they are adjacent each other, to form a saturated or unsaturated five- or six-membered ring which contains 0-2 oxygen or sulfur atoms therein and may be substituted with a halogen atom or an alkyl group of 1-4 carbons;

l is an integer of 1 or 2;
m is an integer of 1-4;
A is a group represented by the formula of $$\underset{R^{17}}{\overset{R^{18}}{\text{N}}}\!\!\!-\!\!\!\overset{}{\underset{Z}{\|}}\!\!\!-$$

$R^{17}$, $R^{18}$ independently are a hydrogen atom, an alkyl group of 1-4 carbons or a haloalkyl group of 1-4 carbons;

X is an oxygen atom or a sulfur atom; Z is oxygen, Y is an oxygen atom, a sulfur atom, a sulfinyl, sulfonyl or methylene group, or a group represented by the formula of $-NR^{20}-$;

$R^{20}$ is a hydrogen atom or an alkyl group of 1-4 carbons; and the ring B is a benzene, pyridine or cyclohexane ring.

2. An amide compound according to claim 1, wherein $R^1$ is a hydrogen atom or alkyl group of 1-4 carbons; $R^3$ is a hydrogen atom; $R^4$ is a hydrogen atom, a halogen atom or a methyl group;

$R^5$ is a halogen atom, an alkyl group of 1-8 carbons, a haloalkyl group of 1-8 carbons, a cycloalkyl group of 3-8 total carbons, an alkenyl group of 2-8 carbons, an alkynyl group of 2-8 carbons, an alkoxy group of 1-8 carbons, a haloalkoxy group of 1-8 carbons, an alkenyloxy group of 2-8 carbons, a haloalkenyloxy group of 2-8 carbons, an alkynyloxy group of 2-8 carbons, an alkylthio group of 1-8 carbons, a haloalkylthio group of 1-8 carbons, an alkenylthio group of 2-8 carbons, a haloalkenylthio group of 2-8 carbons, an alkynylthio group of 2-8 carbons, an alkoxyalkyl group of 2-8 total carbons, an alkylthioalkyl group of 2-8 total carbons, a (haloalkylthio)alkyl group of 2-8 total carbons, an alkylsulfinyl group of 1-8 carbons, a haloalkylsulfinyl group of 1-8 carbons, an alkylsulfonyl group of 1-8 carbons, a haloalkylsulfonyl group of 1-8 carbons, an alkylsulfonyloxy group of 1-8 carbons, a haloalkylsulfonyloxy group of 1-8 carbons, an alkylamino group of 1-8 carbons, a haloalkylamino group of 1-8 carbons or a dialkylamino group of 2-16 total carbons.

3. An amide compound according to claim 2, wherein $R^1$ is a hydrogen atom.

4. An amide compound according to claim 3, wherein $R^5$ is an alkylthio group of 1-8 carbons, a haloalkylthio group of 1-8 carbons, an alkenylthio group of 2-8 carbons, a haloalkenylthio group of 2-8 carbons, an alkynylthio group of 2-8 carbons, an alkoxyalkyl group of 2-8 total carbons, an alkylsulfinyl group of 1-8 carbons, a haloalkylsulfinyl group of 1-8 carbons;

$R^6$ is a hydrogen or halogen atom, or an alkyl group of 1-3 carbons or a haloalkyl group of 1-3 carbons and X is an oxygen atom.

5. An amide compound according to claim 1, selected from the group consisting of:

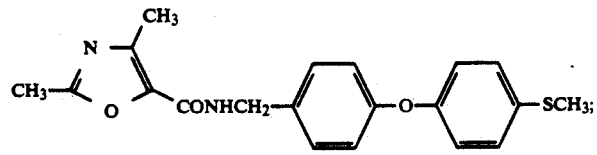

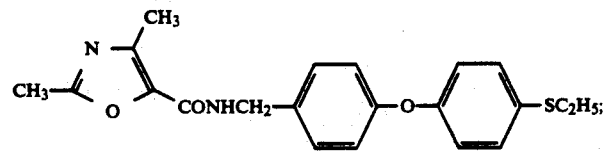

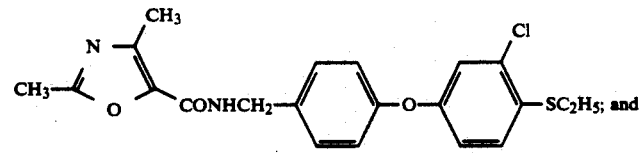

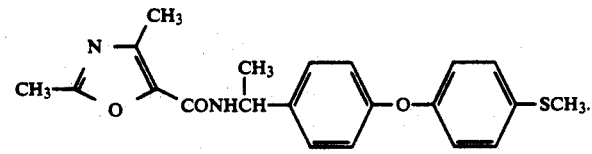

6. An insecticidal and/or acaricidal composition which comprises as an active ingredient an insecticidally and/or acaricidally effective amount of an amide compound according to claim 1, and an inert carrier or diluent.

7. A method for exterminating insects and/or acarids which comprises applying as an active ingredient an insecticidally and/or acaricidally effective amount of an amide compound according to claim 1 to the locus where insects and/or acarids propagate.

* * * * *